(12) United States Patent
Chang et al.

(10) Patent No.: US 9,905,239 B2
(45) Date of Patent: Feb. 27, 2018

(54) METHODS OF DECODING SPEECH FROM THE BRAIN AND SYSTEMS FOR PRACTICING THE SAME

(71) Applicant: The Regents of the University of California, Oakland, CA (US)

(72) Inventors: Edward F. Chang, San Francisco, CA (US); Kristofer E. Bouchard, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/768,416

(22) PCT Filed: Feb. 19, 2014

(86) PCT No.: PCT/US2014/017193
§ 371 (c)(1),
(2) Date: Aug. 17, 2015

(87) PCT Pub. No.: WO2014/130571
PCT Pub. Date: Aug. 28, 2014

(65) Prior Publication Data
US 2015/0380009 A1    Dec. 31, 2015

Related U.S. Application Data

(60) Provisional application No. 61/766,610, filed on Feb. 19, 2013.

(51) Int. Cl.
*G10L 13/00* (2006.01)
*G10L 15/00* (2013.01)
(Continued)

(52) U.S. Cl.
CPC .......... *G10L 21/00* (2013.01); *A61B 5/04001* (2013.01); *A61B 5/4076* (2013.01);
(Continued)

(58) Field of Classification Search
None
See application file for complete search history.

(56) References Cited

U.S. PATENT DOCUMENTS

| 4,084,583 | A | 4/1978 | Hjort |
| 4,709,702 | A | 12/1987 | Sherwin |

(Continued)

FOREIGN PATENT DOCUMENTS

| WO | 2005/057548 | 6/2005 |
| WO | 2012/116232 | 8/2012 |

OTHER PUBLICATIONS

G. N. Jayabhavani and N. R. Raajan, "Silent speech generation using Brain Machine Interface," 2013 IEEE International Conference on Emerging Trends in Computing, Communication and Nanotechnology (ICECCN), Tirunelveli, 2013, pp. 630-633.*

(Continued)

*Primary Examiner* — Paras D Shah
*Assistant Examiner* — Thuykhanh Le
(74) *Attorney, Agent, or Firm* — Edward J. Baba; Khin K. Chin; Bozicevic, Field & Francis LLP

(57) ABSTRACT

Provided are methods of decoding speech from the brain of a subject. The methods include detecting speech production signals from electrodes operably coupled to the speech motor cortex of a subject while the subject produces or imagines producing a speech sound. The methods further include deriving a speech production signal pattern from the detected speech production signals, and correlating the speech production signal pattern with a reference speech production signal pattern to decode speech from the brain of the subject. Speech communication systems and devices for practicing the subject methods are also provided.

19 Claims, 99 Drawing Sheets

(51) Int. Cl.
| | |
|---|---|
| *G10L 15/04* | (2013.01) |
| *G10L 21/00* | (2013.01) |
| *G10L 15/24* | (2013.01) |
| *G10L 25/03* | (2013.01) |
| *G09B 21/00* | (2006.01) |
| *G10L 13/04* | (2013.01) |
| *G10L 25/06* | (2013.01) |
| *A61B 5/04* | (2006.01) |
| *A61B 5/00* | (2006.01) |

(52) U.S. Cl.
CPC ............ *G09B 21/00* (2013.01); *G10L 13/043* (2013.01); *G10L 15/24* (2013.01); *G10L 25/03* (2013.01); *G10L 25/06* (2013.01); *A61B 5/4094* (2013.01); *A61B 5/4803* (2013.01); *A61B 5/7203* (2013.01); *A61B 5/726* (2013.01); *A61B 5/7257* (2013.01)

(56) References Cited

U.S. PATENT DOCUMENTS

| | | | |
|---|---|---|---|
| 4,967,038 A | 10/1990 | Gevins et al. | |
| 5,038,782 A | 8/1991 | Gevins et al. | |
| 5,119,816 A | 6/1992 | Gevins | |
| 5,291,888 A | 3/1994 | Tucker | |
| 5,361,773 A | 11/1994 | Ives | |
| 5,479,934 A | 1/1996 | Imran | |
| 5,724,984 A | 3/1998 | Arnold et al. | |
| 5,724,987 A * | 3/1998 | Gevins ................. | A61B 5/0484 434/258 |
| 5,817,029 A | 10/1998 | Gevins et al. | |
| 6,154,669 A | 11/2000 | Hunter et al. | |
| 6,256,531 B1 | 7/2001 | Ilmoniemi et al. | |
| 6,381,481 B1 | 4/2002 | Levendowski et al. | |
| 6,510,340 B1 | 1/2003 | Jordan | |
| 6,539,354 B1 * | 3/2003 | Sutton ..................... | G10L 21/06 345/423 |
| 7,239,910 B2 | 7/2007 | Tanner | |
| D565,735 S | 4/2008 | Washbon | |
| D603,051 S | 10/2009 | Causevic et al. | |
| 7,715,607 B2 | 5/2010 | Hu et al. | |
| 7,908,009 B2 | 3/2011 | Wyler et al. | |
| D641,886 S | 7/2011 | Causevic et al. | |
| 8,019,142 B2 | 9/2011 | Nowinski et al. | |
| D647,208 S | 10/2011 | Rothman et al. | |
| 8,045,775 B2 | 10/2011 | Volkau et al. | |
| 2003/0023319 A1 * | 1/2003 | Andersen ................. | A61F 2/68 623/24 |
| 2004/0117175 A1 * | 6/2004 | Chu ......................... | G10L 19/07 704/219 |
| 2004/0176950 A1 * | 9/2004 | Chu ......................... | G10L 19/08 704/207 |
| 2004/0181263 A1 * | 9/2004 | Balzer ..................... | A61N 1/0531 607/49 |
| 2004/0249302 A1 * | 12/2004 | Donoghue ........... | A61B 5/04001 600/544 |
| 2005/0144005 A1 * | 6/2005 | Kennedy ................. | G10L 15/24 704/271 |
| 2006/0004422 A1 * | 1/2006 | De Ridder ............. | A61N 1/0529 607/45 |
| 2006/0106431 A1 * | 5/2006 | Wyler ................. | A61N 1/36067 607/48 |
| 2006/0217782 A1 * | 9/2006 | Boveja ................. | A61N 1/0531 607/45 |
| 2006/0241718 A1 * | 10/2006 | Tyler ..................... | A61B 5/0492 607/45 |
| 2007/0088403 A1 * | 4/2007 | Wyler ................. | A61N 1/36082 607/45 |
| 2007/0093706 A1 | 4/2007 | Gevins et al. | |
| 2007/0142862 A1 * | 6/2007 | Dilorenzo ............. | A61N 1/3605 607/2 |
| 2008/0047342 A1 * | 2/2008 | Takano ................. | A61B 5/224 73/379.01 |
| 2008/0096171 A1 * | 4/2008 | Movahhedi ............ | G09B 19/00 434/178 |
| 2008/0270131 A1 * | 10/2008 | Fukuda ............... | G10L 21/0272 704/246 |
| 2009/0118787 A1 * | 5/2009 | Moffitt ............... | A61N 1/36082 607/45 |
| 2009/0131508 A1 * | 5/2009 | Verdru ................ | A61K 31/4015 514/424 |
| 2009/0157751 A1 * | 6/2009 | Jung .................... | A61B 5/0476 |
| 2009/0253982 A1 * | 10/2009 | Wang ..................... | A61B 5/055 600/419 |
| 2009/0281408 A1 | 11/2009 | Lee et al. | |
| 2009/0312817 A1 * | 12/2009 | Hogle .................. | A61B 5/0492 607/54 |
| 2010/0016732 A1 * | 1/2010 | Wells ................... | A61B 5/0059 600/476 |
| 2010/0036191 A1 * | 2/2010 | Walter .................. | A61N 2/006 600/14 |
| 2010/0130844 A1 | 5/2010 | Williams et al. | |
| 2010/0198042 A1 | 8/2010 | Popescu et al. | |
| 2010/0249637 A1 * | 9/2010 | Walter ................... | A61H 23/02 600/544 |
| 2011/0046502 A1 | 2/2011 | Pradeep et al. | |
| 2011/0046503 A1 | 2/2011 | Pradeep et al. | |
| 2011/0046504 A1 | 2/2011 | Pradeep et al. | |
| 2011/0152708 A1 * | 6/2011 | Adachi ............... | A61B 5/04845 600/544 |
| 2011/0237923 A1 | 9/2011 | Picht et al. | |
| 2011/0257464 A1 * | 10/2011 | Kehoe ...................... | A61F 5/58 600/23 |
| 2011/0282231 A1 | 11/2011 | Pradeep et al. | |
| 2011/0282232 A1 | 11/2011 | Pradeep et al. | |
| 2012/0022391 A1 | 1/2012 | Leuthardt | |
| 2012/0136403 A1 * | 5/2012 | Choudury ................ | A01N 1/00 607/2 |
| 2012/0163689 A1 * | 6/2012 | Bottger ................ | A61B 5/0263 382/131 |
| 2012/0296444 A1 | 11/2012 | Greenberg et al. | |
| 2012/0316793 A1 * | 12/2012 | Jung .................. | A61B 5/04842 702/19 |
| 2013/0018596 A1 * | 1/2013 | Bottger ................ | G06T 7/0012 702/21 |
| 2014/0211593 A1 * | 7/2014 | Tyler ...................... | A61B 5/165 367/137 |
| 2014/0213926 A1 * | 7/2014 | Vaidyanathan .... | A61N 1/36067 600/545 |
| 2015/0297106 A1 * | 10/2015 | Pasley .................. | A61B 5/0476 600/378 |

OTHER PUBLICATIONS

L. Wang, X. Zhang and Y. Zhang, "Extending motor imagery by speech imagery for brain-computer interface," 2013 35th Annual International Conference of the IEEE Engineering in Medicine and Biology Society (EMBC), Osaka, 2013, pp. 7056-7059.*
W. Wang, A. D. Degenhart, G. P. Sudre, D. A. Pomerleau and E. C. Tyler-Kabara, "Decoding semantic information from human electrocorticographic (ECoG) signals," 2011 Annual International Conference of the IEEE Engineering in Medicine and Biology Society, Boston, MA, 2011, pp. 6294-6298.*
Ajmone-Marsan (1998) "Electrocorticography: Historical Comments on its Development and the Evolution of its Practical Applications" Electroencephalogr. Clin. Neurophysiol, 48:9-16.
Briggman (2005) "Optical Imaging of Neuronal Populations During Decision-Making" Science 307:896-901.
Brumberg et al. (2010) "Brain-Computer Interfaces for Speech Communication" Speech. Commun. 52(4):367-379.
Mante et al. (2013) "Context-dependent computation by recurrent dynamics in prefrontal cortex" Nature 503:78-84.

* cited by examiner

A

METHODS OF DECODING SPEECH FROM THE BRAIN AND SYSTEMS FOR PRACTICING THE SAME

CROSS-REFERENCE TO RELATED APPLICATIONS

Pursuant to 35 U.S.C. § 119(e), this application claims priority to the filing date of U.S. Provisional Patent Application Ser. No. 61/766,610, filed Feb. 19, 2013, the disclosure of which is incorporated herein by reference in its entirety.

STATEMENT REGARDING FEDERALLY SPONSORED RESEARCH

This invention was made with government support under Grant No. DP2 OD008627 awarded by the National Institutes of Health. The government has certain rights in the invention.

BACKGROUND

Speech communication critically depends on the capacity to produce the large set of sounds that compose a given language. The wide range of spoken sounds results from highly flexible configurations of the vocal tract, which filters sound produced at the larynx via precisely coordinated movements of the lips, jaw and tongue. Each articulator has extensive degrees of freedom, allowing a large number of different realizations for speech movements. How humans exert such exquisite control in the setting of highly variable movement possibilities is a central unanswered question.

The cortical control of articulation is primarily mediated by the ventral half of the lateral sensorimotor (Rolandic) cortex (ventral sensorimotor cortex, vSMC), which provides corticobulbar projections to and afferent innervation from the face and vocal tract. The U-shaped vSMC is composed of the pre- and post-central gyri (Brodmann areas 1, 2, 3, 6b), and the gyral area directly ventral to the termination of the central sulcus called the guenon (Brodmann area 43). Using electrical stimulation, the somatotopic organization of face and mouth representations in human vSMC has been described. However, focal stimulation could not evoke meaningful utterances, implying that speech is not stored in discrete cortical areas. Instead, the production of phonemes and syllables is thought to arise from a coordinated motor pattern involving multiple articulator representations.

SUMMARY

Provided are methods of decoding speech from the brain of a subject. The methods include detecting speech production signals from electrodes operably coupled to the speech motor cortex of a subject while the subject produces or imagines producing a speech sound. The methods further include deriving a speech production signal pattern from the detected speech production signals, and correlating the speech production signal pattern with a reference speech production signal pattern to decode speech from the brain of the subject. Speech communication systems and devices for practicing the subject methods are also provided.

BRIEF DESCRIPTION OF THE DRAWINGS

The invention may be best understood from the following detailed description when read in conjunction with the accompanying drawings. Included in the drawings are the following figures.

Heat maps in Panels D, F and H display single-trial activity during multiple productions of /ja/ (left), /ji/ (center), and /ju/ (right), while plots in Panels E, G and I overlay the across trial mean±s.e. for /ja/, /ji/, and /ju/. Dashed vertical lines in Panels D-I demarcate the 500 ms time window displayed in Panel A. Points immediately above the x-axis in Panels E, G and I demarcate times at which there is a difference between vowels (rank-sum test, P<$10^{-3}$).

Figure 21:
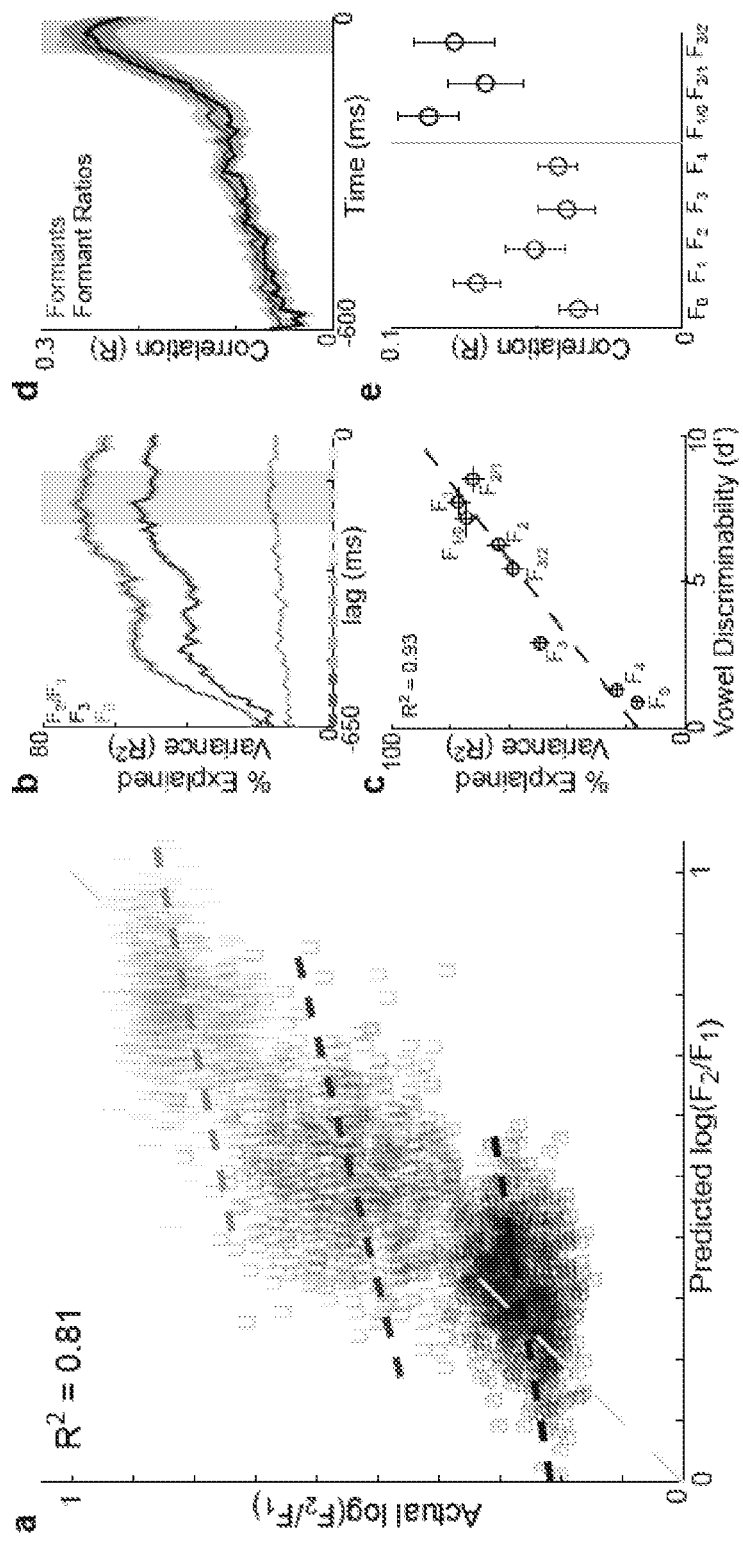

FIG. 21 depicts neural decoding and encoding of single-utterance acoustics across vowel. Panel A is a scatter plot of predicted $F_2/F_1$ vs. actual $F_2/F_1$ for decoders trained to predict the across vowel variability from the cortical data for /a/, /i/, and /u/. The dashed line extending up and to the right from 0,0 is the linear fit across vowels, while the shorter dashed lines correspond to the linear fits within a vowel. Panel B shows the time course of decoding performance (% explained variance, $R^2$) for $F_2/F_1$, $F_3$, and $F_0$. Data are presented as mean±s.e. from N=24 recording sessions in three subjects. The shaded area corresponds to time points at which model performance for different features were compared. Tick marks on the ordinate demarcate distinct temporal epochs in the structure of the underlying cortical data, corresponding to a vowel epoch, a consonant epoch, and early times. Time-point zero corresponds to the beginning of the acoustic measurement. Panel C shows vowel discriminability (d') vs. decoding performance (% explained variance, $R^2$) for the eight formant features. Data are presented as mean±s.e. from N=24 sessions for both d' and $R^2$. The dashed line is the best linear fit between the two. Panel D shows the time course of neural encoding performance (correlation coefficient, R) for individual electrodes (N=25 electrodes across three subjects). Traces correspond to separate linear models using formants and formant ratios to predict high-gamma activity. The shaded area corresponds to time points at which model performance was compared. Time-point zero corresponds to the beginning of the acoustic measurement. Panel E shows the correlation coefficients associated with individual acoustic features in the formant and formant ratio encoding models. Data are presented as mean±s.e., N=25 electrodes.

Figure 22:
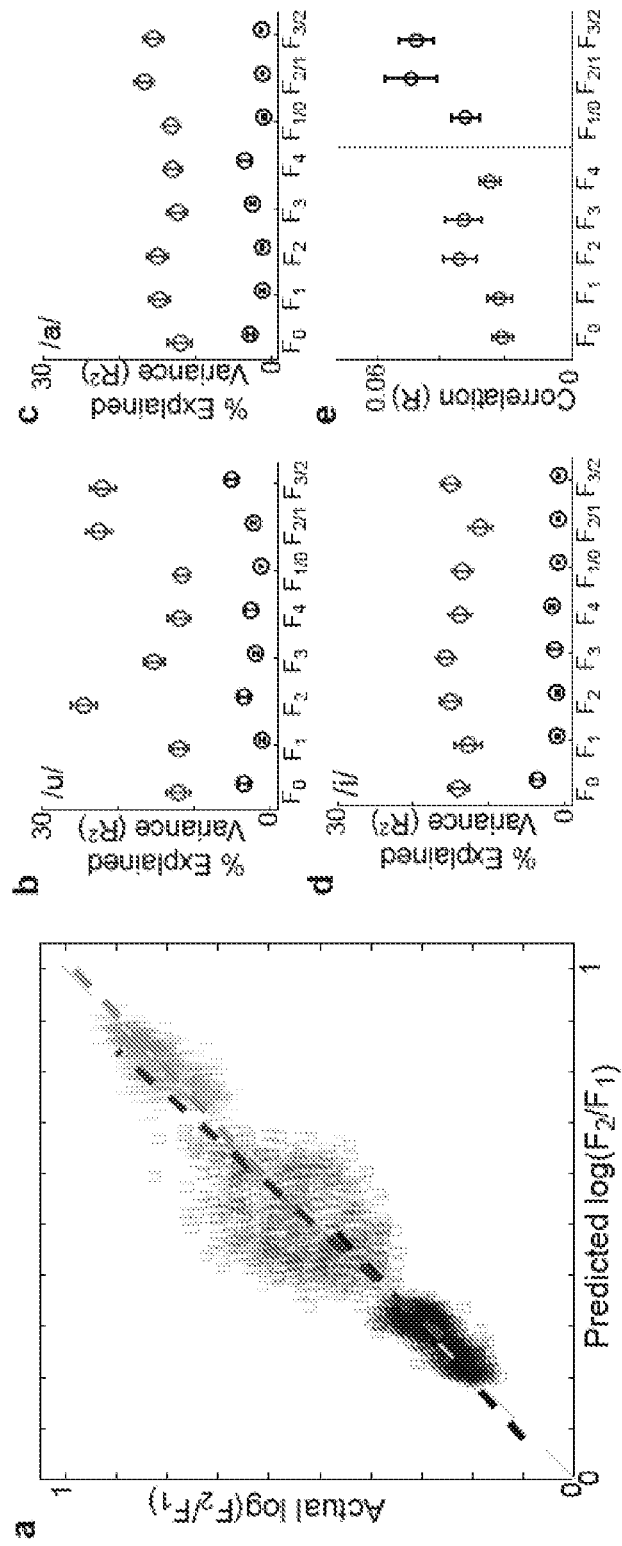

FIG. 22 provides data relating to neural decoding and encoding of single-utterance acoustics within vowels. Panel A shows a scatter plot of predicted $\log(F_2/F_1)$ vs. actual $\log(F_2/F_1)$ for decoders trained to predict the within vowel variability from the cortical data for /a/, /i/, and /u/ individually. The thin dashed line is the linear fit across vowels; the shorter dashed lines correspond to the linear fits within a vowel. Panels B-D show average decoding performance (% Explained Variance, $R^2$) across formant features for decoders trained within a vowel and across vowels for /u/ (Panel B), /a/ (Panel C), and /i/ (Panel D). Data are presented as mean±s.e., N=24 recording sessions. Panel E shows correlation coefficients associated with individual acoustic features in the formant (left of the vertical line) and formant ratio (right of the vertical line) encoding models. Data are presented as mean±s.e., N=25 electrodes.

Figure 23:
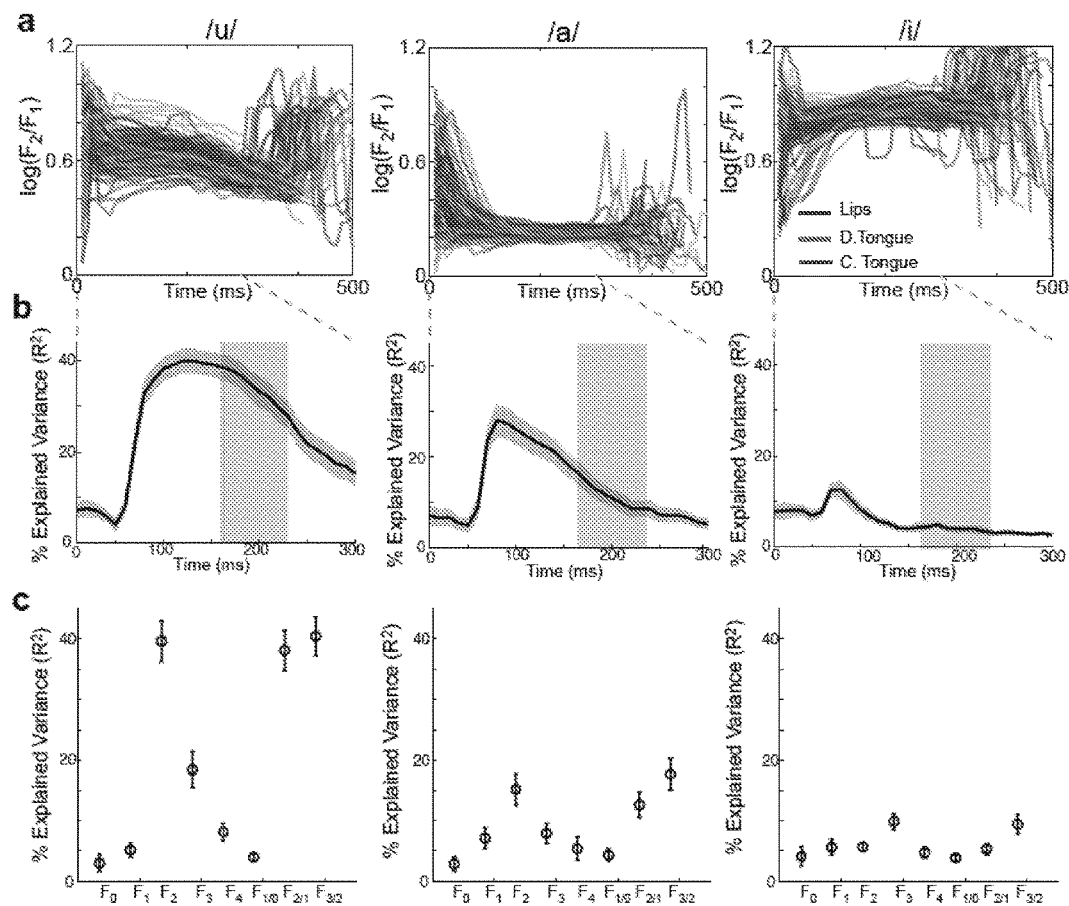

FIG. 23 provides data relating to perseveratory coarticulation of vowel acoustics. Panel A shows traces of $F_2/F_1$ vs. time for /u/, /a/, and /i/ from one recording session. Individual traces correspond to the articulator engaged during the production of the preceding consonant (lips, dorsal tongue, or coronal tongue). Time-point zero is the acoustic onset of the consonant-to-vowel transition. Panel B shows the time-course of percent of variance in $F_2/F_1$ explained ($R^2$) by the primary articulator engaged by the preceding consonant for the three vowels (/u/, left; /a/, center; /i/, right). Data are presented as mean±s.e.; N=24 recording sessions. Shaded area demarcates approximate times of extracted formant values (central $\frac{1}{5}^{th}$ of each vowel utterance). Time-point zero is the acoustic onset of the consonant-to-vowel transition. Panel C shows the percent variance explained ($R^2$) by the articulator engaged by the preceding consonant for the eight formant features.

Figure 24:
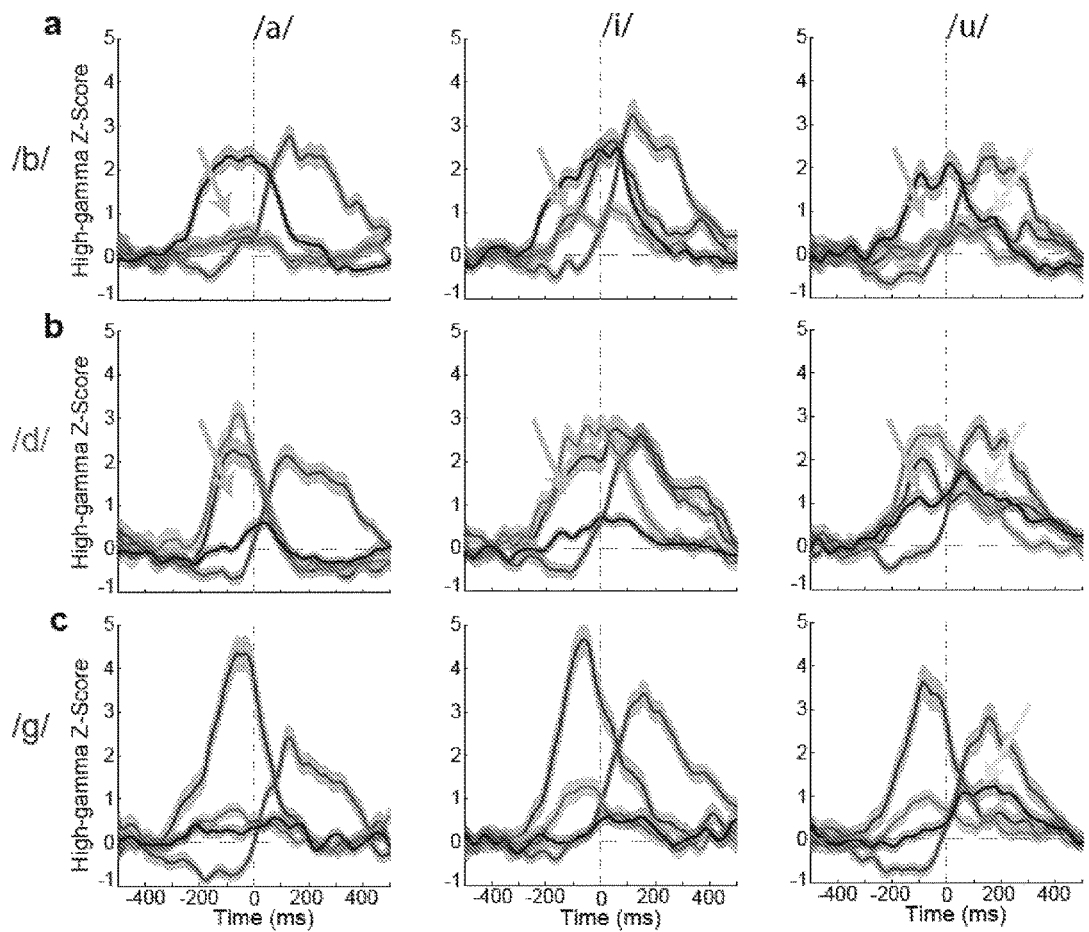

FIG. 24 provides data showing coarticulation in cortical activity for individual phonemes. Panels A-C show cortical data (mean±s.e.) from four electrodes distributed along the dorsal-ventral extent of vSMC (colored with increasing dorsal distance from Sylvian fissure) during the production of /ba/, /bi/, /bu/ (Panel A); /da/, /di/, /du/ (Panel B); and /ga/, /gi/, /gu/ (Panel C) Dashed vertical and horizontal lines demarcate 0 for time and high-gamma z-scores, respectively. Time point 0 is the acoustic onset of the consonant-to-vowel transition. Arrows point downward to the left demarcate vowel times for /u/ with different activity depending on the preceding consonant; arrows pointing downward to the right demarcate consonant times during /b/ and /d/ with differential activity depending on the upcoming vowel.

Figure 25:
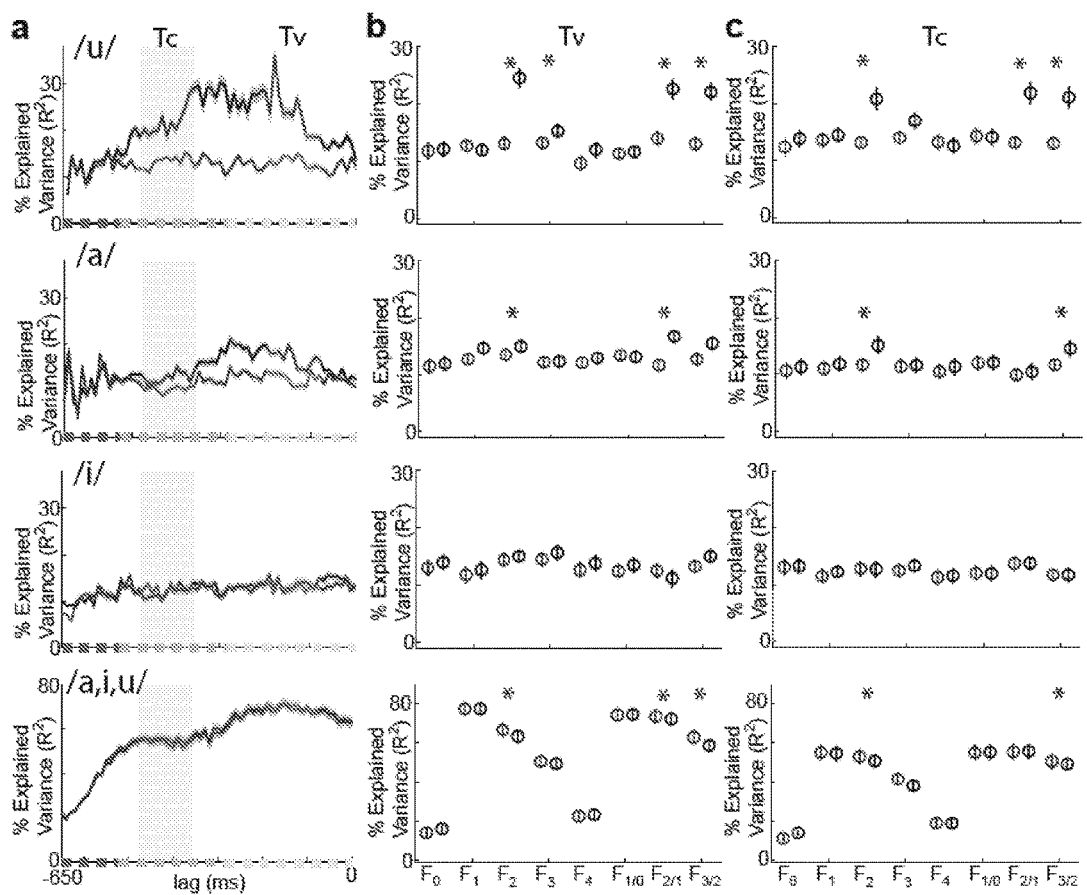

FIG. 25 shows data establishing a cortical source for co-articulation. Panel A shows time-courses of decoding performance (% Variance Explained, mean±s.e.) for raw $\log(F_2/F_1)$ and residual $\log(F_2/F_1)$ after removing the effects of perseverative co-articulation due to the articulator engaged by the preceding consonant. Tick marks on the ordinate correspond to distinct temporal epochs in the structure of the underlying cortical data. The shaded region corresponds to time points at which decoding performance was calculated for vowel times (Tv) and consonant times (Tc). Time-point zero corresponds to the beginning of the acoustic measurement window. Panel B shows decoding performance (mean±s.e.) during vowel times (Tv) for raw formant features and the feature residuals after removing the effects of perseveratory coarticulation. *: P<$10^{-3}$ between decoding performance of raw formants and residual formants, Wilcoxon Signed-Rank test, N=24. Panel C shows decoding performance (mean±s.e.) during consonant times (Tc) for raw formant features and the feature residuals after removing the effects of perseveratory coarticulation. *: P<$10^{-3}$ between decoding performance of raw formants and residual formants, Wilcoxon Signed-Rank test, N=24.

Figure 26:
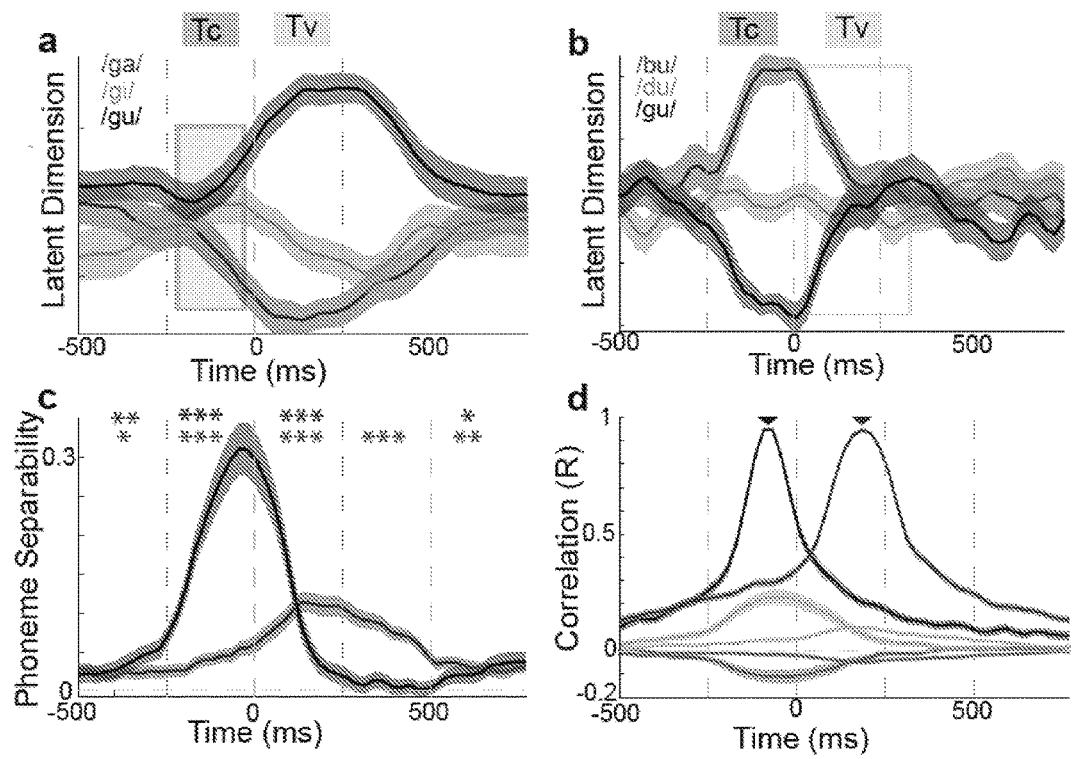

FIG. 26 shows data relating to anticipatory and perseveratory vSMC network dynamics during speech. Panel A shows average (mean±s.e.) consonant-vowel trajectories in the single dimension that best separates the vowels derived from dimensionality-reduction of single-trial cortical activity associated with /ga/, /gi/, and /gu/. The box on the left depicts the consonant time. Time-point zero is the acoustic onset of the consonant-to-vowel transition in all plots. Panel B shows average (mean±s.e.) consonant-vowel trajectories in the single dimension that best separates the consonants derived from dimensionality-reduction of single-trial cortical activity associated with /bu/, /du/, and /gu/. The box on the right depicts the vowel time. Panel C shows average (mean±s.e.) time course of phoneme separability: phoneme separability of the labial, coronal tongue, and dorsal tongue consonants transitioning to individual vowels (n=78); phoneme separability of the vowels /a/, /i/, and /u/ transitioning from individual consonants (n=162). Panel D shows average (mean±s.e.) state-space autocorrelations for consonant-vowel syllables: correlation coefficients for consonant states (left-most triangle) during the production of individual vowels (n=78); state-space autocorrelation for vowel states (right-most triangle) during the production of individual consonants (n=162). Also plotted are the correlation for within syllable randomizations, as well as the results of the across syllable randomizations.

DETAILED DESCRIPTION

Provided are methods of decoding speech from the brain of a subject. The methods include detecting speech production signals from electrodes operably coupled to the speech motor cortex of a subject while the subject produces or imagines producing a speech sound. The methods further include deriving a speech production signal pattern from the detected speech production signals, and correlating the speech production signal pattern with a reference speech production signal pattern to decode speech from the brain of the subject. Speech communication systems and devices for practicing the subject methods are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the signal" includes reference to one or more signals, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods of decoding speech from the brain of a subject. In certain aspects, the methods include detecting speech production signals from at least three electrodes operably coupled to the speech motor cortex of a subject while the subject produces or imagines producing a speech sound, deriving a speech production signal pattern from the detected speech production signals, and correlating the speech production signal pattern with a reference speech production signal pattern to decode speech from the brain of the subject. Various steps and aspects of the methods will now be described in greater detail below.

As set forth above, methods of the present disclosure include detecting speech production signals from at least three electrodes operably coupled to the speech motor cortex of a subject. By "speech production signals" is meant neural signals, generated by one or more neurons in the speech motor cortex, which relate to the movement of one or more speech articulators (e.g., the larynx, lips, jaws, tongue, and the like) during the production of actual or imagined speech sound(s) such as phonemes, a formant (e.g., formant acoustics of a vowel(s)), diphones, triphones, consonant vowel transitions, syllables, words, sentences, and any combinations thereof. In certain aspects, the speech production signals include neural signals relating to formants (e.g., spectral peaks of the sound spectrum $|P(f)|$ of the voice) and pitch (e.g., how "high" or "low" the speech sound is depending on the rate of vibration of the vocal chords). For example, with respect to formants, the speech production signals (e.g., vSMC activity) correlate to the acoustic parameters of different vowels, as well as different renditions of the same vowel (as demonstrated in Example 7 below).

The speech production signals are detected using at least three electrodes operably coupled to the speech motor cortex of the subject. By "operably coupled" is meant the at least three electrodes are of a suitable type and position so as to detect the desired speech production signals in the speech motor cortex. According to one embodiment, the at least three electrodes are operably coupled to the speech motor cortex by implantation on the surface of the speech motor cortex. In one aspect, an array of electrocorticography electrodes (ECoG array) is disposed on the surface of the speech motor cortex (e.g., the vSMC) for detection of speech production signals (e.g., local field potentials) generated in the speech motor cortex. According to certain embodiments, the at least three electrodes are operably coupled to the speech motor cortex by insertion of the electrodes into the speech motor cortex (e.g., at a desired depth).

The specific location at which to position an electrode may be determined by identification of anatomical landmarks in the subject's brain, such as the pre-central and post-central gyri and the central sulcus. Identification of anatomical landmarks in a subject's brain may be accomplished by any convenient means, such as magnetic resonance imaging (MRI), functional magnetic resonance imaging (fMRI), and visual inspection of a subject's brain while undergoing a craniotomy. Once a suitable location for an electrode is determined, the electrode may be positioned (e.g., implanted) according to any convenient means. Suitable locations for positioning or implanting the at least three electrodes may include, but are not limited to, one or more regions of the ventral sensorimotor cortex (vSMC), including the pre-central gyrus, the post-central gyrus, the guenon (the gyral area directly ventral to the termination of the central sulcus), and any combination thereof. Correct placement of the at least three electrodes may be confirmed by any convenient means, including visual inspection or computed tomography (CT) scan. In some aspects, after electrode positions are confirmed, they may be superimposed on a surface reconstruction image of the subject's brain. In certain aspects, the electrodes are positioned such that the speech production signals are detected from one or more regions of the vSMC, e.g., the speech production signals are detected from a region of the vSMC selected from the pre-central gyrus, the post-central gyrus, the guenon, and combinations thereof (see FIG. 1, panels B and C).

Methods of interest for positioning electrodes further include, but are not limited to, those described in U.S. Pat. Nos. 4,084,583; 5,119,816; 5,291,888; 5,361,773; 5,479,934; 5,724,984; 5,817,029; 6,256,531; 6,381,481; 6,510,340; 7,239,910; 7,715,607; 7,908,009; 8,045,775; and 8,019,142; the disclosures of which are incorporated herein by reference in their entireties for all purposes.

The number of electrodes operably coupled to the speech motor cortex may be chosen so as to provide the desired resolution and information about the speech production signals being generated in the speech motor cortex, as each electrode may convey information about the activity of a particular region (e.g., the somatotopic regions in the vSMC identified and described in the Examples section herein below). By comparing differences between the signals of each electrode, speech production signal patterns may be derived from the speech production signals. Accordingly, in certain embodiments, at least 10 electrodes (e.g., at least 20 electrodes) are employed. Between about 3 and 1024 electrodes, or more, may be employed. In some embodiments, the number of electrodes positioned is about 3 to 10 electrodes, about 10 to 20 electrodes, about 20 to 30 electrodes, about 30 to 40 electrodes, about 40 to 50 electrodes, about 60 to 70 electrodes, about 70 to 80 electrodes, about 80 to 90 electrodes, about 90 to 100 electrodes, about 100 to 110 electrodes, about 110 to 120 electrodes, about 120 to 130 electrodes, about 130 to 140 electrodes, about 140 to 150 electrodes, about 150 to 160 electrodes, about 160 to 170 electrodes, about 170 to 180 electrodes, about 180 to 190 electrodes, about 190 to 200 electrodes, about 200 to 210 electrodes, about 210 to 220 electrodes, about 220 to 230 electrodes, about 230 to 240 electrodes, about 240 to 250 electrodes, about 250 to 300 electrodes (e.g., a 16×16 array of 256 electrodes), about 300 to 400 electrodes, about 400 to 500 electrodes, about 500 to 600 electrodes, about 600 to 700 electrodes, about 700 to 800 electrodes, about 800 to 900 electrodes, about 900 to 1000 electrodes, or about 1000 to 1024 electrodes, or more. The electrodes may be homogeneous or heterogeneous.

Electrodes may be arranged in no particular pattern or any convenient pattern to facilitate detection of speech production signals. For example, a plurality of electrodes may be placed in a grid pattern, in which the spacing between adjacent electrodes is approximately equivalent. Such spacing between adjacent electrodes may be, for example, about 2.5 cm or less, about 2 cm or less, about 1.5 cm or less, about 1 cm or less, about 0.5 cm or less, about 0.1 cm or less, or about 0.05 cm or less. Electrodes placed in a grid pattern may be arranged such that the overall plurality of electrodes forms a roughly geometrical shape. In certain embodiments, a grid pattern may be roughly square in overall shape, roughly rectangular, roughly trapezoidal, or roughly oval in shape, or roughly circular.

Electrodes may be pre-arranged into an array, such that the array includes a plurality of electrodes that may be placed on or in a subject's brain. Such arrays may be miniature- or micro-arrays, a non-limiting example of which may be a miniature ECoG array. For a general review of ECoG technology, see Ajmone-Marsan, C. Electrocorticography: Historical Comments on its Development and the Evolution of its Practical Applications, Electroencephalogr. Clin. Neurophysiol, Suppl. 1998, 48: 10-16; the disclosure of which is incorporated herein by reference.

Also of interest are electrodes that may receive electroencephalography (EEG) data. One or more wet or dry EEG electrodes may be used in practicing the subject methods. Electrodes and electrode systems of interest further include, but are not limited to, those described in U.S. Patent Publication Numbers 2007/0093706, 2009/0281408, 2010/0130844, 2010/0198042, 2011/0046502, 2011/0046503, 2011/0046504, 2011/0237923, 2011/0282231, 2011/0282232 and U.S. Pat. Nos. 4,709,702, 4,967,038, 5,038,782, 6,154,669; the disclosures of which are incorporated herein by reference.

An array may include, for example, about 5 electrodes or more, e.g., about 5 to 10 electrodes, about 10 to 20 electrodes, about 20 to 30 electrodes, about 30 to 40 electrodes, about 40 to 50 electrodes, about 50 to 60 electrodes, about 60 to 70 electrodes, about 70 to 80 electrodes, about 80 to 90 electrodes, about 90 to 100 electrodes, about 100 to 125 electrodes, about 125 to 150 electrodes, about 150 to 200 electrodes, about 200 to 250 electrodes, about 250 to 300 electrodes (e.g., a 256 electrode array in 16×16 format), about 300 to 400 electrodes, about 400 to 500 electrodes, or about 500 electrodes or more. In certain embodiments, the array may cover a surface area of about 1 cm$^2$, about 1 to 10 cm$^2$, about 10 to 25 cm$^2$, about 25 to 50 cm$^2$, about 50 to 75 cm$^2$, about 75 to 100 cm$^2$, or 100 cm$^2$ or more. Arrays of interest may include, but are not limited to, those described in U.S. Pat. Nos. USD565735; USD603051; USD641886; and USD647208; the disclosures of which are incorporated herein by reference.

Electrodes may be platinum-iridium electrodes or be made out of any convenient material. The diameter, length, and composition of the electrodes to be employed may be determined in accordance with routine procedures known to those skilled in the art. Factors which may be weighted when selecting an appropriate electrode type may include but not be limited to the desired location for placement, the type of subject, the age of the subject, cost, duration for which the electrode may need to be positioned, and other factors.

Figure 2:
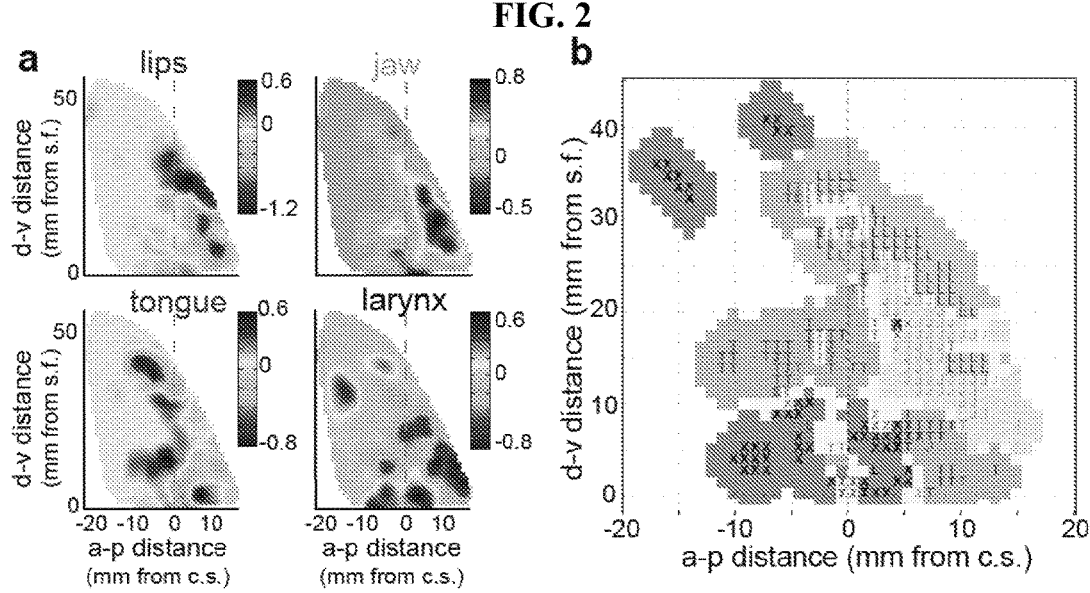
FIG. 2 shows spatial representation of articulators. Panel A depicts localization of lips, jaw, tongue, and larynx representations. Average magnitude of articulator weightings plotted as a function of anterior-posterior (AP) distance from the central sulcus and dorsal-ventral (DV) distance from the Sylvian fissure (n=3 subjects). Panel B shows functional somatotopic organization of speech articulator representations in vSMC. Lips (L); jaw (J); tongue (T,); larynx (X,), mixed. Letters correspond to locations based upon direct measurement-derived regression weights, shaded rectangles correspond to regions classified by k-nearest neighbor.
Figure 19:
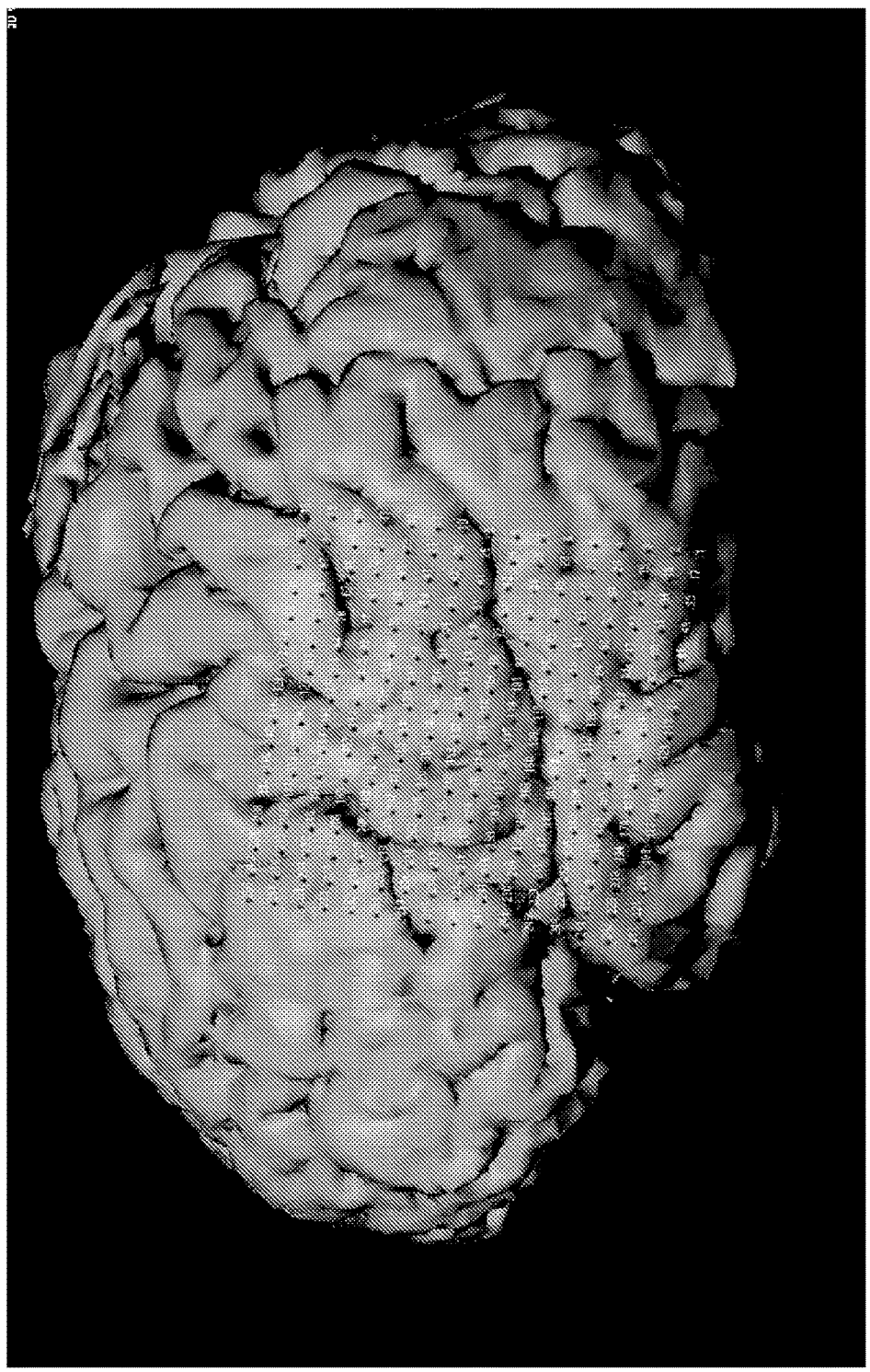
FIG. 19 shows the spatiotemporal patterns of speech motor cortex speech production signals/neural activity for 256 channels (a 16×16 ECoG electrode array) for consonant-vowel syllables. Panel A shows the position of the array relative to the subject's brain. Panels B-T represent a single consonant as indicated with vowels superimposed on each plot (a—solid line; i—dashed line; u—dotted line).
Figure 19:
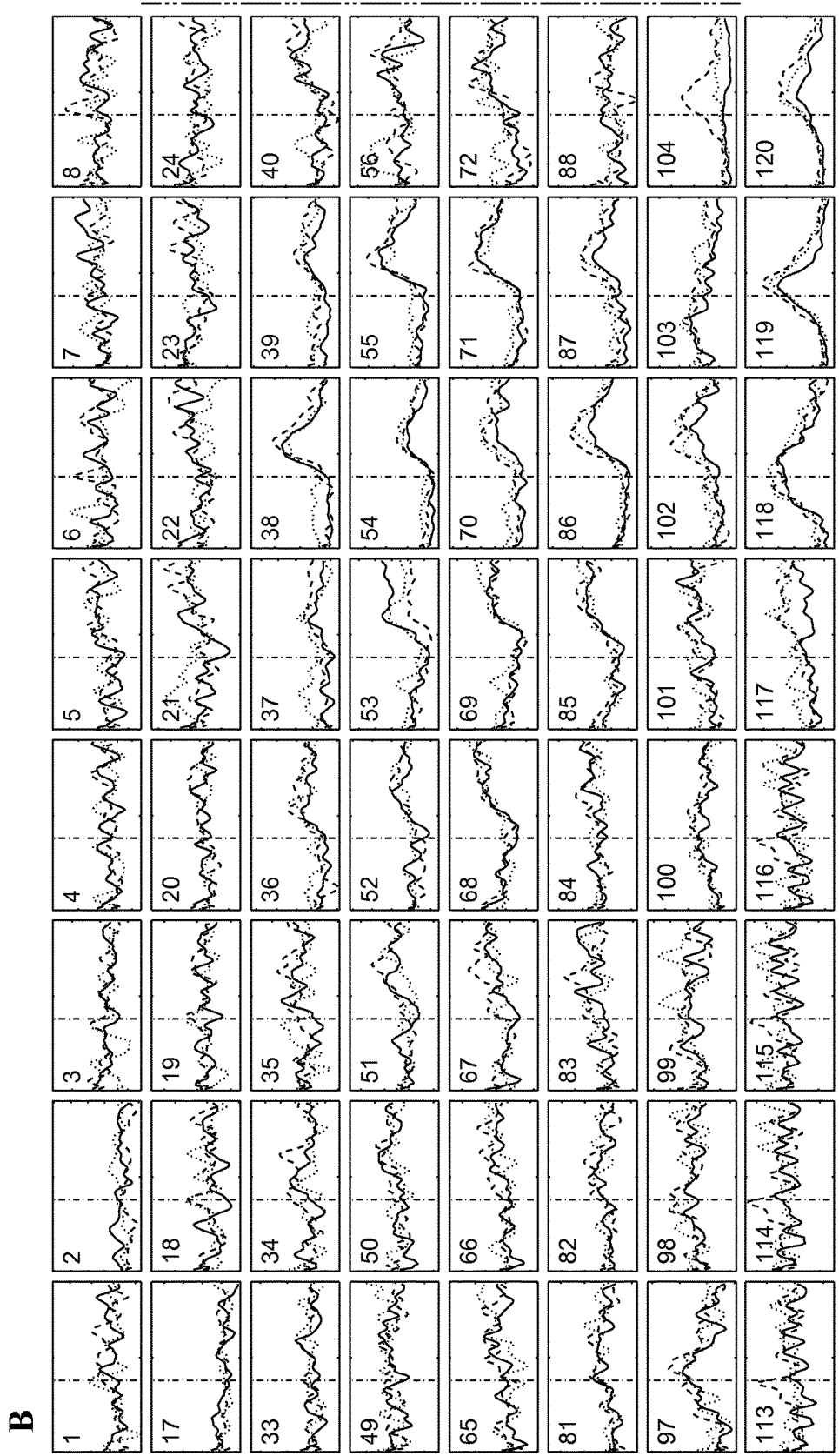
Figure 19:
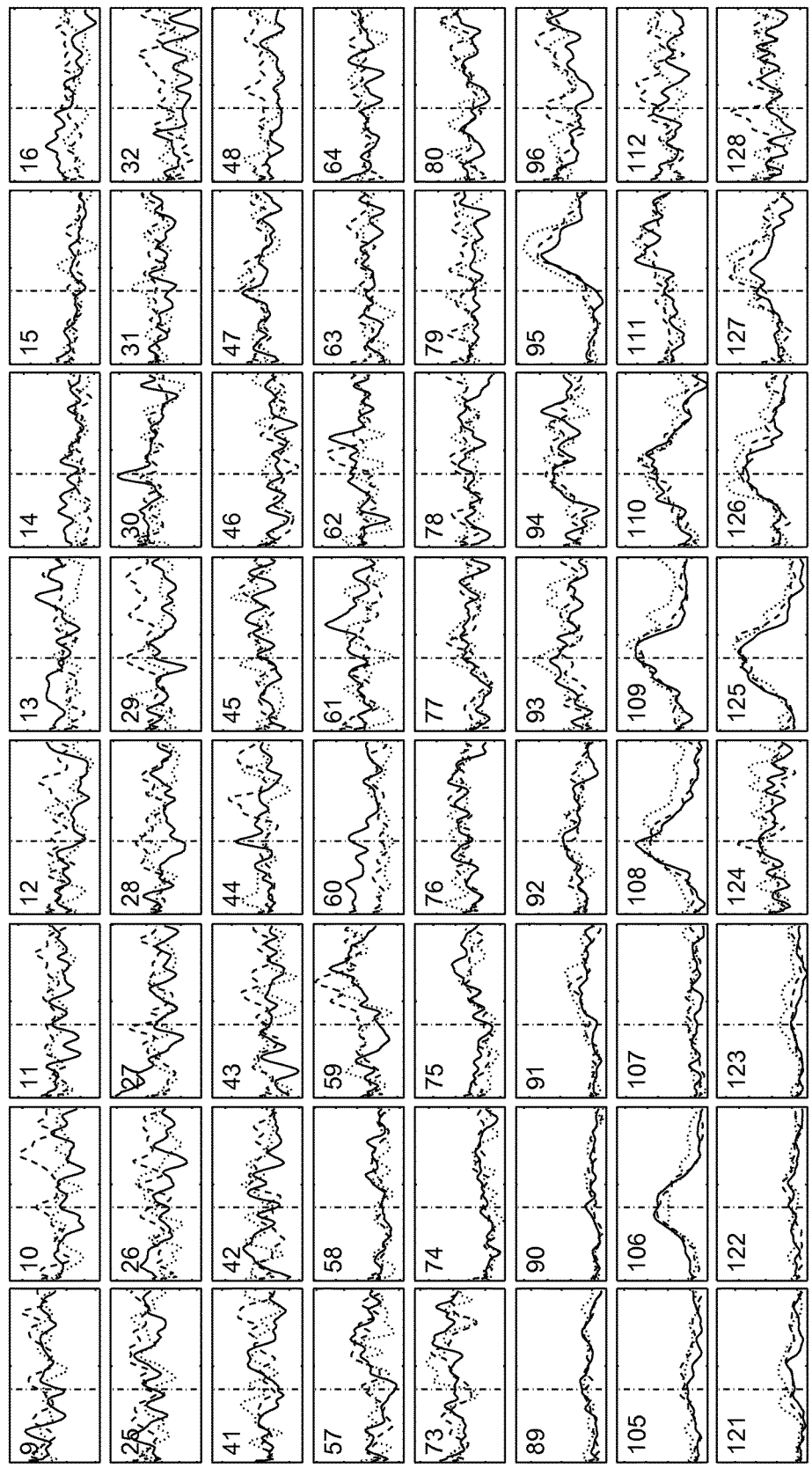
Figure 19:
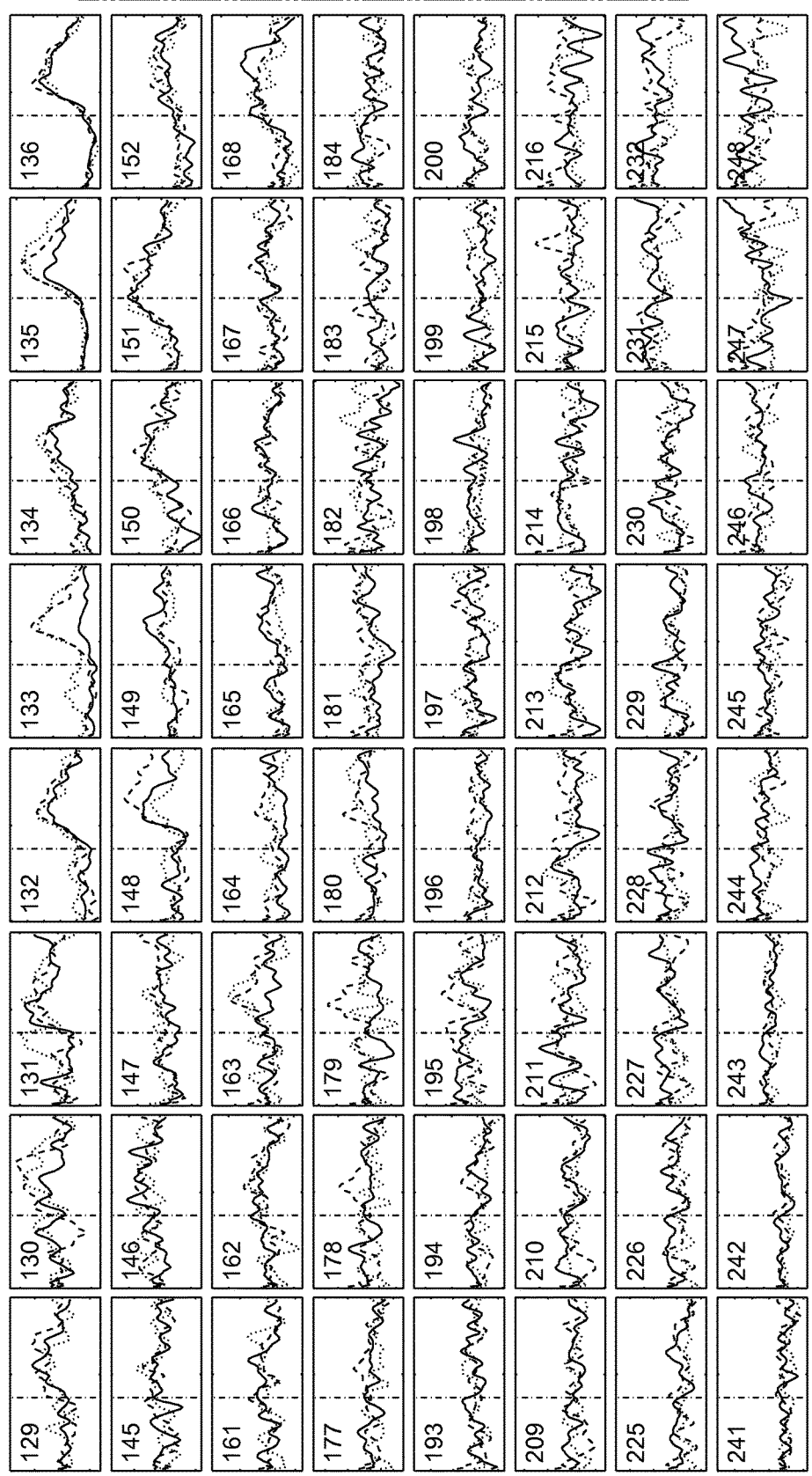
Figure 19:
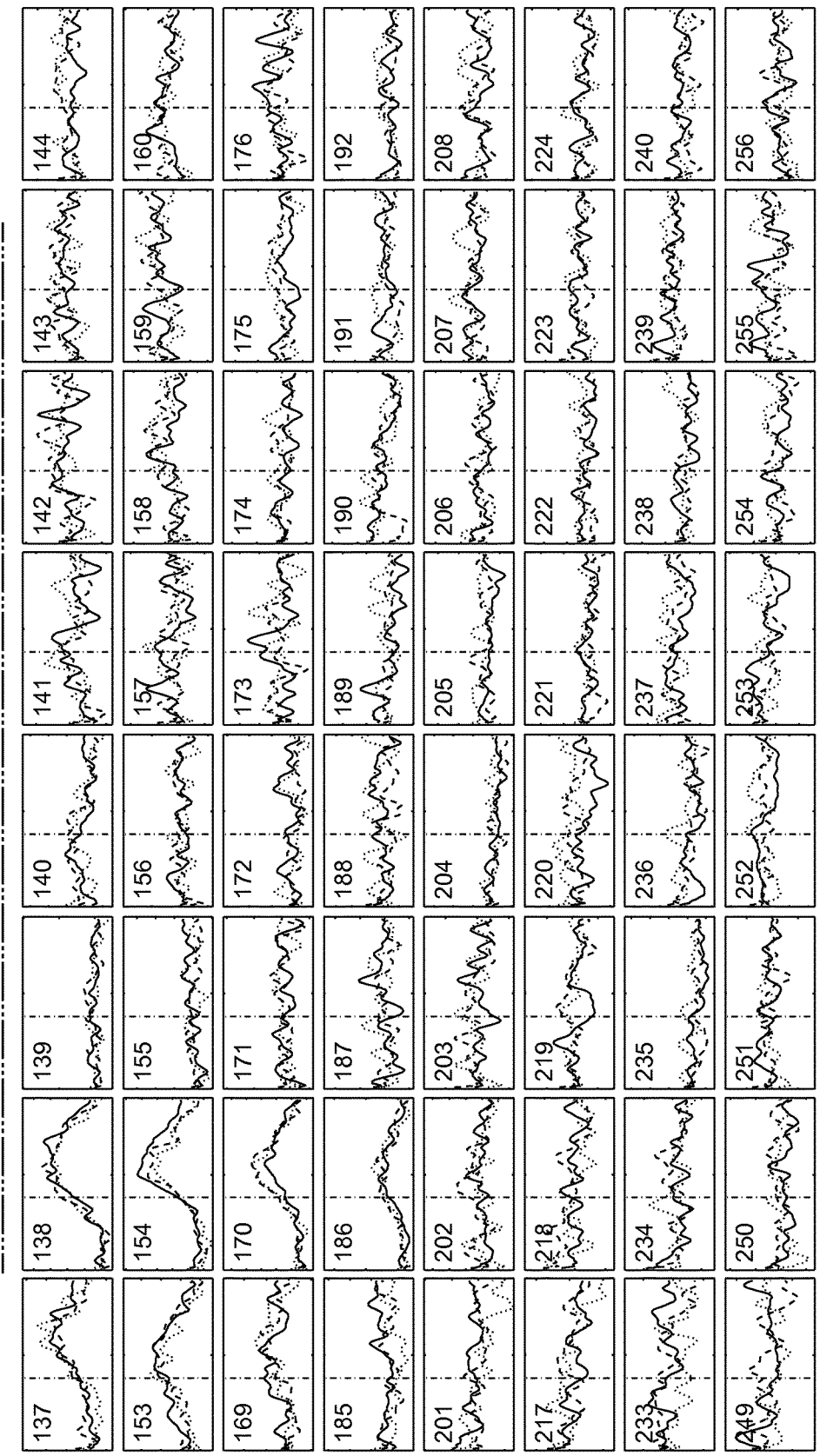
Figure 19:
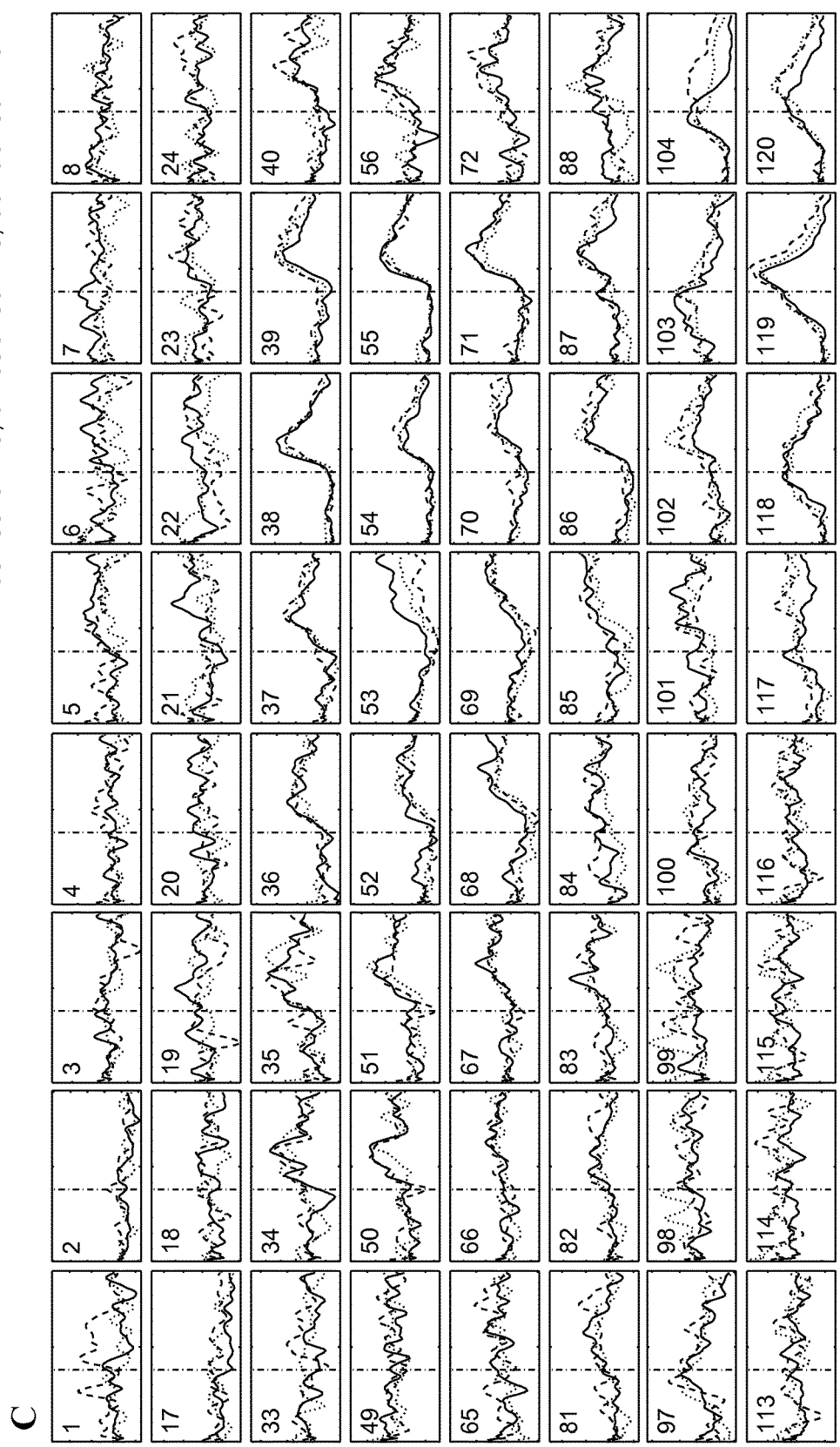
Figure 19:
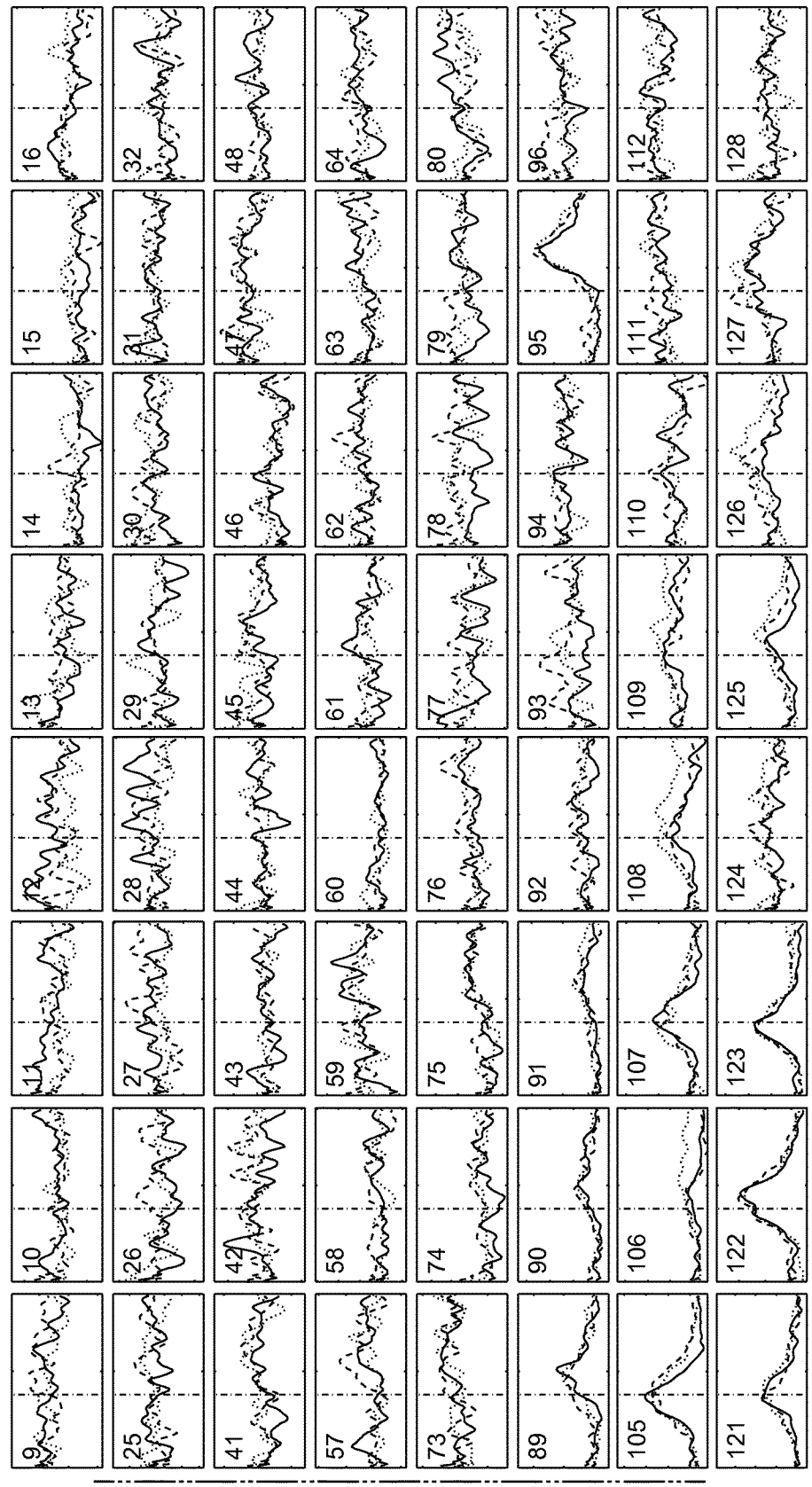
Figure 19:
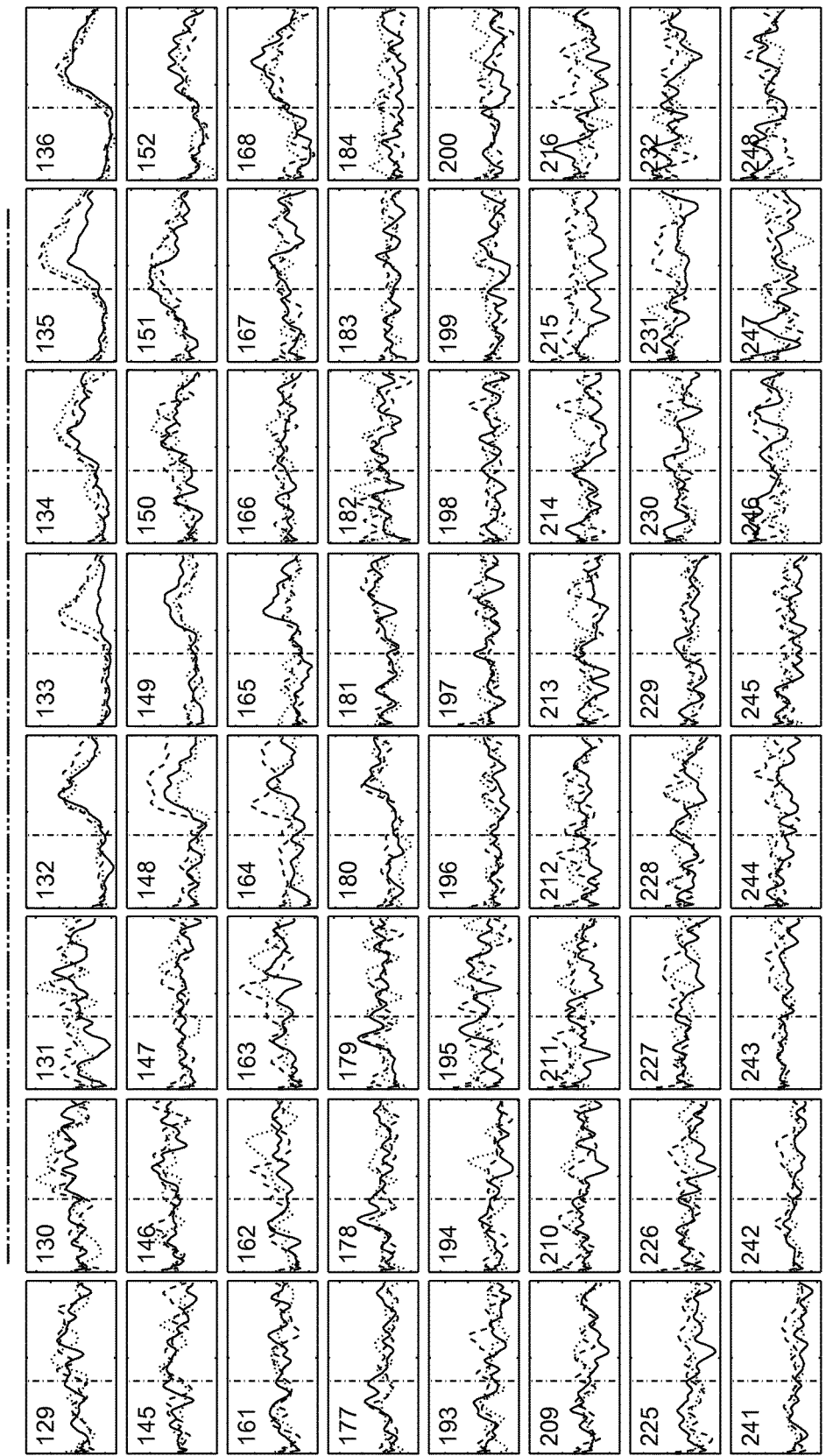
Figure 19:
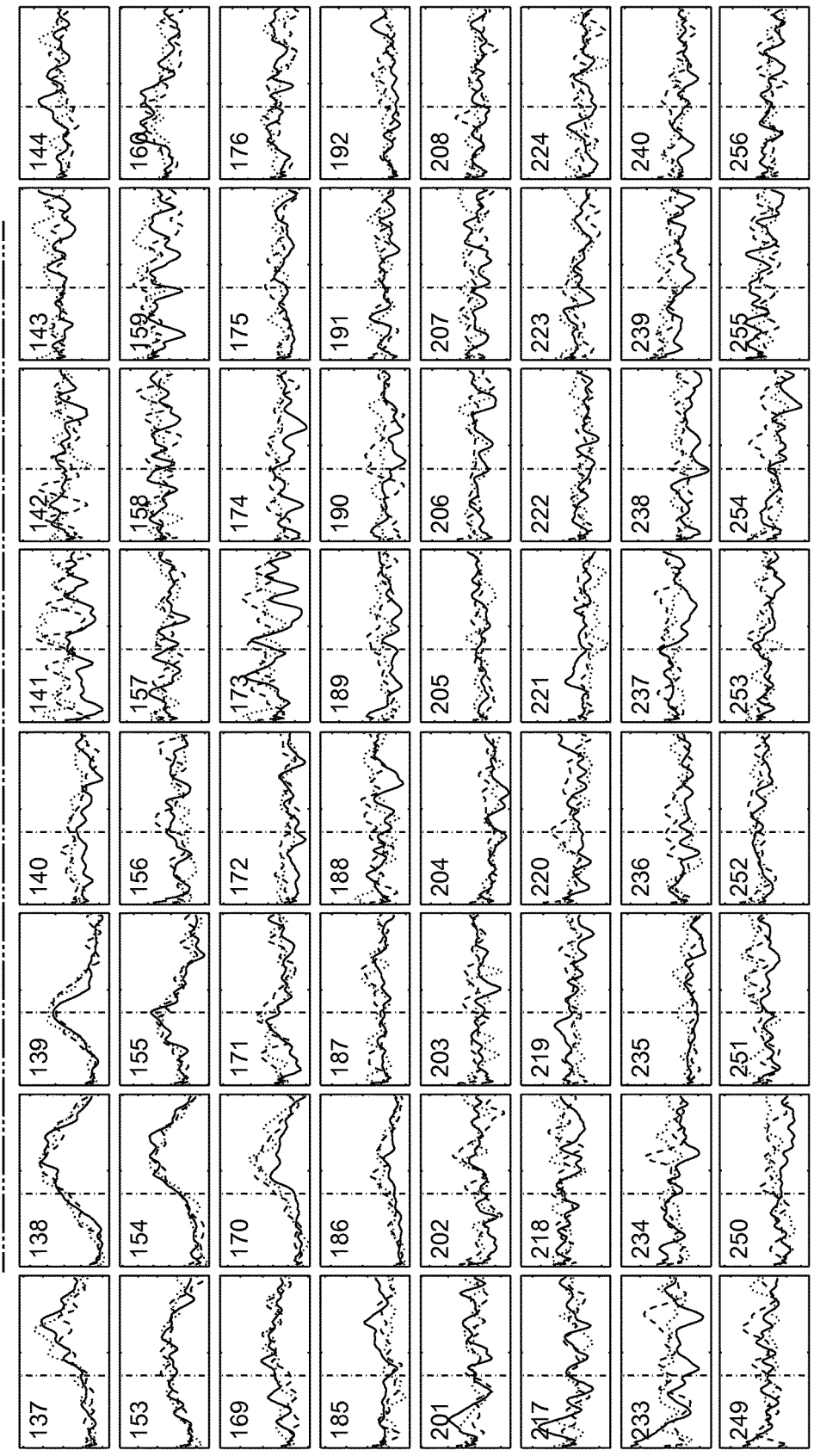
Figure 19:
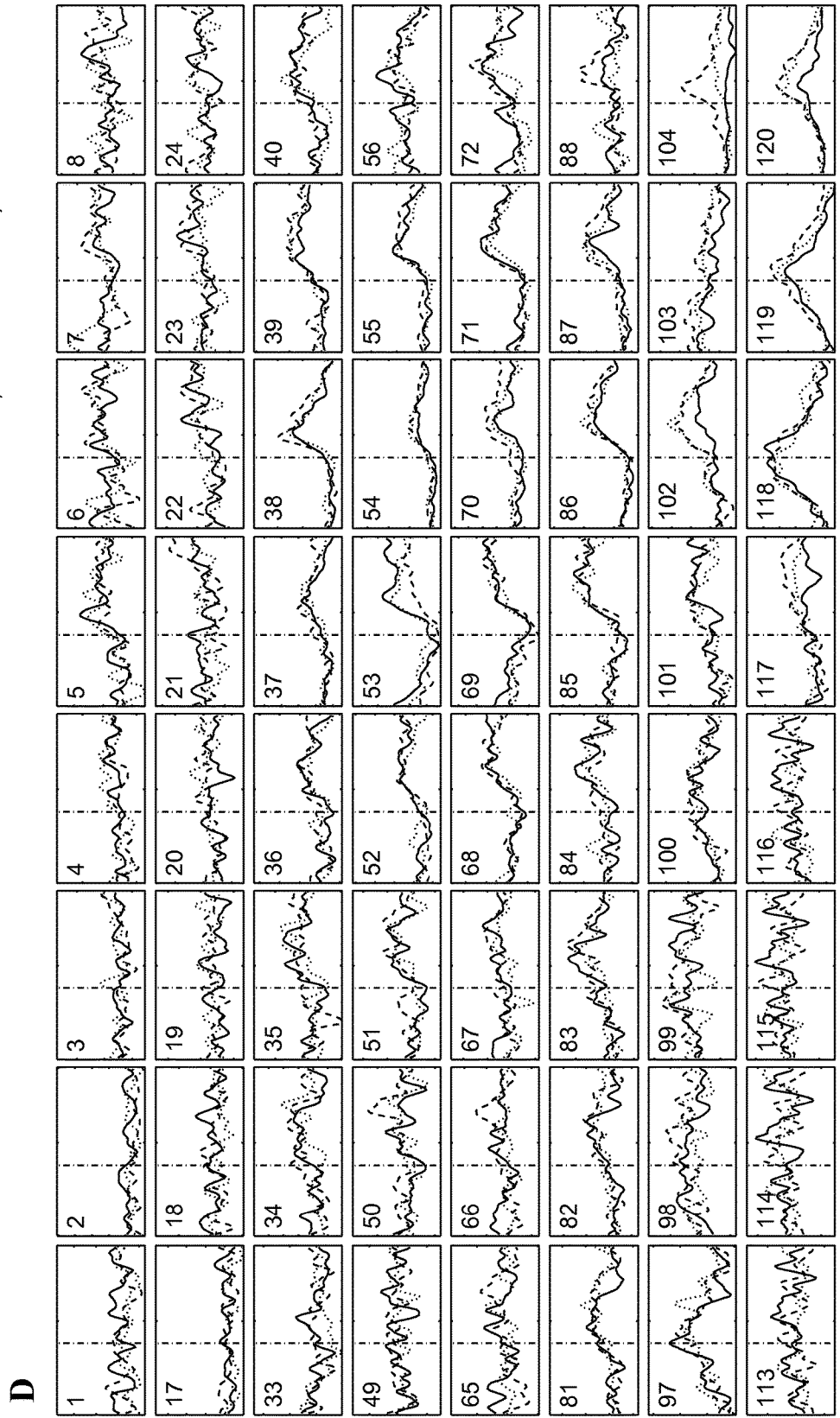
Figure 19:
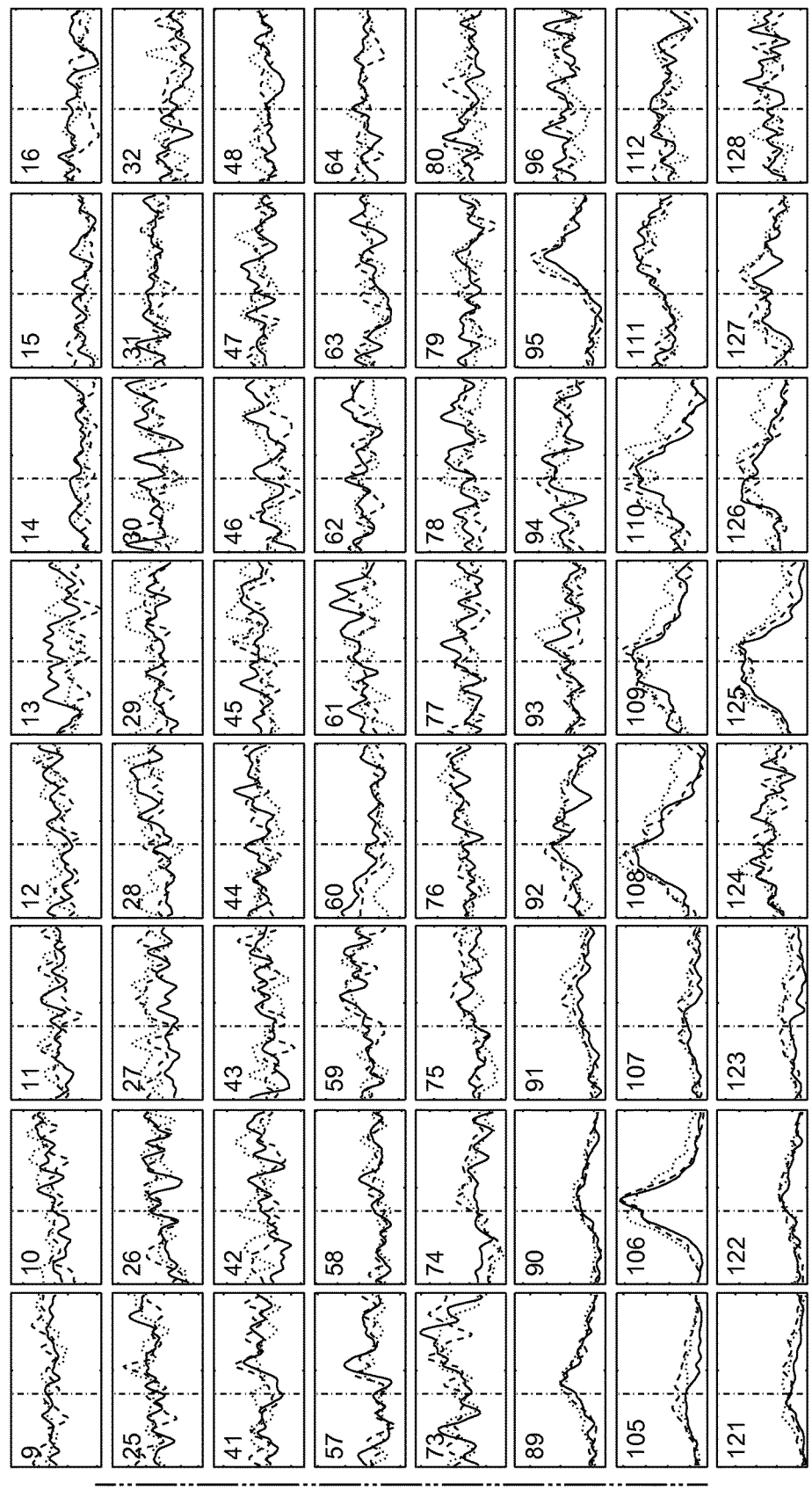
Figure 19:
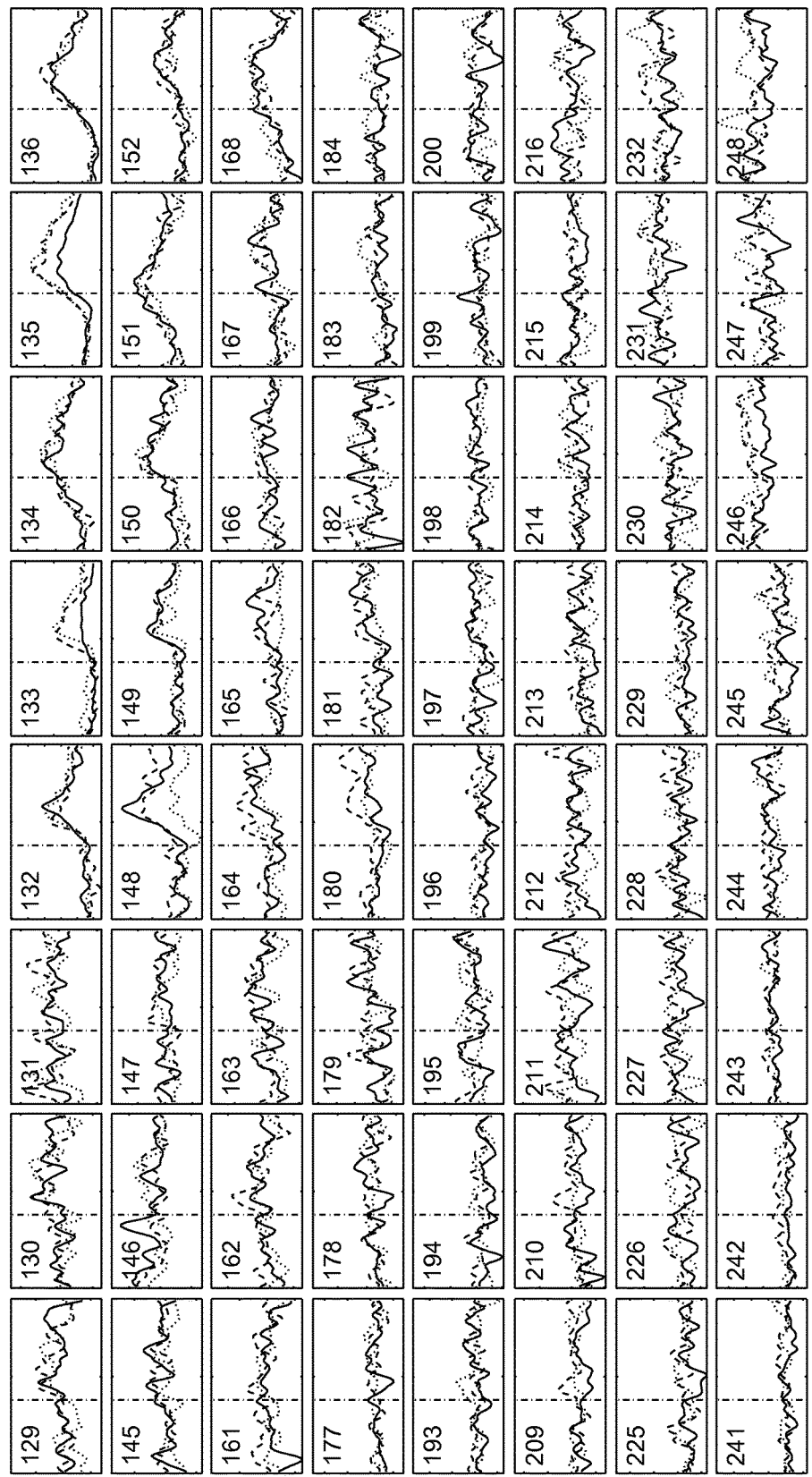
Figure 19:
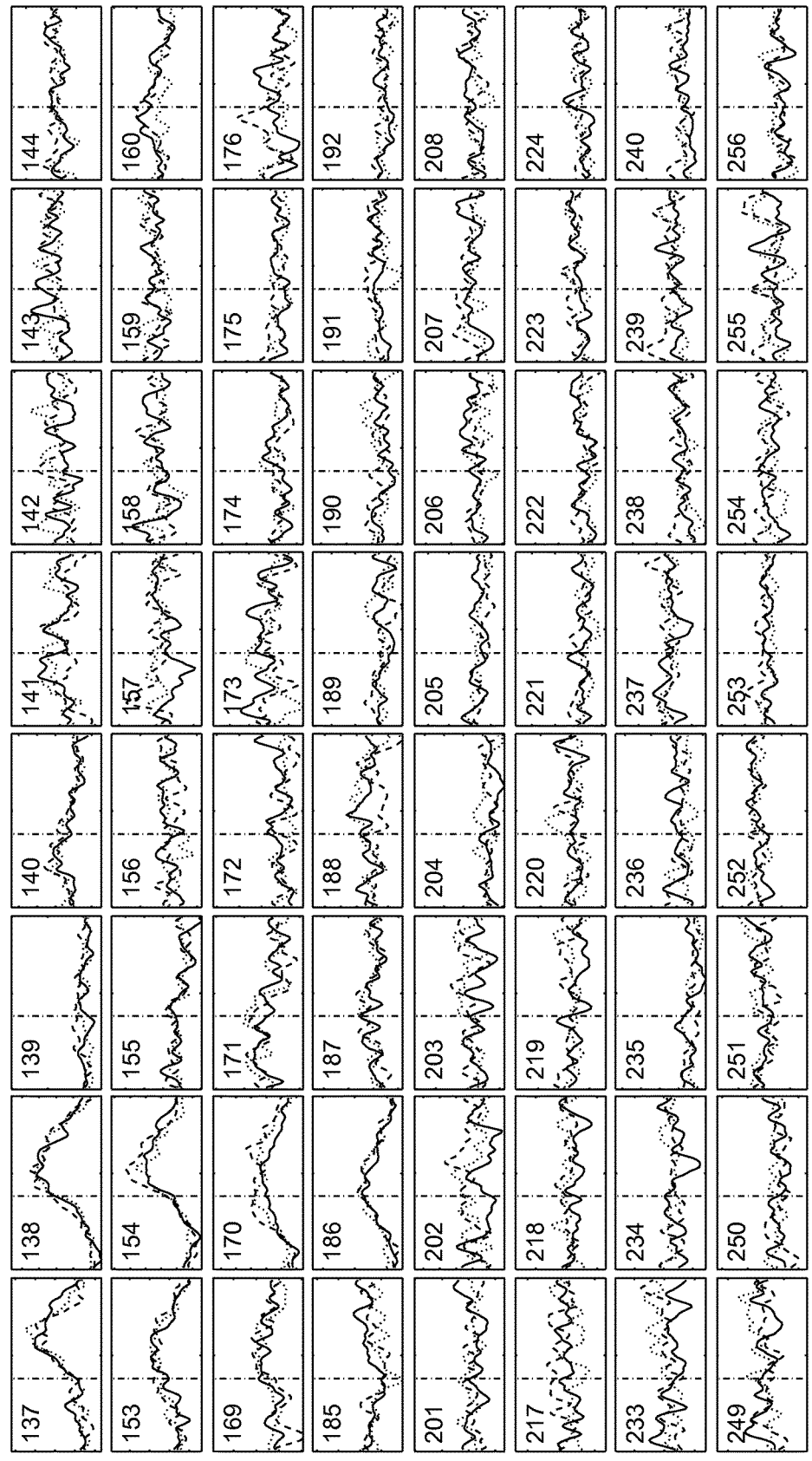
Figure 19:
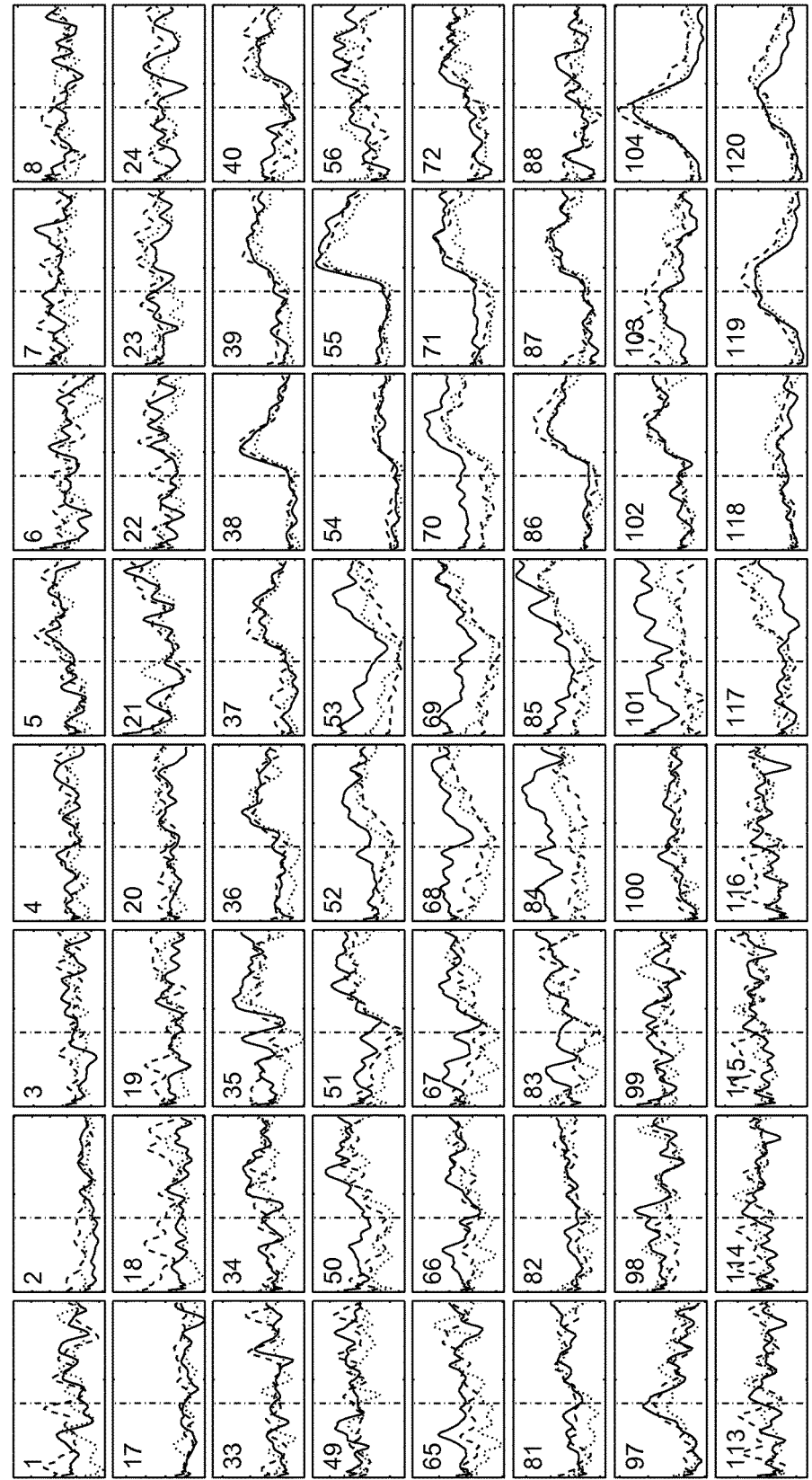
Figure 19:
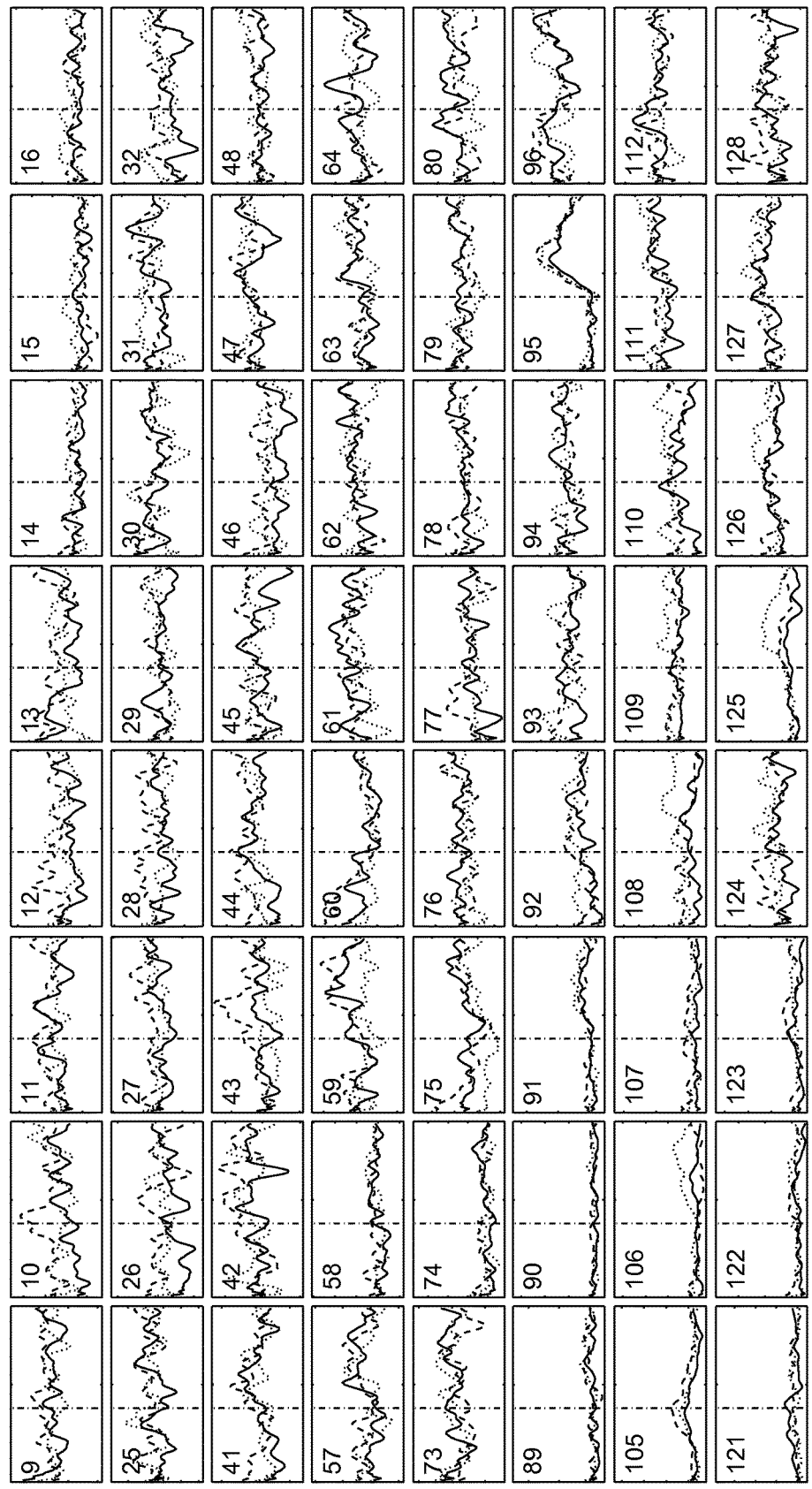
Figure 19:
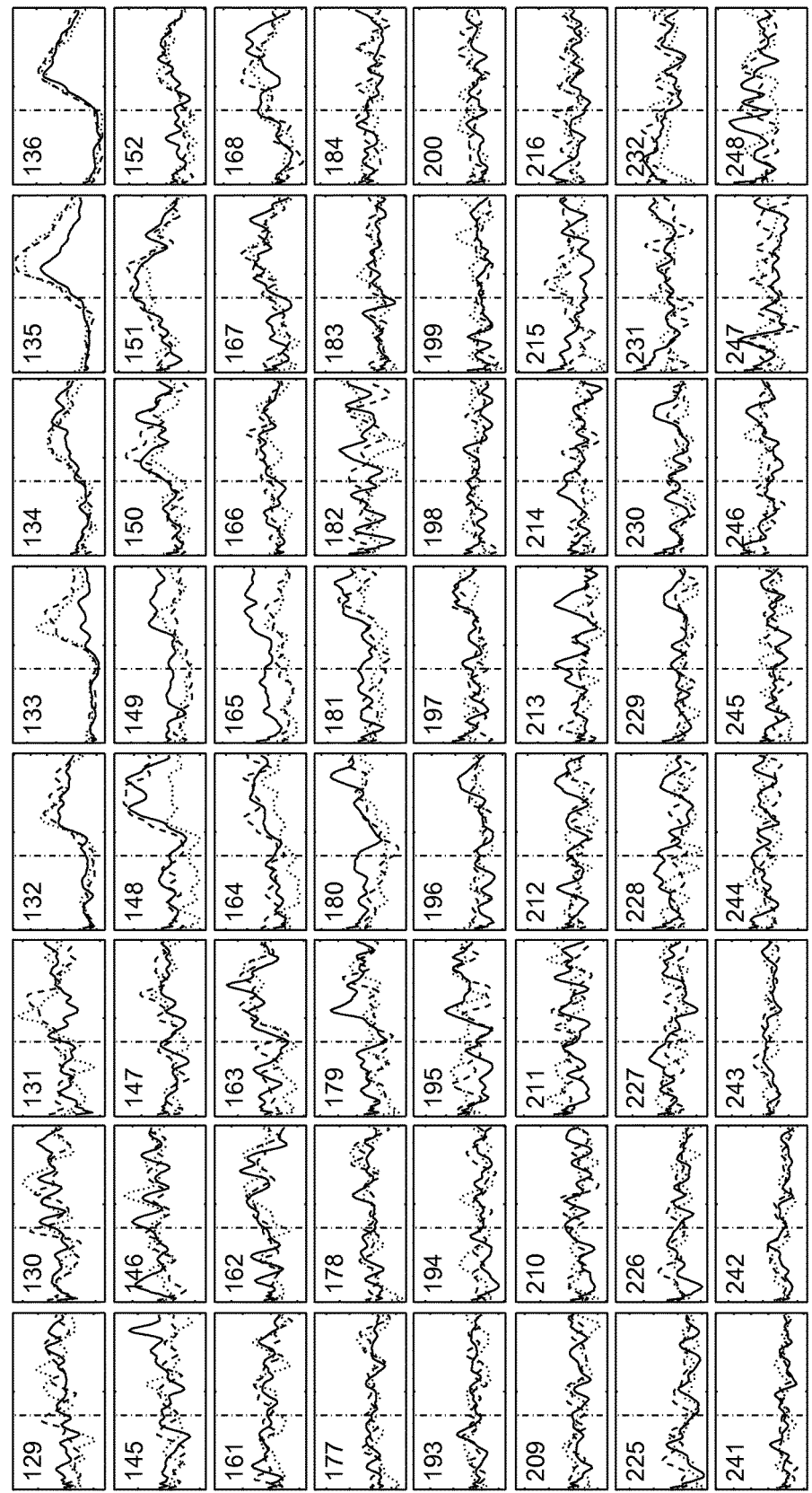
Figure 19:
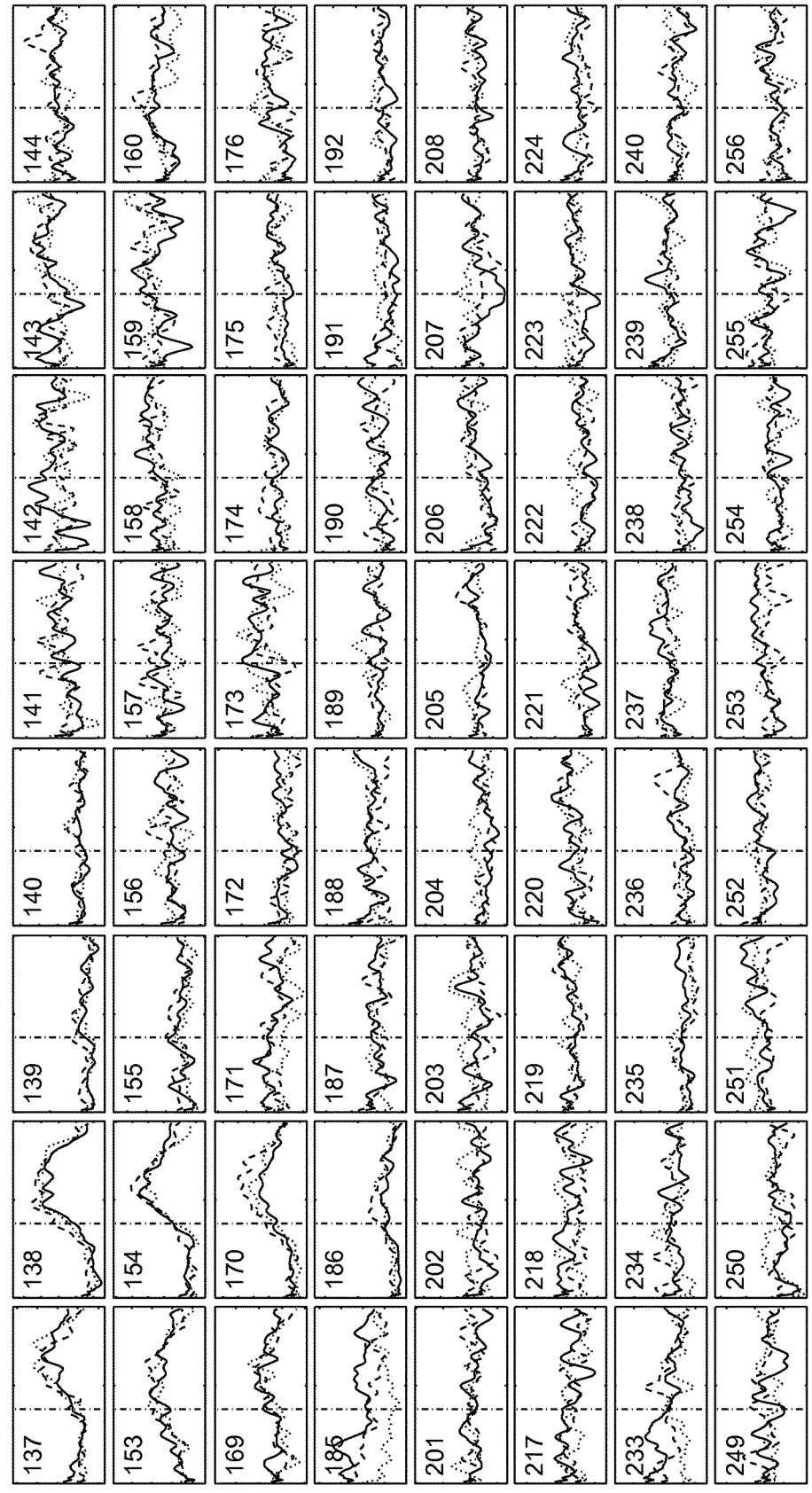
Figure 19:
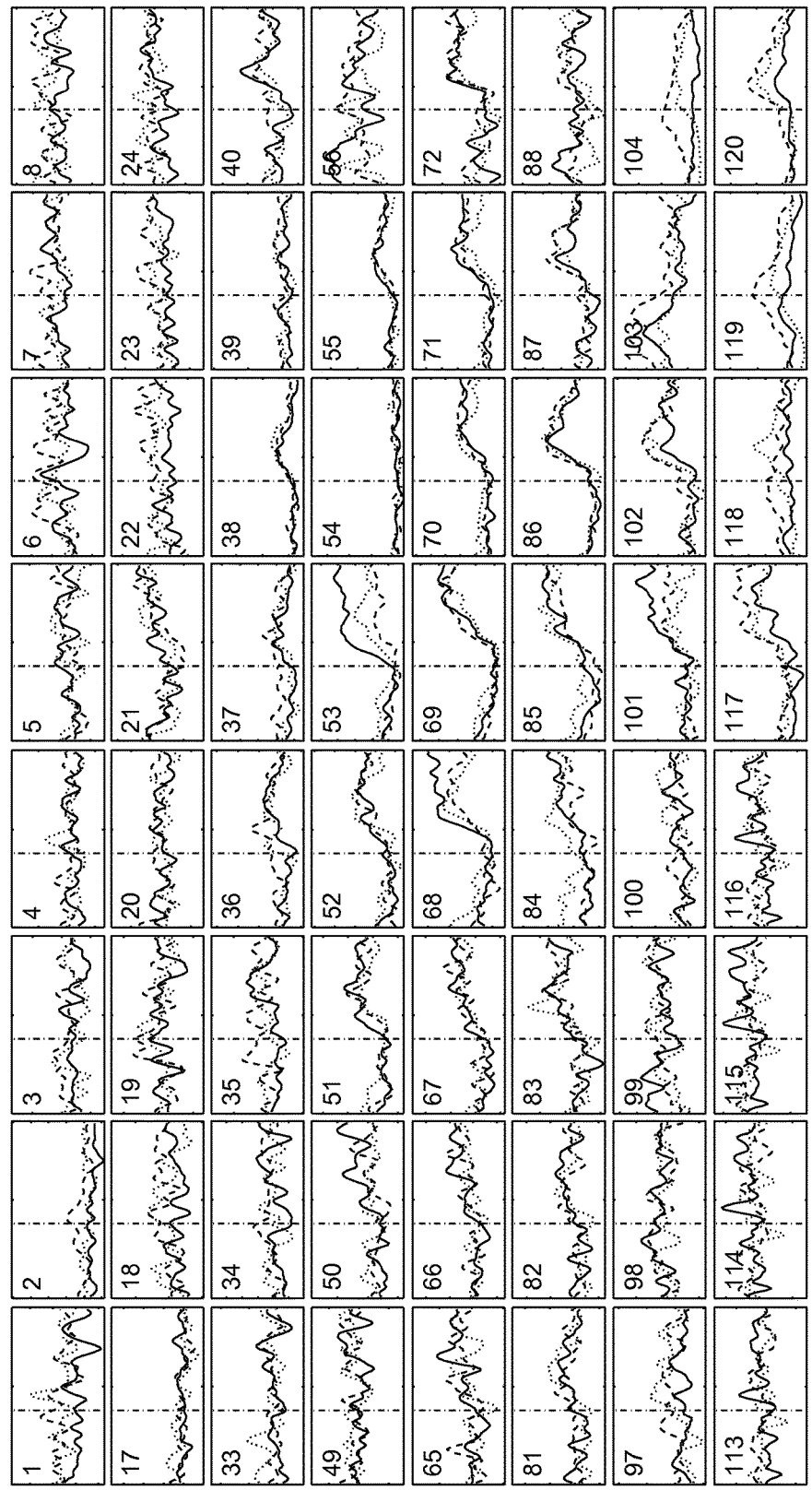
Figure 19:
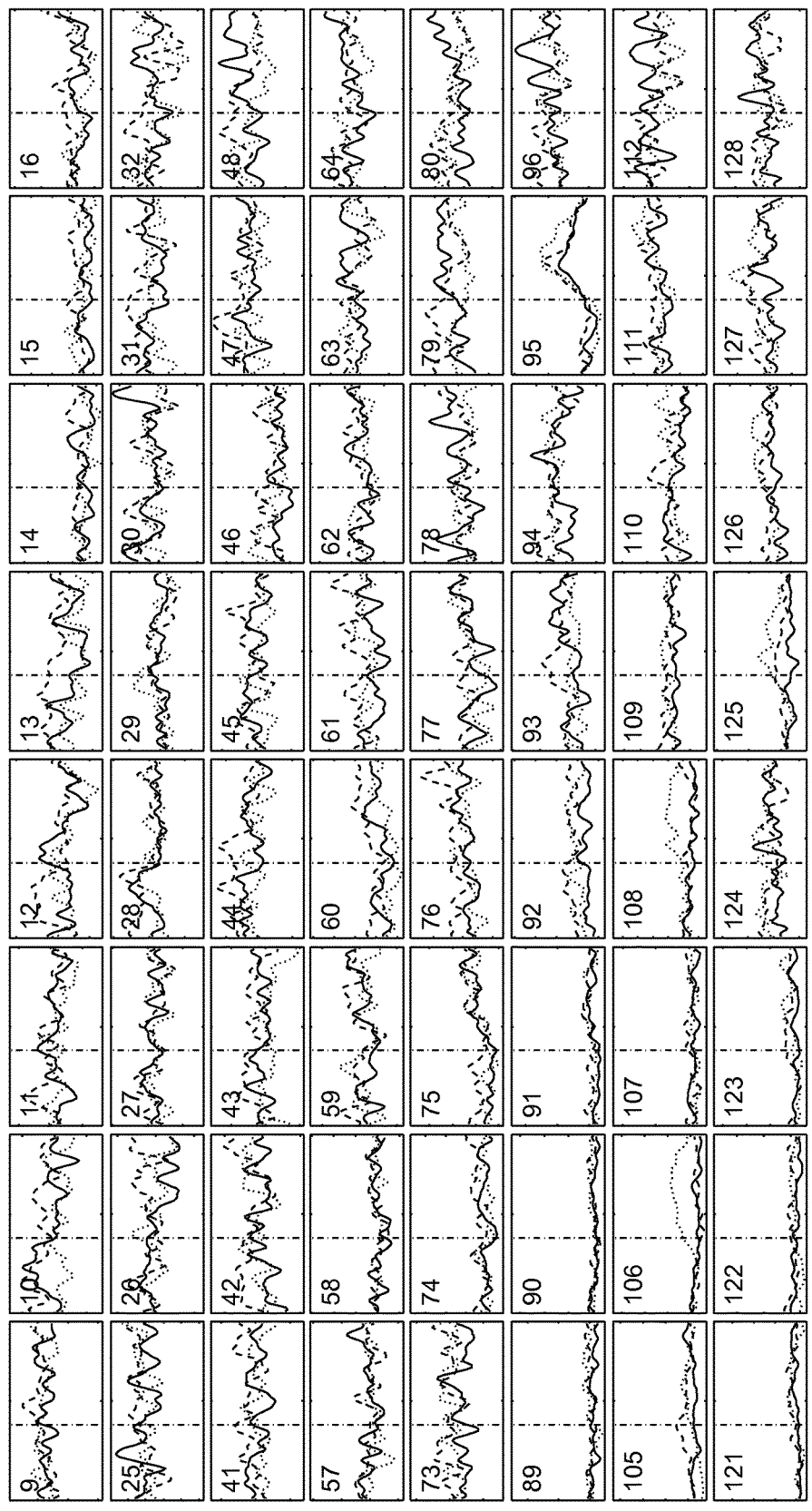
Figure 19:
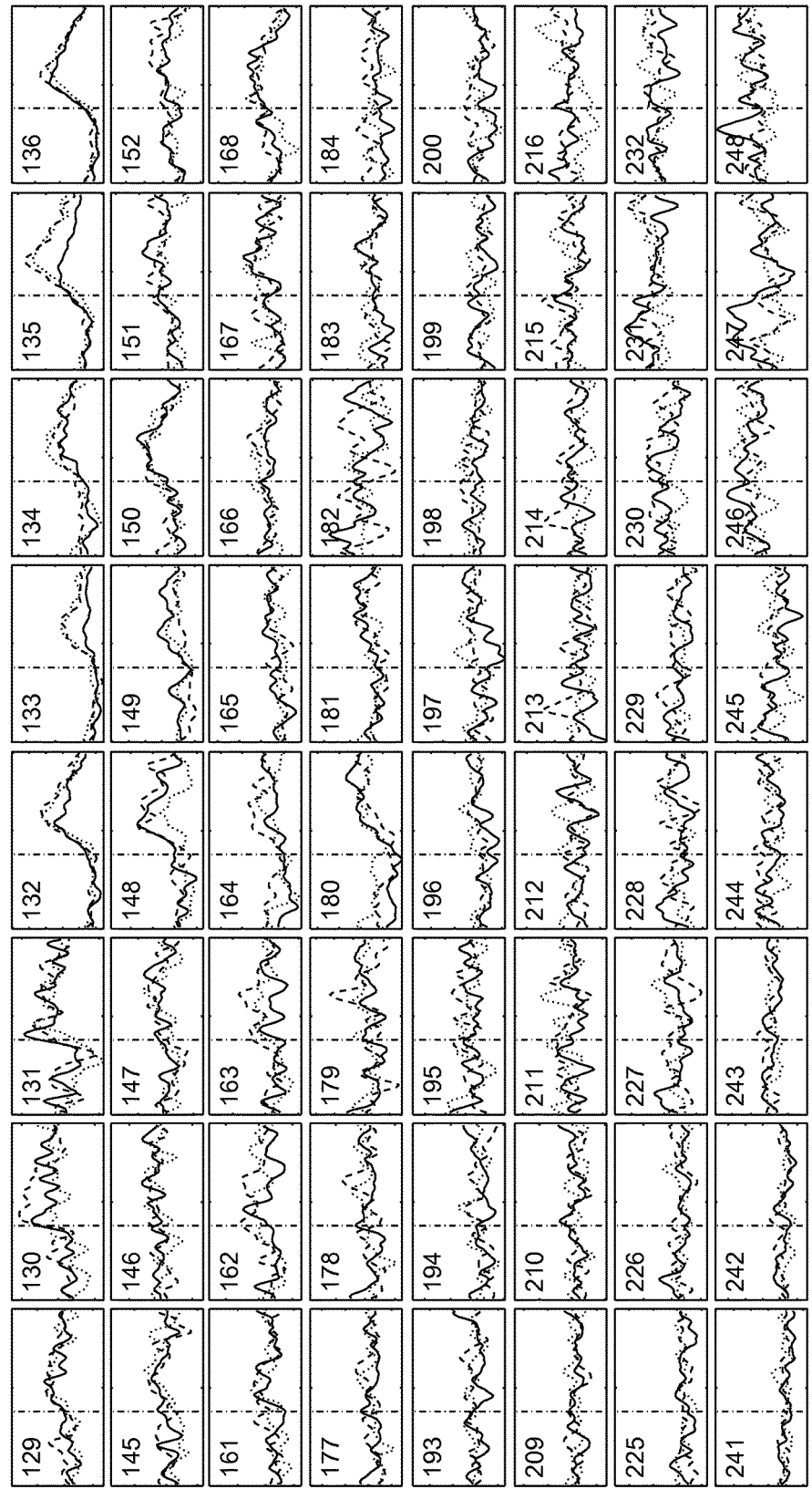
Figure 19:
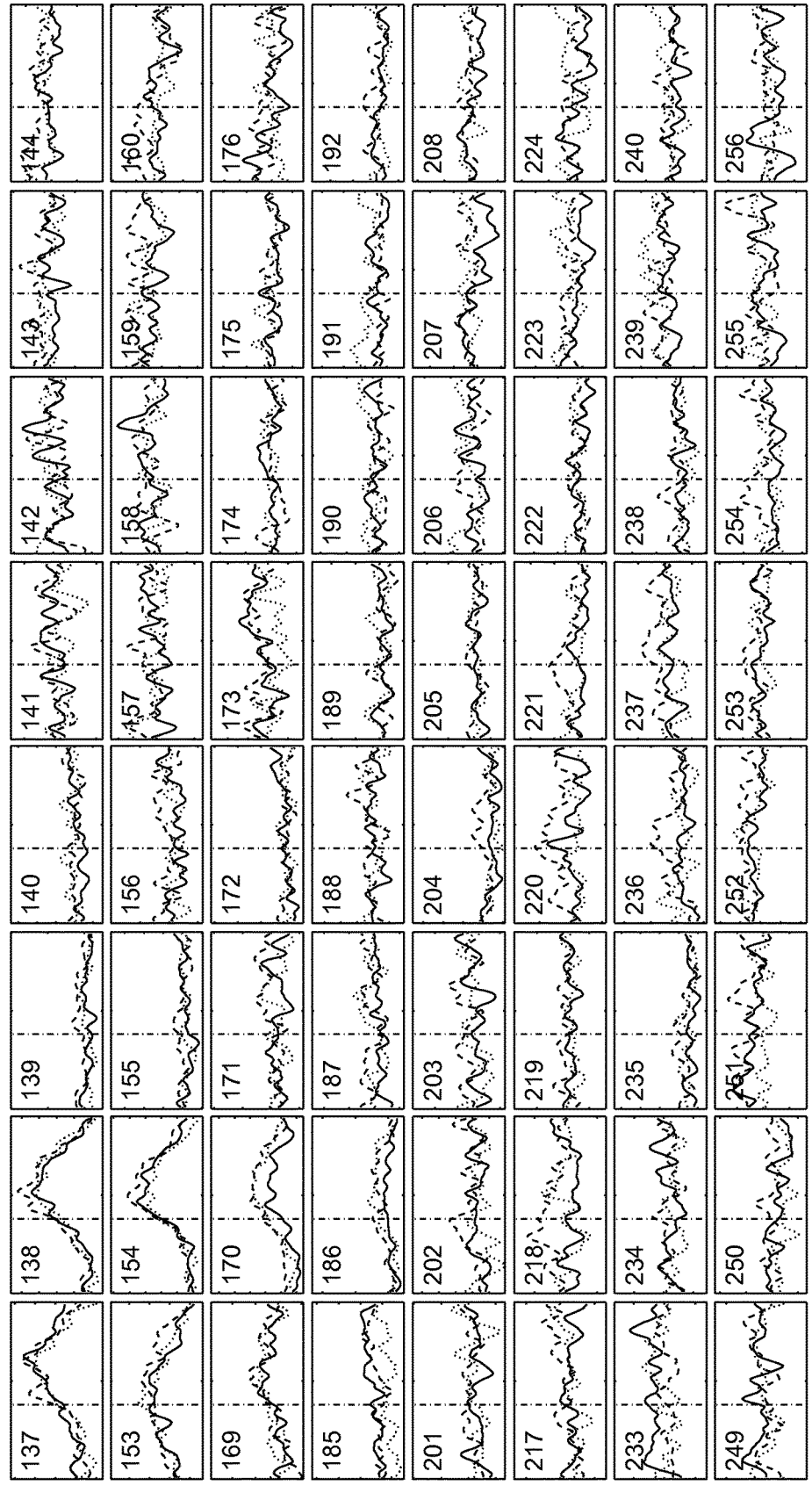
Figure 19:
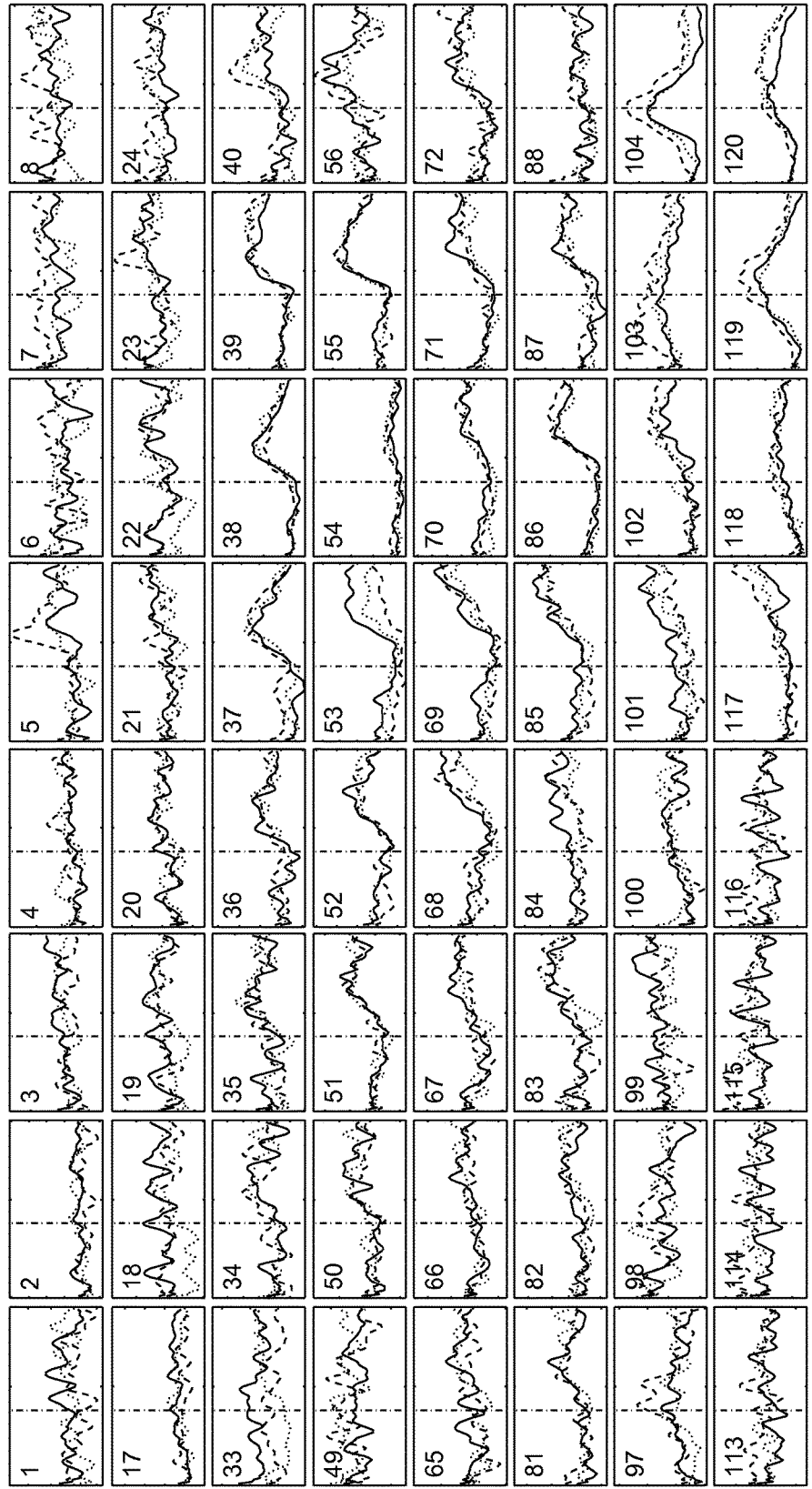
Figure 19:
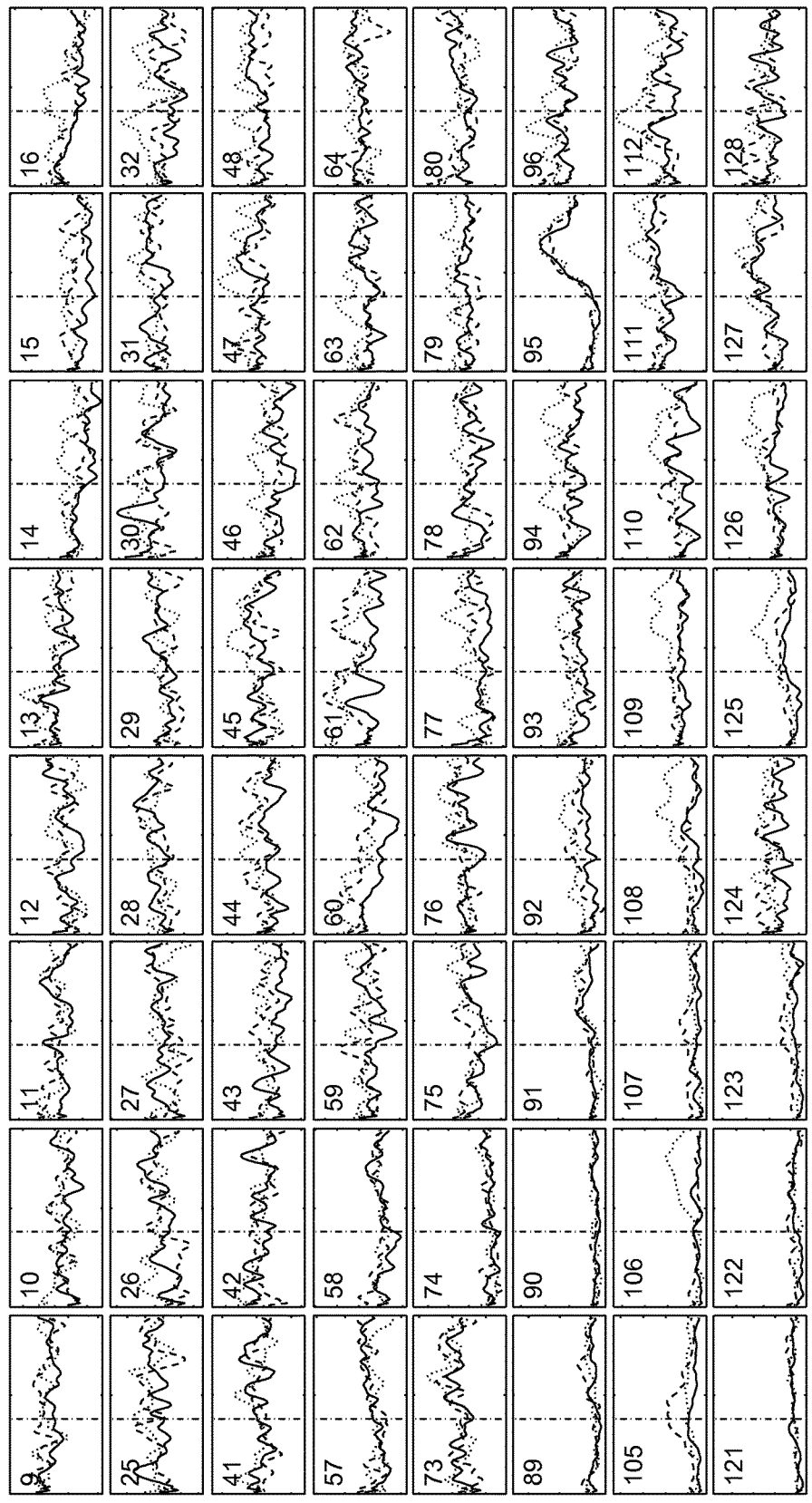
Figure 19:
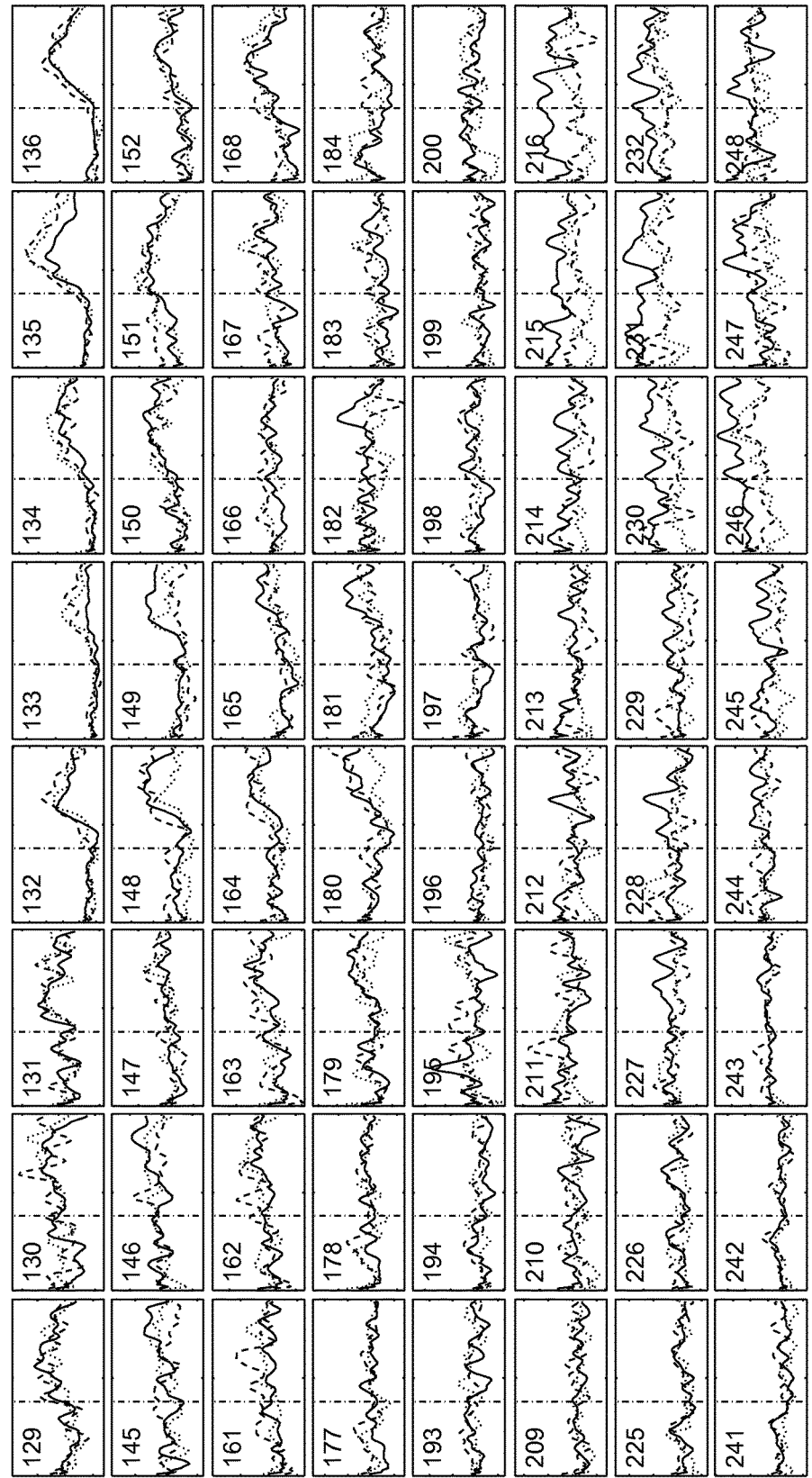
Figure 19:
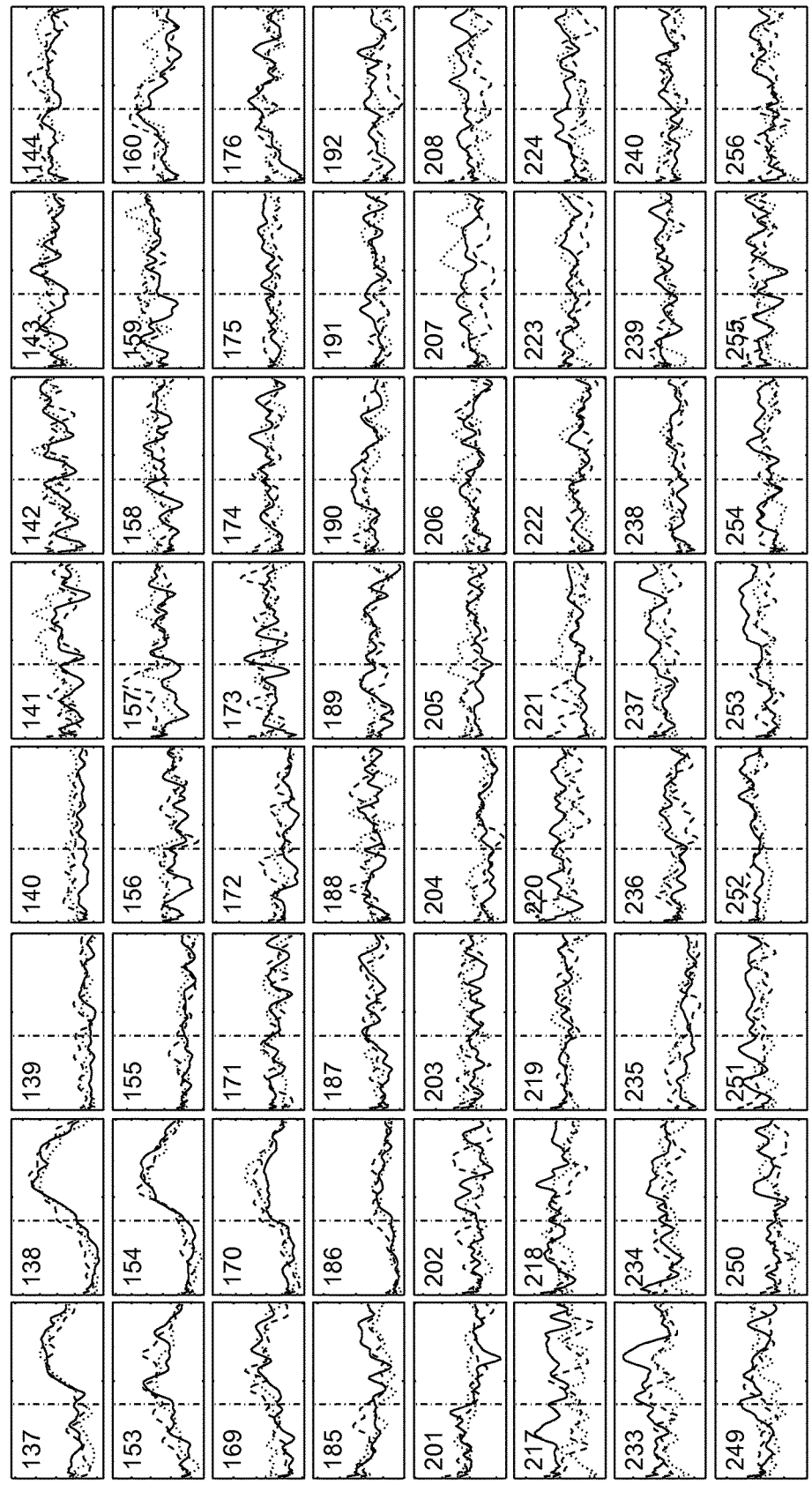
Figure 19:
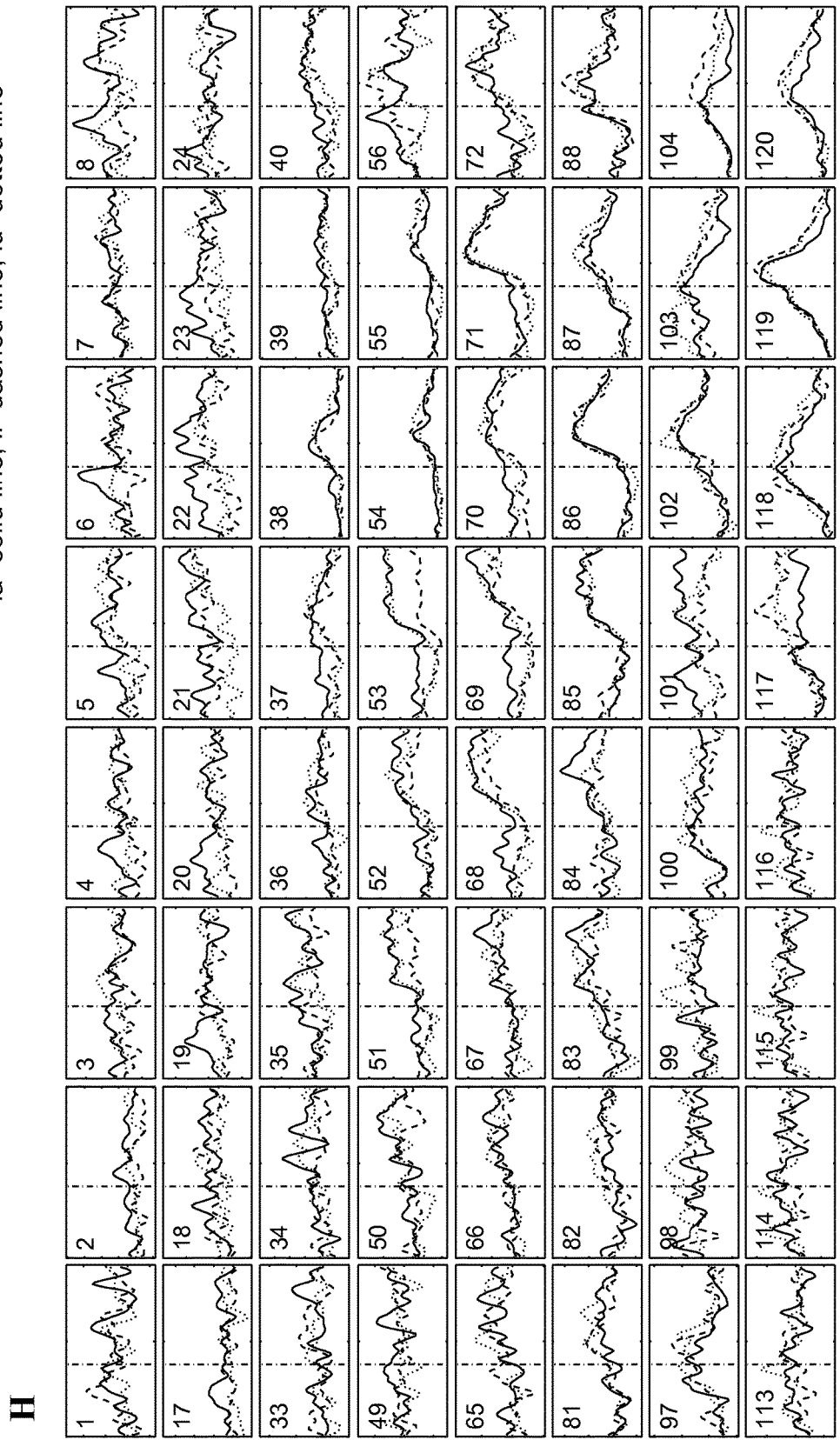
Figure 19:
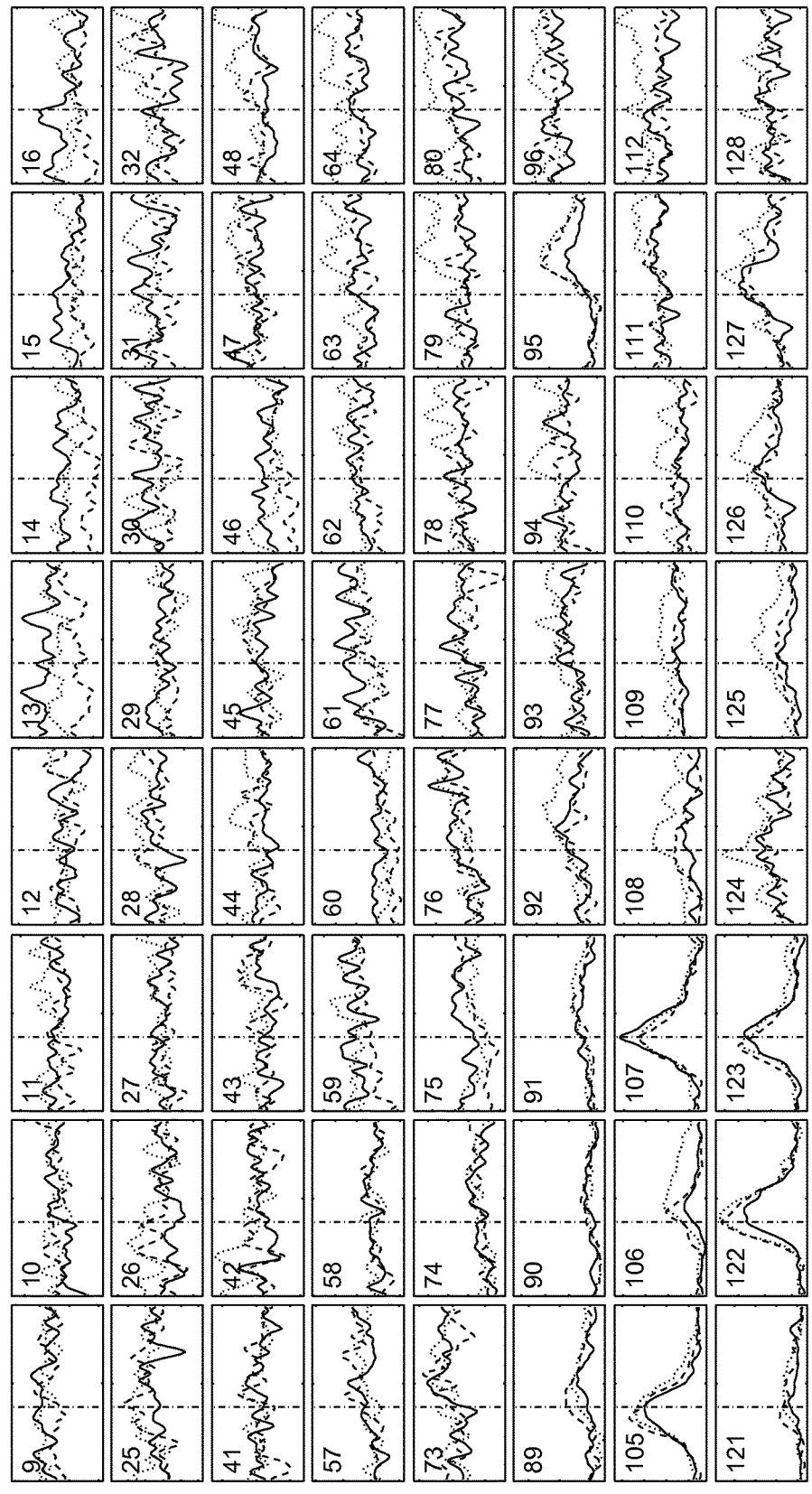
Figure 19:
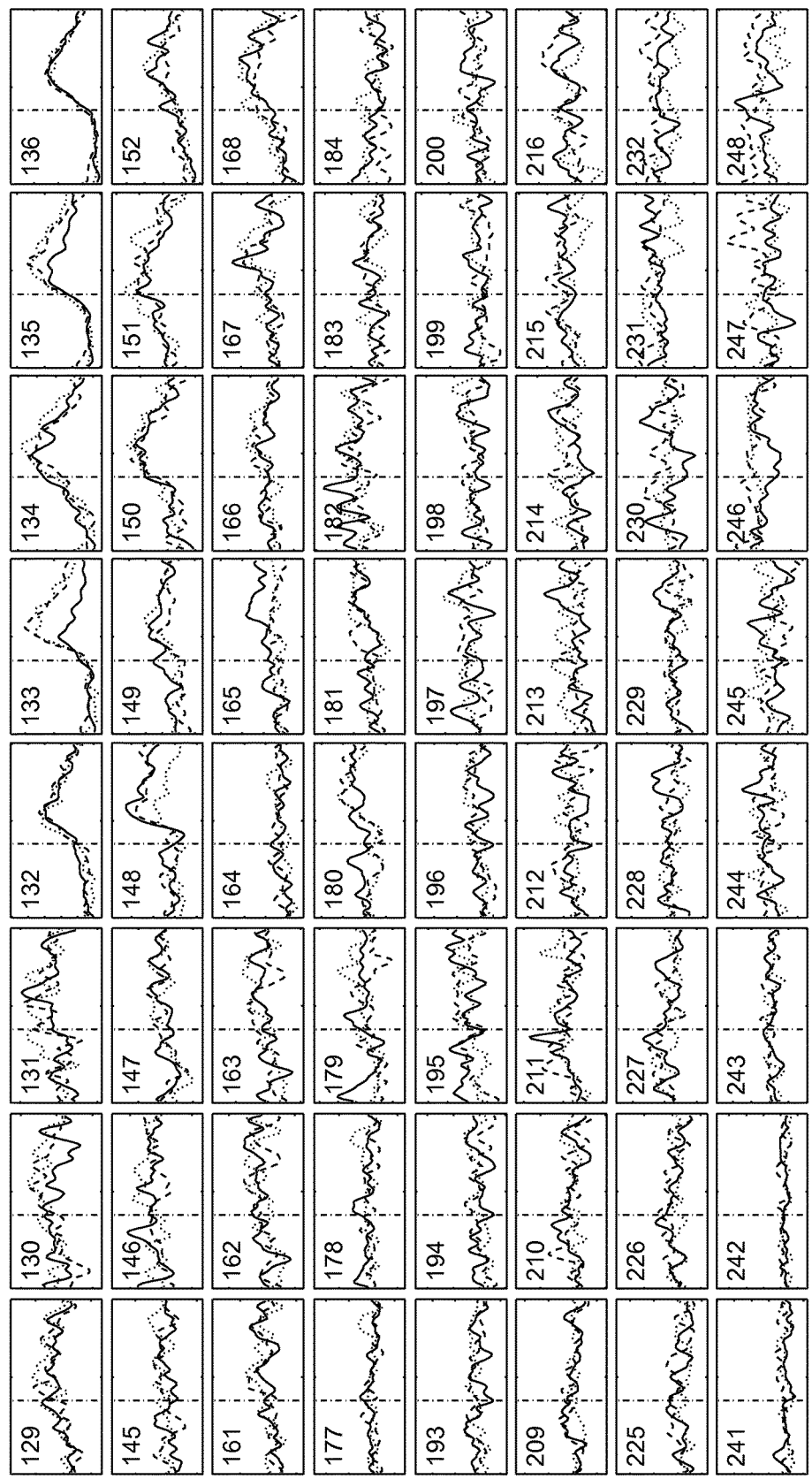
Figure 19:
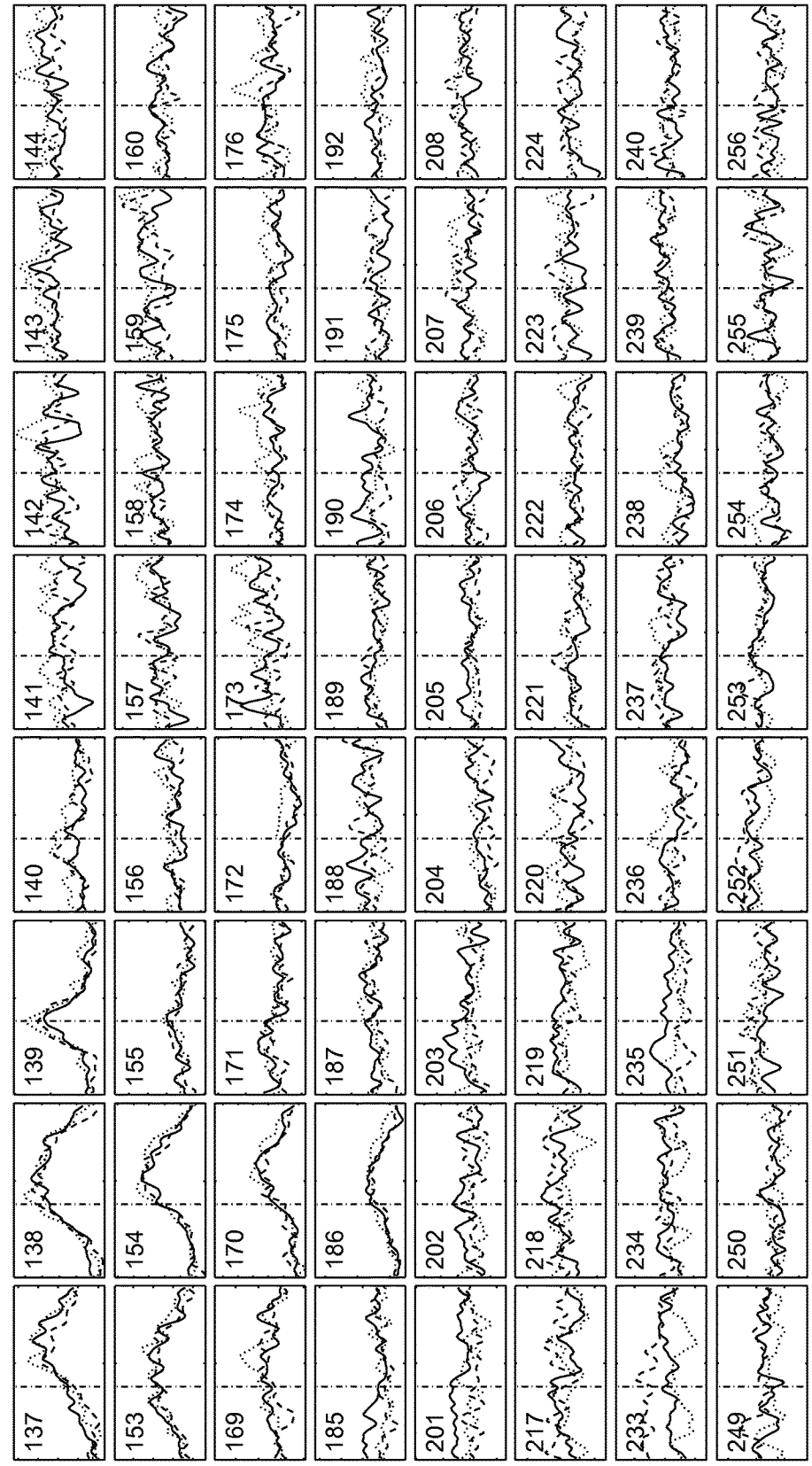
Figure 19:
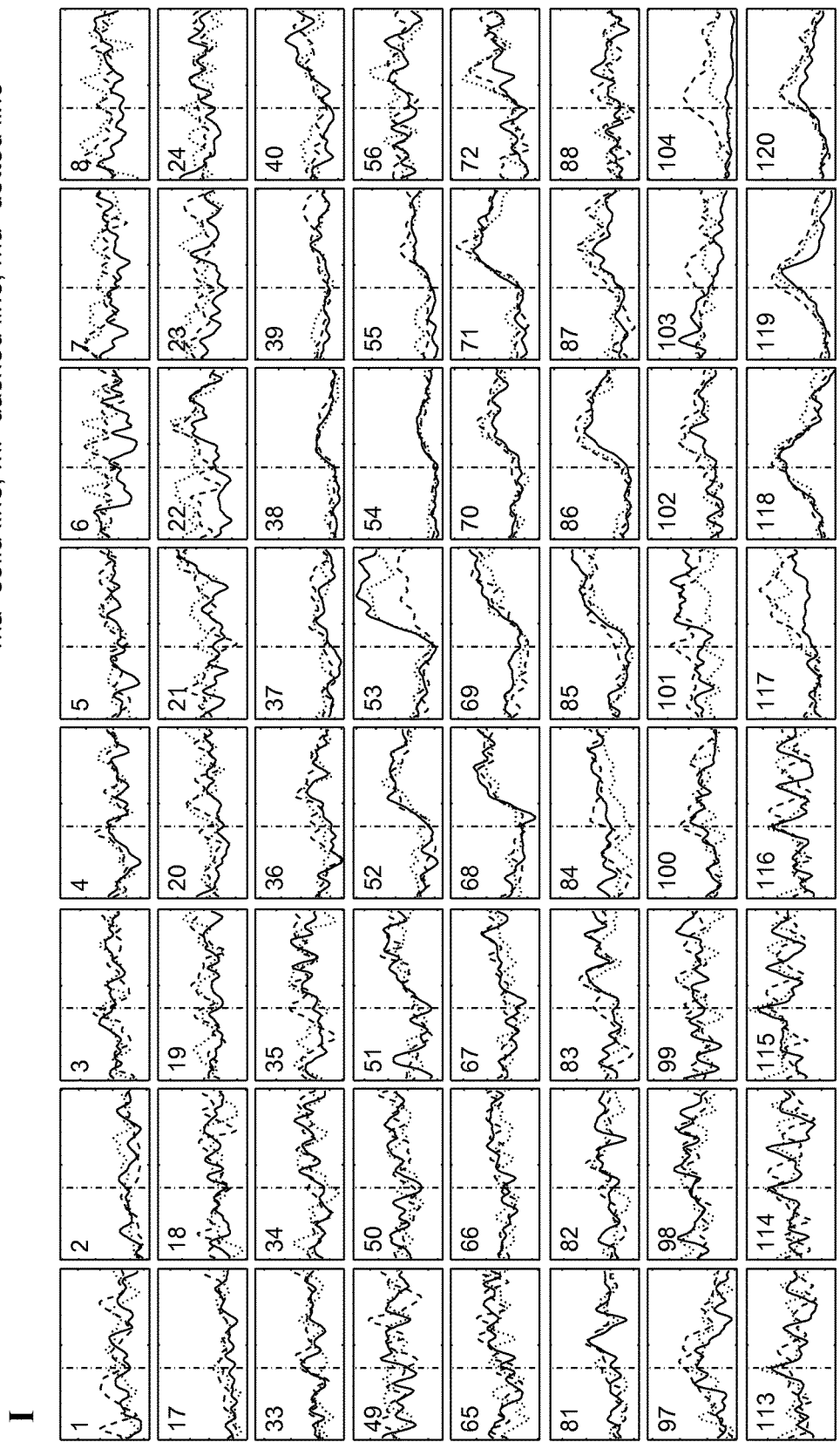
Figure 19:
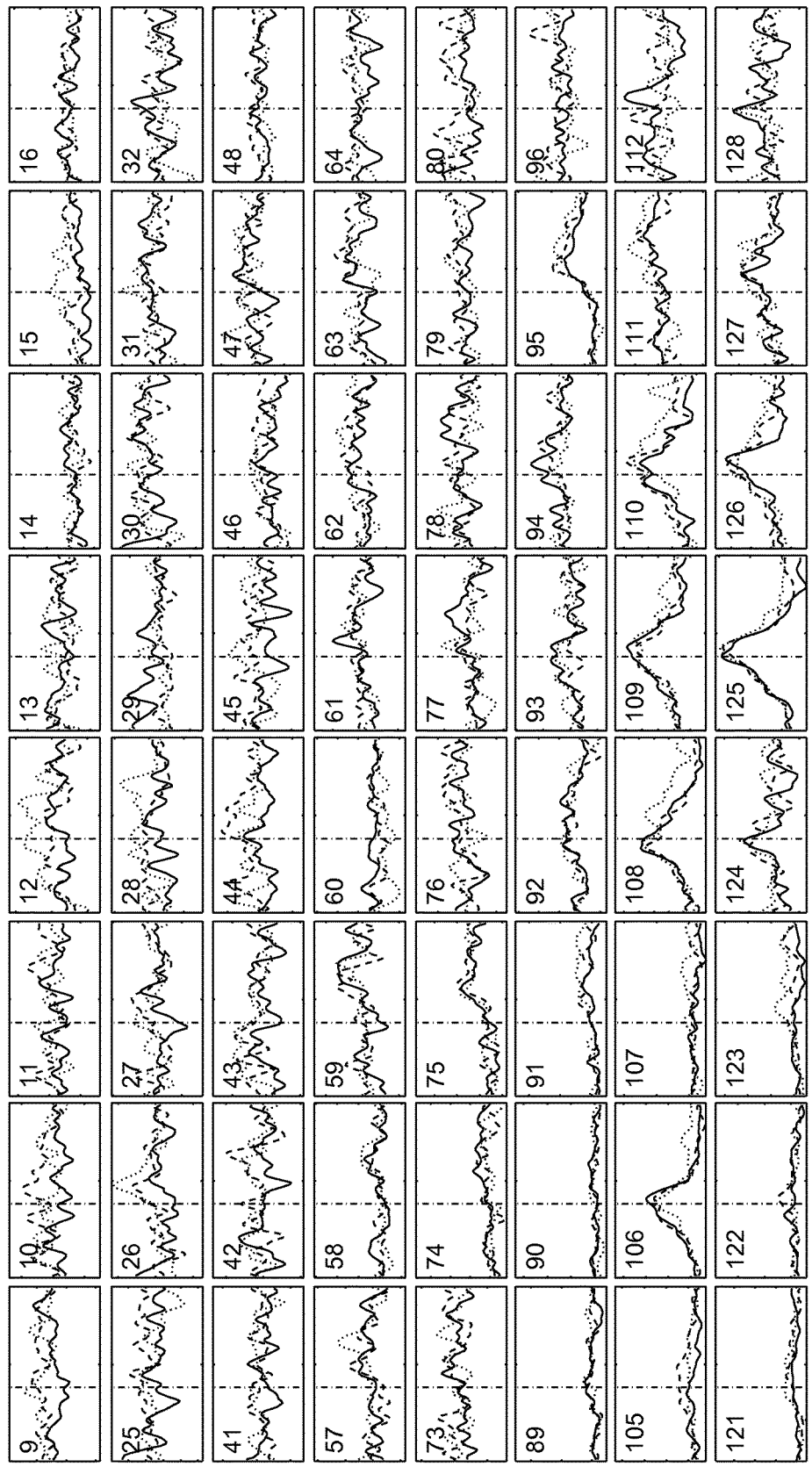
Figure 19:
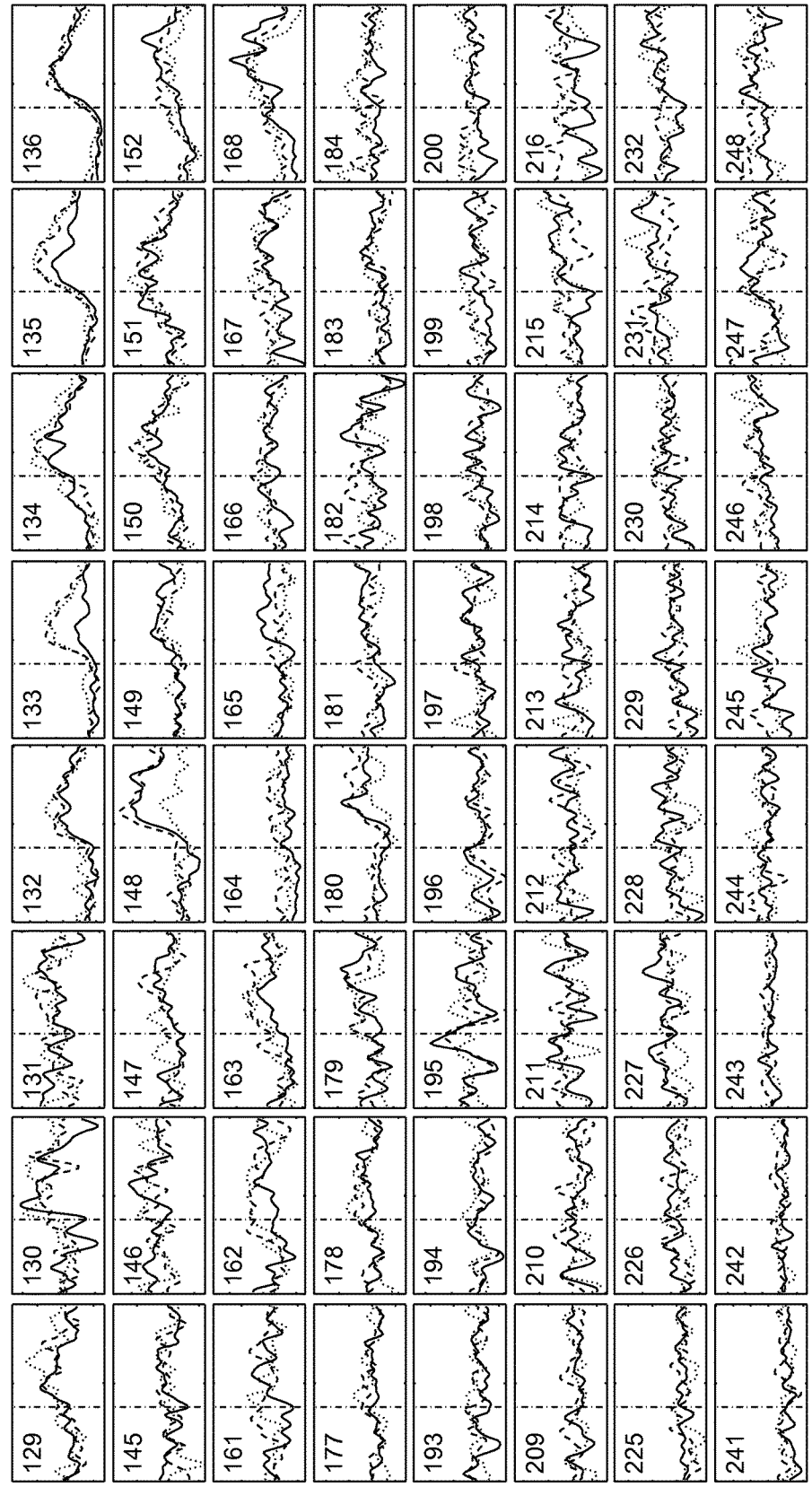
Figure 19:
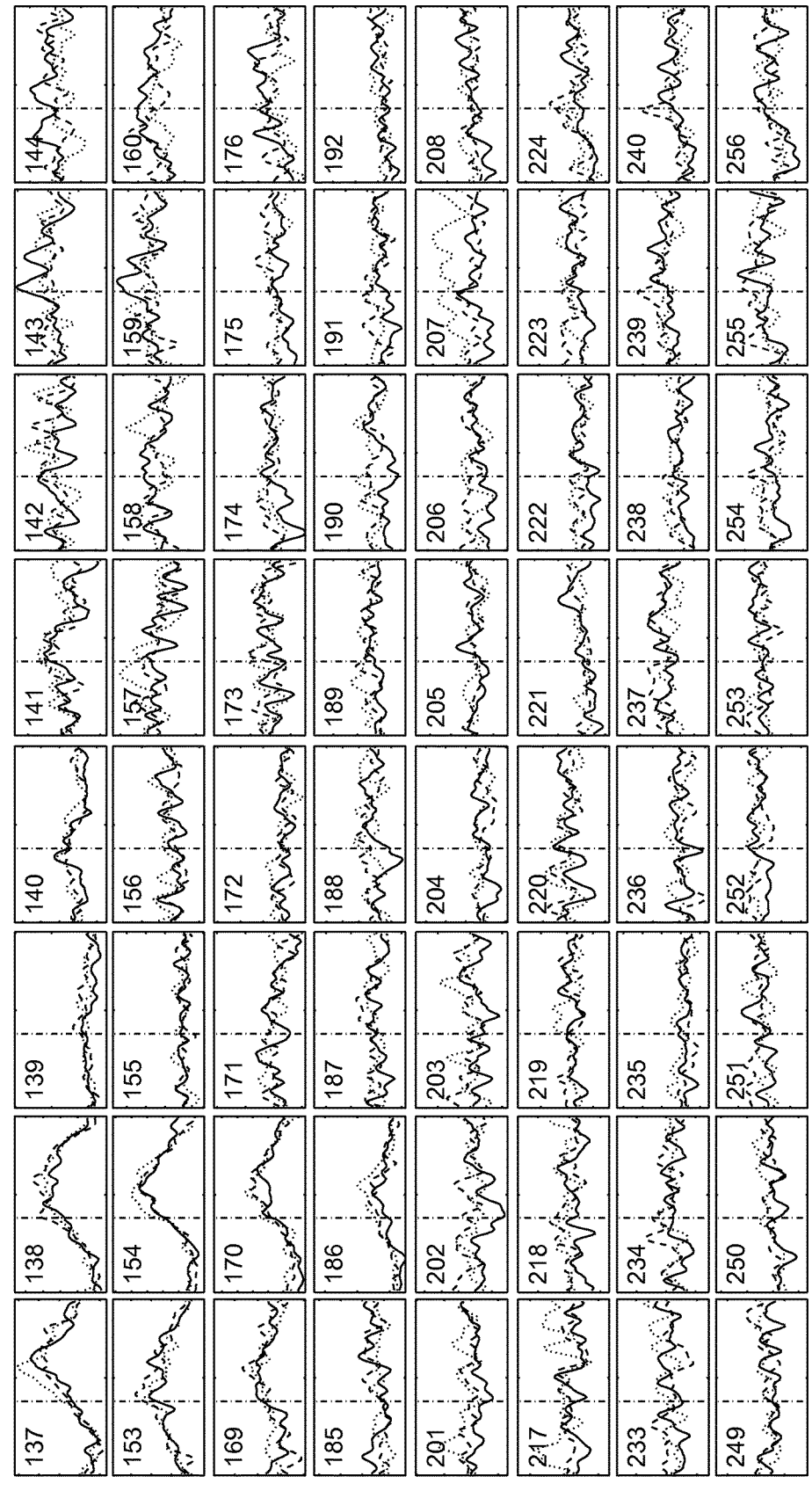
Figure 19:
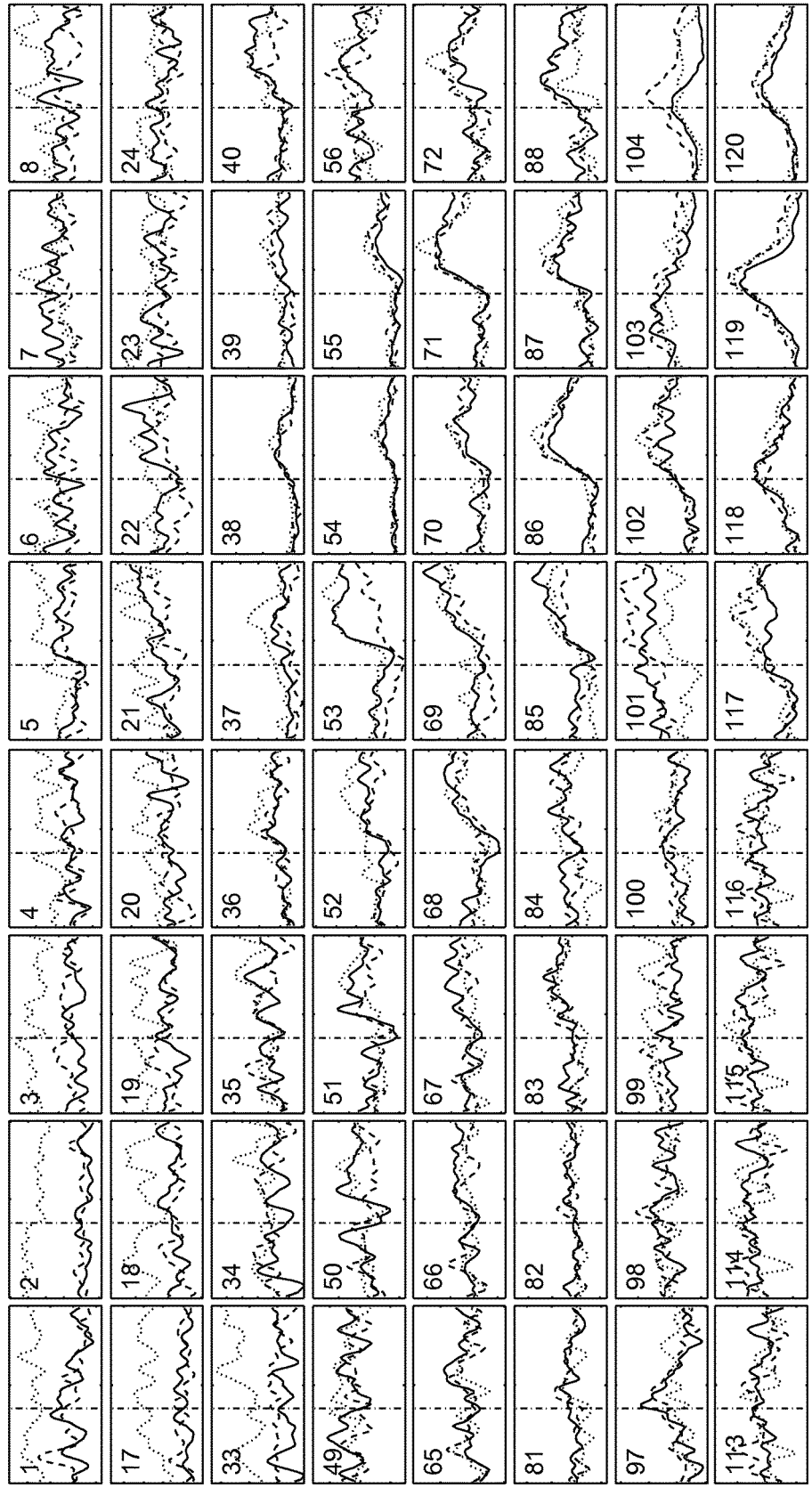
Figure 19:
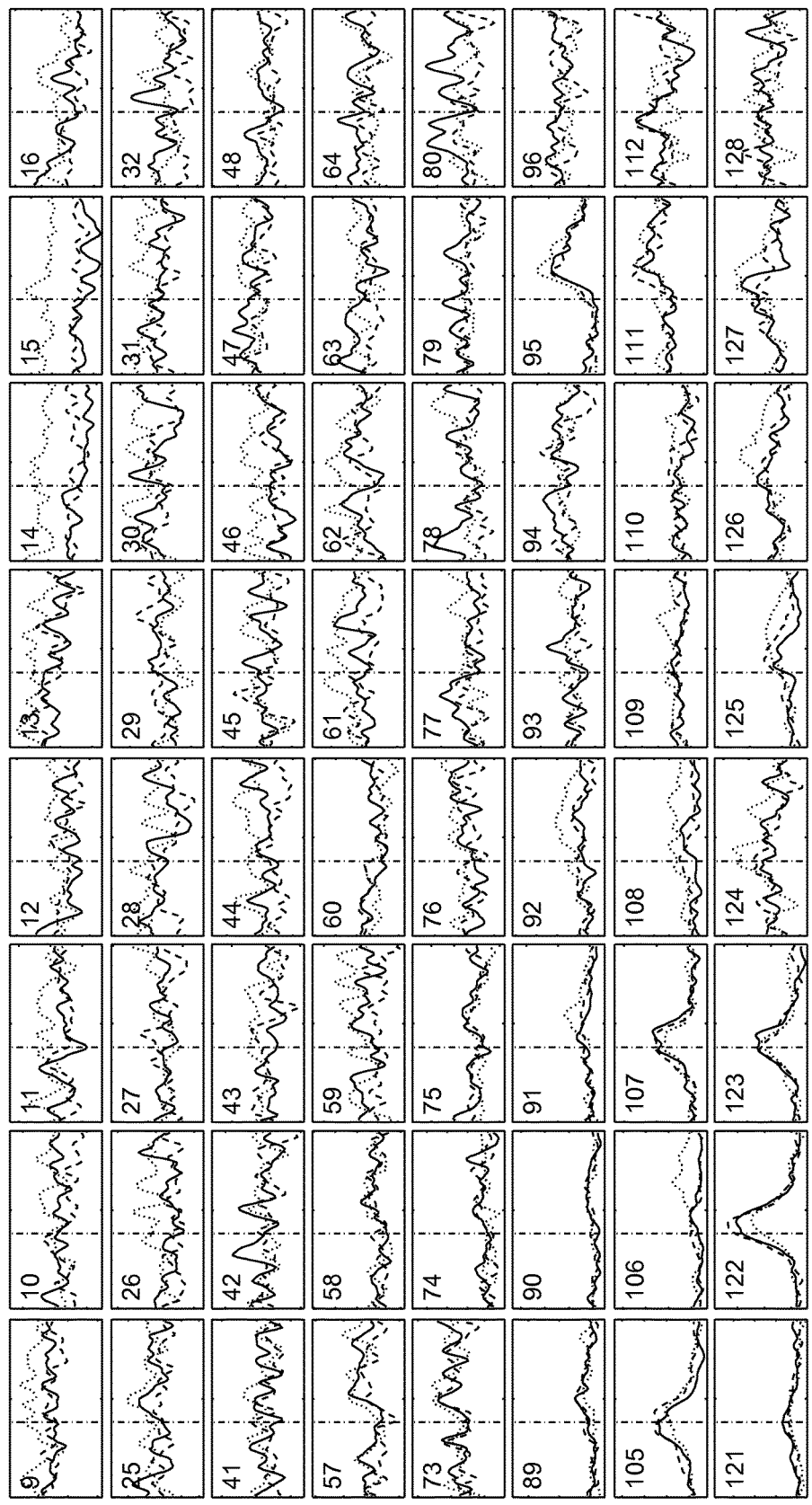
Figure 19:
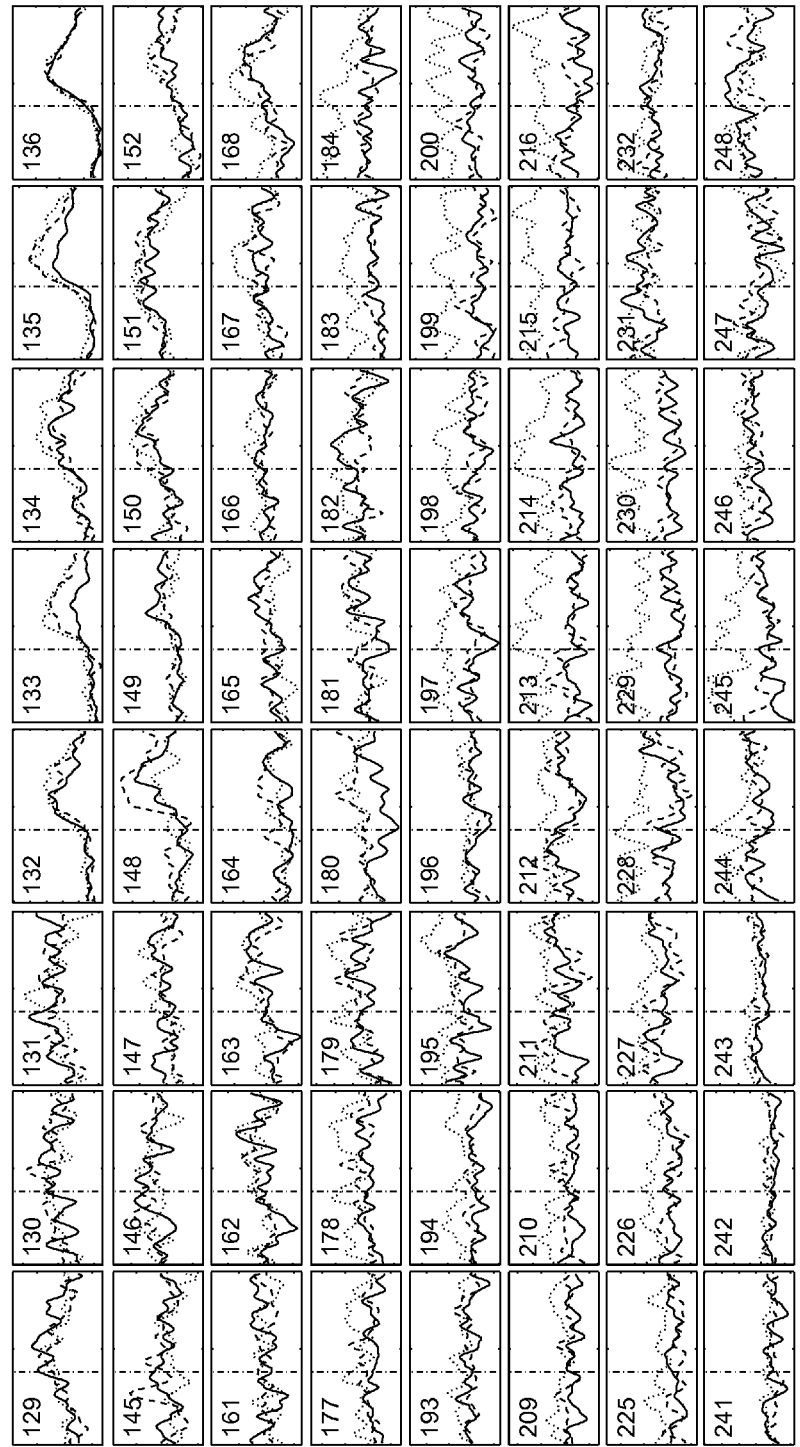
Figure 19:
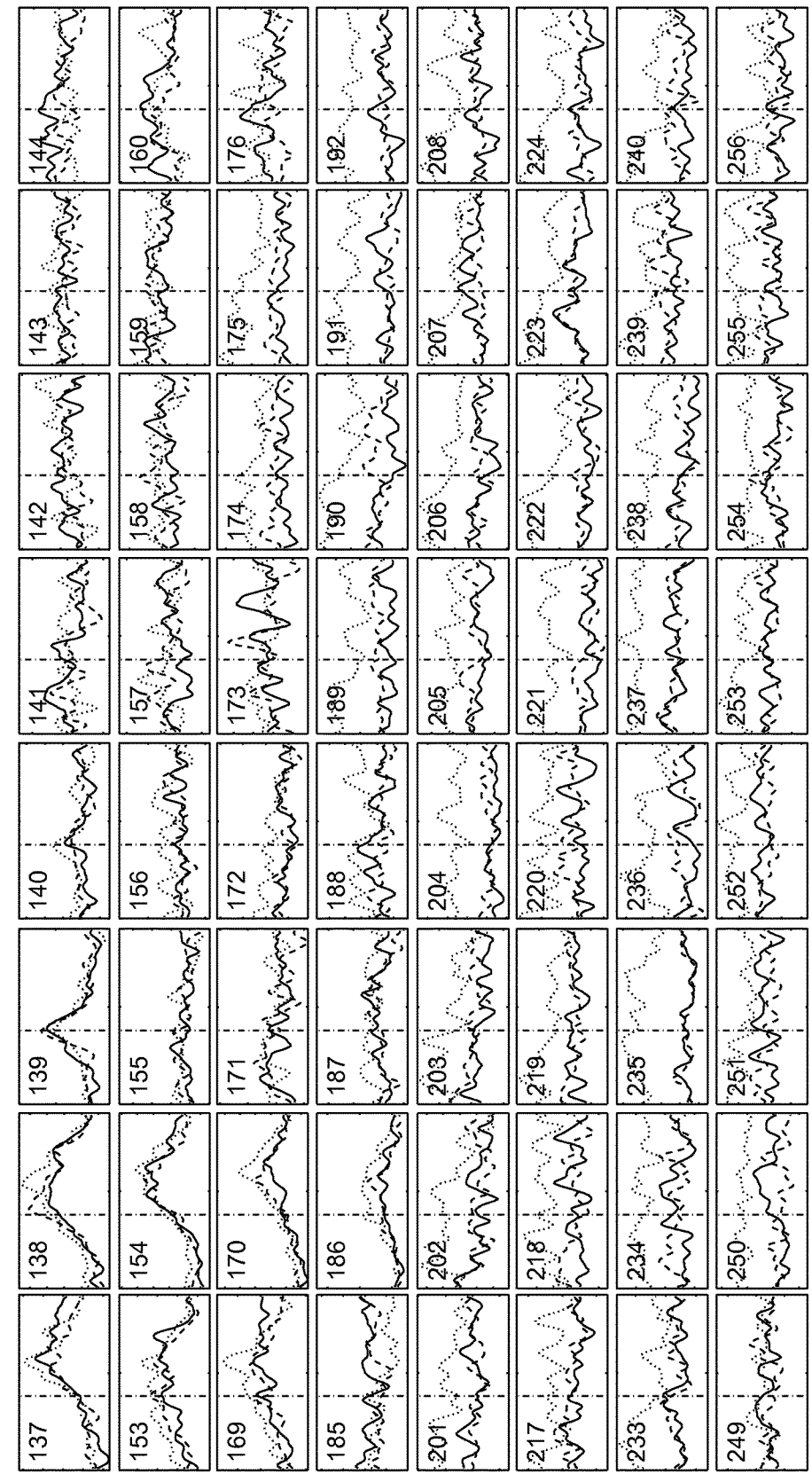
Figure 19:
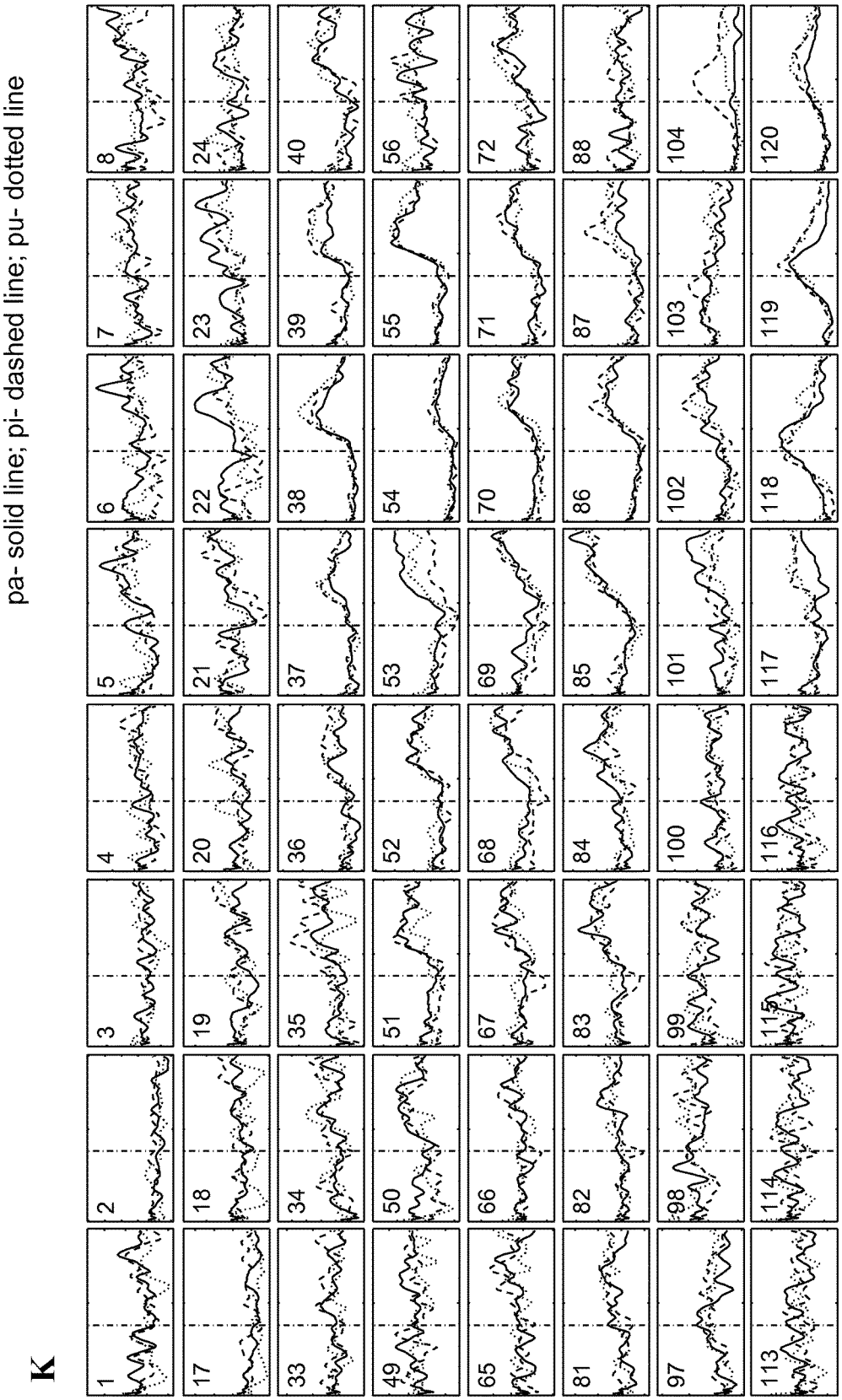
Figure 19:
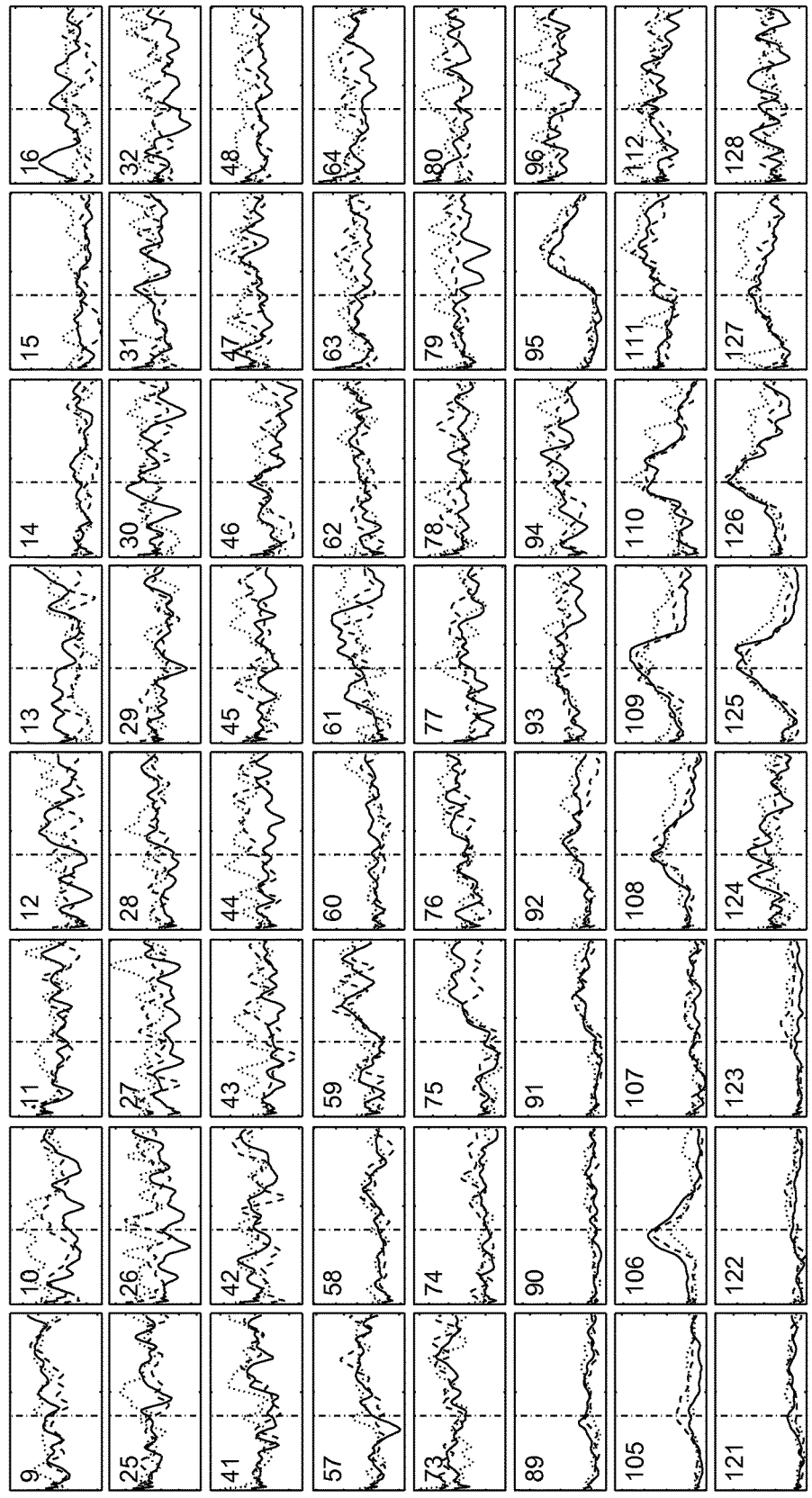
Figure 19:
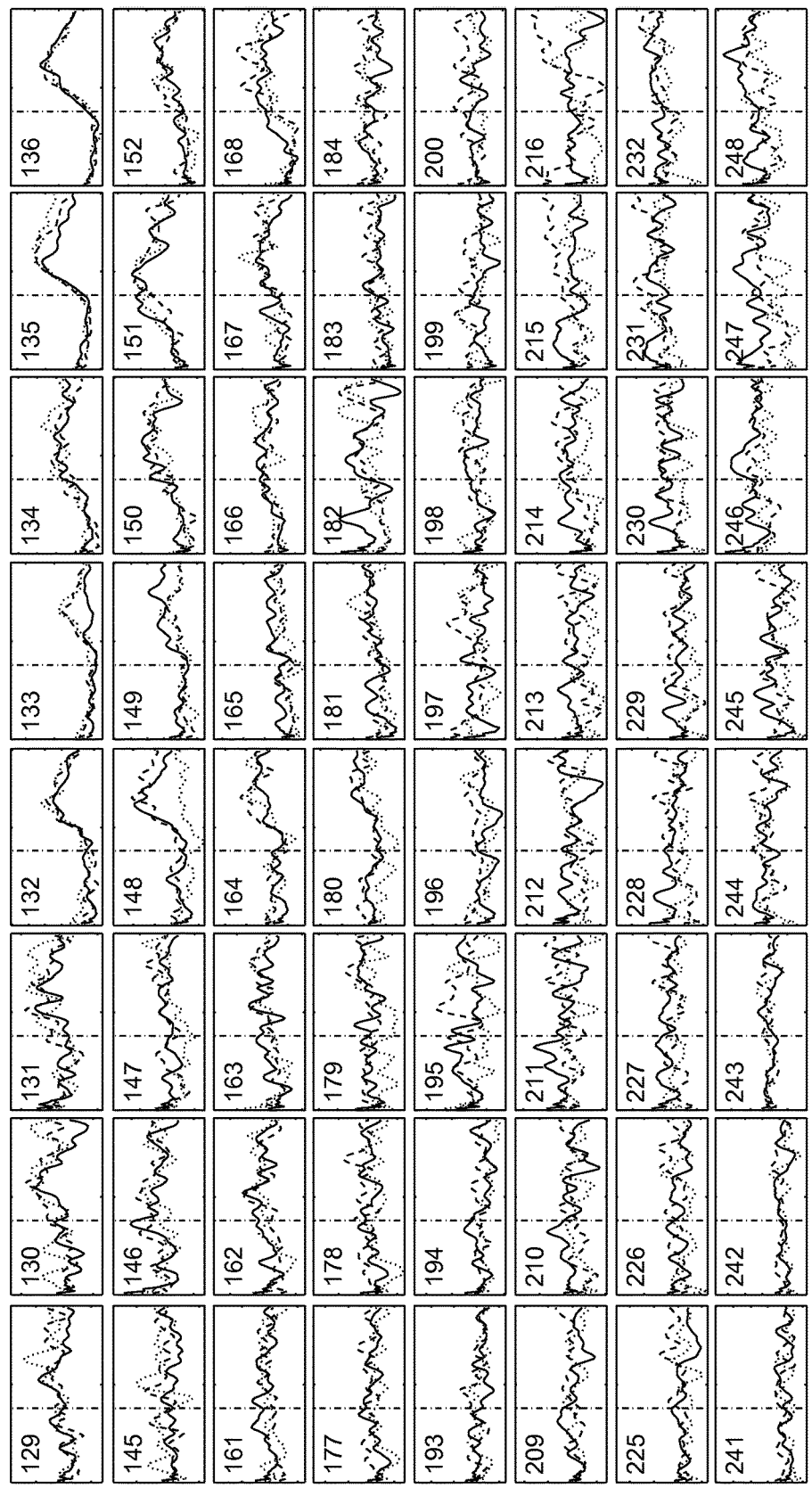
Figure 19:
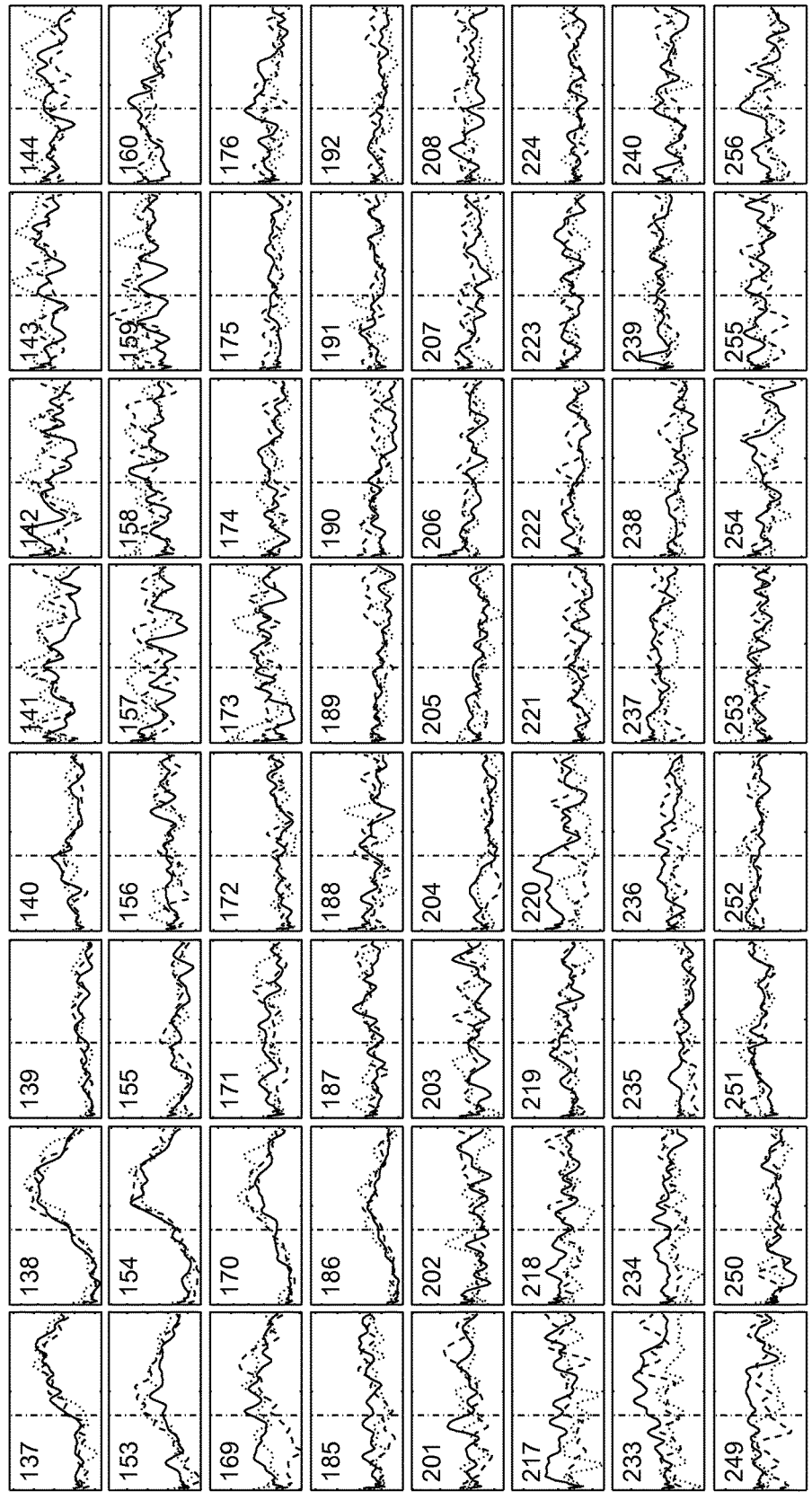
Figure 19:
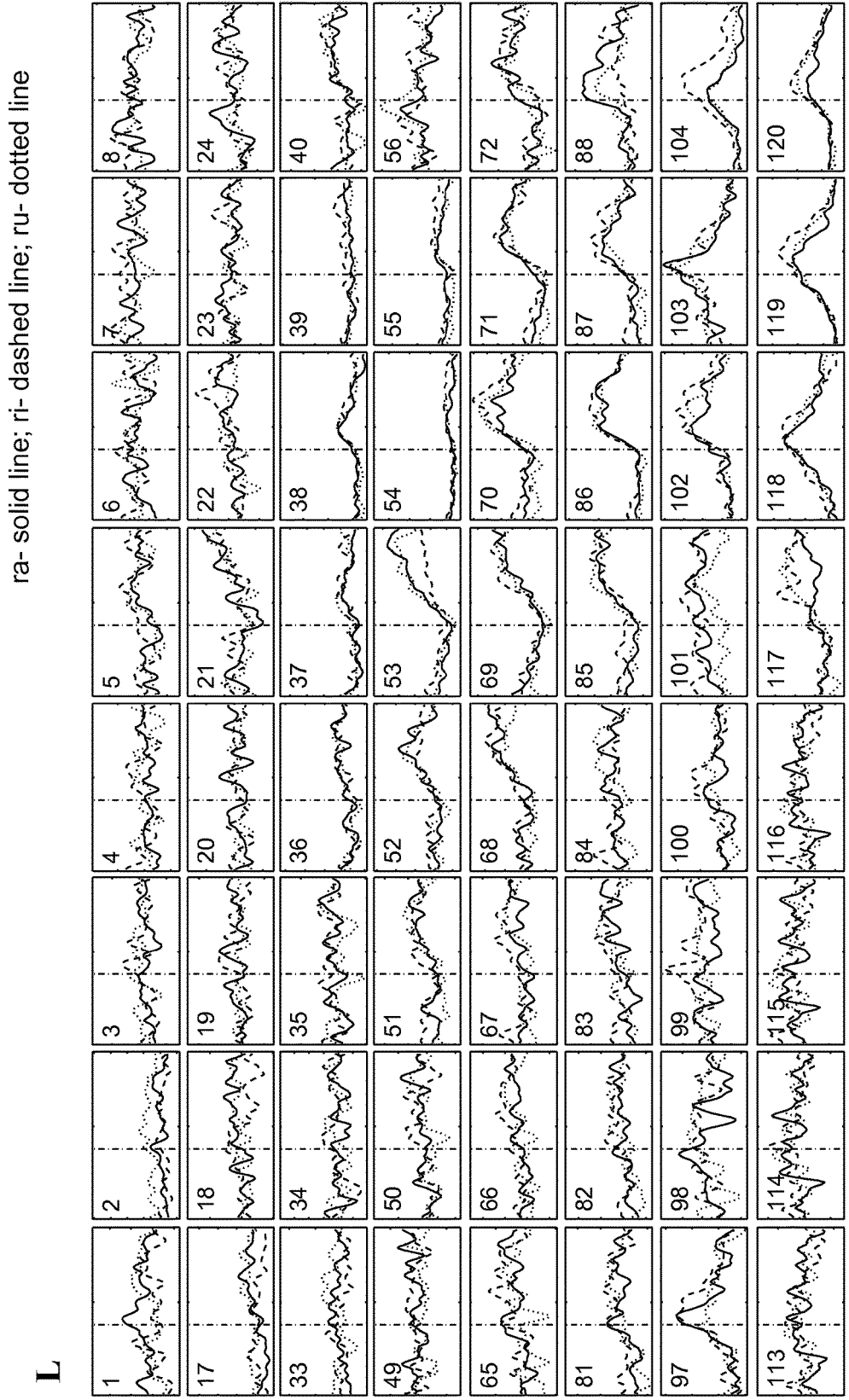
Figure 19:
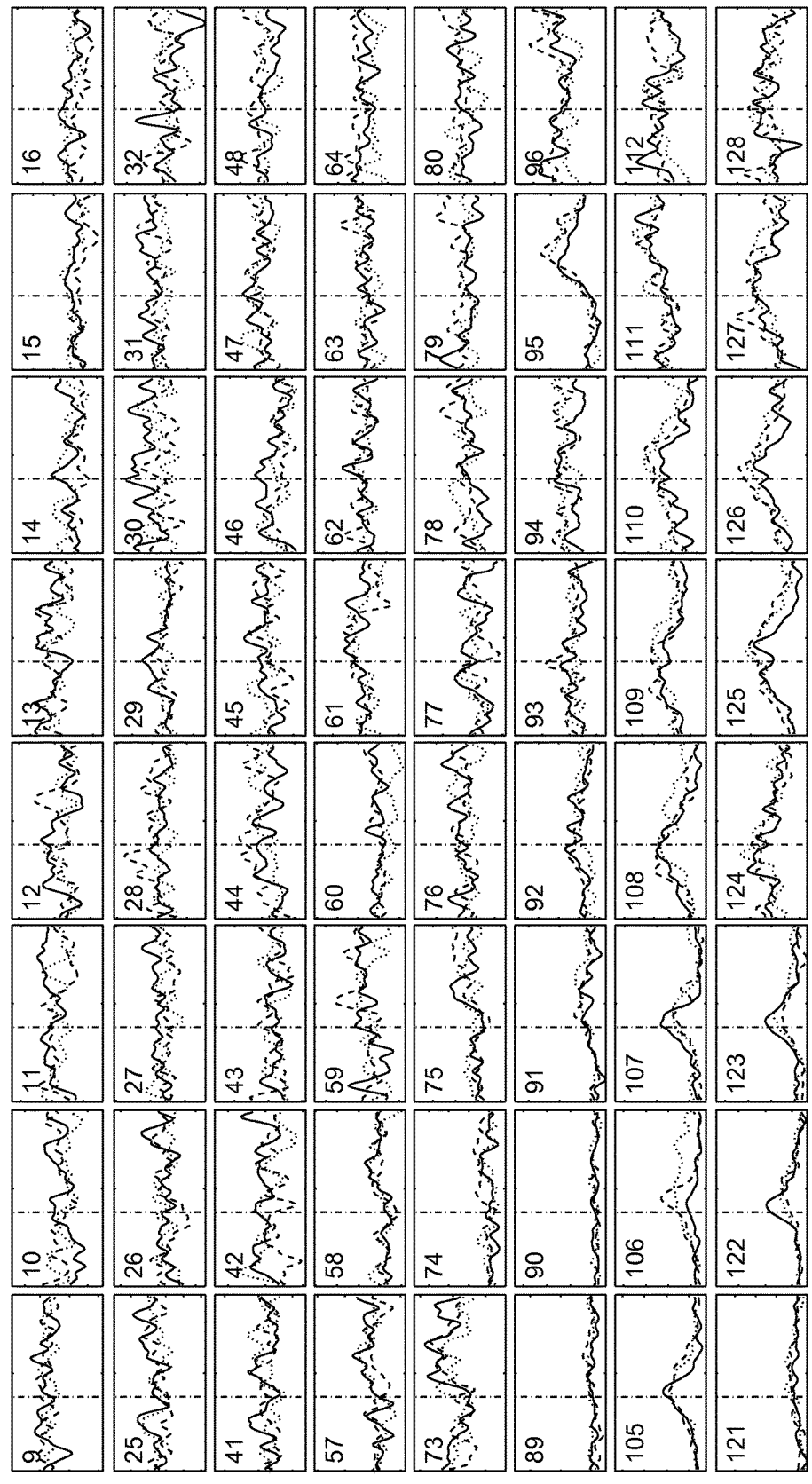
Figure 19:
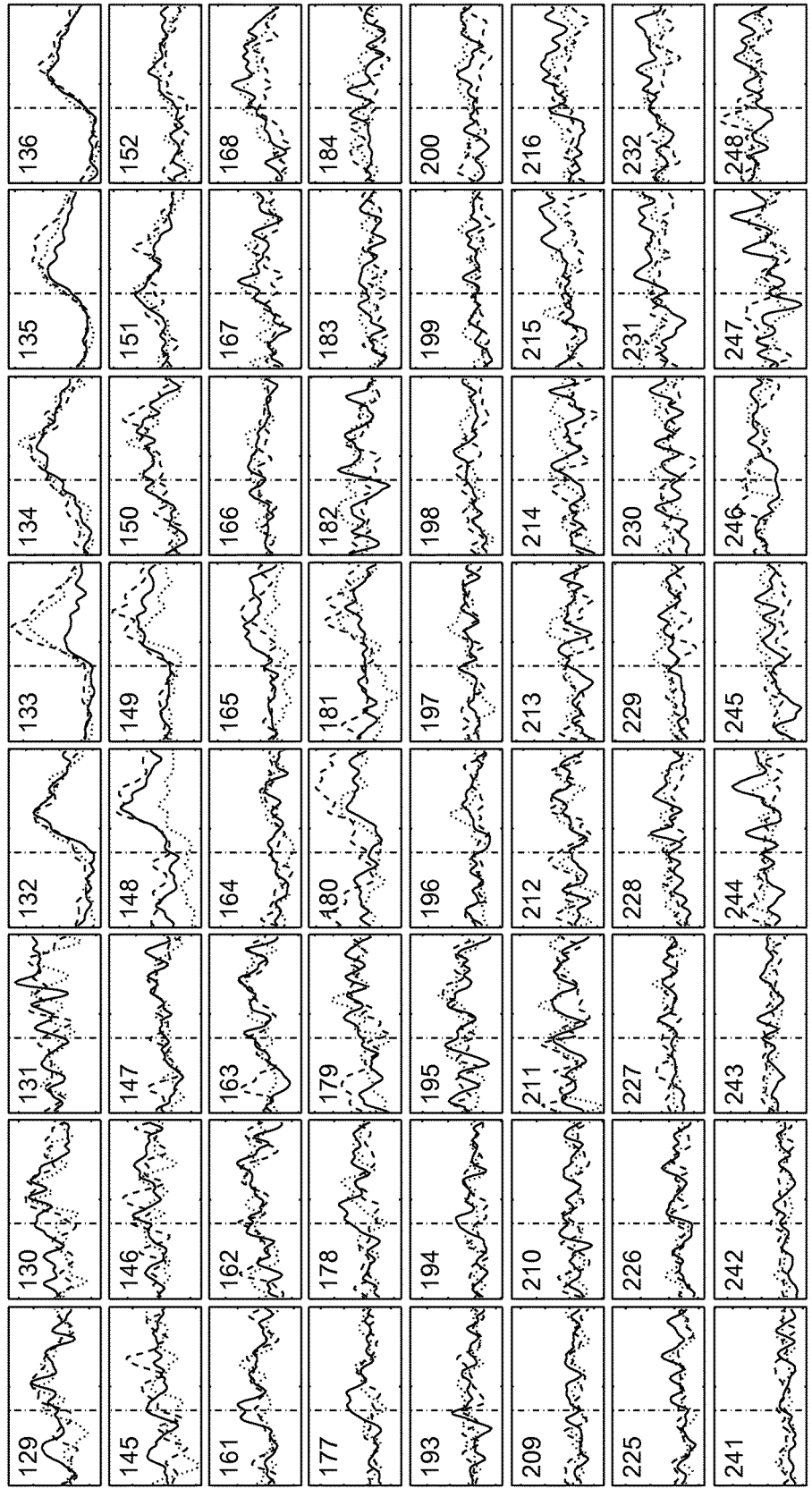
Figure 19:
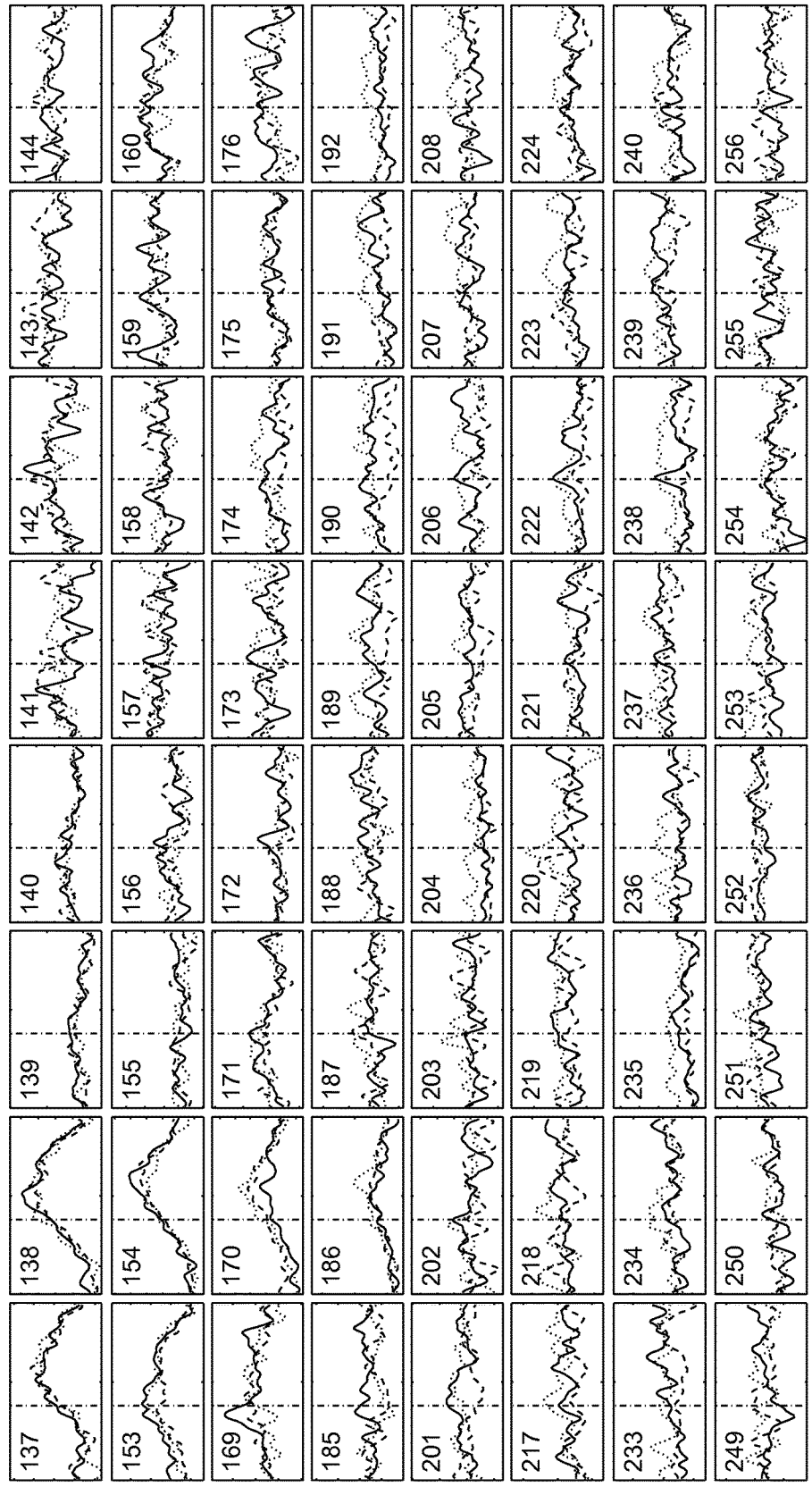
Figure 19:
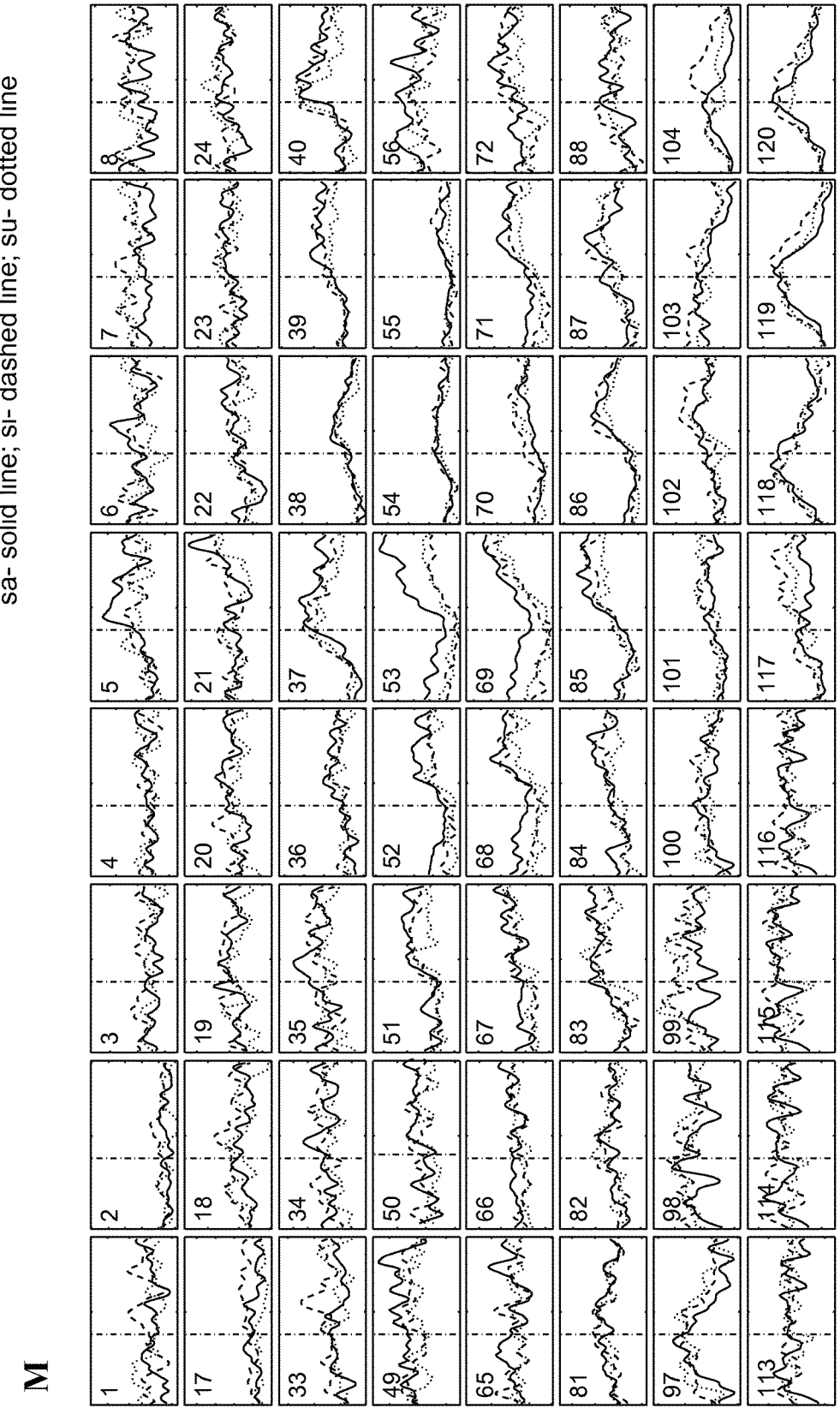
Figure 19:
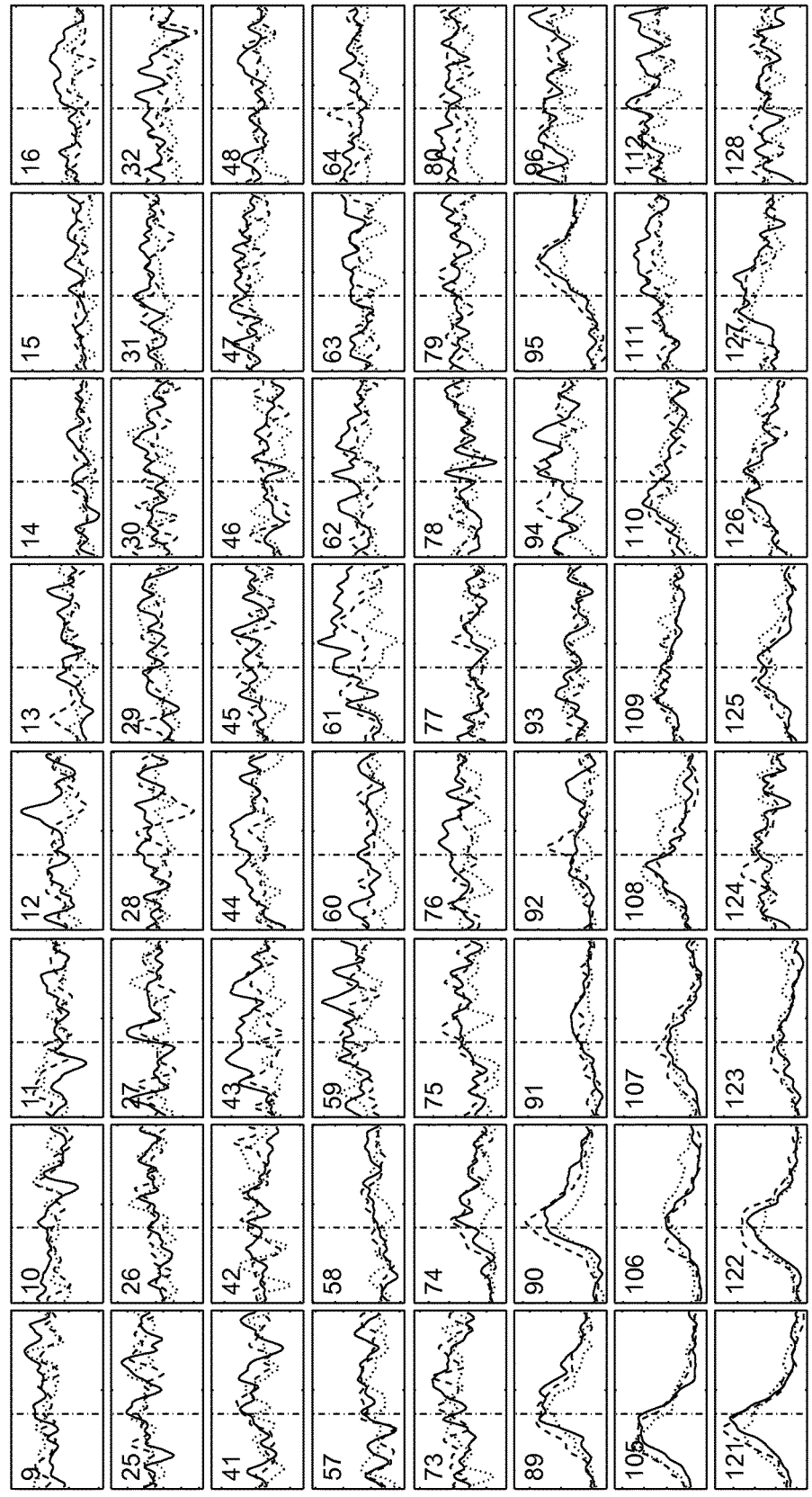
Figure 19:
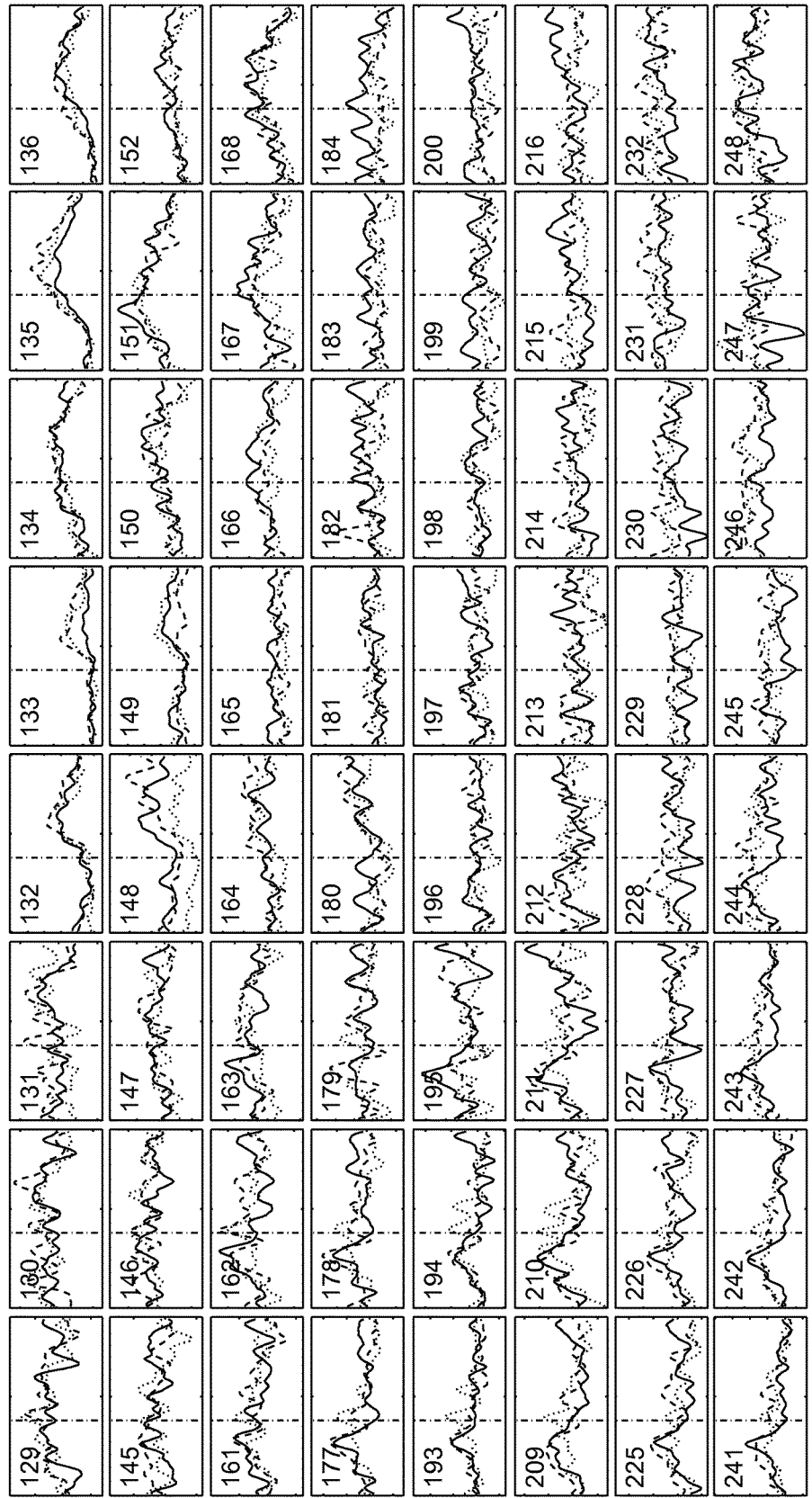
Figure 19:
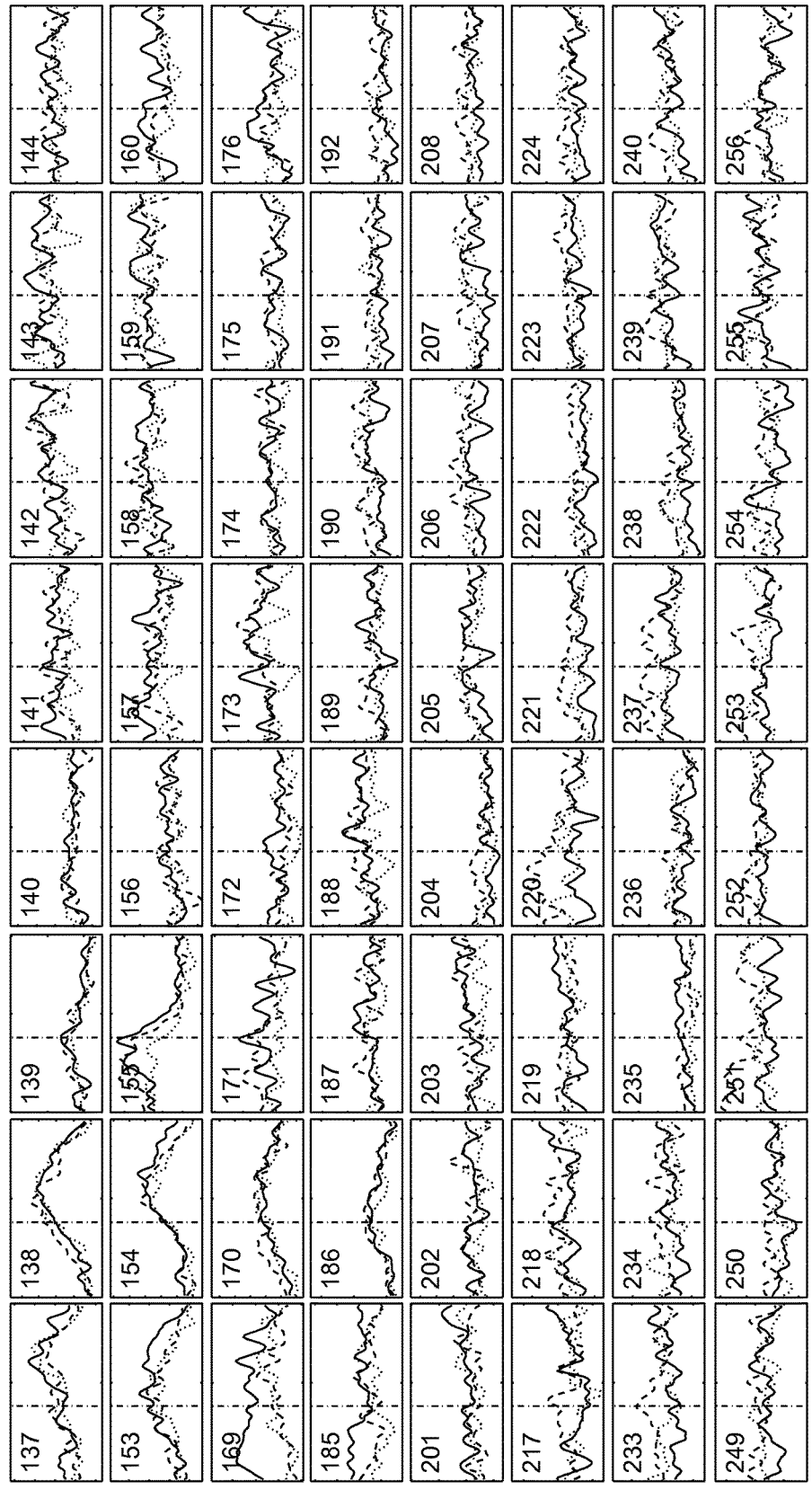
Figure 19:
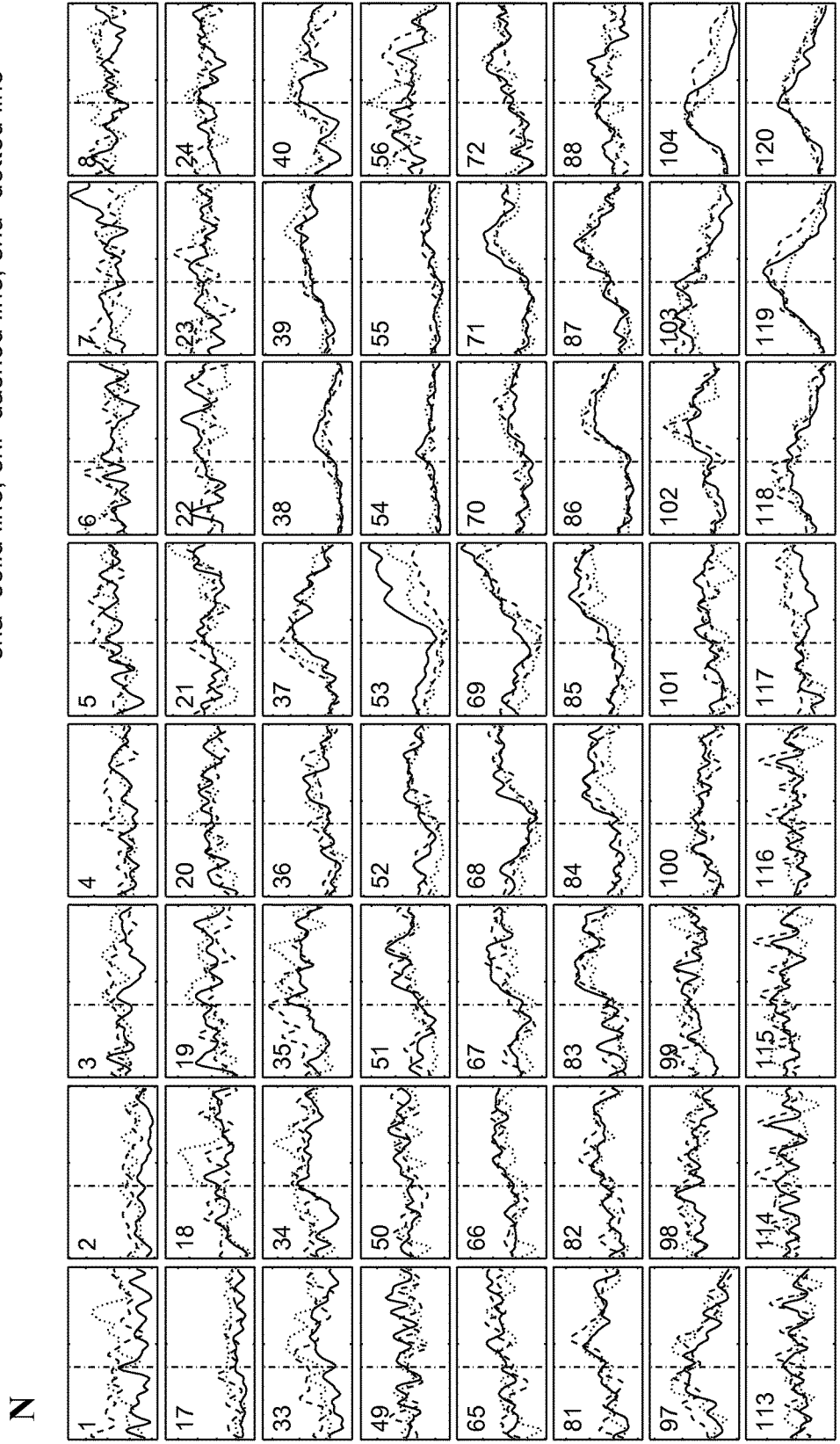
Figure 19:
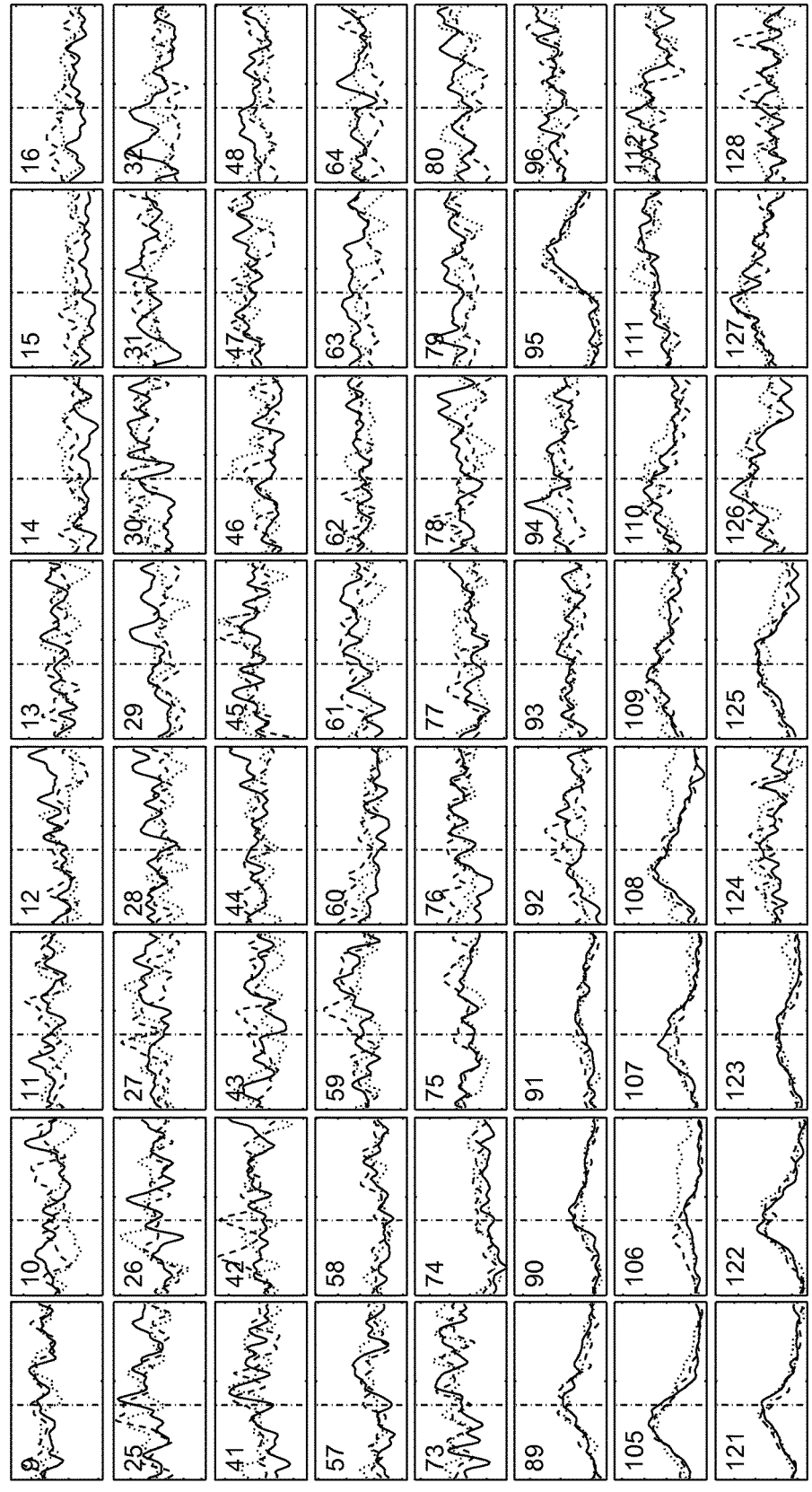
Figure 19:
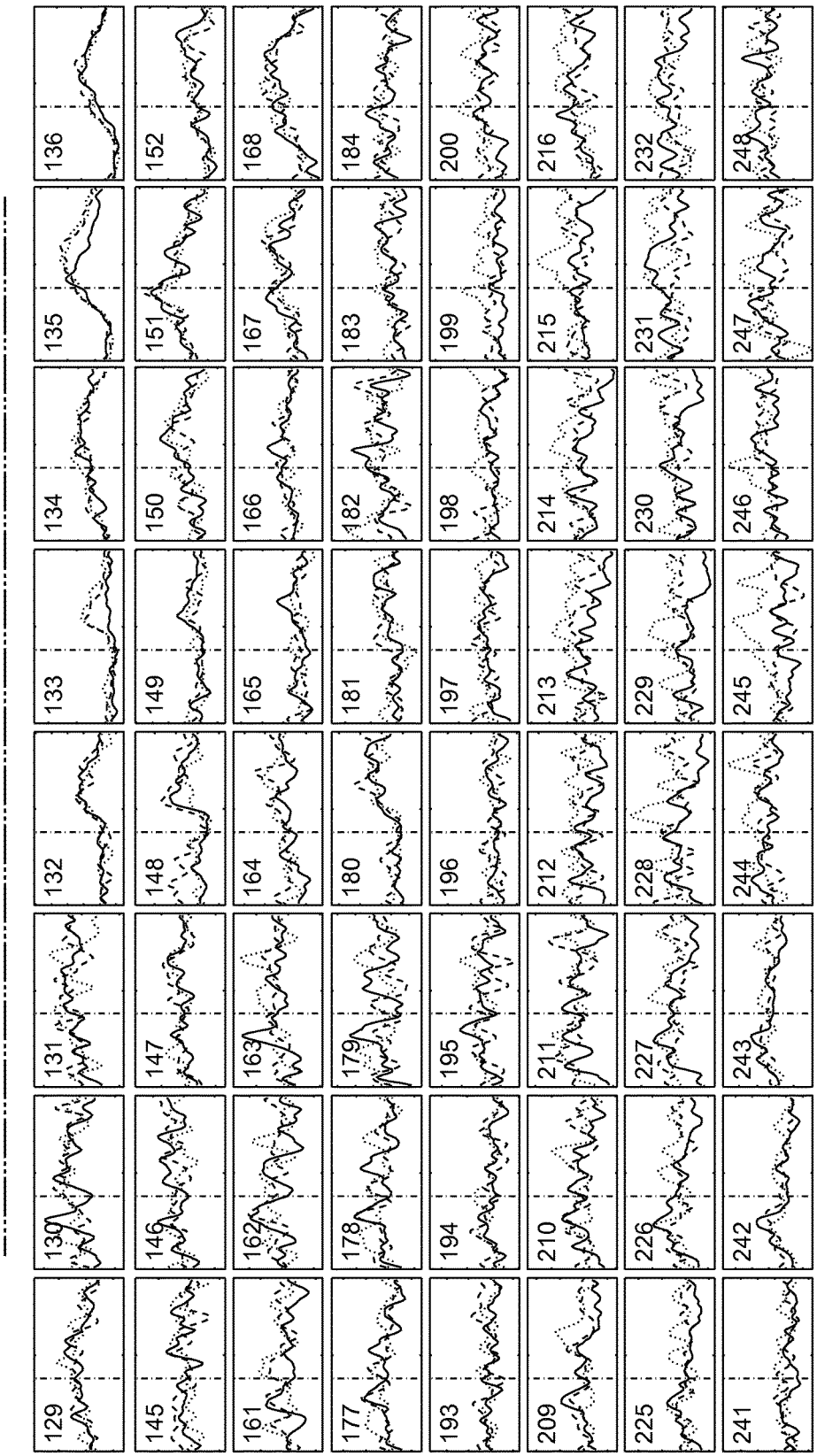
Figure 19:
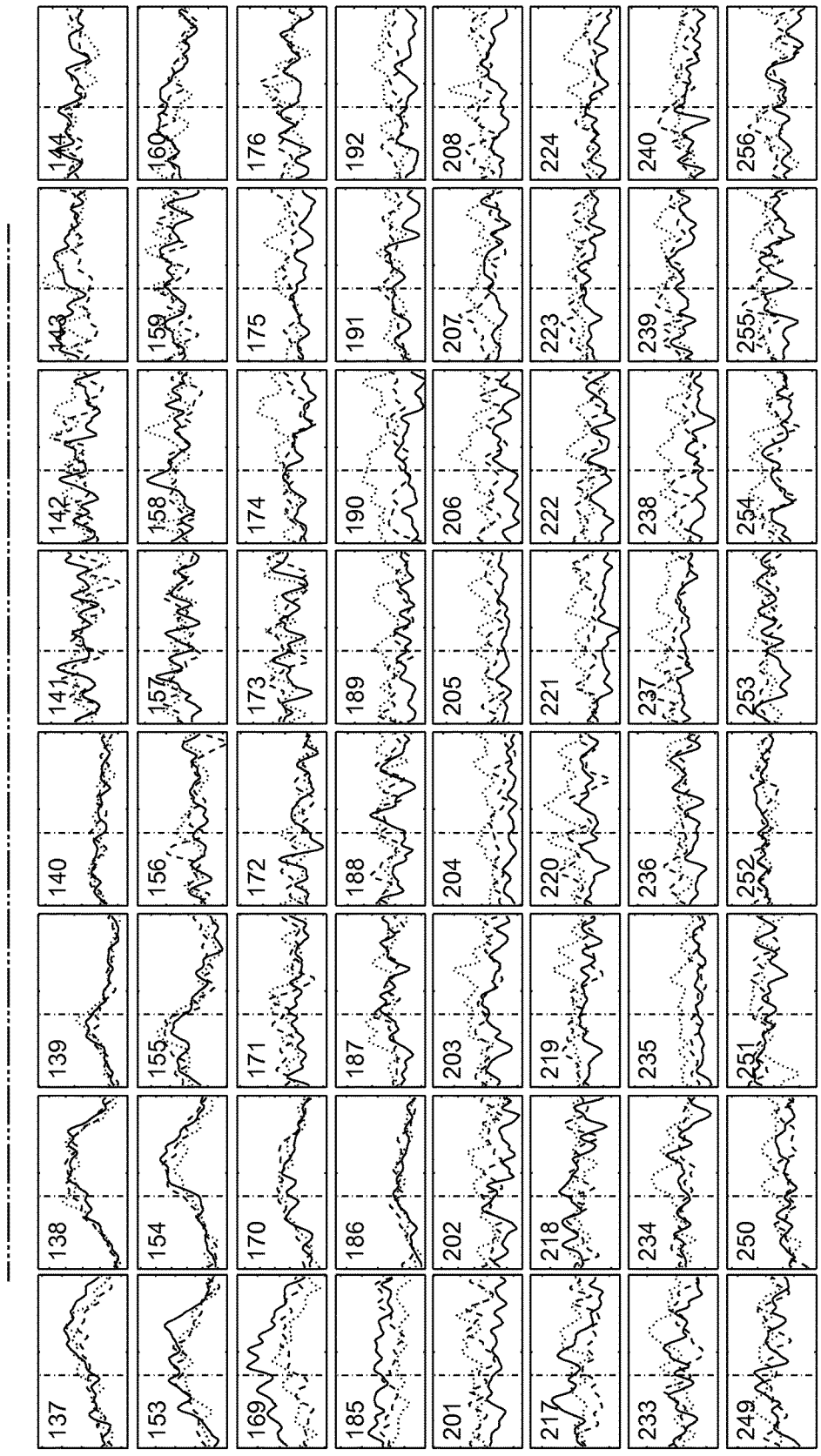
Figure 19:
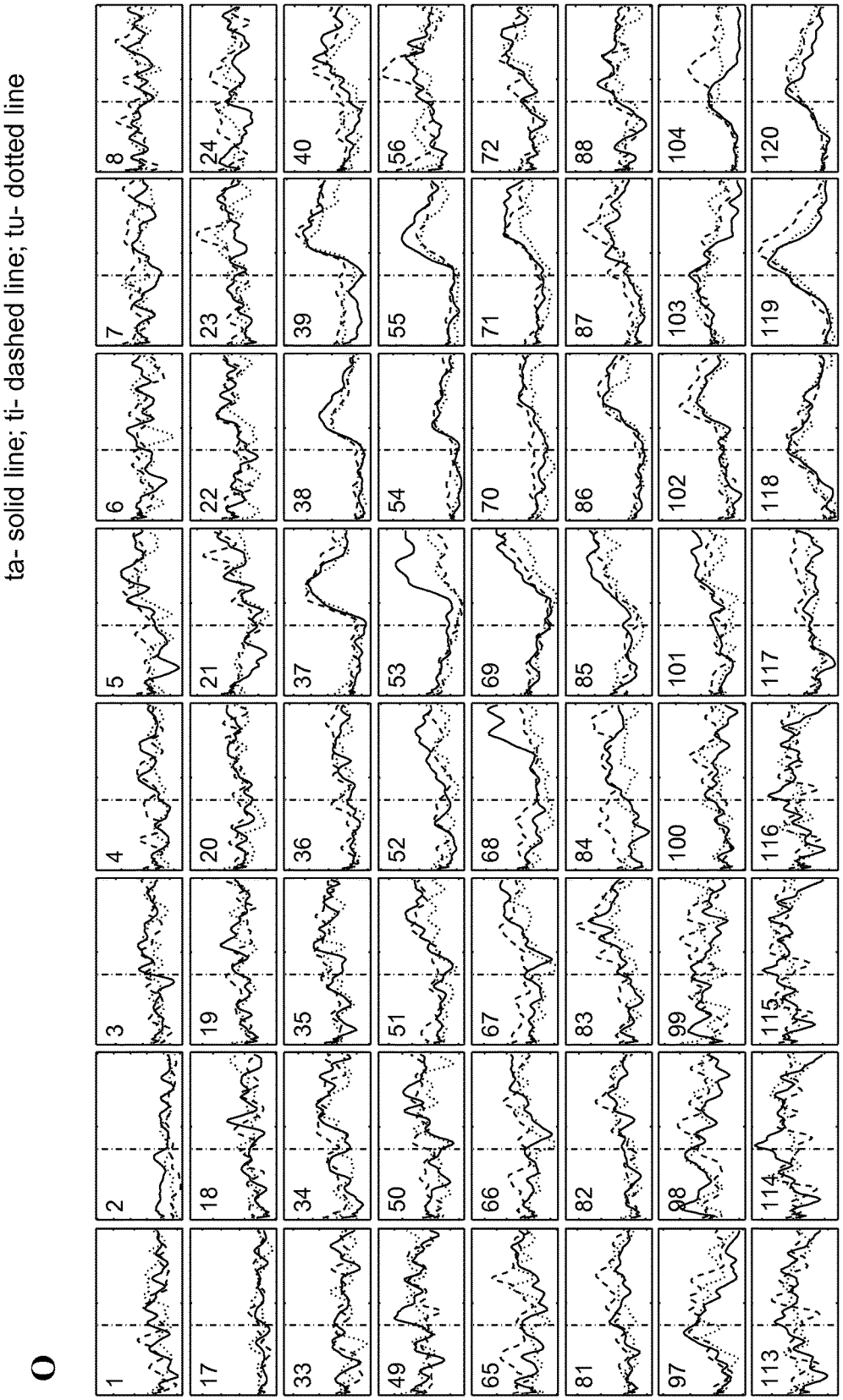
Figure 19:
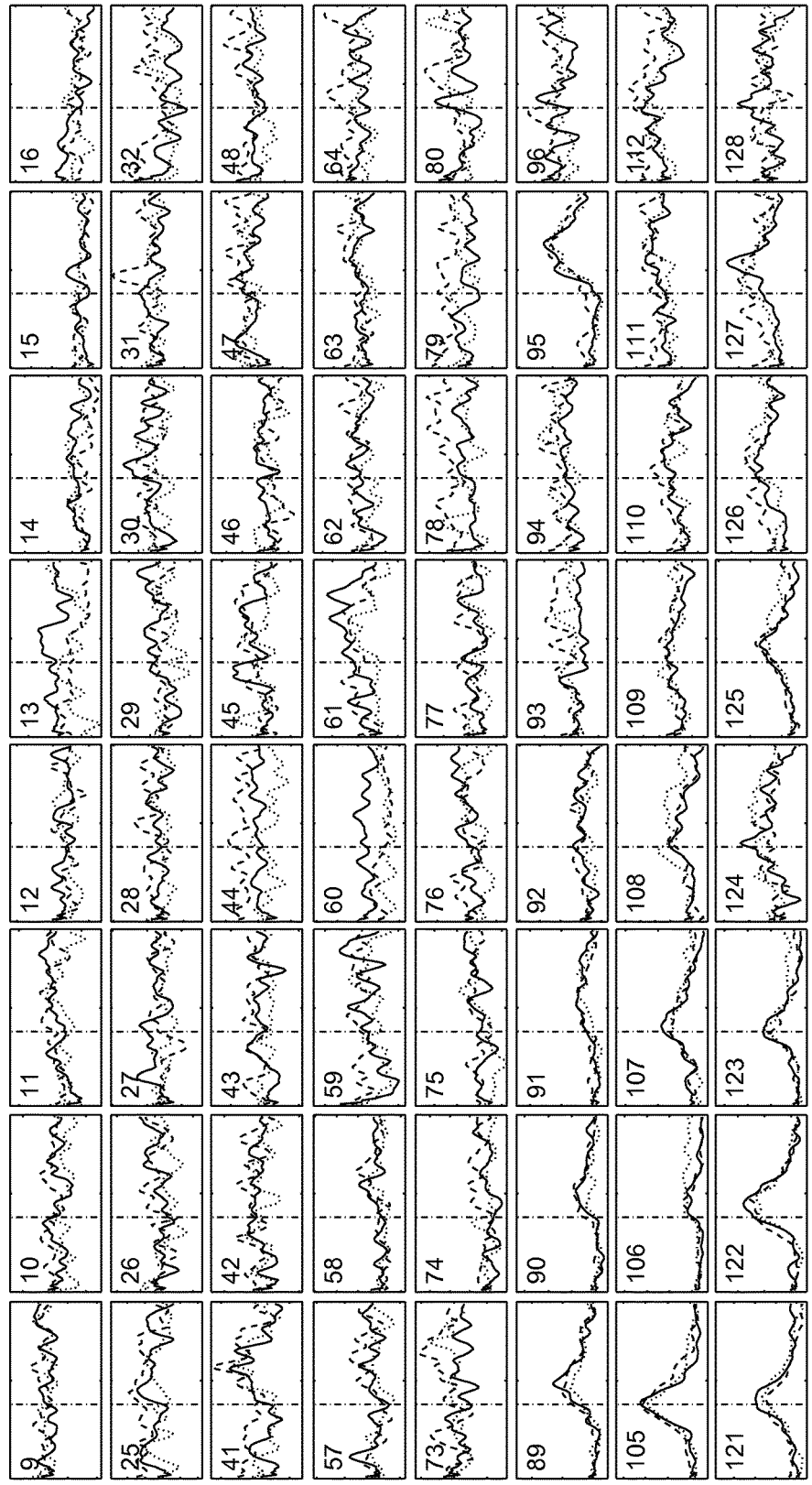
Figure 19:
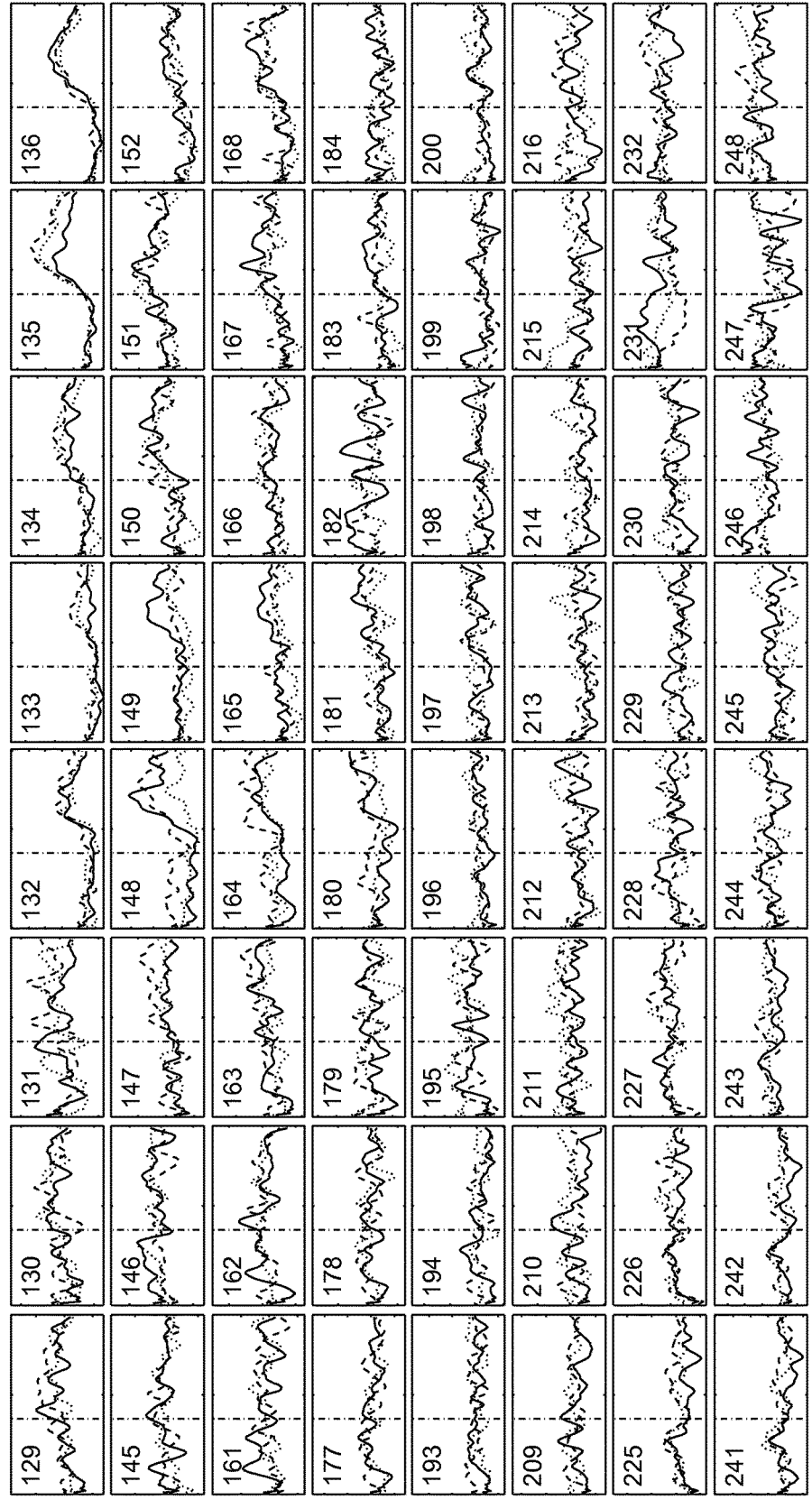
Figure 19:
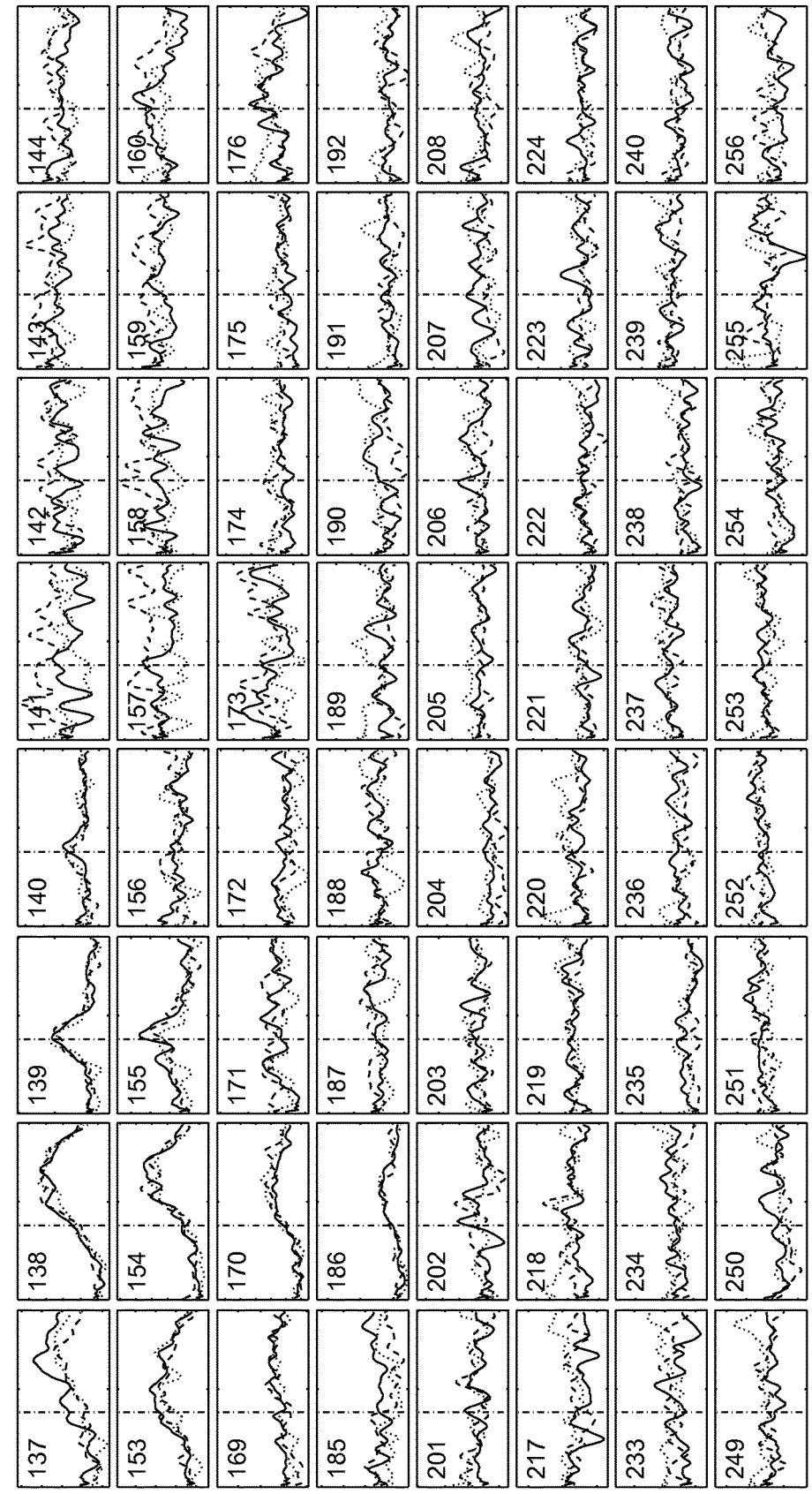
Figure 19:
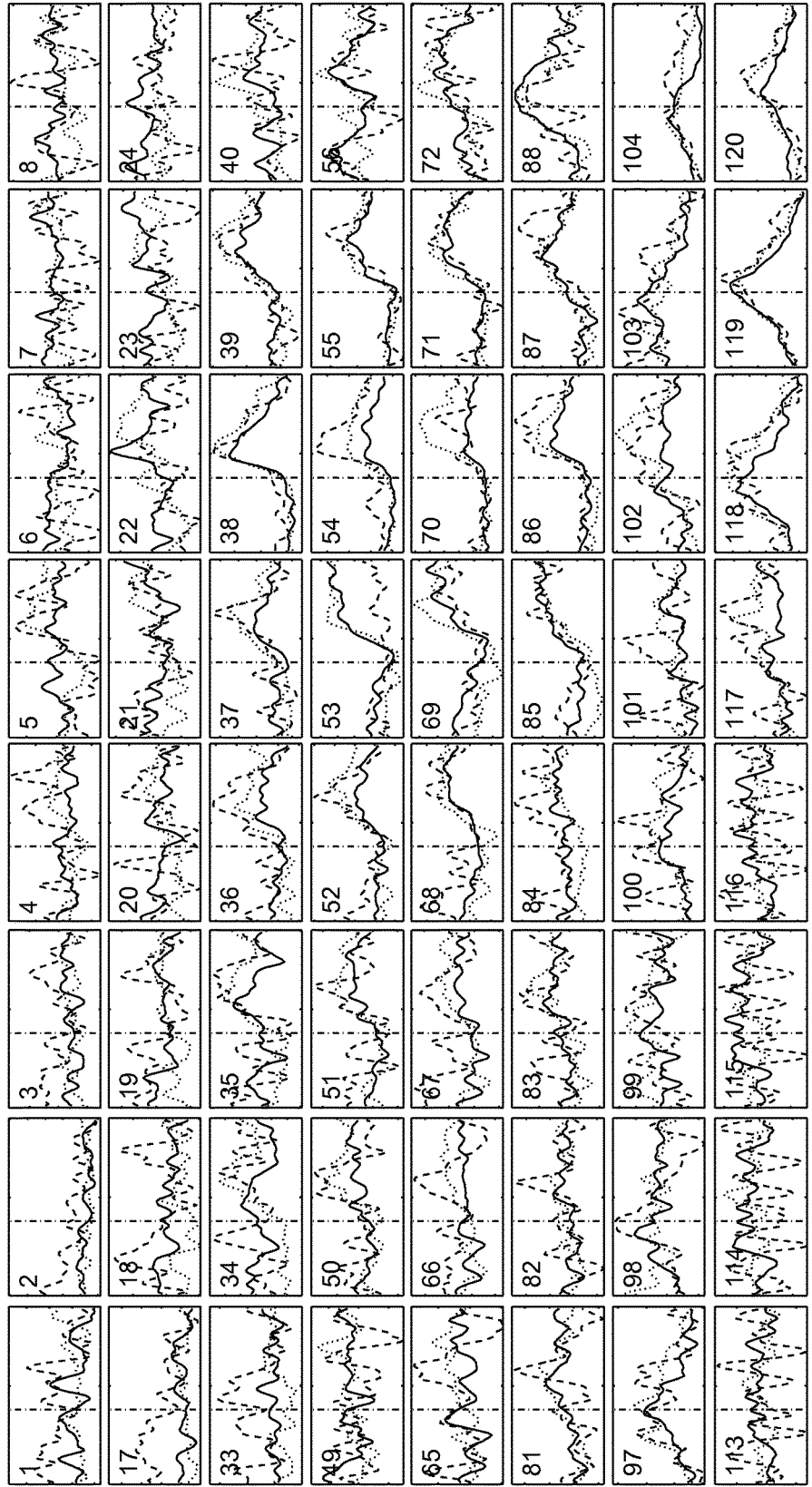
Figure 19:
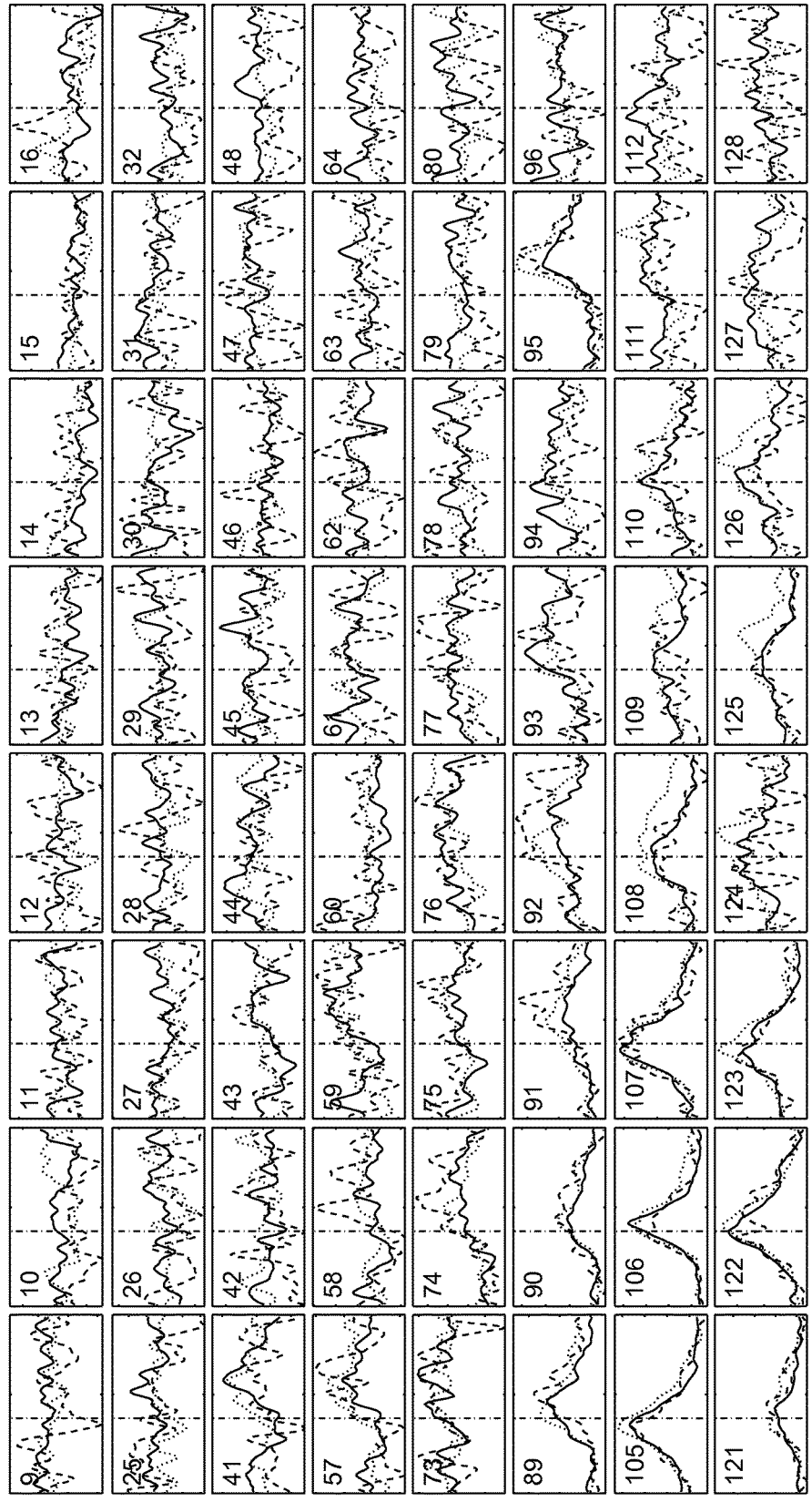
Figure 19:
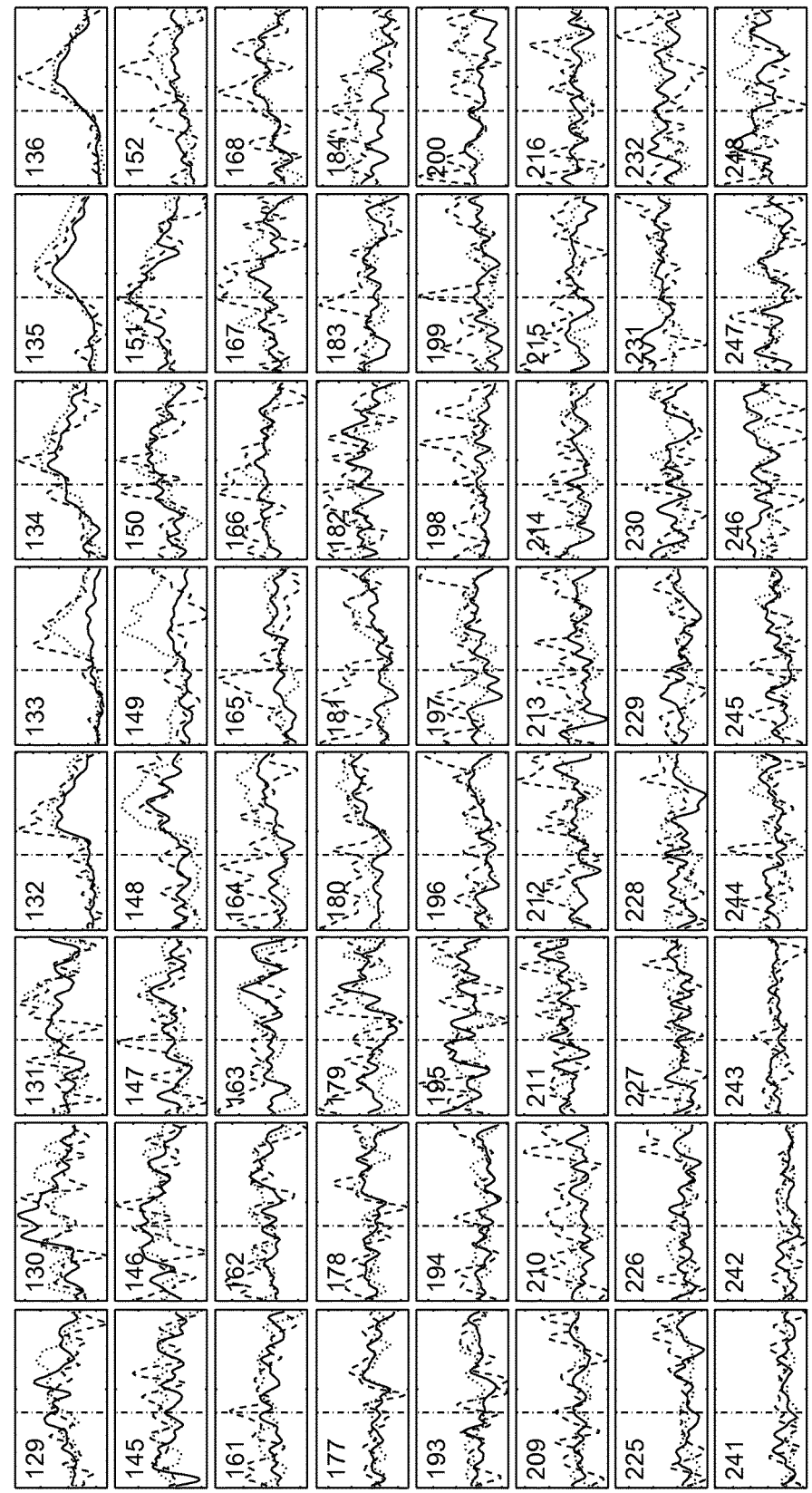
Figure 19:
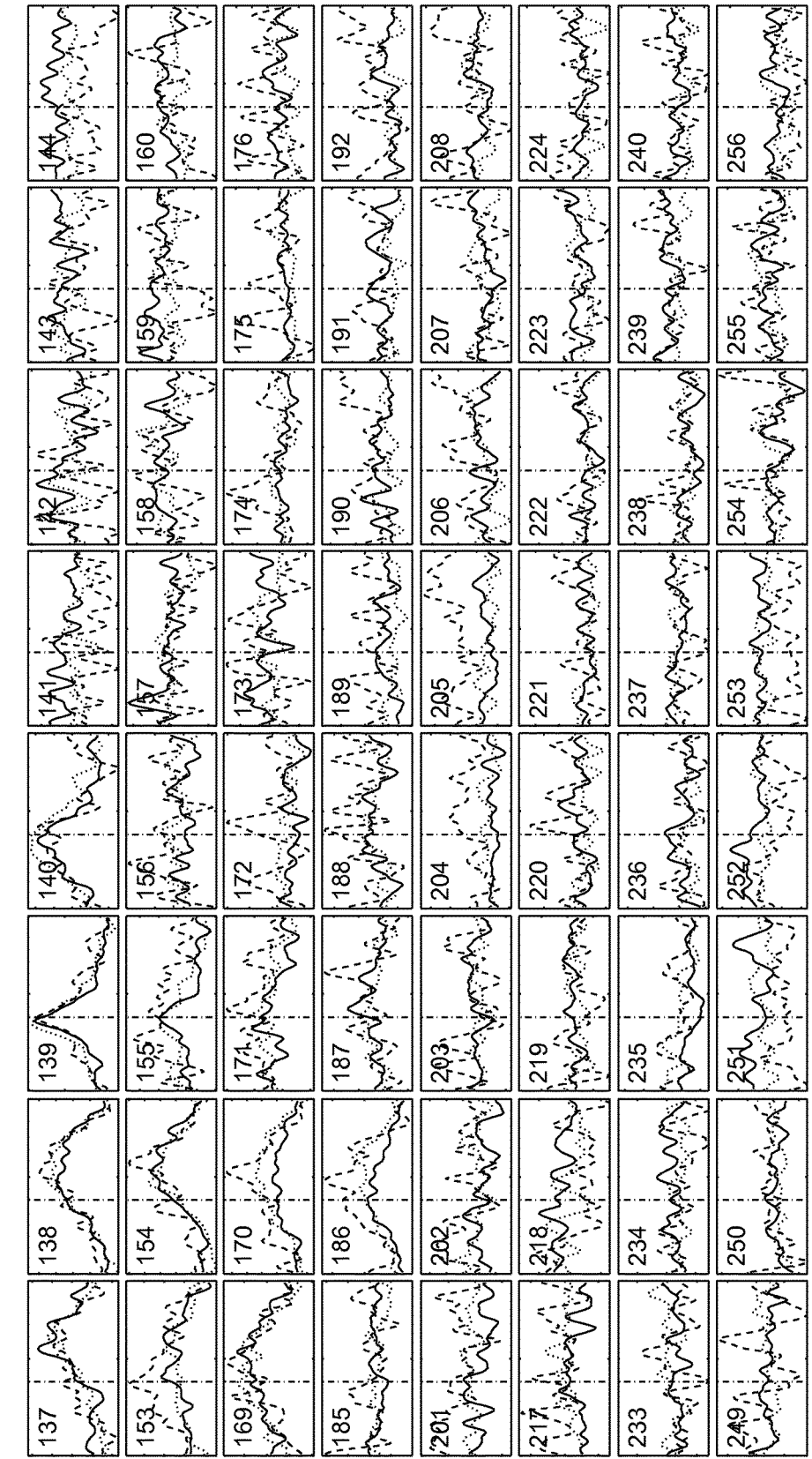
Figure 19:
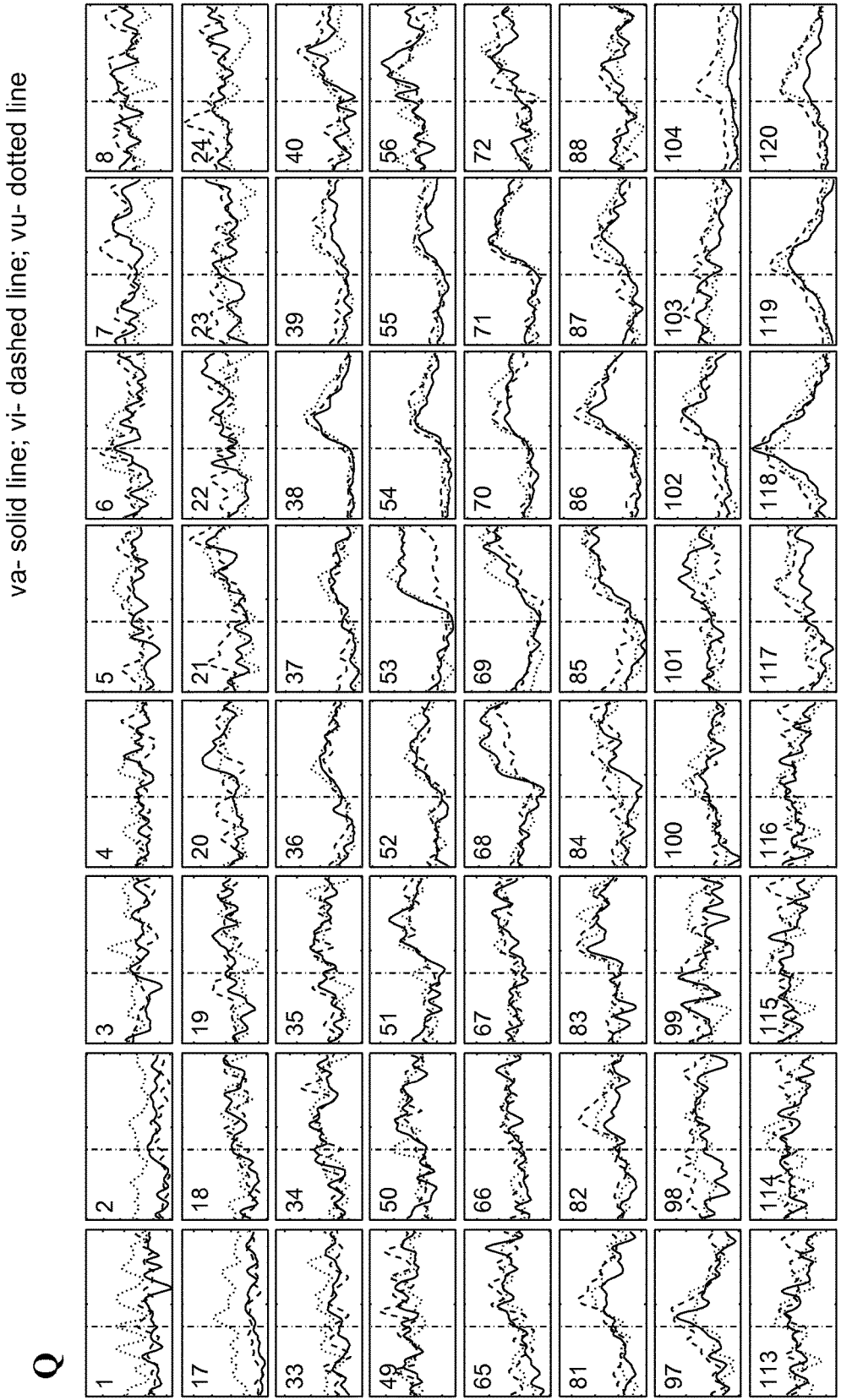
Figure 19:
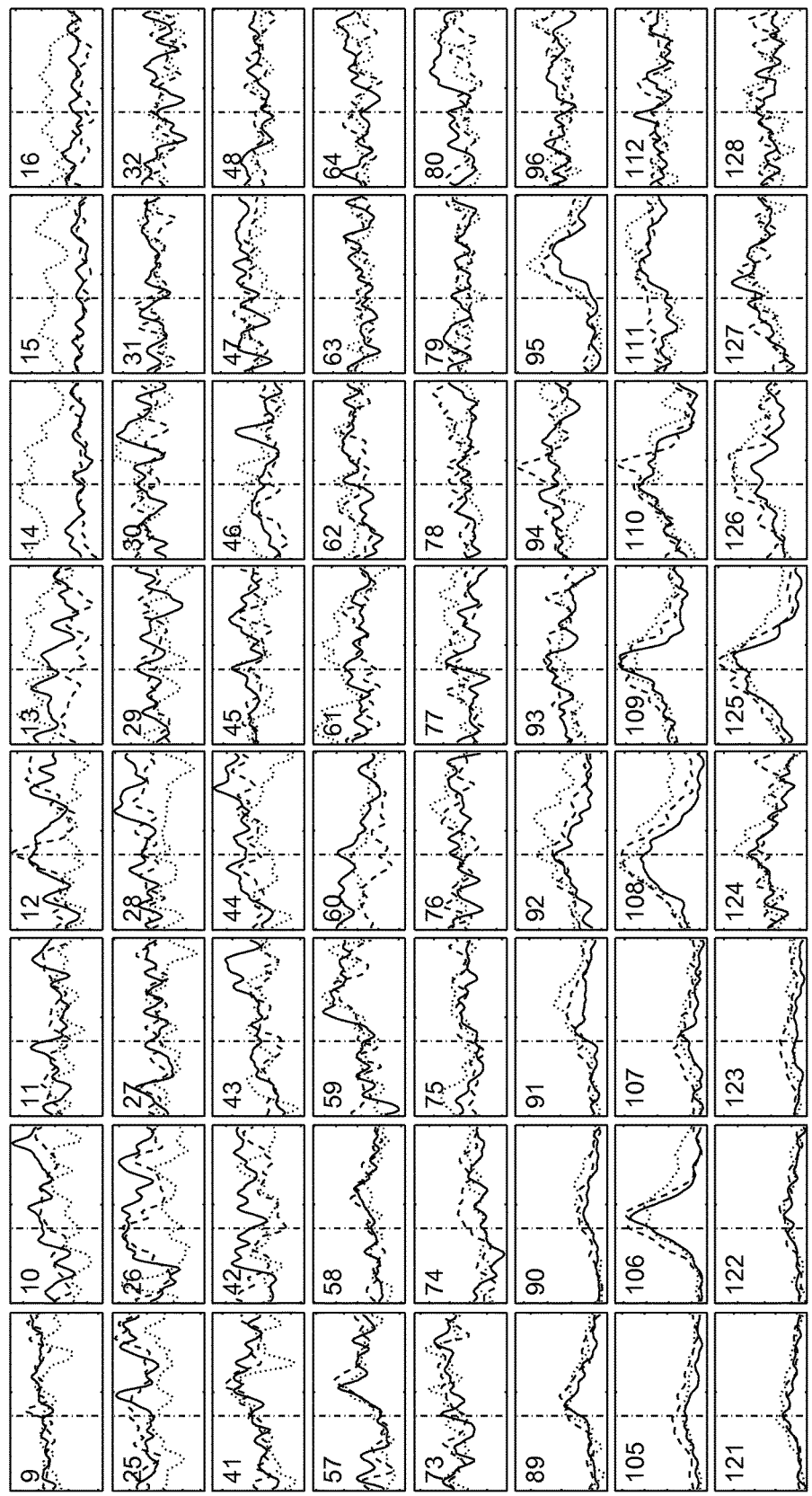
Figure 19:
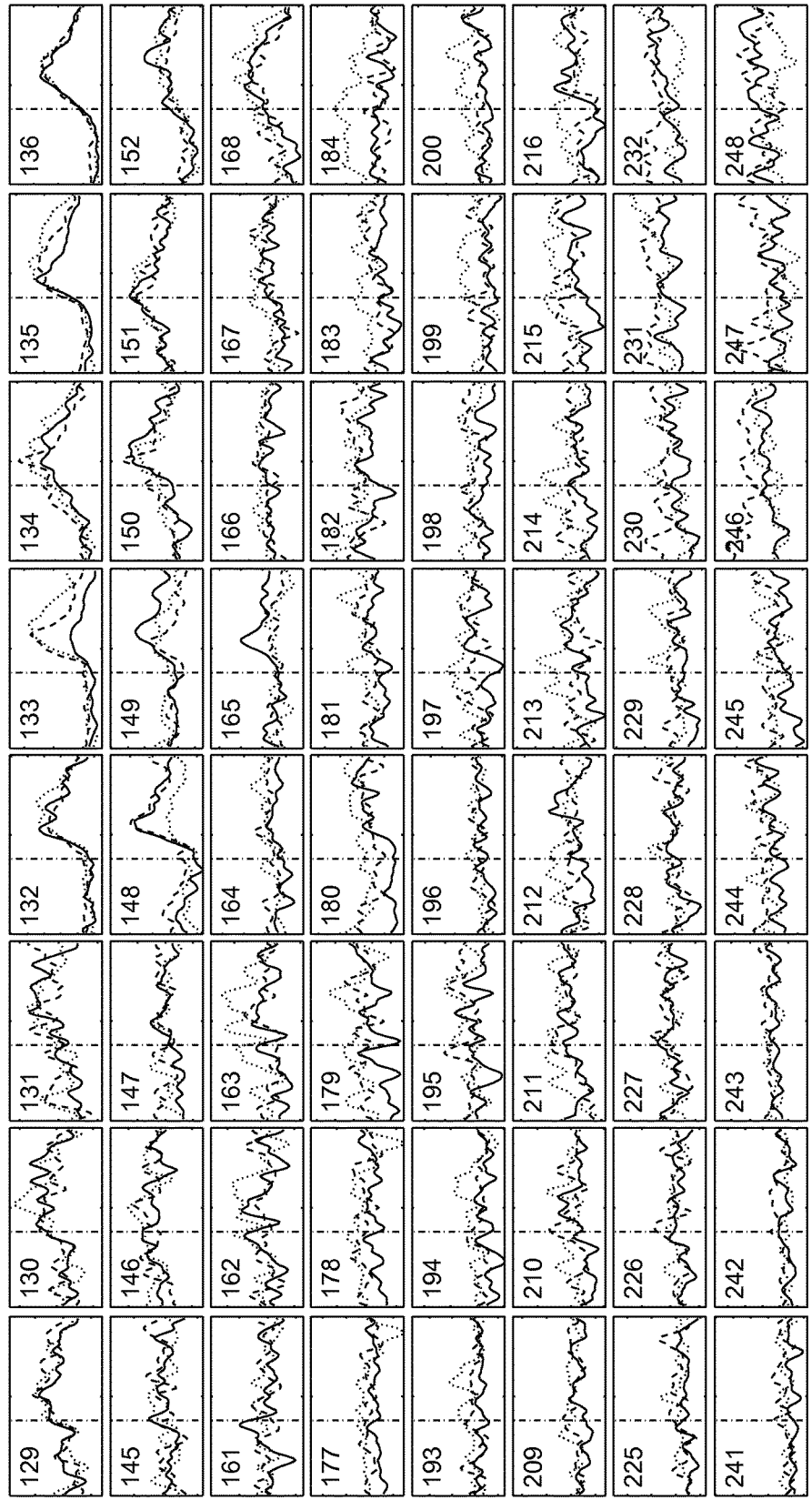
Figure 19:
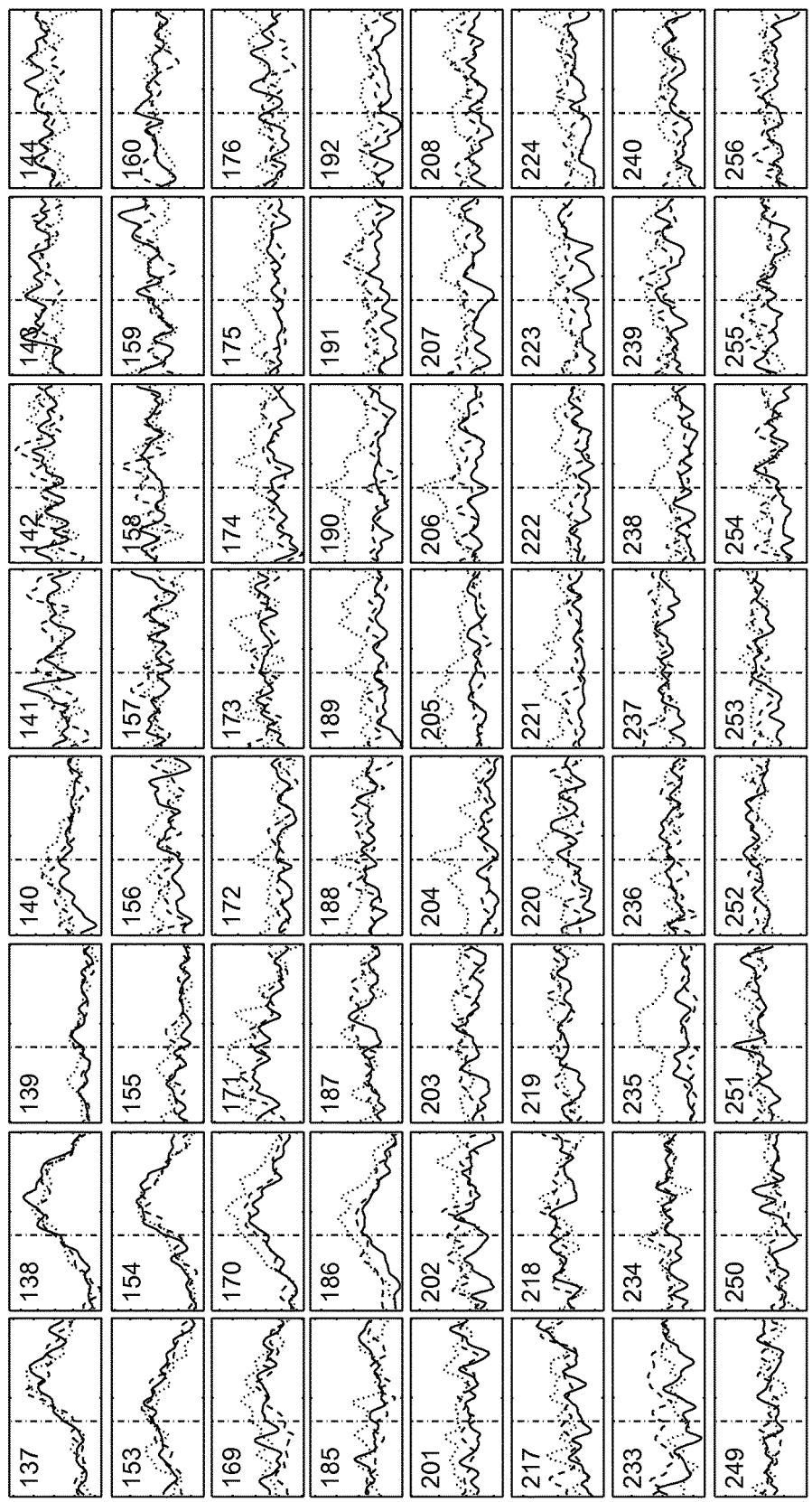
Figure 19:
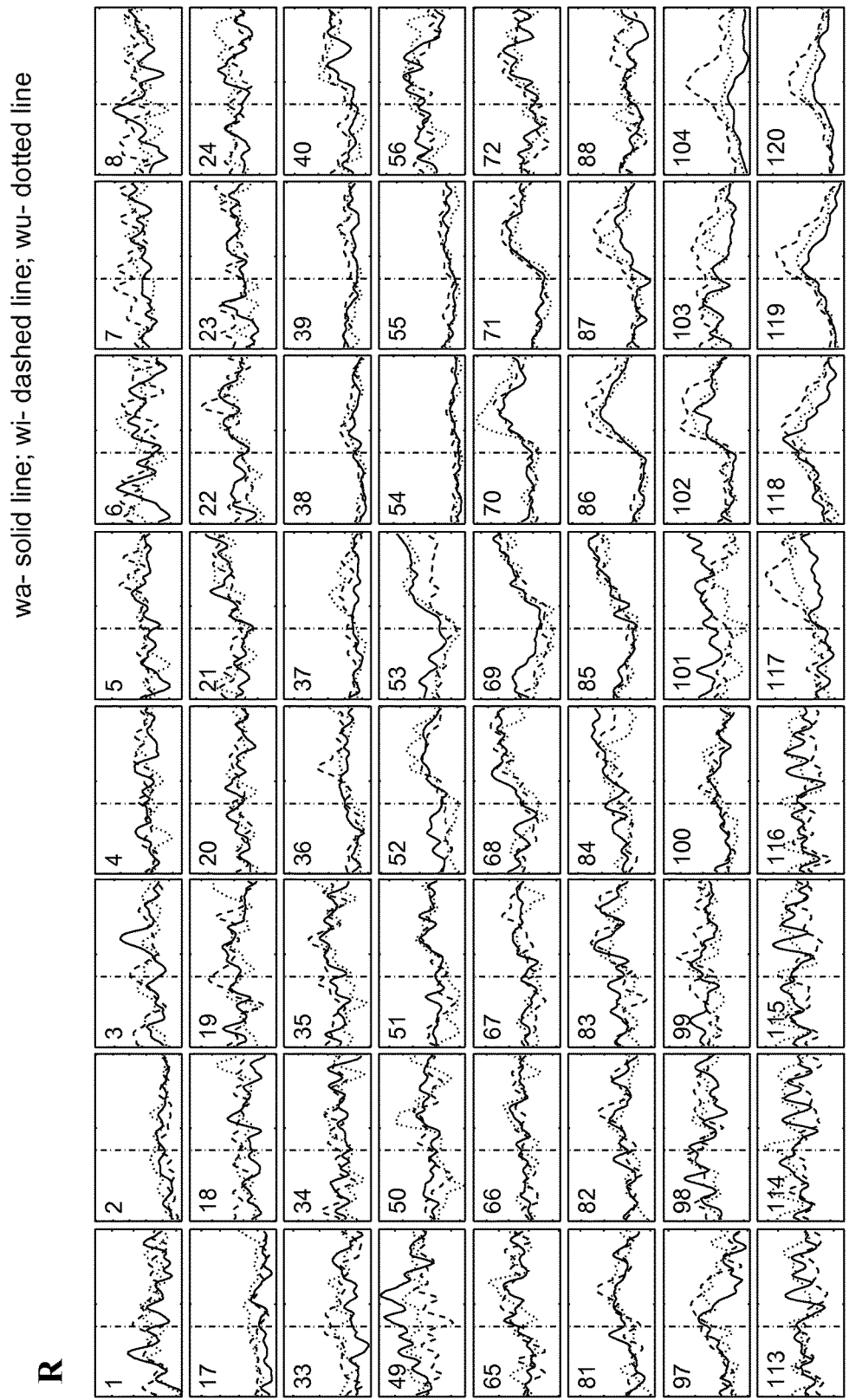
Figure 19:
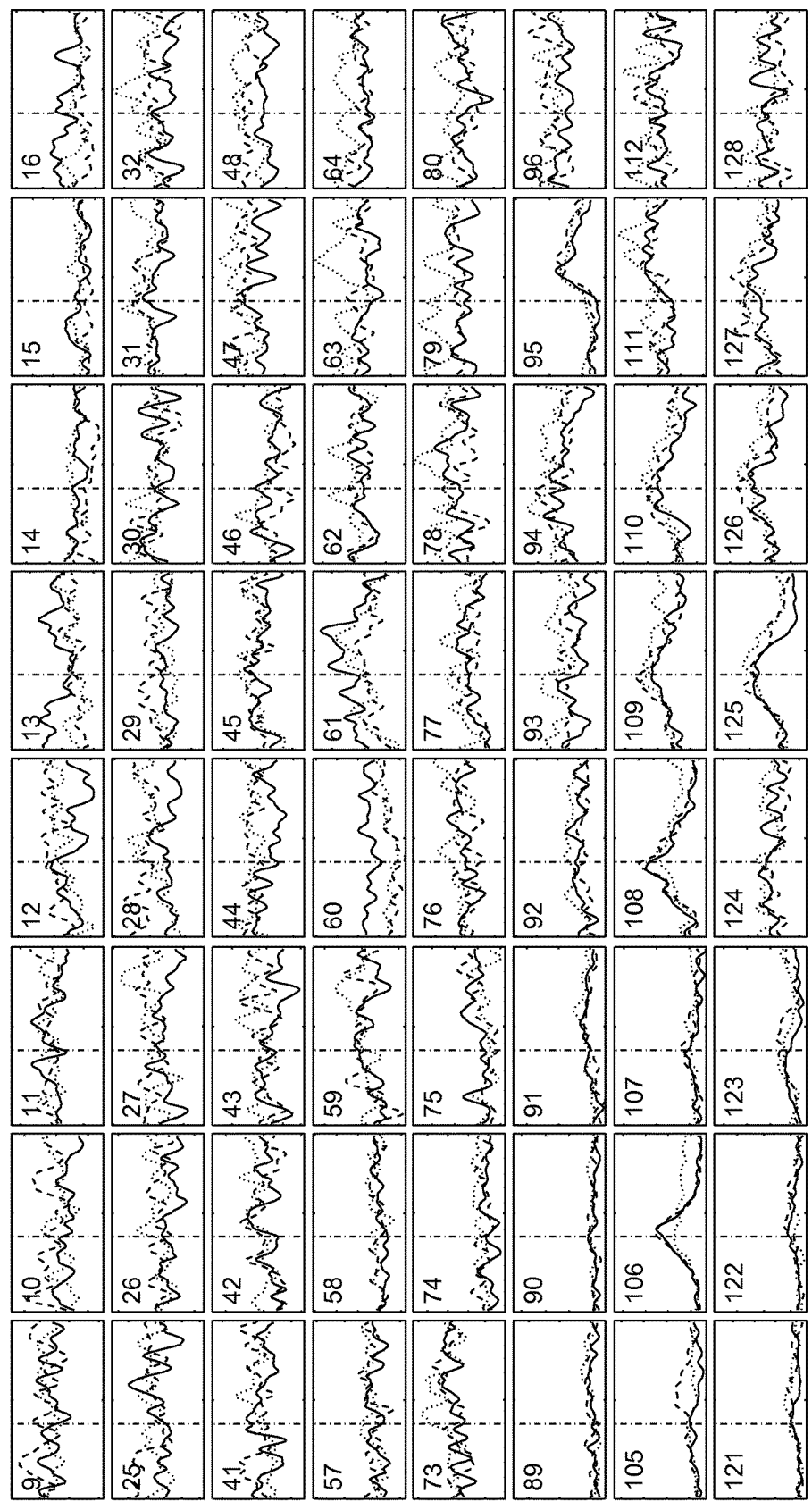
Figure 19:
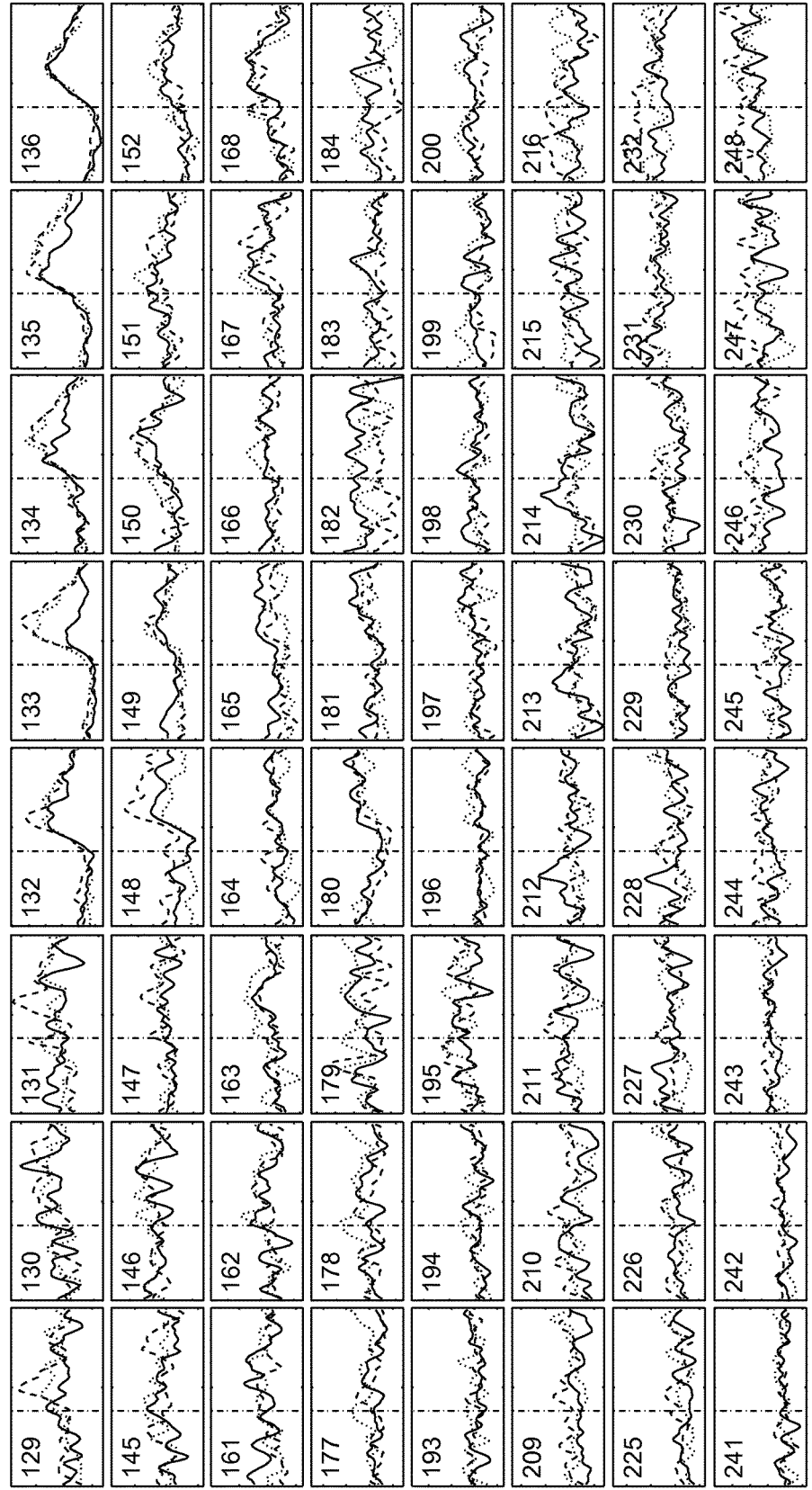
Figure 19:
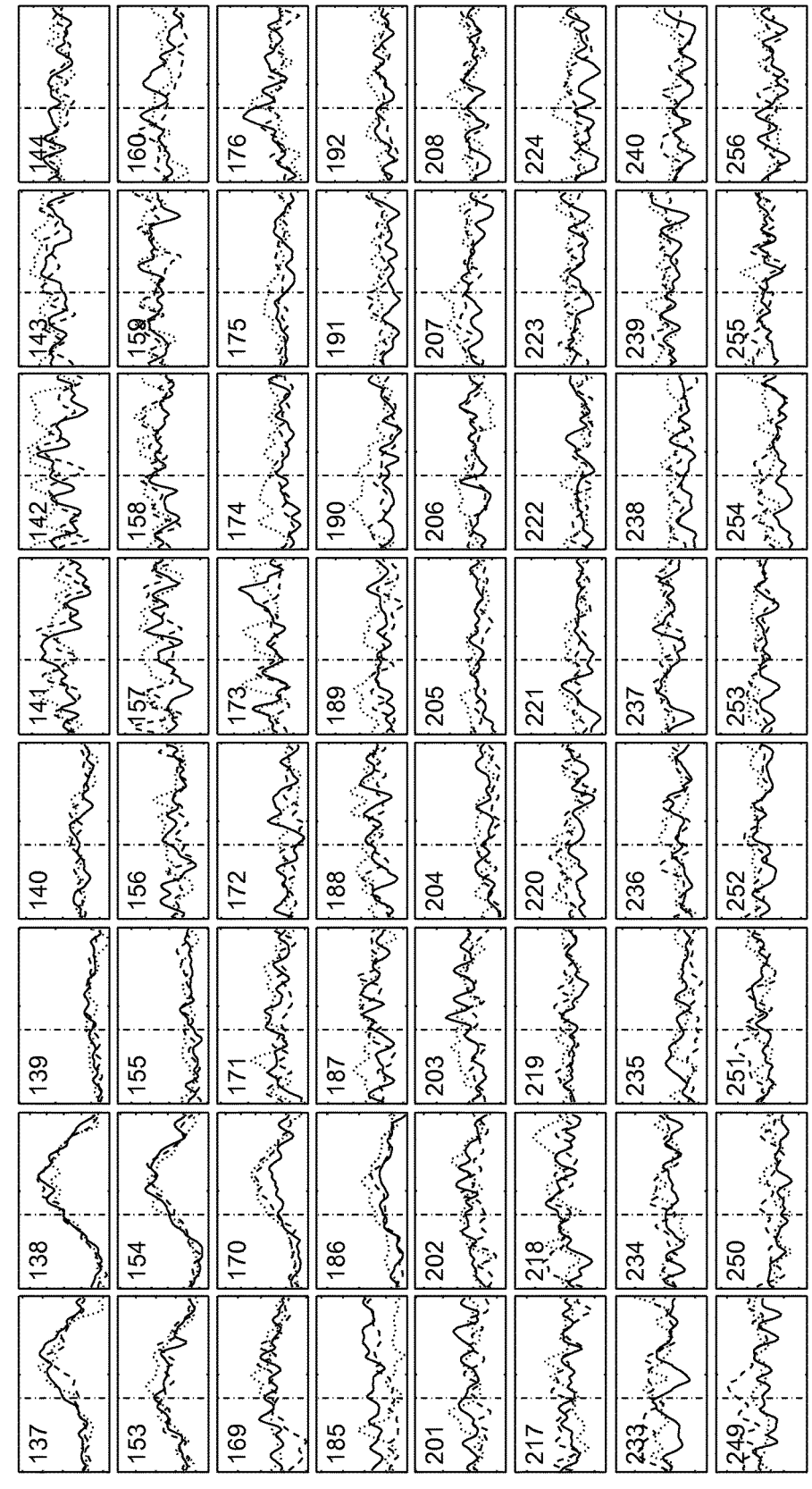
Figure 19:
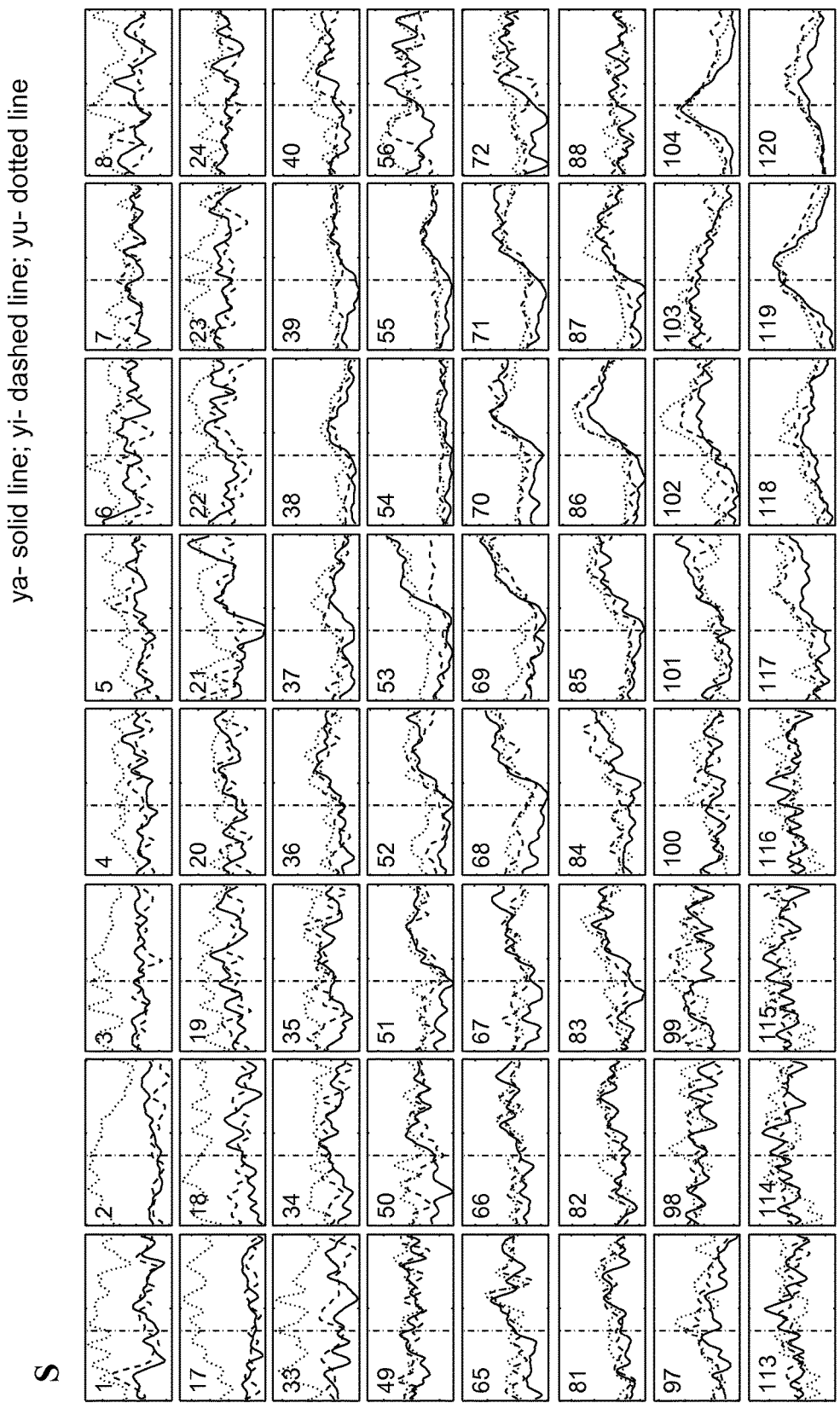
Figure 19:
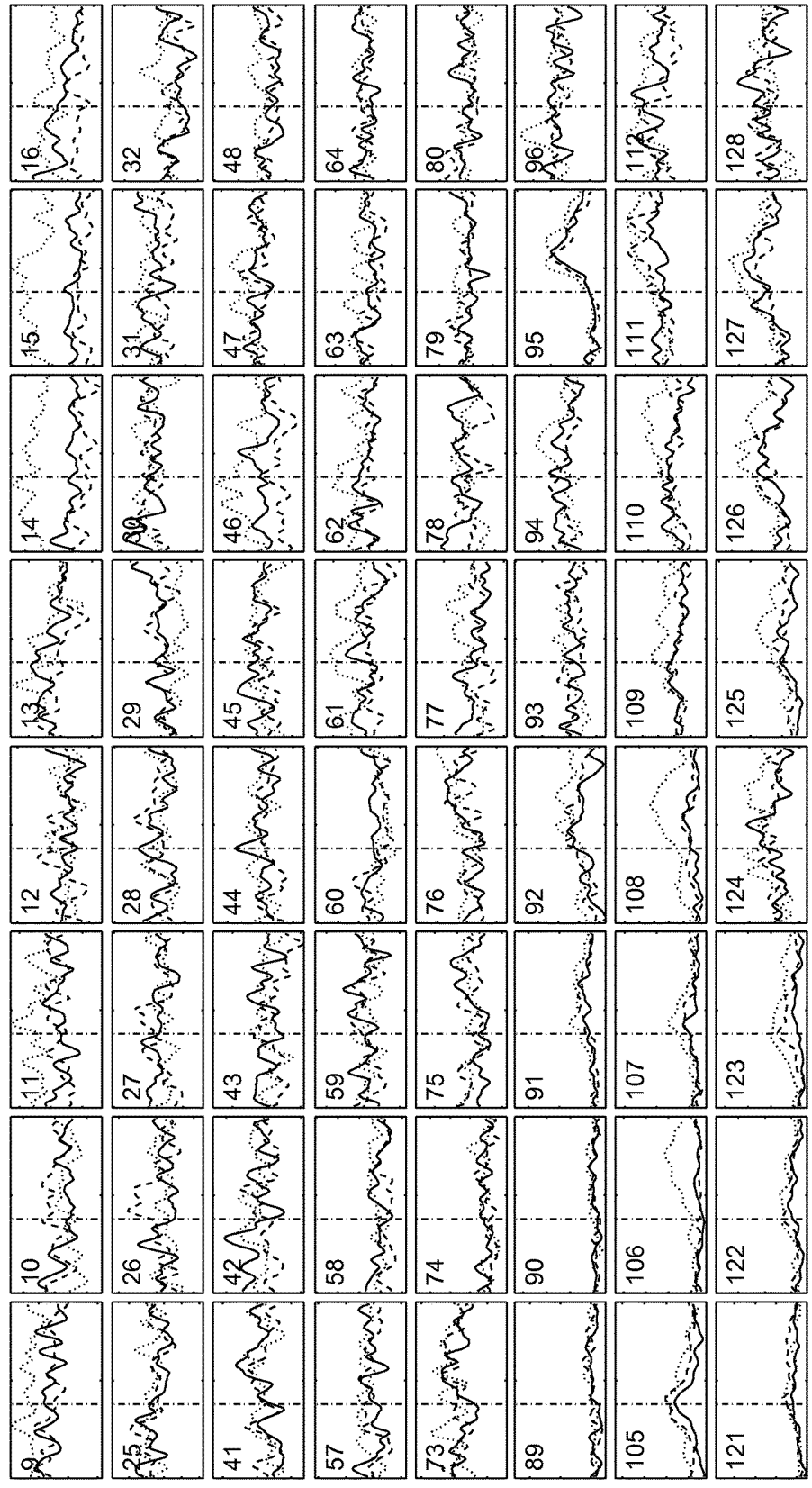
Figure 19:
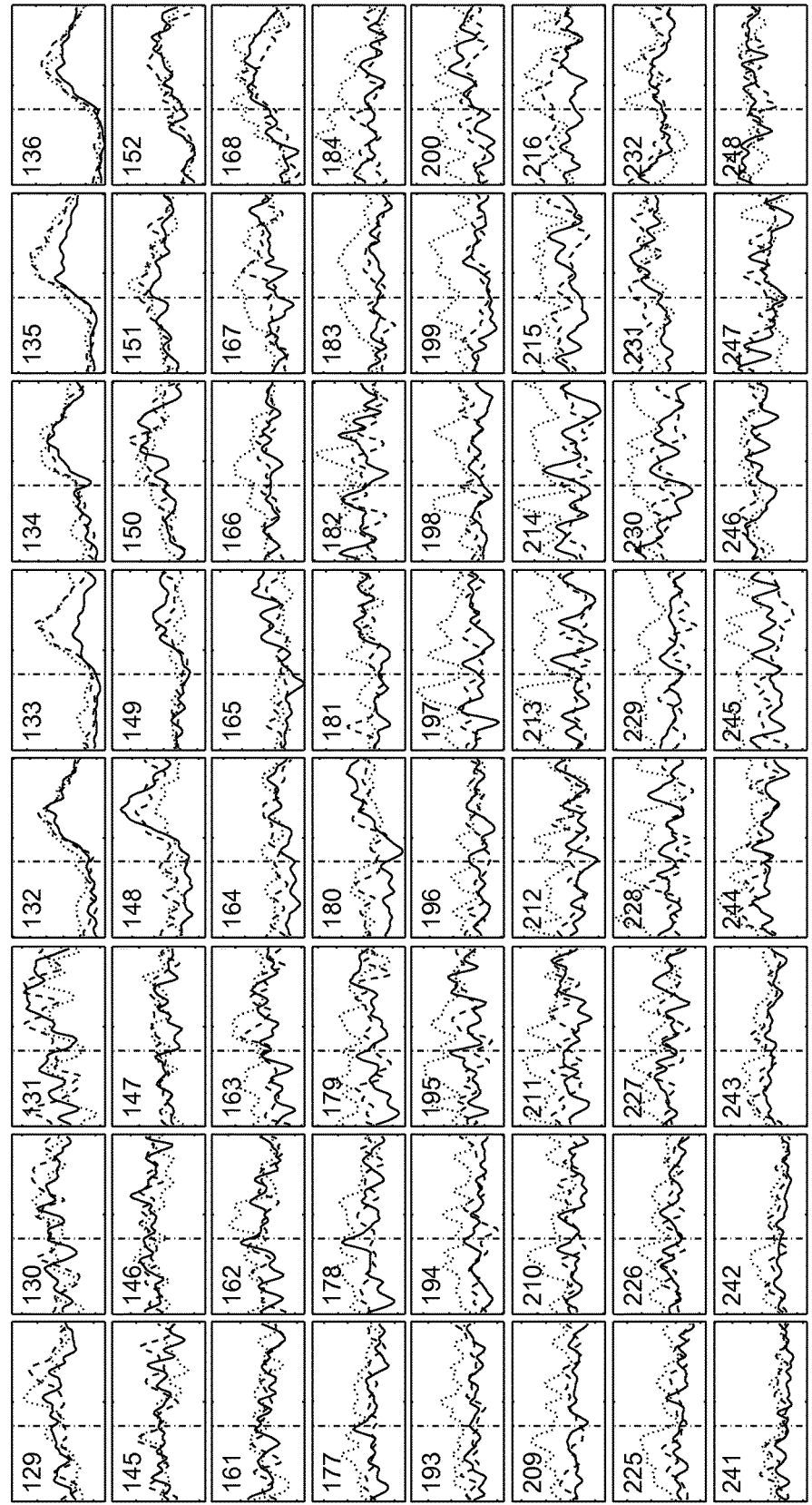
Figure 19:
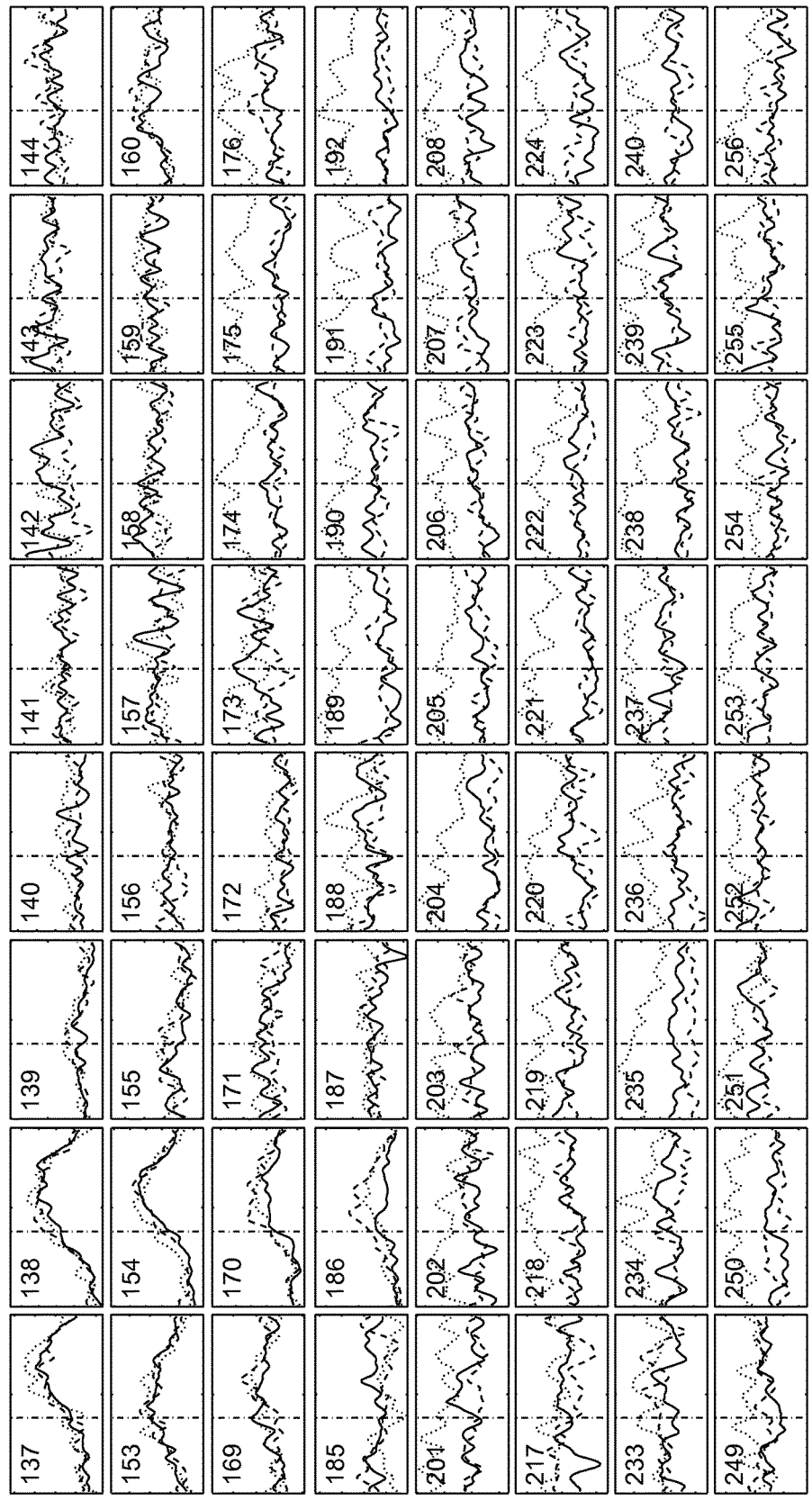
Figure 19:
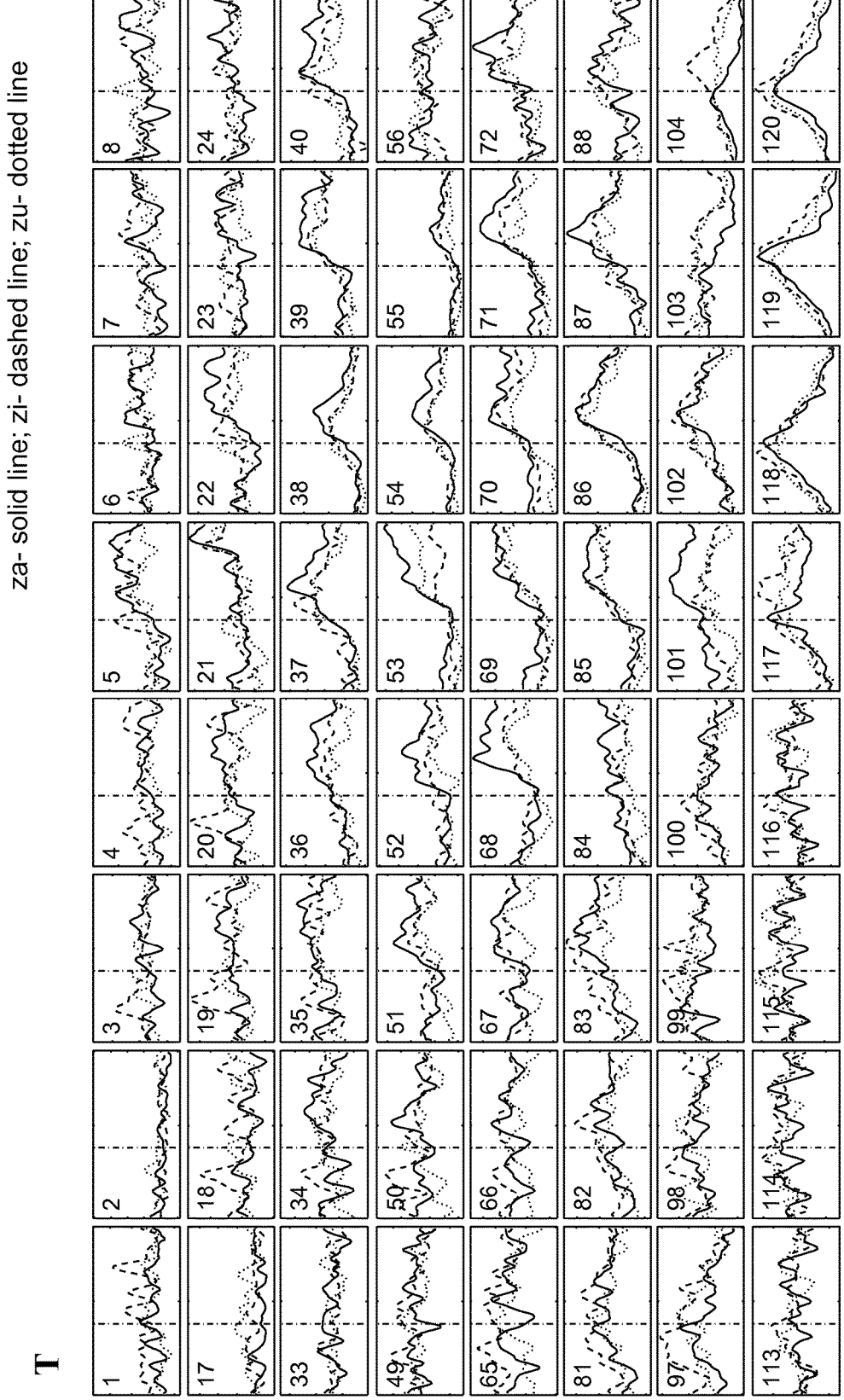
Figure 19:
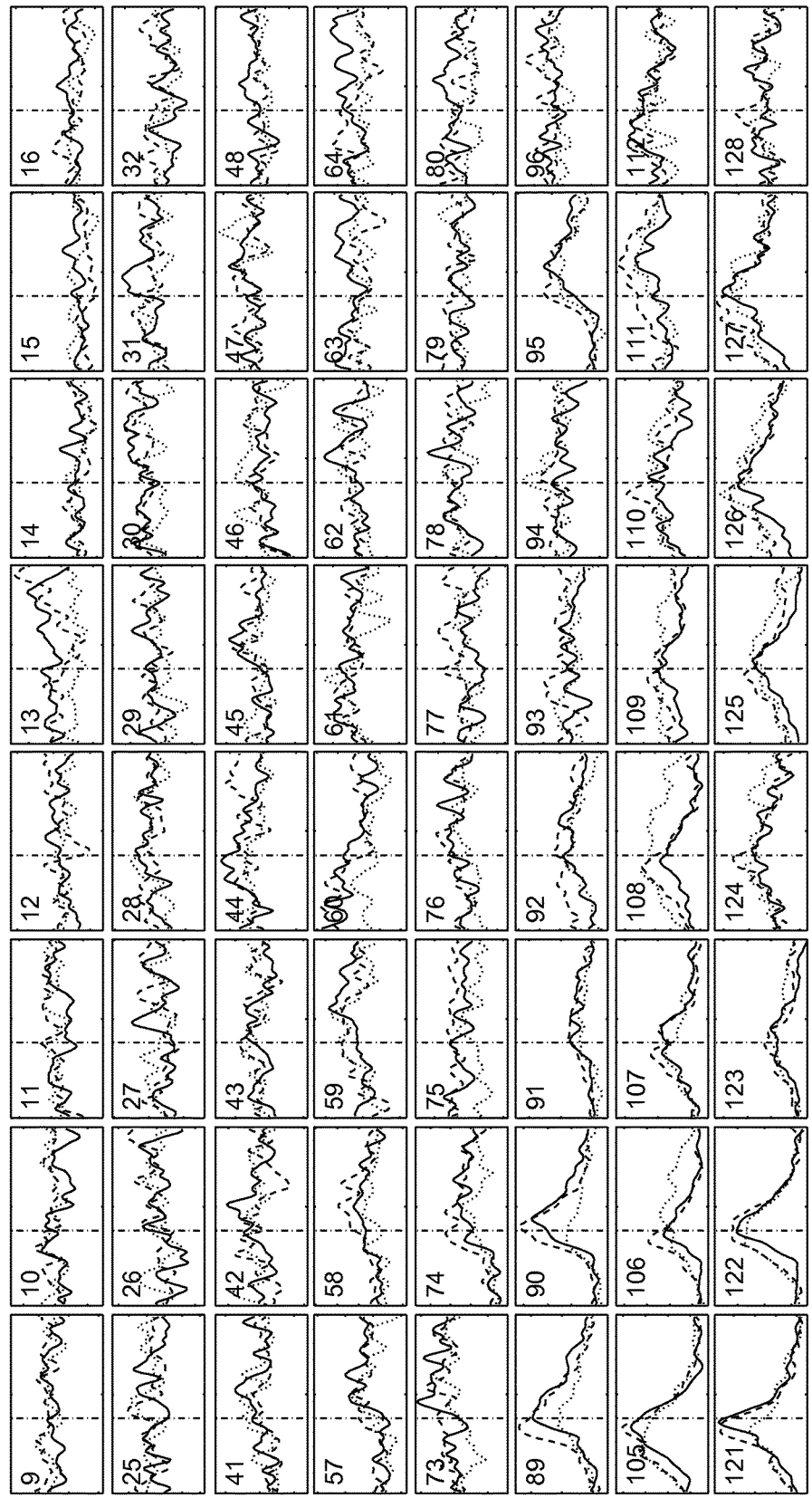
Figure 19:
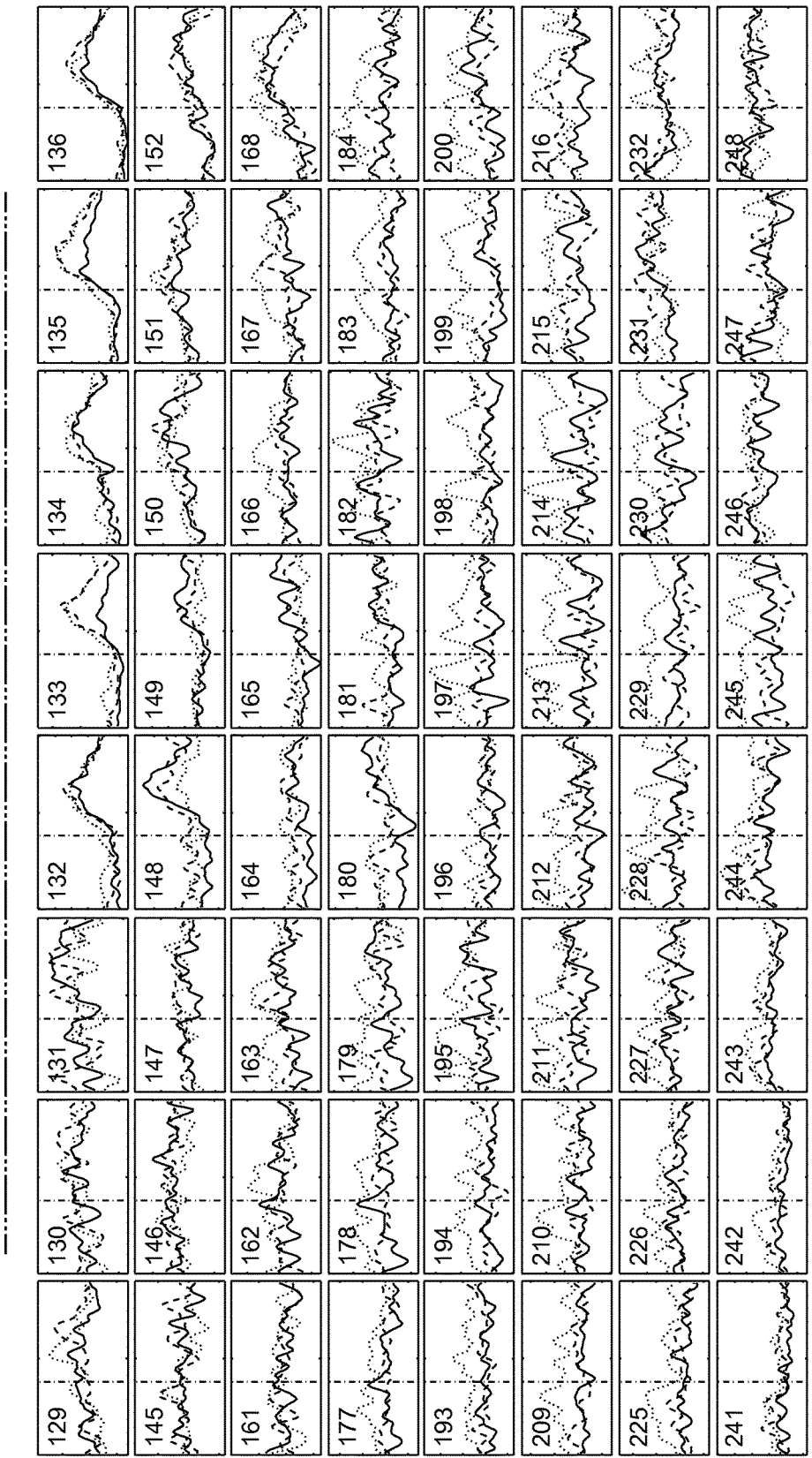
Figure 19:
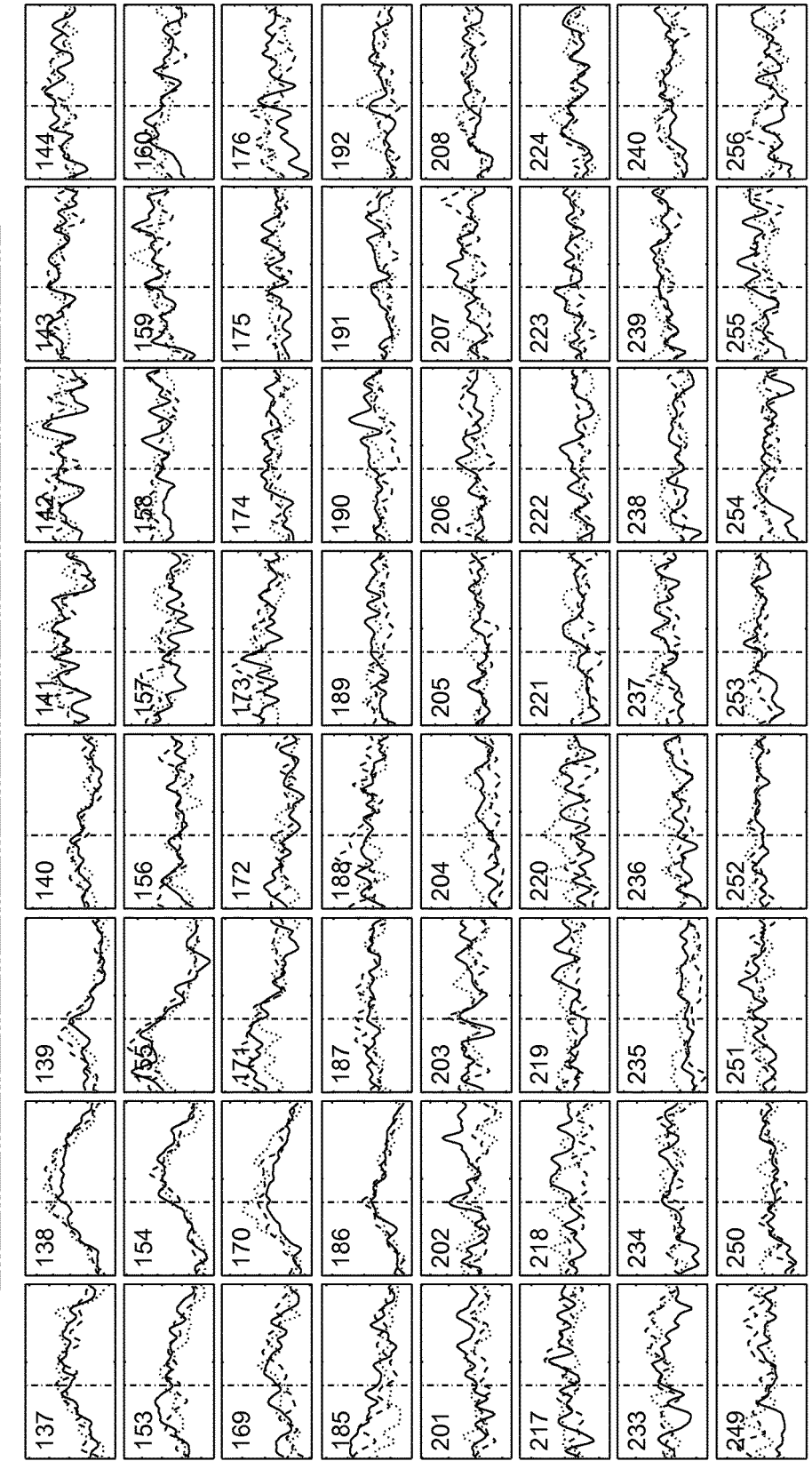

In certain aspects, an array of electrodes (e.g., an ECoG array) is positioned on the surface of the speech motor cortex such that the array covers the entire or substantially the entire region of the speech motor cortex corresponding to the somatotopic arrangement of articulator representations of the subject (see, e.g., FIG. 2, panel B). For example, the electrode array may be disposed on the surface of the speech motor cortex from −100 mm to +100 mm, from −80 mm to +80 mm, from −60 mm to +60 mm, from −40 mm to +40 mm, or from −20 mm to +20 mm relative to the central sulcus along the anterior-posterior axis. Alternatively, or additionally, the electrode array may be disposed on the surface of the speech motor cortex from a location at or proximal to the Sylvian fissure to a distance of 500 mm or less, 400 mm or less, 300 mm or less, 200 mm or less, 100 mm or less, 90 mm or less, 80 mm or less, 70 mm or less, 60 mm or less, 50 mm or less, or 40 mm or less from the Sylvian fissure along the dorsal-ventral axis. One example array and example positioning thereof is shown in FIG. 19, panel A.

In certain embodiments, a ground electrode or reference electrode may be positioned. A ground or reference electrode may be placed at any convenient location, where such locations are known to those of skill in the art. In certain embodiments, a ground electrode or reference electrode is a scalp electrode. A scalp electrode may be placed on a subject's forehead or in any other convenient location.

Figure 1:
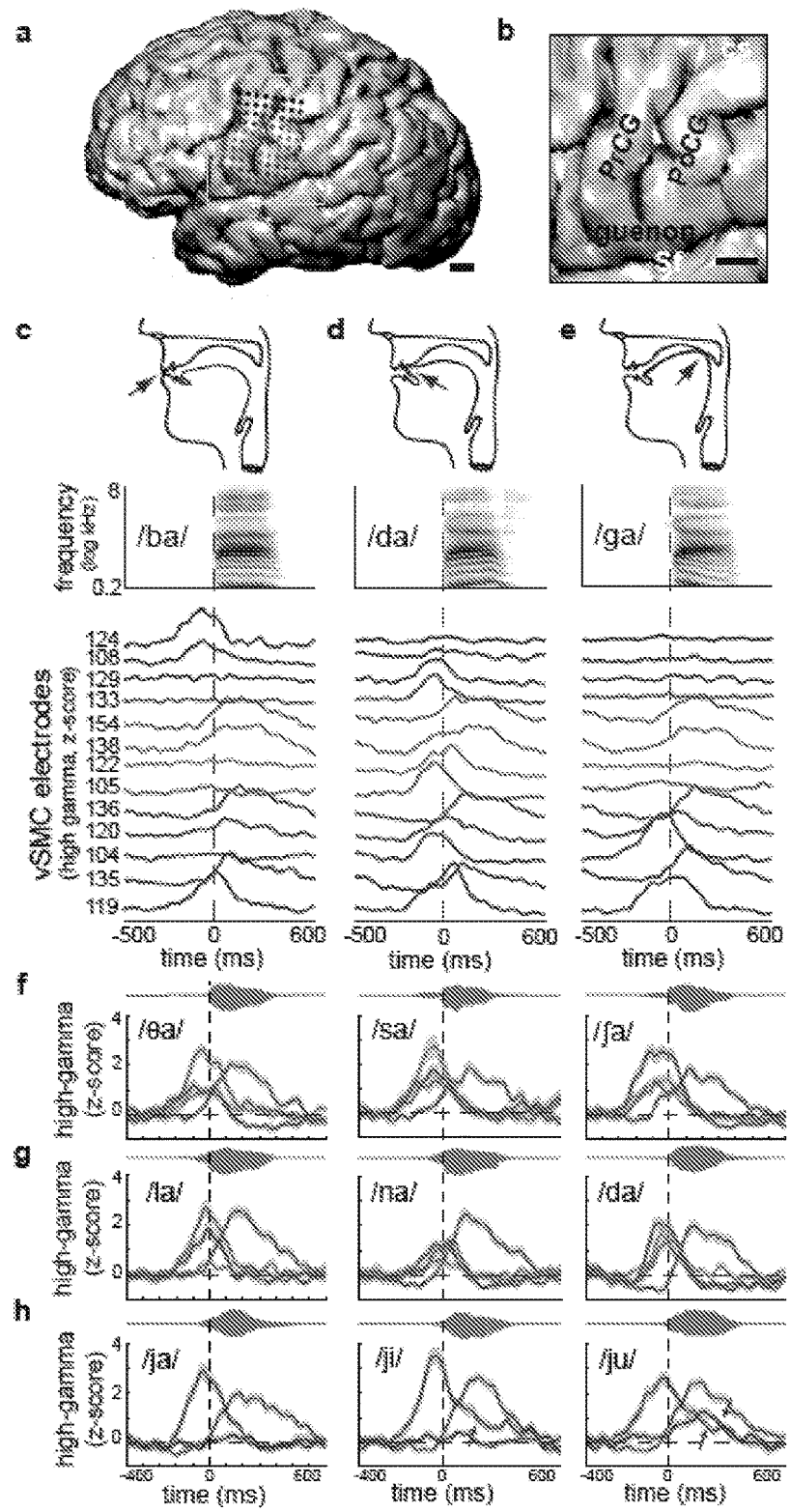
FIG. 1, Panel A depicts an MRI reconstruction of a single subject brain with vSMC electrodes (dots), by distance from Sylvian fissure. Panel B shows an expanded view of vSMC anatomy: pre- and post-central gyri (PrCG and PoCG), central sulcus (cs), Sylvian fissure (Sf). Scale bar=1 cm. Panels C-E depict: (top) vocal tract schematics for three consonants (/b/, /d/ and /g/), produced by occlusion at the lips, tongue tip, and tongue body, respectively (arrow); (middle) spectrograms of spoken consonant-vowel (CV) syllables; and (bottom) average cortical activity from a subset of electrodes. Vertical, dashed line is acoustic onset of CV transition. Panels F-H show cortical activity at selected electrodes for different phonetic contrasts (mean±s.e.) (acoustic waveforms displayed above). Fricatives [/θ/("th" of "thin"), /s/, /ʃ/("sh" of "shin")] with different constriction locations are shown in Panel F. Front tongue consonants (/l/, /n/, /d/) with different constriction degree/shapes are shown in Panel G. Single consonant [/j/ ("y" of "yes")] with different vowels (/a/, /i/, /u/) are shown in Panel H. Arrows pointing substantially upward correspond to a tongue electrode with prolonged activity for /i/ and /u/ vowels. Arrows pointing substantially downward correspond to an active lip electrode for /u/.

In certain aspects, speech production signals are detected for a duration of time and may be detected for a duration beginning prior to the onset of the produced or imagined speech sound and ending after production (or imagined production) of the speech sound. That is, detecting speech production signals may include detecting a time-course of speech production signals from each of the least three electrodes. In certain aspects, speech production signals are detected beginning from 250 milliseconds or more prior to the onset of the produced or imagined speech sound. Example time-courses of speech production signals of individual electrodes are shown in FIG. 1 (panels D-I), where the high-gamma frequency component (85-175 Hz) of local field potentials of the vSMC are detected and aligned to acoustic onsets of consonant-to-vowel transitions (CVs).

In certain aspects, detecting speech production signals includes using a signal amplifier and analog to digital converter (ADC). The digital signal may be recorded at a sampling rate of from 0.1 to 20,000 Hz, such as from 0.15 to 10,000 Hz, including from 0.2 to 5,000 Hz, e.g., from 0.25 to 3,000 Hz.

According to certain embodiments, deriving a speech production signal pattern comprises performing time-frequency analysis of speech production signals detected from each of the at least three electrodes. In certain aspects, the time-frequency analysis is performed using a method selected from the group consisting of: Fast Fourier Transform (FFT), wavelet transform, Hilbert transform, and band-pass filtering. Signal noise and artifacts may be removed by filtering and visual identification. According to certain embodiments, the high frequency, broadband, and low frequency components are extracted, as well as single and multi-unit firing action potentials.

The speech production signals are detected while the subject produces or imagines producing a speech sound. By "speech sound" is meant a phonetic component of a word (e.g., a phoneme, a formant (e.g., formant acoustics of a vowel(s)), a diphone, a triphone, a syllable (such as a consonant-to-vowel transition (CV)), two or more syllables, a word (e.g., a single-syllable or multi-syllable word), a phrase, a sentence, or any combination of such speech sounds. In certain aspects, the speech sound includes speech information such as formants (e.g., spectral peaks of the sound spectrum |P(f)| of the voice) and pitch (e.g., how "high" or "low" the speech sound is depending on the rate of vibration of the vocal chords) which are encoded in the speech production signals and capable of being decoded from the detected speech production signals and/or patterns thereof. For example, with respect to formants, the speech production signals (e.g., vSMC activity) correlate to the acoustic parameters of different vowels, as well as different renditions of the same vowel (as demonstrated in Example 7 herein).

Deriving a speech production signal pattern from the detected speech production signals may be performed using any suitable approach. For example, the speech production signals may be detected for a desired duration of time using a plurality of electrodes (e.g., at least three, 10 or more, 20 or more, 256, etc. as described above) positioned on the surface of the speech motor cortex at desired locations, e.g., locations representing the entire or substantially entire region corresponding to the somatotopic arrangement of articulator representations of the subject as shown by way of example in FIG. 2, panel B. As such, in certain aspects, the speech production signal pattern is a spatiotemporal pattern of activity and/or inactivity in regions of the vSMC identified by the present inventor as corresponding to regions associated with the control of particular speech articulators. Examples of speech production signal spatiotemporal patterns for consonant-vowel syllables are shown in FIG. 19, panels B-T (with the positions of 256 electrodes of a 16×16 ECoG array disposed on the speech motor cortex of the subject shown in panel A). Upon establishment of reference speech production signal patterns (e.g., during a training period) corresponding to various speech sounds (e.g., the various phonemes, diphones, triphones, syllables (e.g., CVs), words, sentences and the like as described in detail in the Examples section below), the speech sound produced or imaginarily produced by the subject may be decoded by correlating the derived speech production signal pattern(s) to the reference speech production signal pattern(s). That is, the reference speech production signal pattern that correlates (e.g., is most similar with respect to spatiotemporal activity pattern in the vSMC) to the derived speech production signal pattern may be identified. Upon identification of the corresponding reference speech production signal pattern, the derived speech production signal pattern is decoded as the speech sound associated with the reference speech production signal pattern, thereby decoding speech from the brain of the subject. In certain aspects, a decoding algorithm is trained on recorded data (e.g., a database of reference speech production signal patterns, such as that shown in FIG. 19) and then applied to novel neural signal inputs for real-time implementation.

Multichannel population neural signals may be analyzed using methods including, but not limited to, general linear regression, correlation, linear quadratic estimation (Kalman-Bucy filter), dimensionality reduction (e.g., principal components analysis), clustering, pattern classification, and combinations thereof.

According to certain embodiments, the subject has a speech impairment or inability to communicate. Subjects of interest include, but are not limited to, subjects suffering from paralysis, locked-in syndrome, Lou Gehrig's disease, aphasia, dysarthria, stuttering, laryngeal dysfunction/loss, vocal tract dysfunction, and the like.

In certain aspects, the methods of the present disclosure further include producing the speech sound in audible form (e.g., through a speaker), displaying the speech sound in text format (e.g., on a display), or both.

Systems

Also provided are systems for performing the methods of the present disclosure. Such systems include speech communication systems. According to one embodiment, a speech communication comprising a neurosensor and a receiver unit is provided. The neurosensor includes at least three electrodes that detect speech production signals when operably coupled to the speech motor cortex of a subject while the subject produces or imagines producing a speech sound, and a transmitter (e.g., a wireless transmitter) that transmits the detected speech production signals. The receiver unit includes: a receiver (e.g., a wireless receiver) in communication with the transmitter that receives the detected speech production signals; a speech generator, a processor and a memory (e.g., a non-transitory memory) that includes instructions which, when executed by the processor, derive a speech production signal pattern from the detected speech production signals, correlates the speech production signal pattern with a reference speech production signal pattern to decode the speech sound, and communicates the speech sound using the speech generator.

As set forth above, systems of the present disclosure include a neurosensor which includes a transmitter that transmits the detected speech production signals. In certain aspects, the transmitter is a wireless transmitter. Wireless transmitters of interest include, but are not limited to, WiFi-based transmitters, Bluetooth-based transmitters, radio frequency (RF)-based transmitters, and the like. The wireless receiver of the receiver unit is selected such that it is compatible with the wireless format of the wireless transmitter.

Systems of the invention include a speech generator. In certain aspects, the speech generator comprises a speaker that produces the speech sound in audible form. For example, the speaker may produce the speech sound in a manner that replicates a human voice. Alternatively, or additionally, the speech generator may include a display that displays the speech sound in text format. According to certain embodiments, the speech generator includes both a speaker that produces the speech sound in audible form and a display that displays the speech sound in text format. In certain aspects, the receiver unit includes a control that enables the subject to toggle between producing the speech sound in audible form, displaying the speech sound in text format, and both. The speech generator is capable of generating any of the speech sounds actually or imaginarily produced by the subject, e.g., a phoneme, a diphone, a triphone, a syllable, a consonant-vowel transition (CV), a word, a phrase, a sentence, or any combination of such speech sounds. In certain aspects, the speech generator is capable of generating the formants and/or pitch of the speech sound(s) actually or imaginarily produced by the subject, e.g., based on information relating to formants and pitch encoded in the speech production signals and patterns thereof (see, e.g., Example 7 below). For example, speech production signal patterns which include information relating to formants and pitch may be correlated to reference speech production signal patterns associated with known formants and pitches (e.g., as established during a training period), and the speech generator may produce the speech sound (e.g., in audible form or text format) with the correlated formants and pitch. Inclusion of the formants and pitch in the speech sound produced by the speech generator is useful, e.g., to make the speech sound more natural and/or understandable to those with whom the subject is communicating.

In certain aspects, the receiver unit is a unit dedicated solely to receiving and processing speech production signals detected by the neurosensor, deriving and decoding speech production signal patterns, and the like. In other aspects, the receiver unit is a device commonly used among the subject's population which is capable of performing the functions of the receiver unit. For example, the receiver unit may be a desktop computer, a laptop computer, a tablet computer, a smartphone, or a TTY device. According to certain embodiments, the receiver is a tablet computer or smartphone, e.g., a tablet computer or smartphone which runs an operating system selected from an iOS™ operating system, an Android™ operating system, a Windows™ operating system, or any other tablet- or smartphone-compatible operating system.

Speech communication systems of the subject disclosure may include any components or functionalities described hereinabove with respect to the subject methods. For example, the neurosensor may include the number, types, and positioning of electrodes as described above in regard to the methods of the present disclosure such that speech production signals sufficient to derive speech production signal patterns may be detected. Also by way of example, the memory (e.g., a non-transitory memory) of the receiving unit may include instructions for performing time-frequency analysis (e.g., by Fast Fourier Transform (FFT), wavelet transform, Hilbert transform, bandpass filtering, and/or the like) of speech production signals detected from each of the at least three electrodes.

The memory (e.g., a non-transitory memory) includes instructions for deriving a speech production signal pattern from the detected speech production signals, and correlating the speech production signal pattern with a reference speech production signal pattern. In certain aspects, the speech production signal pattern is a spatiotemporal pattern of activity and/or inactivity in regions of the vSMC identified by the present inventor as corresponding to regions associated with the control of particular speech articulators. Upon establishment of reference speech production signal patterns (such as the spatiotemporal signal patterns shown by way of example in FIG. 19, panels B-T) corresponding to various speech sounds (e.g., the various phonemes, syllables (e.g., CVs), words, and the like as described in detail in the Examples section below) which may be included in the same or a separate memory, the speech sound produced or imaginarily produced by the subject may be decoded by correlating the derived speech production signal pattern(s) to the reference speech production signal pattern(s). That is, the reference speech production signal pattern that correlates (e.g., is most similar with respect to the spatiotemporal activity pattern in the vSMC) to the derived speech production signal pattern may be identified. Upon identification of this reference speech production signal pattern, the derived speech production signal pattern is decoded as the speech sound associated with the reference speech production signal pattern, thereby decoding speech from the brain of the subject. In certain aspects, a decoding algorithm is trained on recorded data (e.g., a database of reference speech production signal patterns), stored in the memory, and then applied to novel neural signal inputs for real-time implementation.

Utility

The subject methods and systems find use in any application in which it is desirable to decode speech from the brain of a subject (e.g., a human subject). Subjects of interest include those in which the ability to communicate via spoken language is lacking or impaired. Examples of such subjects include, but are not limited to, subjects who may be suffering from paralysis, locked-in syndrome, Lou Gehrig's disease, aphasia, dysarthria, stuttering, laryngeal dysfunction/loss, vocal tract dysfunction, and the like. An example application in which the subject methods and systems find use is providing a speech impaired individual with a speech communication neuroprosthetic system which detects and decodes speech production signals and/or patterns thereof from the speech motor cortex of the subject and produces audible speech and/or speech in text format, enabling the subject to communicate with others without using speech articulators or writing/typing the speech for display to others. The methods and systems of the present disclosure also find use in diagnosing speech motor disorders (e.g., aphasia, dysarthria, stuttering, and the like). In addition, the subject methods and systems find use, e.g., in enabling individuals to communicate via mental telepathy.

In certain aspects, methods and systems of the present disclosure utilize population neural analyses to decode individual speech sounds (phonemes, including consonants and vowels). These speech sounds are the building block units of human speech. Phonemes can be concatenated into syllables, words, phrases and sentences to provide the full combinatorial potential of spoken language. This approach based on the natural neurophysiologic mechanisms of speech production has distinct advantages over present technologies for, e.g., communication neuroprostheses, which either focus on purely acoustic parameter control (e.g. formant) or spelling devices, neither of which are robust or efficient for communication.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Efforts have been made to ensure accuracy with respect to numbers used (e.g. amounts, temperature, etc.) but some experimental errors and deviations should be accounted for.

Materials and Methods

The following are general materials and protocols used in Examples 1-6 below.

Subjects and Experimental Task

To understand the functional organization of vSMC in articulatory sensorimotor control, neural activity was recorded directly from the cortical surface in three human subjects implanted with high-density multi-electrode arrays as part of their work-up for epilepsy surgery[17] (FIG. 1, Panel A). Intracranial cortical recordings were synchronized with microphone recordings as subjects read aloud consonant-vowel (CV) syllables (19 consonants followed by either /a/, /u/, or /i/, FIG. 6) commonly used in American English. This task was designed to sample across a range of phonetic features, including different constriction locations (place of articulation), and different constriction degree/shape (manner of articulation) for a given articulator.

Three native English speaking human subjects underwent chronic implantation of a high-density, subdural electrocortigraphic (ECoG) array over the left hemisphere (two subjects) or right hemisphere (one subject) as part of their clinical treatment of epilepsy (Table 1). Subjects gave their written informed consent before the day of surgery. All subjects had self-reported normal hearing and underwent neuropsychological language testing (including the Boston Naming and verbal fluency tests) and were found to be normal. Each subject read aloud consonant-vowel syllables (CVs) composed of 18-19 consonants (19 consonants for two subjects, 18 consonants for one subject), followed by one of three vowels. Each CV was produced between 15 and 100 times. Microphone recordings were synchronized with the multichannel ECoG data.

TABLE 1

| Subect ID | Grid Placement | Cerebral Language Dominance by Wada Testing | MRI | Seizure Focus Location | Speech Articulation | Postoperative Seizure Control |
| --- | --- | --- | --- | --- | --- | --- |
| EC2 | Left Perisylvian Cortex | Left | Normal | Posterior temporal cortex | Normal fluency, No dysarthria | Seizure-free |
| EC33 | Right Perisylvian Cortex | Right | Normal | Hippocampus, Medial Temporal Lobe | Normal fluency, No dysarthria | Seizure-free |
| EC31 | Left Perisylvian Cortex | Left | Normal | No seizures during prolonged hospitalization | Normal fluency, No dysarthria | Seizure-free* |

Data Acquisition and Signal Processing

Cortical local field potentials (LFP) were recorded with ECoG arrays and a multichannel amplifier optically connected to a digital signal processor (Tucker-Davis Technologies, Alachua, Fla.). The spoken syllables were recorded with a microphone, digitally amplified, and recorded inline with the ECoG data. ECoG signals were acquired at 3052 Hz.

The time series from each channel was visually and quantitatively inspected for artifacts or excessive noise (typically 60 Hz line noise). These channels were excluded from all subsequent analysis and the raw recorded ECoG signal of the remaining channels were then common average referenced and used for spectro-temporal analysis. For each (useable) channel, the time-varying analytic amplitude was extracted from eight bandpass filters (Gaussian filters, logarithmically increasing center frequencies (85-175 Hz) and semi-logarithmically increasing band-widths) with the Hilbert transform. The high-gamma (high-γ) power was then calculated by averaging the analytic amplitude across these eight bands, and then this signal was down-sampled to 200

Hz. High-γ power was z-scored relative to the mean and standard deviation of baseline data for each channel. Throughout the Methods, High-γ power refers to this z-scored measure, denoted below as Hγ.

Acoustic Analysis

The recorded speech signal was transcribed off-line using WaveSurfer (www.speech.kth.se/wavesurfer/). The onset of the consonant-to-vowel transition (C→V) was used as the common temporal reference point for all subsequent analysis (see FIG. 6). This was chosen because it permits alignment across all of the syllables and allows for a consistent discrimination of the consonantal and vocalic components. Post-hoc analysis of acoustic timing revealed the onset of the consonant-to-vowel transition to be highly reproducible across multiple renditions of the same syllable. As such, alignment at C→V results in relatively small amounts of inter-syllable jitter in estimated times of acoustic onset, offset and peak power.

For temporal analysis of the CV acoustic structure, each individual vocalization was first converted to a cochlear spectrogram by passing the sound-pressure waveform through a filter bank emulating the cochlear transfer function. As the current analysis of cortical data leverages the cross-syllabic variability in (average) Hγ (see below), the dataset of produced vocalizations was reduced to a single exemplar for each CV syllable. For each unique CV syllable, the cochlear spectrograms associated with each utterance of that CV ($S_i(t,f)$) were analyzed to find a single proto-typical example (Pspct), defined as the syllable that had the minimum spectral-temporal difference from every other syllable of that kind:

$$Pspct = \min_{S_i} \left( \sum_j \sum_{t,f} (S_j(t,f) - S_i(t,f))^2 \right) \quad (1)$$

The onset, peak, and offset of acoustic power were extracted for each syllable prototype using a thresholding procedure.

Articulator State Matrix and Phonetic Feature Matrix

Figure 4:
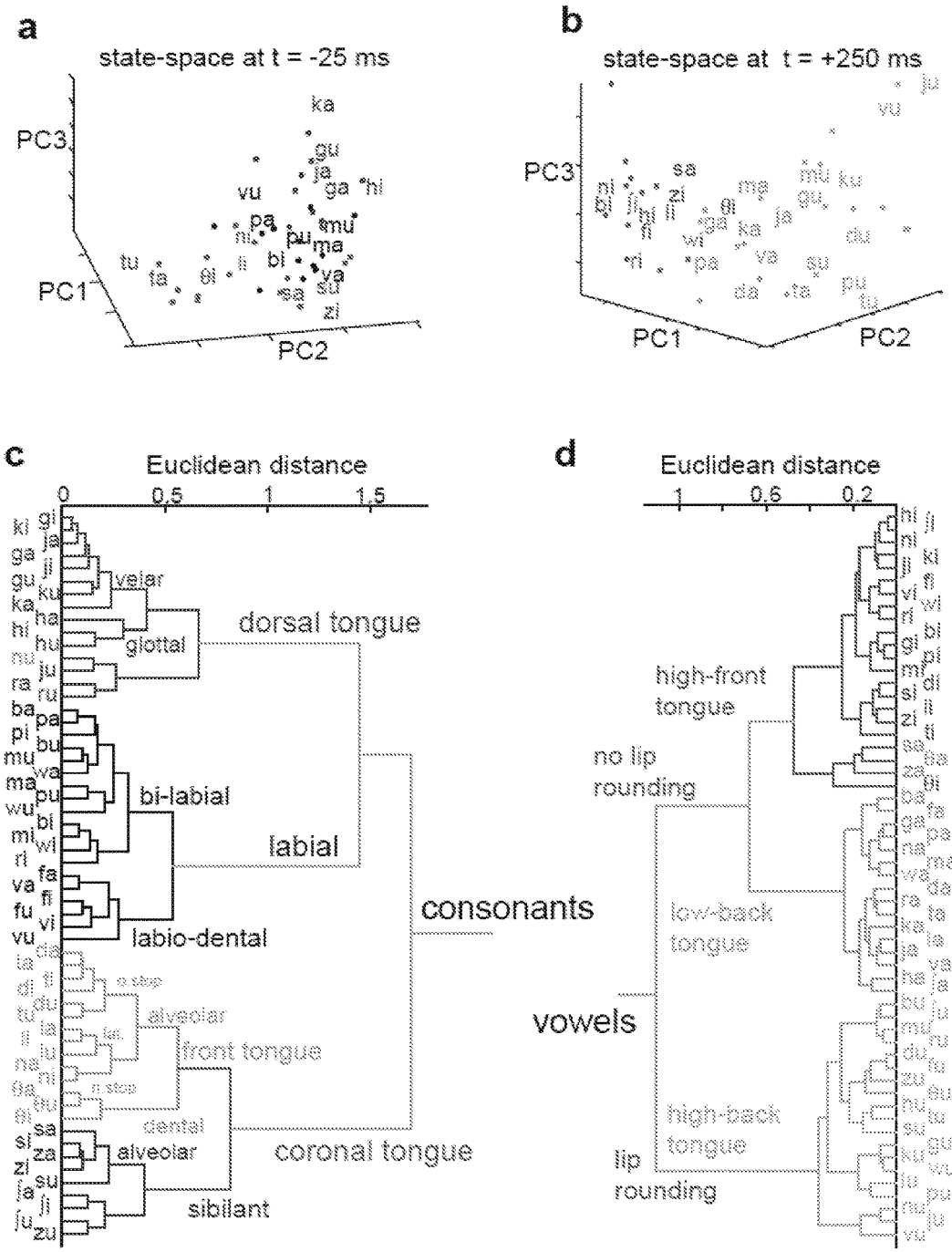
FIG. 4 shows the phonetic organization of spatial patterns. Scatterplots of CV syllables in the first three principal components for consonants (t=−25 ms) and vowels (t=+250 ms) are shown in Panels A and B, respectively. A subset of CVs are labeled, all others have dots. Hierarchical clustering of cortical state-space at consonant and vowel time points is shown in Panels C and D. Individual syllables are color-coded and dendrogram branches are labeled by known linguistic categories. Correlations between cortical state-space and phonetic features are shown in Panels E and F. Black line: median; grey box: 25th and 75th percentile. ***: $P<10^{-10}$, WSRT; n=297 for both consonants and vowels.
Figure 4:
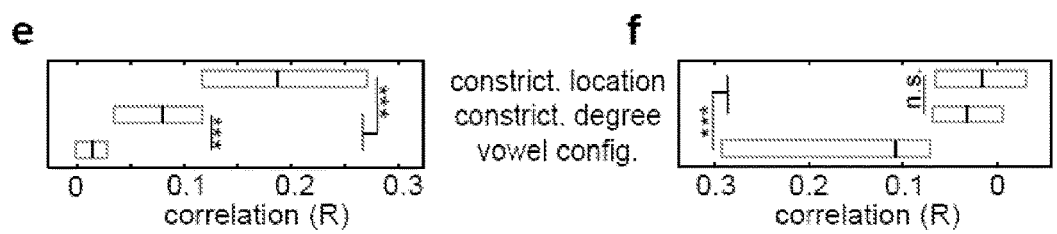
Figure 5:
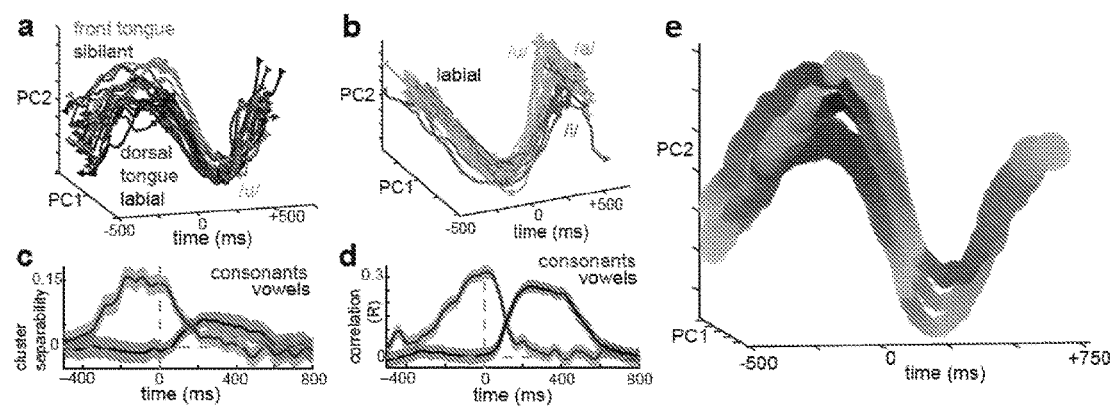
FIG. 5 depicts the dynamics of phonetic representations. Cortical state-space trajectories are shown in Panels A and B. Panel A shows consonants transitioning to the vowel /u/ (sibilant, coronal tongue, dorsal tongue, labial). Each line corresponds to a single CV trajectory. Symbols; left triangle: t=−500 ms, square: t=−25 ms, circle: t=250 ms, right triangle: t=750 ms. Panel B shows trajectories of the labial consonants transitioning to /a/, /i/ and /u/. Panels C and D show across-subject averages of cluster separability (Panel C) and correlation between cortical state-space structure and phonetic features (Panel D) for consonants and vowels (mean±s.e). Panel E shows the time-course of CV syllable trajectories for Subject 1.
Figure 6:
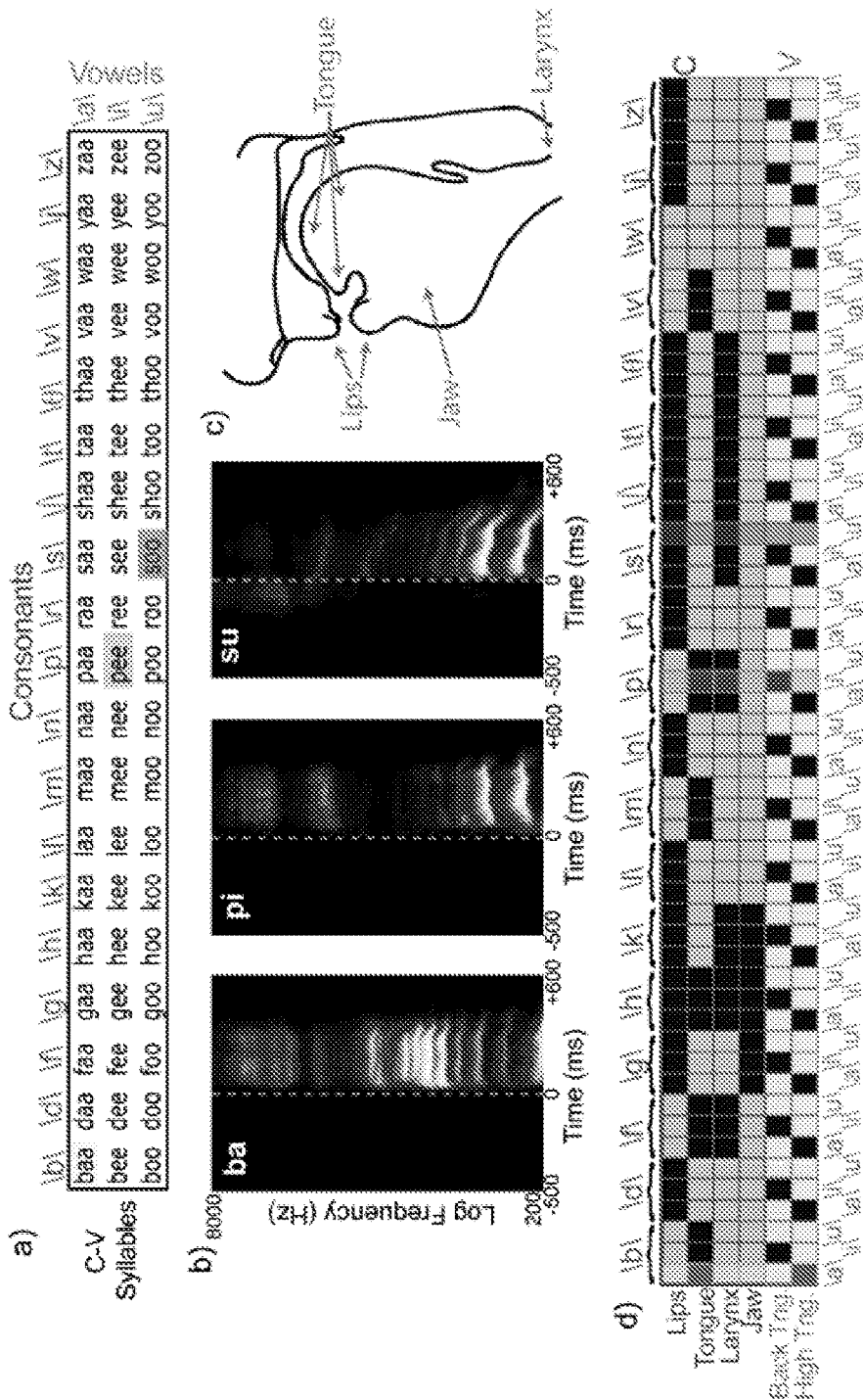
FIG. 6 shows task design and behavioral analysis. Panel A depicts a Consonant-Vowel Matrix and IPA phonetic symbols. Neurosurgical patients read aloud from a list of consonant-vowel syllables (CVs), consisting of 19 consonants followed by one of three vowels (/a/, /u/, or /i/). The IPA notations for the consonant and vowel are displayed as column and row headings, respectively, with entries in the matrix specifying the American English pronunciation. Panel B shows cochlear spectrograms for three syllables aligned at the acoustic onset of the consonant-to-vowel transition. To analyze the consonant and vowel phases of our CVs from a common temporal reference point, all behavioral and electrophysiological data are aligned at the acoustic onset of the consonant-to-vowel transition (t=0). The acoustic onset of the C-V transition is displayed as the dashed grey line overlaid on the cochlear spectrograms for three syllables with temporally distinct consonants (/b/, /p/, /s/). Panel C depicts a diagram of the vocal tract with respect to the four major articulator organs analyzed: tongue, lips, jaw, and larynx. Panel D shows an articulator state matrix, where each CV is described by a six element binary vector indicating its articulatory organ engagement. Each vector consisted of four variables corresponding to the four main upper-vocal tract articulatory organs (Lips, Tongue, Larynx, Jaw) for consonants and two variables describing the tongue configuration for vowels (Back Tongue and High Tongue). Furthermore, they constitute a linearly independent basis set with which to describe the CVs in our dataset. This linear independence is preferred given the linear methods used for articulatory analysis (general linear models and partial correlation analysis).
Figure 14:
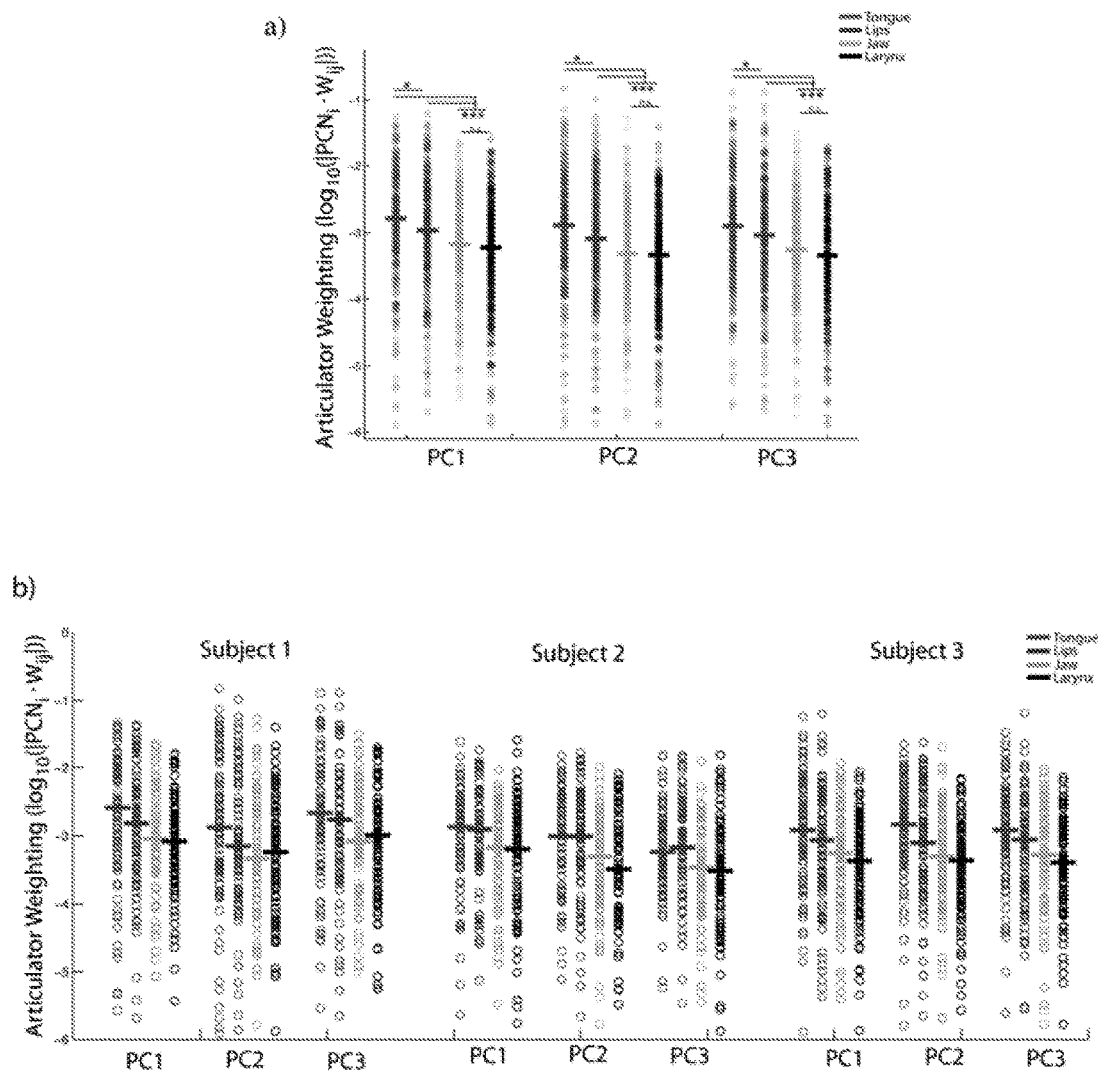
FIG. 14 shows that the structure of principal components is weighted towards modulations of tongue and lips over larynx and jaw. Panel A depicts the magnitude of articulator weightings in the $1^{st}$ three PCs across all subjects (tongue, lips, jaw and larynx are presented from left to right). To understand the contribution of each articulator to the principal components that define the cortical state-space, the articulator weightings for each electrode were projected onto each principal component. This is possible because both PCA used to define the cortical state-space and the GLM analyses are linear descriptions of the recorded high-gamma activity. Articulator weightings correspond to a linear transformation of the articulator state into high-gamma activity, while the weightings of each electrode in each PC corresponds to a linear transformation of those electrode's high-Gamma activity into PC space. Across PCs, it was determined that the magnitude of the articulator weightings ($\log_{10}(|PCNi*Wij|)$)) was significantly biased towards tongue over lips (P<0.05) over jaw and larynx (P<0.001 for each), while the difference between jaw and larynx was not significant (P>0.2). This demonstrates that the structure of phonetic representations in the cortical state-space will be more heavily organized by the tongue and lips features than the jaw and larynx. This systematic bias in articulator weightings is in line with the organization of the cortical state-space described in the text, which is clustered according to the major oral articulators (i.e. tongue and lip). Statistical significance determined by Wilcoxon signed-rank test, n=266 electrodes across subjects for each PC, with post-hoc bonferroni correction for m=6 comparisons per PC. Panel B shows the magnitude of articulator weightings in the first 3 PCs for the subjects individually. The rank-ordering of articulator weightings in PCs is a general feature of the individual subjects.

To describe the engagement of the articulators in the production of different CV syllables, standard descriptions of the individual consonant and vowel sounds in the International Phonetic Alphabet (IPA) were drawn from. Each CV syllable was associated with a binary vector describing the engagement of the speech articulators utilized to produce the CV. For the linear analysis presented in FIGS. 2 and 3, the articulator state vector ($B_i$) for each CV syllable $s_i$ was defined by six binary variables describing the four main articulator organs (Lips, Tongue, Larynx, Jaw) for consonant production and two vocalic tongue configurations (High Tongue, Back Tongue) (FIG. 6). Although more detailed descriptions are possible (e.g. alveolar-dental), the linear methods utilized for these analyses necessitate that the articulator variables be linearly independent (no feature can be completely described as a linear combination of the others), though the features may have correlations. An expanded phonetic feature matrix (nine consonant constriction location variables, four tongue configuration variables, and six consonant constriction degree/shape variables, again derived from IPA, FIG. 14), was used in the non-parametric analysis of the cortical state-space (FIGS. 4 and 5).

Analysis of Articulator Representations

Spatial Organization Derived from a General Linear Model

To examine the spatial organization with which Hγ was modulated by the engagement of the articulators, it was determined how the activity of each electrode varied with consonant articulator variables using a general linear model. Here, at each moment in time (t), the general linear model described the Hγ of each electrode as an optimally weighted sum of the articulators engaged during speech production. Hγ(t) recorded on each electrode ($e_i$), during the production of syllable $s_j$, $H\gamma_{ij}(t)$, was modeled as a linear weighted sum of the binary vector associated with the consonant component of $s_j$ ($B_j^c$):

$$H\gamma_{ij}(t) = \beta_i(t) \cdot B_j^C + \beta_{i0}(t) \quad (2)$$

The coefficient vector $\beta_i(t)$ that resulted in the least-mean square difference between the levels of activity predicted by this model and the observed Hγ(t) across all syllables was found by linear regression. For each electrode $e_i$ at time t, the associated 1×4 slope vector ($\beta_i(t)$) quantifies the degree to which the engagement of a given articulator modulated the cross-syllable variability in Hγ(t) at that electrode. Coefficients of determination ($R^2$) were calculated from the residuals of this regression. In the current context, $R^2$ can be interpreted as the amount of cross-syllabic variability in Hγ that can be explained by the optimally weighted linear combination of articulatory state variables.

The spatial organization of the speech articulators was examined using the assigned weight vectors ($\beta_i(t)$) from the GLM described above. First, the fit of the GLM at each electrode $e_i$ was determined of interest if, on average, the associated p-value was less than 0.05 for any one of the four consonant articulator time windows ($T_A$) determined from the partial-correlation analysis below. This time window was defined to be the average onset-to-offset time of significant partial correlations for each individual articulator in each subject (see Partial Correlation Analysis). This method identifies electrodes whose activity is well predicted by the GLM for any of the individual articulators, as well as combinations thereof, for extended periods of time. As these time windows extend for many points this is a rather stringent criterion in comparison to a peak-finding method or single significant-crossings. In practice, the minimum (across time) p-values associated with the vast majority of these electrodes are several orders of magnitude less than 0.05. For the electrodes gauged to be significant in each subject, the weights were averaged for each articulator (A) in that articulators time window ($T_A$). Thus, each electrode of interest ($e_i$) is assigned four values, with each value corresponding to the weighting for that articulator (A)

$$W_i^A = \frac{1}{|T_A|} \sum_{t \in T_A} \beta_i(t), \quad (3)$$

averaged across that articulator's time window ($T_A$):

For the analysis of representational overlap at individual electrodes (FIG. 2c), each electrode was classified according to the dominant articulator weight in a winner-take-all manner. The fractional articulator weighting was calculated based off of the positive weights at each electrode, and is plotted as average percent of summed positive weights.

Figure 7:
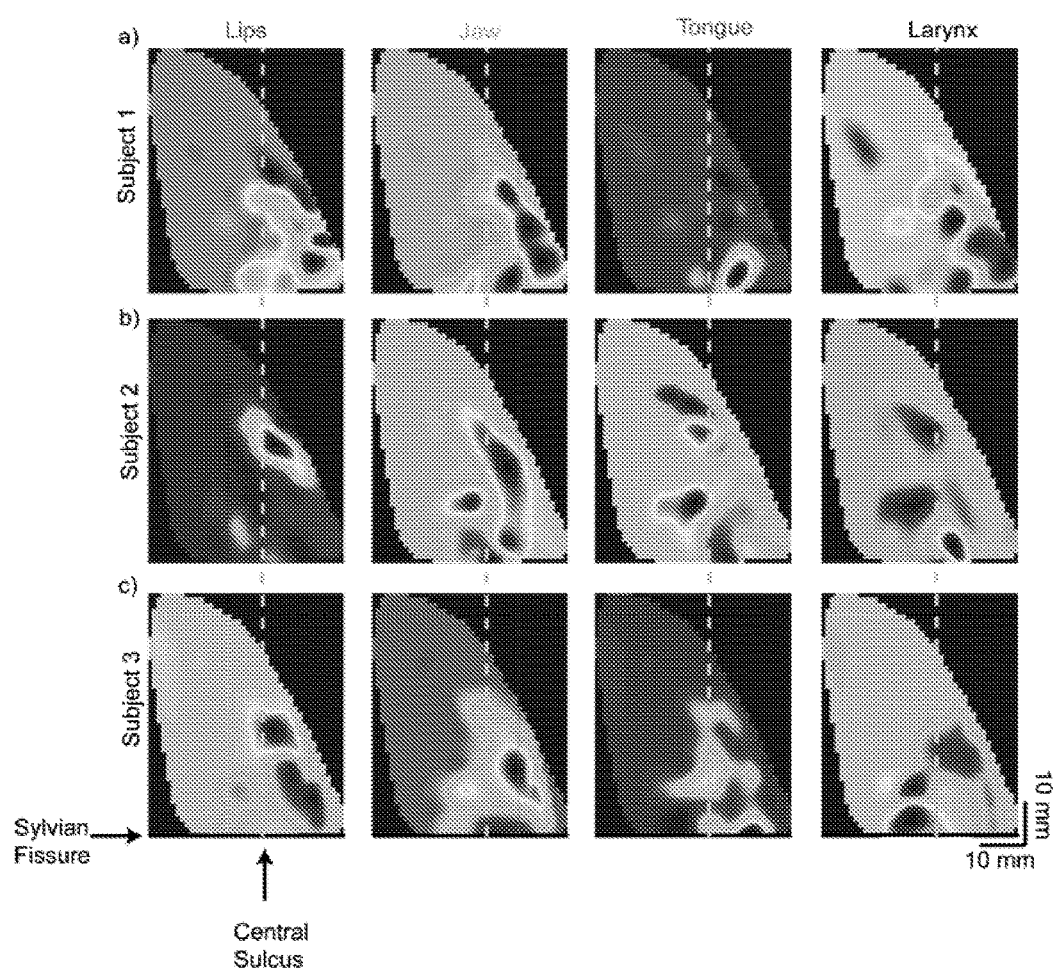
FIG. 7 depicts the spatial topographic organization of articulator representations in vSMC for individual subjects. Panels A-C show the topographic organization of articulator weightings for each subject. The optimal weighting assigned to each articulator (lips, jaw, tongue, and larynx) by the general linear model analysis presented as a heat map in Cartesian space, defined by distance from Central Sulcus (ordinate) and Sylvian Fissure (azimuth). Dashed vertical gray line corresponds to the Central Sulcus.

For spatial analysis, the data for each subject was smoothed using a 2 mm uniform circular kernel. The maps presented and analyzed in FIGS. 7 and 8 correspond to these average weights for the Lips, Tongue, Larynx, and Jaw. The maps presented and analyzed in FIG. 2 correspond to these average weights for each articulator averaged across subjects. The spatial organization of vSMC is described by plotting the results of the GLM for an individual on the cortex of that individual. A Cartesian plane was used to defined by the Anterior-Posterior distance from the Central Sulcus (ordinate) and the Dorsal-Ventral distance from the Sylvian Fissure (azimuth). This provides a consistent reference frame to describe the spatial organization of each subject's cortex and to combine data across subjects while preserving the individual differences.

Somatotopic Map and k-Nearest Neighbors Algorithm

Figure 9:
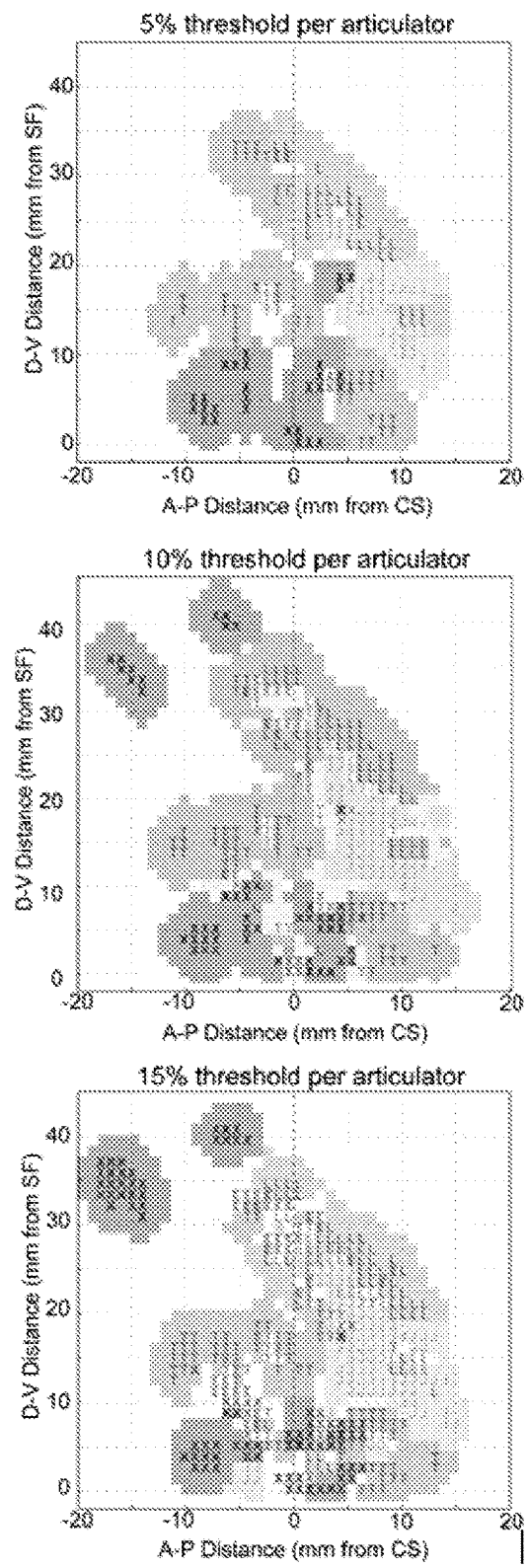
FIG. 9 depicts combined articulator maps for different thresholds of individual articulator weights. To provide complementary visualizations of articulator representations presented in FIG. 2, Panel B, articulator maps derived from the k-nearest neighbor classification scheme are presented based off of articulator locations for three different weighting thresholds. Panel A, 5%; Panel B, 10%; Panel C, 15%. As would be expected from the analysis presented in FIG. 2, high thresholds resulted in the most delineated articulator maps (5%), and as the threshold for data inclusions is lowered, the maps exhibit more articulator overlap and became more 'fractured', with different articulator representations being spatially interdigitated.

To construct the summary somatotopic map of FIG. 2b, the spatial location of the top 10% of weights for each articulator (averaged across subjects, data in FIG. 2A) was first extracted. Then, a k-nearest neighbor algorithm was used to classify the surrounding cortical tissue based on the nearest k=4 neighbors within a spatial extent of 3 mm of each spatial location; if no data points were present within 3 mm, the location is un-classified. Locations where no clear majority (>50%) of the nearest-neighbors belonged to a single articulator were classified as mixed. These values were chosen to convey, in summary form, the visual impression of the individual articulator maps, and to 'fill-in' spatial gaps in our recordings. The summary map changed smoothly and as expected with changes in threshold of individual articulator maps, k (number of neighbors), spatial extent, and minimum number of points. Results are qualitatively insensitive to the details of this analysis, including the choice of 10% as a threshold, as changes in the clustering algorithm could be made to accommodate subtle differences in data inclusion. For visual comparison, displayed are the somatotopic maps derived from the same algorithm derived from the top 5%, top 10% and top 15% of weights in FIG. 9.

Partial Correlation Analysis

To quantify the temporal structure with which single-electrode Hγ was correlated with the engagement of a single articulator, partial correlation analysis was used. Partial correlation analysis is a standard statistical tool that quantifies the degree of association between two random variables (here, Hγ(t) and the engagement of a given articulator, $A_i$), while removing the effect of a set of other random variables (here, the other articulators, $A_j$, j≠i). For a given electrode, the partial correlation coefficient between Hγ(t) across syllables at time t and articulator $A_i(\rho(H\gamma(t),A_i))$ is calculated as the correlation coefficient between the residuals $r(H\gamma(t),A_j)$, j≠i, resulting from de-correlating the Hγ(t) and every other articulator $A_j$, i≠j, and the residuals $r(A_i,A_j)$, i≠j, resulting from de-correlating the articulators from one another:

$$\rho(H\gamma(t), A_i) = \frac{\text{cov}(r(H\gamma(t), A_j), r(A_i, A_j))}{\sigma_1 \cdot \sigma_2}, i \neq j \quad (4)$$

where $\sigma_1$ and $\sigma_2$ are the standard deviations of $r(H\gamma(t),A_j)$ and $r(A_i,A_j)$, respectively. In the current context, the partial correlation coefficients quantify the degree to which the cross-syllabic variability in Hγ at a given moment in time was uniquely associated with the engagement of a given articulator during speech production. For each articulator, those electrodes whose peak partial correlation coefficient (ρ) exceeded the mean±2.5 σ of ρ values across electrodes and time (>mean($\rho(e_i,t)$)+2.5σ($\rho(e_i,t)$)) were analyzed. The focus is on the positive correlations (denoted as R), because there were typically a larger number of positive values (mean ρ>0), the temporal profiles are grossly similar for negative values, and for expositional simplicity. Results did not qualitatively change with changes in this threshold of ~±0.2 σ. The onset, offset, and peak times were extracted for each articulator for each electrode that crossed this threshold. The data presented in FIG. 3d are the mean±s.e. of these timing variables across electrodes pooled across subjects. The average onset and offset for each of the four consonant articulators (A [Lips,Tongue,Jaw,Larynx]) in each subject was used to define the articulator time window ($T_A$) used in the spatial analysis described above.

Cortical State-Space and State-Space Analysis

PCA and Cortical State-Space

Figure 11:
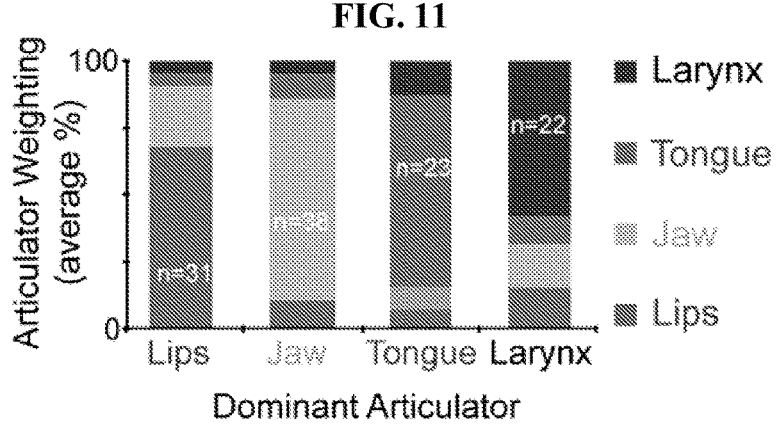
FIG. 11 depicts the distribution of fractional articulator weightings at individual electrodes. Distributions of articulator weightings were characterized at a finer spatial scale by calculating the fractional representation of all articulators at single electrodes. This figure displays the functional distribution of articulator representations at individual electrodes, categorized according to dominant articulator representation. Displays give average articulator weightings as percentage of total. This analysis revealed clear preferred tuning for individual articulators at single electrodes (FIG. 2, Panel C, electrodes categorized according to the strongest articulator representation), and also demonstrated that single electrodes had functional representations of multiple articulators.

Principal components analysis (PCA) was performed on the set of all vSMC electrodes for dimensionality reduction and orthogonalization. PCA was performed on the n×m*t covariance matrix Z with rows corresponding to channels (of which there are n) and columns corresponding to concatenated Hγ(t) (length t) for each CV (of which there are m). Each electrode's time series was z-scored across syllables to normalize response variability across electrodes. The singular-value decomposition of Z was used to find the eigenvector matrix M and associated eigenvalues λ. The PCs derived in this way serve as a spatial filter of the electrodes, with each electrode $e_j$ receiving a weighting in $PC_i$ equal to $M_{ij}$, where M is the matrix of eigenvectors. Across subjects, it was observed that the eigenvalues (λ) exhibited a fast decay with a sharp inflection point at the ninth eigenvalue, followed by a much slower decay thereafter (FIG. 11). The first nine eigenvectors (PC's) were therefor used as the cortical state-space for each subject.

The cortical state-space representation of syllable $s_k$ at time t, $\kappa(s_k,t)$, is defined as the projection of the vector of cortical activity associated with $s_k$ at time t, $H\gamma_k(t)$, onto M:

$$K(s_k,t) = M \cdot H\gamma_k(t) \quad (5)$$

The contribution of articulators to the cortical state-space ($PCw_{ij}$) was calculated by projecting each electrodes weight vector ($\beta_j$) derived from the GLM model above into the first three dimensions of the cortical state-space (i=1:3):

$$PCw_{ij} = M_{ij} \cdot \beta_j \quad (6)$$

Figure 13:
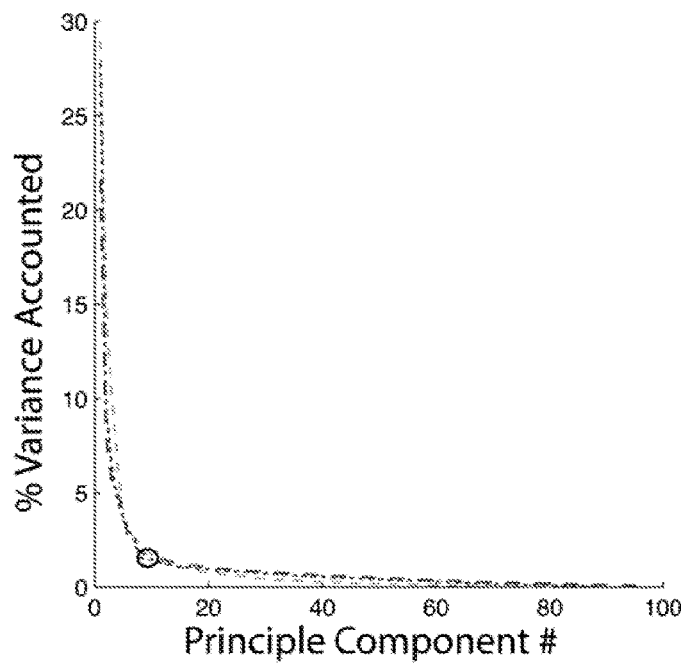
FIG. 13 shows that the structure of spatial principal components is similar across subjects. Percent variance accounted for by each spatial PC for all three subjects. Across subjects, the amount of accounted for variance decreased sharply over the first nine PC's (black circle) and exhibited a very gradual decline thereafter. This indicates that the first nine PCs correspond to the dimensions that discriminate the CVs. The $1^{st}$ nine PCs were therefore used as the cortical state-space. The across-subject differences in the decay after nine components can be explained by the different number of electrodes recorded in each subject. Small changes in the number of dimensions did not qualitatively change the results.

Here, $PCw_{ij}$ is a four-element vector of the projected articulator weights for electrode $e_j$ into $PC_i$. Plotted in FIG. 13 is the $\log_{10}$ of the absolute value of $PCw_{ij}$ across electrodes, which describes the distribution of magnitudes of the representations associated with the four articulators in a given PC.

Clustering Analysis k-means and hierarchical clustering were performed on the cortical state-space representations of syllables, $\kappa(s_k,t)$, based on the pair-wise Euclidean distances calculated between CV syllable representations. Agglomerative hierarchical clustering used Ward's Method. All analyses of the detailed binary phonetic feature matrix were performed using both Hamming and Euclidean distances; results did not change qualitatively or statistically between metrics. Silhouette analysis was utilized to validate the claim that there were three clusters at the consonant time. The silhouette of a cluster is a measure of how close (on average) the members of that cluster are to each other, relative to the next nearest cluster. For a particular data set, the average silhouette for a given number of clusters describes the parsimony of the number of clusters in the data. Hence, examining the silhouette across different number of clusters gives a quantitative way to determine the most parsimonious number of clusters. Higher values correspond to more parsimonious clustering. On average across subjects, this analysis validated the claim that three clusters (Average Silhouette=0.47) was a more parsimonious clustering scheme than either two (Average Silhouette=0.45) or four clusters (Average Silhouette=0.43).

Correlation of Cortical State-Space Structure with Phonetic Structure

At each moment in time, a goal was to quantify the similarity of the structure of cortical state-space representations of phonemes and the structure predicted by different phonetic feature sets. To this end, measured was the linear correlation coefficient between vectors of unique pair-wise Euclidean distances between phonemes calculated in the cortical state-space (DC(t)) and in the phonetic feature matrix (DP):

$$R(t) = \frac{\mathrm{cov}(DC(t), DP)}{\sigma_{DC(t)} \cdot \sigma_{DP}} \quad (7)$$

As described above, the phonetic feature matrix was composed of three distinct phonetic feature sets, (consonant constriction location, consonant constriction degree/shape, vowel configuration). Distances were calculated independently in these three sub-sets and correlated with DC. Standard error measures of the correlation coefficients were calculated using a bootstrap procedure (1000 iterations).

Cluster Separability

"Cluster separability" is defined at any moment in time as the difference between the average of cross-cluster distances and the average of within cluster distances. This quantifies the average difference of the distance between syllables in different clusters and the tightness of a given cluster. The variability in cluster separability estimation was quantified through a 1000 iteration bootstrap procedure of the syllables used to calculate the metric.

Cluster Density

The average cluster density was quantified by calculating the average inverse of all unique pair-wise distances between CVs in a given cortical state-space cluster. It is a proper density because the number of elements in a cluster does not change with time.

Spatial Cross-Correlation Analysis

Figure 8:
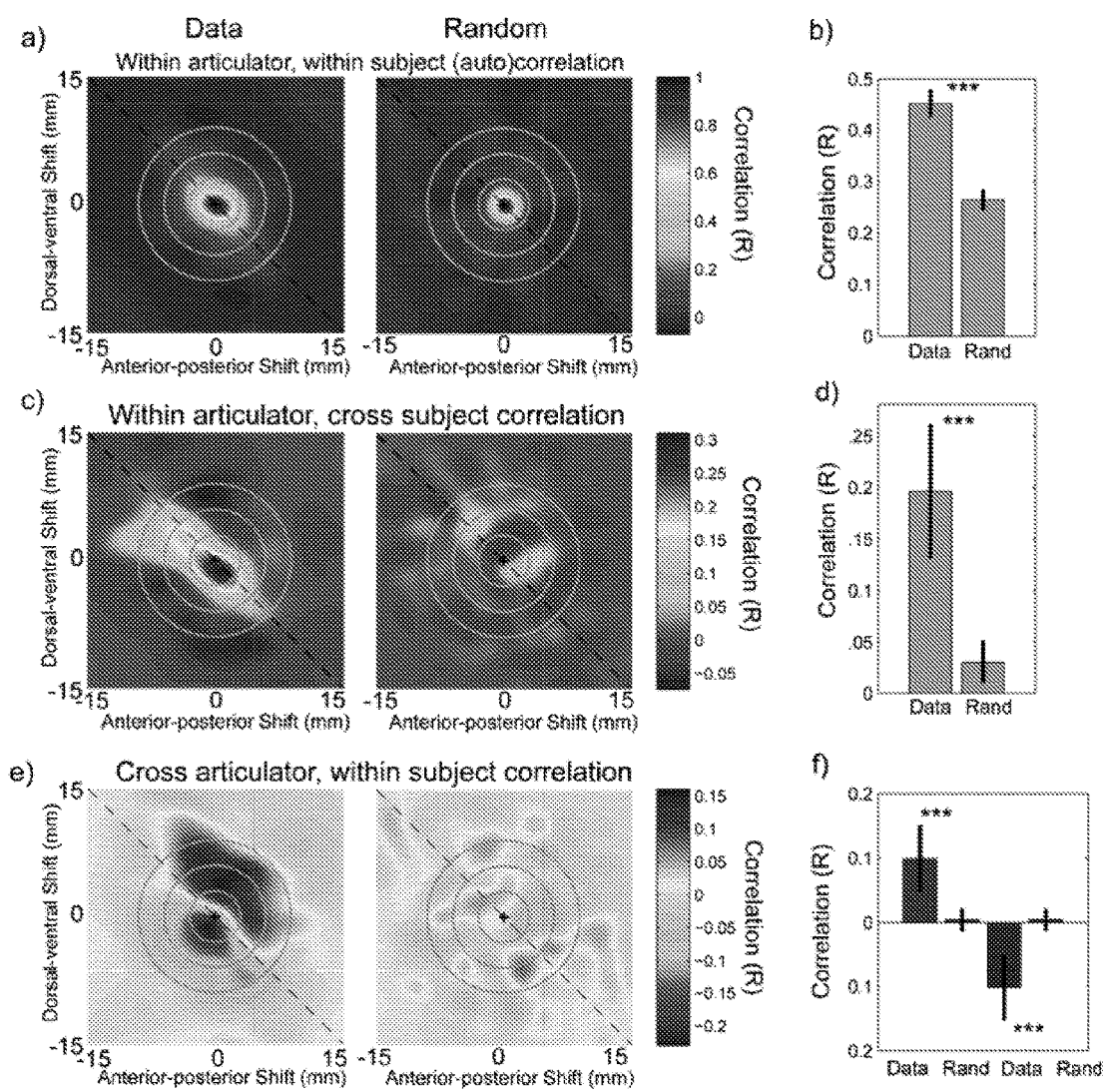
FIG. 8 shows the spatial structure of articulator representations is statistically similar across subjects. The spatial structure of individual articulator representations is shown in Panels A and B. Panels C and D show that the spatial location of individual articulator representations is statistically similar across subjects. The spatial sequence of articulator representations is statistically observed for each subject in Panels E and F.

The spatial organization of articulator representations was quantitatively analyzed using a two-dimensional cross-correlation analysis (FIG. 8). This quantifies the similarity of spatial structure of two matrices as they are 'slid' over each other at different spatial shifts in the x-direction (e.g. anterior-posterior direction) and the y-direction (e.g. dorsal-ventral direction). Generally speaking, two-dimensional cross-correlation analysis is capable of revealing important spatial characteristics, and has been utilized in the analysis of grid cells in entorhinal cortex. Here, it is used primarily to examine two key features of the somatotopic map: 1) the consistency of spatial location of individual articulators across subjects, and 2) the consistency of the dorsal-ventral sequence of articulator representations within an individual. To gauge the significance of these analyses, the results derived from analysis of observed data were compared to a null data set created by randomly permuting the spatial location of selected electrodes prior to any analysis or processing. The structure of the with-in articulator was first examined, with-in subject autocorrelation. This provides information regarding the spatial contiguity of articulator representations, and any reproducible repeating structure (e.g. grid cells), or anisotropies (i.e. preferred angles of orientation). To address the consistency of the spatial location of individual articulators across subjects, the maps for a single articulator were cross-correlated across pair-wise comparisons of subjects (i.e. Lips in S1 vs. Lips in S2, etc). To address the consistency of the spatial ordering of articulators along the dorsal-ventral axis, neighboring articulator representations were cross-correlated across pair-wise sequential comparisons (i.e. Larynx vs. Tongue, Tonuge vs. Jaw, Jaw vs. Lips) within a subject. The results of these analyses, presented in FIG. 8, demonstrate that the key features of the summary articulator maps are statistically reproduced in individual subjects.

As shown in FIG. 8, panels A and B, the spatial structure of individual articulator representations were examined by taking the spatial autocorrelation of each map in each subject (S1-S3). If individual electrodes for specific articulators are randomly organized with respect to one another, expected is a single large peak at zero shift ([0,0]) that falls off symmetrically with (x,y) shifts and has a radius of ~2 mm (size of smoothing kernel)(a, Random). It was found that the representations of individual articulators were spatially well isolated in each subject (large single peak at [0,0]), but tended to be spatially clustered (correlation has greater spatial extent than random scattering). There also appeared to be a relatively consistent anisotropy along the anterior-dorsal/posterior-ventral axes (dashed line). These features are summarized in the left plot in (a, Data) by averaging the individual articulator×subject spatial autocorrelation functions. For comparison, an example of the average autocorrelation function derived from a single random permutation of the spatial location of each subject's electrodes is presented on the right (a, Random). (b) the difference between the observed and random autocorrelations were quantified by averaging the values with in a 3 mm radius (innermost ring) for each comparison. The correlation values for the data (0.45±0.03, mean±s.e., 3 subjects×4 articulators, n=12) were significantly greater than for the randomized data (0.26±0.02, mean±s.d., 1000 randomizations for each subject; $P<10^{-3}$). Therefore, electrodes with similar representations are spatially closer to one-another than expected by chance.

As shown in FIG. 8, panels C and D, the spatial location of individual articulator representations is statistically similar across subjects. The across-subject similarity of spatial location was examined for individual articulator representations by taking the spatial cross-correlation of each articulators map across pair-wise subject comparisons (S1-2, S2-S3, and S1-S3). If the representation of an individual articulator occupies a similar spatial location across subjects, large correlations centered at [0,0] and that fall off with distance are expected. This analysis revealed that the representations of individual articulators were in similar locations across subjects, as evidence by the large values (red) very near the center of the heat map, corresponding to zero relative shift. The similarity in spatial localization is summarized in (panel C) by averaging the individual with-in articulator, cross-subject cross-correlations functions, which exhibits a peak near [0,0]. Given the anisotropy described in (panel A), a similar anisotropy is expected to be seen here. For comparison, an example of the average with-in articulator, cross-subject correlation function derived from a single random permutation of the spatial location of each subject's electrodes is presented on the right (panel C, Random). In panel D, the difference between the observed and random correlations were quantified by averaging the values with in a 3 mm radius for individual comparisons.

The correlation values for the data (0.195±0.064, mean±s.e., 3 subjects×4 articulators, n=12) were significantly greater than for the randomized data (0.031±0.021, mean±s.d., $P<10^{-3}$, 1000 iteration permutation test). Therefore, the representation of individual articulators is more consistently located across subjects than expected by chance.

Panels E and F of FIG. 8 show the spatial sequence of articulator representations is statistically observed for each subject. The with-in subject spatial sequence of articulator representations was examined by taking the spatial cross-correlation between spatially adjacent representations (Larynx→Tongue, Tongue→Jaw, Jaw→Lips), within each subject. Given the anisotropy of individual articulator representations (panel A), if the dorsal-ventral sequence of articulator representations described in FIG. 2 is robust at the single subject level, then a negative-to-positive transition of the correlations about the main diagonal (dashed black line) is expected to be seen. This analysis revealed that the representations of individual articulators were spatially sequenced along the dorsal-ventral axis, as evidenced by the negative-to-positive transition across the dashed line. The similarity in spatial sequencing is summarized in (panel E) by averaging the individual cross-articulator, with-in subject cross-correlation functions. The change in sign of the spatial cross-correlation function about the diagonal is the telltale signature of a spatially sequenced organization. For comparison, an example of the average cross-articulator, within-subject correlation function derived from a single random permutation of the spatial location of each subject's electrodes is presented on the right (panel E, random). In panel F, the difference between the observed and random correlations were quantified by averaging the values within the 6 mm semi-circle above and below the diagonal separately for individual comparisons. The correlation values for the above diagonal data were positive (0.099±0.052, mean±s.e., 3 subjects×3 cross-articulator comparisons, n=9) and significantly greater than for the randomized data (0.004±0.018, mean±s.d., 1000 permutations for each subject; $P<10^{-3}$); in contrast, the correlation values for the below diagonal data were negative (−0.102±0.052, mean±s.e., n=9) and significantly greater (in magnitude) than for the randomized data (0.005±0.017, mean±s.d., $P<10^{-3}$, 1000 permutations for each subject). Therefore, the dorsal-ventral sequence of articulator representations is stronger than expected by chance. Together, the data and analysis presented in Supplementary FIGS. 2-3 demonstrate that the representational organization of the articulators in individual subjects is statistically similar. Furthermore, these analyses suggest that the coordinate system used here (anterior-posterior distance relative to the central sulcus and dorsal-ventral distance relative to Sylvian Fissure), is an important organizational reference frame for the Rolandic cortex.

Spatial Organization Analysis

To further understand the observed functional organization of articulator representations, the average Euclidean distance (in mm) was measured between electrodes categorized according to their preferred articulator (winner-take-all categorization). Compared were the distributions of average intra-articulator distances and cross-articulator distances to predictions from a perfect linear somatotopy and from a completely random scattering (1000 maps each). These null models had similar parameters to the observed organization (same number of points per articulator, approximately the same range of spatial values and total area covered) and were used as bounding conditions to set the scale for possible outcomes (FIG. 10).

Figure 10:
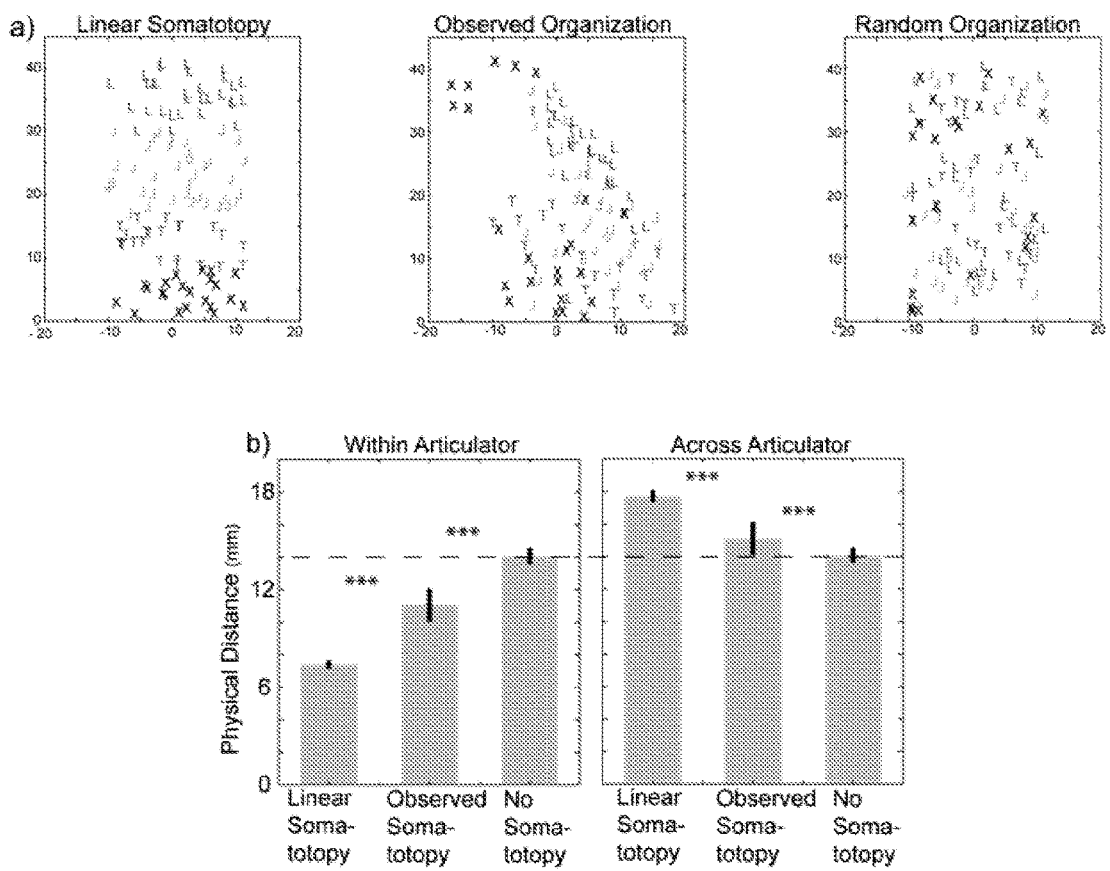
FIG. 10 shows that the observed articulator organization is neither a perfect linear somatotopy nor a random distribution (Panel A). The average Euclidean distance (in mm) between electrodes categorized according to their preferred articulator (winner-take-all categorization) were measured to further understand the observed functional organization of articulator representations (Panel B).

As shown in FIG. 10, the distributions of average intra-articulator distances and cross-articulator distances were compared to predictions from a perfect linear somatotopy and from a completely random distribution (1000 simulated maps each). These null models had similar parameters to the observed organization (same number of points per articulator, approximately the same range of spatial values and total area covered) and were used as bounding conditions to set the scale for possible outcomes. The observed map is presented in the middle panel of panel A, and is flanked by an example perfect linear somatotopy (left) and an example random scattering (right). Panel B of FIG. 10 shows distributions of intra-articulator distances (left) and cross-articulator distances (right). The perfect linear somatotopy minimizes the intra-articulator distances (7.43±0.25 mm, mean±s.d., 1000 maps) at the expense of maximizing the cross-articulator distances (17.7±0.38 mm, mean±s.d., 1000 maps); conversely, on average, the random scattering has equal distances with-in and across articulators (14.08±0.48 mm vs. 14.07±0.44 mm, mean±s.d., 1000 maps, dashed grey line). The observed intra-articulator distances (11.06±1.01 mm. mean±s.e., n=3188 pair-wise distances) and across articulator distances (15.11±1.01 mm, mean±s.e., n=4587 pair-wise distances) are both intermediate to these bounding values and are significantly different from both the perfect linear somatotopy and the random scattering ($P>10^{-3}$). These results suggest that the observed anatomical organization of articulator representations may reflect a weighted balance of simultaneous constraints on intra-articulator and cross-articulator distances. This may support the integration of multi-articulator information by reducing the physical distance between different articulators, perhaps decreasing delays in neuronal transmission.

Co-Clustering Coefficient

The co-clustering coefficient (FIG. 12) is defined over a set of n tokens and describes the degree of overlap between cluster memberships when these tokens are separated into clusters in different ways (e.g. clustered in different spaces). Each CV syllable, $s_i$, can be clustered in both the cortical state-space and according to the major oral articulators. This clustering will give rise to an assignment of $s_i$ to cortical cluster j ($NC_j$) and articulator cluster k ($AC_k$), where $NC_j$ and $AC_k$ are the sets of syllable assignments to cortical cluster j and articulator cluster k, respectively, and can be of different sizes ($|NC_j|\neq|AC_k|$). Defined here are the articulator clusters according to the known major articulator for the consonants, and according to vowel identity for vowels. For each $s_i$, the associated co-clustering coefficient, $\kappa(s_i) \in [0\ 1]$, is defined in terms of the normalized, symmetric set theoretic difference between $NC=NC_j \backslash s_i$ (i.e. the syllables in $NC_j$ other than $s_i$) and $AC=AC_k \backslash s_i$:

$$\kappa(s_i) = 1 - \frac{|NC \Delta AC|}{|NC| + |AC|} \qquad (8)$$

Where $\Delta$ is the symmetric difference operator: for two sets A and B, $A \Delta B = (A \backslash B) \cup (B \backslash A)$. $\kappa(s_i)$ takes the value 1 if every syllable that is in the same cluster as $s_i$ defined in one space is also in the same cluster as $s_i$ defined in the other space (e.g. NC=AC). Conversely, $\kappa(s_i)$ takes the value 0 if every syllable that is in the same cluster as $s_i$ defined in one space is in a different cluster than $s_i$ defined in the other space (e.g. NC ∩ AC=0).

It is estimated the expected value of $\kappa(s_i)$ under the null hypothesis of no relationship between clustering in cortical state-space and clustering according to major articulator by randomly permuting cluster identity according to articulator while leaving the clustering in the cortical state-space unchanged. This procedure was repeated independently 1000 times for every CV syllable for each subject, and the average of the repetitions was used as the estimate of $\kappa(s_i)$ under the null hypothesis.

LDA Projection of Cortical State-Space

Multiclass LDA was performed on the cortical state-space representations (K) at consonant and vowel times by computing the matrix $A^* = AB^{-1/2}$, where A and B are the class centroids and common with-in class covariance matrices, respectively. Syllables were classified according to major oral articulators (labial, coronal, dorsal) for consonant times and the three vowels (/a/, /i/, and /u/) for vowel times. SVD was then performed on the covariance matrix of $A^*$, and projected the state-space representations of syllables into the first two dimensions of the corresponding eigenspace.

Example 1: vSMC Physiology During Syllable Production

Cortical readings were aligned to acoustic onsets of consonant-to-vowel transitions (t=0) to provide a common reference point across CVs (FIG. 1, panels C-E). The focus was on the high-gamma frequency component of local field potentials (85-175 Hz), which correlates well with multi-unit firing rates. For each electrode, the time-varying high-gamma amplitude was normalized to baseline statistics by transforming to z-scores.

During syllable articulation, approximately 30 active vSMC electrode sites were identified per subject (~1200 mm², change in z-score>2 for any syllable). Cortical activity from selected electrodes distributed along the vSMC dorso-ventral axis is shown for /ba/, /da/, and /ga/ (FIG. 1, panels C-E). The plosive consonants (/b/, /d/, /g/) are produced by transient occlusion of the vocal tract by the lips, front tongue, and back tongue, respectively, whereas the vowel /a/ is produced by a low, back tongue position during phonation. Dorsally located electrodes (e.g. e124, e108; black) were active during production of /b/, which requires transient closure of the lips. In contrast, mid-positioned electrodes (e.g. e129, e133, e105; grey) were active during production of /d/, which requires forward tongue protrusion against the alveolar ridge. A more ventral electrode (e.g. e104; red) was most active during production of /g/, which requires a posterior-oriented tongue elevation towards the soft palate. Other electrodes appear to be active during the vowel phase for /a/ (e.g. e154, e136, e119).

Cortical activity at different electrode subsets was superimposed to visualize spatiotemporal patterns across other phonetic contrasts. Consonants produced with different constriction locations of the tongue tip, (e.g. /θ/ [dental], /s/ [alveolar], and /ʃ/ [post-alveolar]), showed specificity across different electrodes in central vSMC (FIG. 1, panel F), though were not as categorical as those shown for articulators shown in FIG. 1, panels C-E. Consonants with similar tongue constriction locations, but different constriction degree/shape, were generated by overlapping electrode sets exhibiting different relative activity magnitudes (FIG. 1, panel G, /l/ [lateral] vs. /n/ [nasal stop] vs. /d/ [oral stop]). Syllables with the same consonant followed by different vowels (FIG. 1, panel H, /ja/, /ji/, /ju/) revealed similar activity patterns preceding the CV transition. During vowel phonation, a dorsal electrode is clearly active during /u/ (black arrow), but not /i/ or /a/, whereas another electrode in the middle of vSMC had prolonged activity during /i/ and /u/ vowels compared to /a/ (red arrow). These contrastive examples illustrate that important phonetic properties can be observed qualitatively from the rich repertoire of vSMC spatiotemporal patterns.

Example 2: Spatial Representation of Articulators

To determine the spatial organization of speech articulator representations, how cortical activity at each electrode depended upon the movement of a given articulator (using a general linear model) was examined. Binary variables were assigned to four articulatory organs (lips, tongue, larynx, and jaw) used in producing the consonant component of each CV (FIG. 6). In FIG. 2, panel A, spatial distribution of optimal weightings for these articulators (averaged over time and subjects) are plotted as a function of dorsal-ventral distance from the Sylvian fissure and anterior-posterior distance from the central sulcus. Representations were found for each articulator distributed across vSMC (FIG. 2, panel A). For example, the lip representation was localized to the dorsal aspect of vSMC, whereas the tongue representation was more distributed across the ventral aspect.

To determine topographic organization of articulators across subjects, the greatest 10% of weightings from individual articulator distributions were extracted (FIG. 2, panel A) and used a clustering algorithm (k-nearest neighbor) to classify the surrounding cortex (FIG. 2, panel B). An overall somatotopic dorsal-ventral arrangement of articulator representations was found laid out in the following sequence: larynx (X), lips (L), jaw (J), tongue (T), and larynx (X) (FIG. 2, panels A and B; FIGS. 7-10). An analysis of the fractional representation of all articulators at single electrodes revealed clear preferred tuning for individual articulators at single electrodes and also demonstrated that single electrodes had functional representations of multiple articulators (FIG. 11).

Example 3: Timing of Articulator Representations

Because the time-course of articulator movements is on the scale of tens of milliseconds, previous approaches have been unable to resolve temporal properties associated with individual articulator representations. The timing of correlations between cortical activity and specific consonant articulators (using partial correlation analysis) was examined, and included two vowel articulatory features (back tongue & high tongue; FIG. 6).

Figure 3:
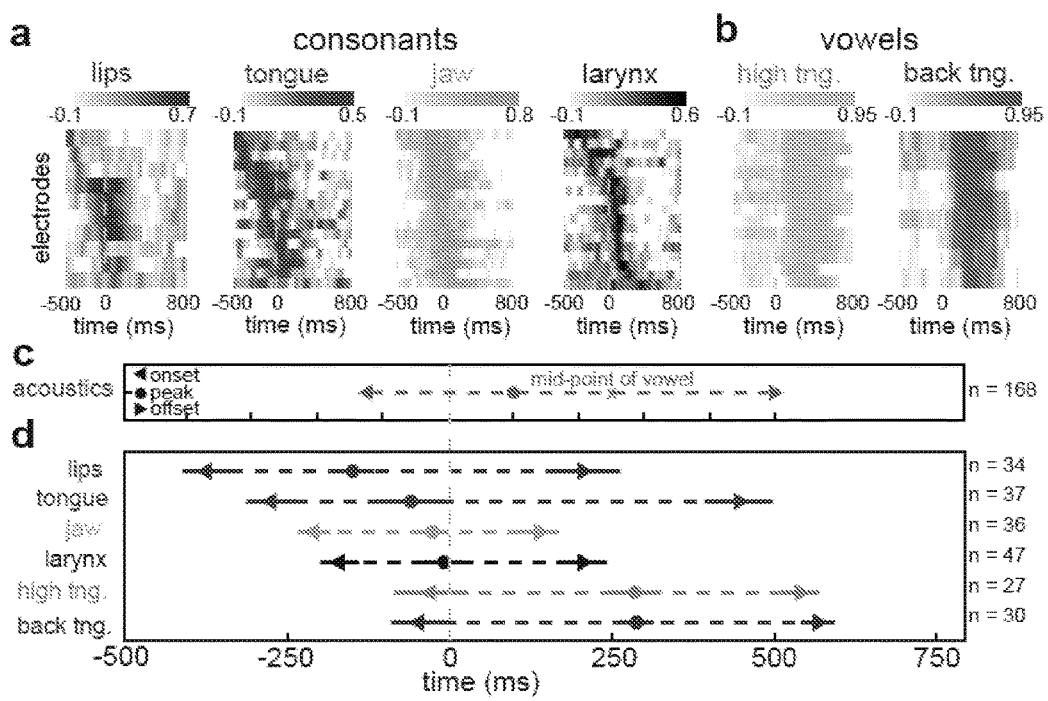
FIG. 3 depicts temporal representation of articulators. Timing of correlations between cortical activity and consonant and vowel articular features is shown in Panel A and Panel B, respectively. Heat maps display correlation coefficients (R) for a subset of electrodes. Acoustic landmarks are shown in Panel C. Onset (<), peak power (o) and offset (>) for CV syllables (mean±s.e., n=168 syllables, all subjects); (x) is vowel midpoint; s.e. bars are smaller than symbols. Panel D shows temporal sequence and range of correlations. Symbols are the same as in Panel C. Data are mean (symbol)±s.e. (solid line) across electrodes from all subjects. The number of electrodes contributing to each articulator is displayed on the right.
Figure 12:
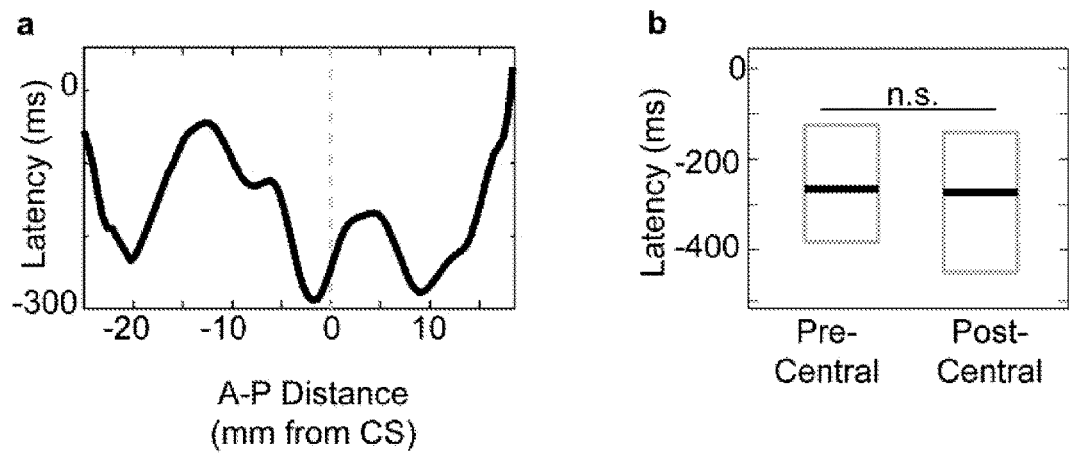
FIG. 12 shows that activation latencies (Panel A) are similar between the pre-central gyrus, the post-central gyrus, and across the guenon (Panel B). Whether activation timing differences could be dissociated between motor and somatosensory processing was examined. For each electrode, the onset latency of the coefficient of determination (R2) was calculated, which quantifies how well the linear articulator model fit the cortical data. It was observed that onset latencies occurred before the CV transition, and no significant latency differences were found in those areas immediately anterior and posterior to the central sulcus (±10 mm), or across the guenon (a-b, P>0.4, Rank-Sum test; n=71 and n=67 electrodes respectively, from three subjects). This suggests that cortical activity recorded throughout the vSMC has significant motor components that are difficult to disambiguate from afferent sensory processes.

Time-courses of correlations for electrodes with highest values were plotted, sorted by onset latency, are shown in FIG. 3, panel A. It was found that jaw, high tongue, and back tongue had very consistent timing across electrodes. Similar results were found for tongue, lips, and larynx, but with more variable latencies. Timing relationships between articulator representations were staggered, reflecting a temporal organization during syllable production: lip and tongue correlations began well before sound onset (FIG. 3, panels A, C and D); jaw and larynx correlations were aligned to the CV transition (FIG. 3, panels A, C and D); high tongue and back tongue features showed high temporal specificity for the vowel phase, peaking near the acoustic mid-point of the vowels (~250 ms, FIG. 3, panels B-D). This sequence of articulator correlations was consistent across subjects (FIG. 3, panel D, $P<10^{-10}$, ANOVA, F=40, df=5, n=211 electrodes from 3 subjects) and accords with timing of articulator movement shown in speech kinematic studies. No significant onset latency differences were found in those areas immediately anterior and posterior to the central sulcus (±10 mm), or across the geunon (FIG. 12). This is consistent with mixed sensory and motor orofacial responses throughout the vSMC, which are also seen in stimulation experiments.

Example 4: Phonetic Organization of Spatial Patterns

Figure 15:
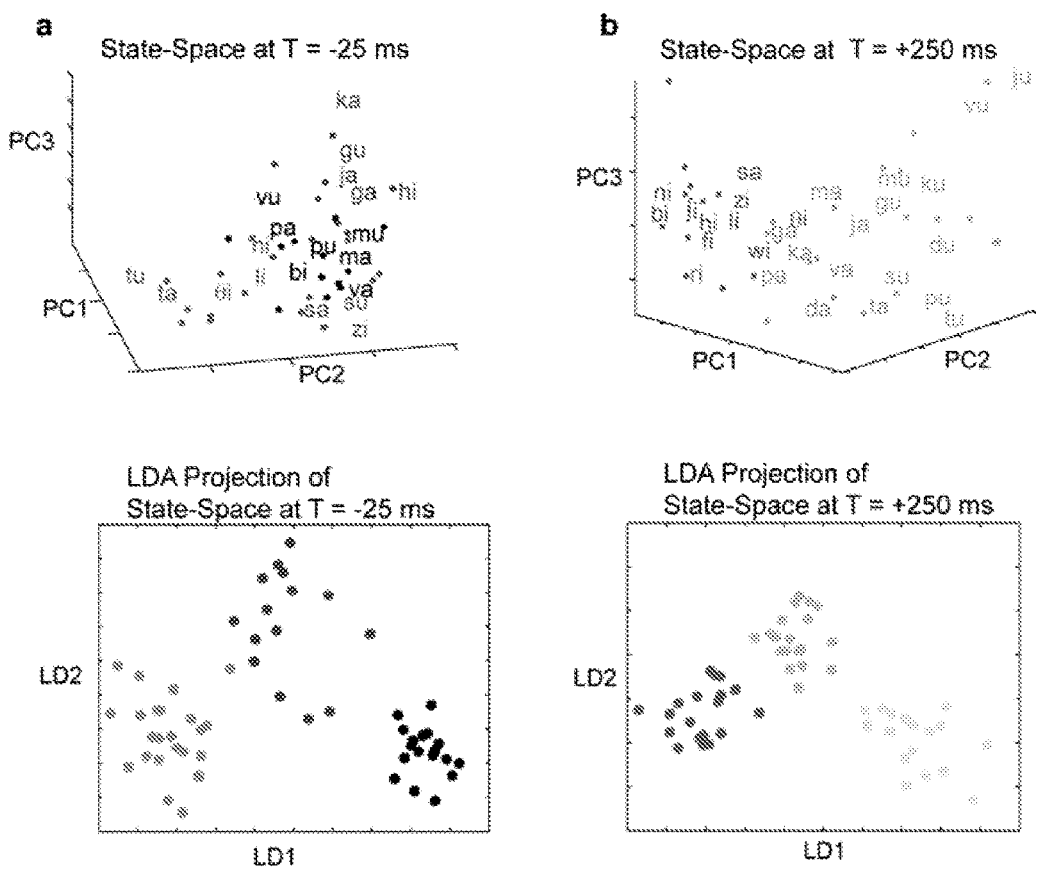
FIG. 15 provides a visualization of linear discriminate analysis (LDA) projection of cortical state-space. LDA was performed on the 9 dimensional principle components space at the consonant and vowel time points, using the major oral articulators and vowel identity as labels (i.e. labial, dorsal tongue, coronal tongue for consonants and /a/, /i/, and /u/ for vowels, k=3 clusters for both). Top: the cortical state-space defined by the first three principal components derived from the covariance matrix of the high-gamma z-scores at the consonant time (Panel A) and at the vowel time (Panel B) were re-plotted. In this display, unsupervised k-means clustering was used to group syllables according to distances in the full nine-dimensional PC state-space. Bottom: projection of the cortical state-space onto the first two linear discriminate axes designed to accentuate the major oral articulator clusters (Panel A) and the vowel clusters (Panel B). The three major clusters are more separated in the LDA rotation than in the original, unsupervised PCA projection. This is to be expected as LDA explicitly looks for rotations of the axes that maximize the (linear) discriminability of these (experimentally defined) clusters.
Figure 16:
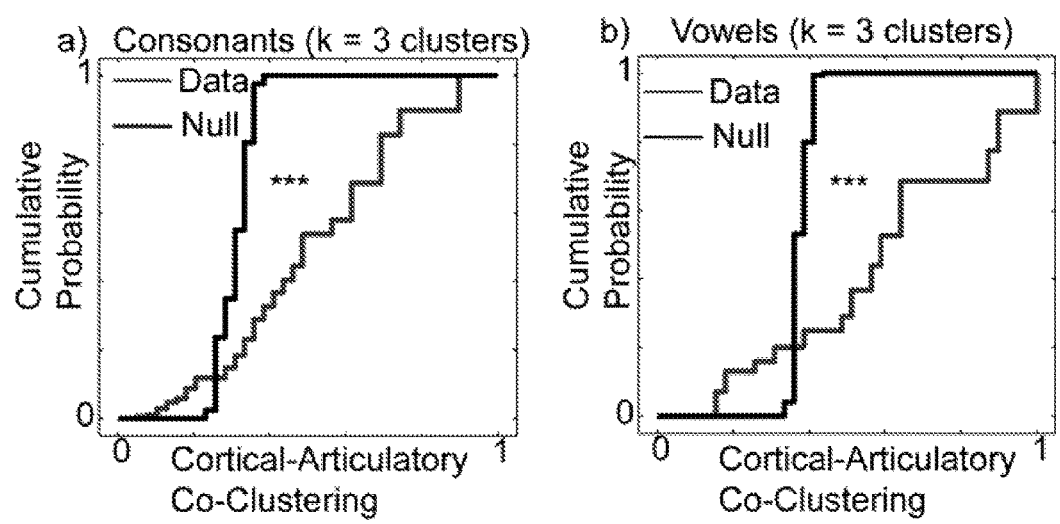
FIG. 16 depicts clustering of CVs in cortical state-space co-clusters with distinguishing articulator features for consonants and vowels. To quantify the degree to which CVs were clustered in cortical state-space according to articulatory constraints, the co-clustering coefficient of CV syllables were calculated. The co-clustering coefficient quantifies the set theoretic overlap between two separate assignments of the same set of tokens to categories. Coefficients are one if and only if the two separate categorical assignments of tokens induce identical clusters of the tokens (100% overlap). Coefficients are zero if and only if every token clustering with a given token in one categorization is in a different cluster in the other categorization (0% overlap). Panel A shows the cumulative distribution of co-clustering coefficients for each CV across subjects for consonants. The co-clustering coefficient for each CV was calculated when categorized by k-means (k=3) clustering in the cortical state-space at a consonant time in each subject, and when categorized according to the three major articulators (Labial, Dorsal Tongue, Coronal Tongue). Across subjects, it was found that clustering of CV's in the cortical state-space co-clustered with the major articulators significantly more than expected by chance. The line with the more gradually rising cumulative probability from left to right is the observed distribution, median=0.50. The line with the more sharply rising cumulative probability from left to right is the null distribution from 1000 random permutations of articulator assignments of CVs, median=0.32; ***: $P<10^{-20}$, Wilcoxon signed-rank test, n=168 syllables from three subjects). Similar results were obtained for each subject individually (Wilcoxon signed-rank test, $P<10^{-6}$, bonferroni corrected for m=3 comparisons, data not shown). Panel B shows the cumulative distribution of co-clustering coefficients for each CV across subjects for vowels. The co-clustering coefficient for each CV was calculated when categorized by k-means (k=3) clustering in the cortical state-space at a vowel time in each subject, and when categorized according to the three vowels (/a/, /i/, and /u/). Across subjects, it was found that clustering of CV's in the cortical state-space co-clustered with the three vowels significantly more than expected by change. The line with the more gradually rising cumulative probability from left to right is the observed distribution, median=0.65. The line with the more sharply rising cumulative probability from left to right is the null distribution, median=0.37; $P<10^{-15}$, Wilcoxon signed-rank test, n=168 syllables from three subjects, not all subjects had all syllables). Similar results were obtained for each subject individually (Wilcoxon signed-rank test, P<0.05, bonferroni corrected for m=3 comparisons, data not shown).

It was hypothesized that the coordination of multiple articulators required for speech production would manifest as spatial patterns of cortical activity. Here, this population-derived pattern is referred to as the phonetic representation. To determine its organizational properties, principal components analysis was used to transform the observed cortical activity patterns into a 'cortical state-space' (9 spatial principal components (PCs) for all subjects, ~60% of variance explained, FIGS. 13 and 14). K-means clustering during the consonant phase (−25 ms prior to the release of the consonant) showed that the cortical state-space was organized according to the major oral articulators (quantified by Silhouette analysis): labial (lips), coronal (front) tongue, and dorsal (back) tongue (FIG. 4, panel A, FIG. 15). During the vowel phase, clear separation of /a/, /i/, and /u/ vowel states was found (FIG. 4, panel B). Similar clustering of consonants and vowels was found across subjects ($P<10$-10 for clustering of both consonants and vowels, FIG. 16).

Theories of speech motor control and phonology have speculated a hierarchical organization of phoneme representations given anatomical and functional dependencies of the vocal tract articulators during speech production. To evaluate such organization in vSMC, hierarchical clustering to the cortical state-space (FIG. 4, panels C and D) was applied. For consonants, this analysis confirmed that the primary tier of organization was defined by the major oral articulator features: dorsal, labial, or coronal (FIG. 4, panel C). These major articulators were superordinate to the constriction location within each articulator. For example, the labial cluster could be subdivided into bi-labial and labio-dental. Only at the lowest level were suggestions observed of organization according to constriction degree/shape, such as the sorting of nasal (/n/ syllables), oral stops (/d/, /t/), and lateral approximants (/l/). Analogously, during the vowel period, a primary distinction was based upon the presence/absence of lip-rounding (/u/ vs. /a/ & /i/) and secondary distinction based on tongue posture (height and front/back position) (FIG. 4, panel D). Therefore, the major oral articulator features that organize consonant representations are similar to those for vowels.

Figure 17:
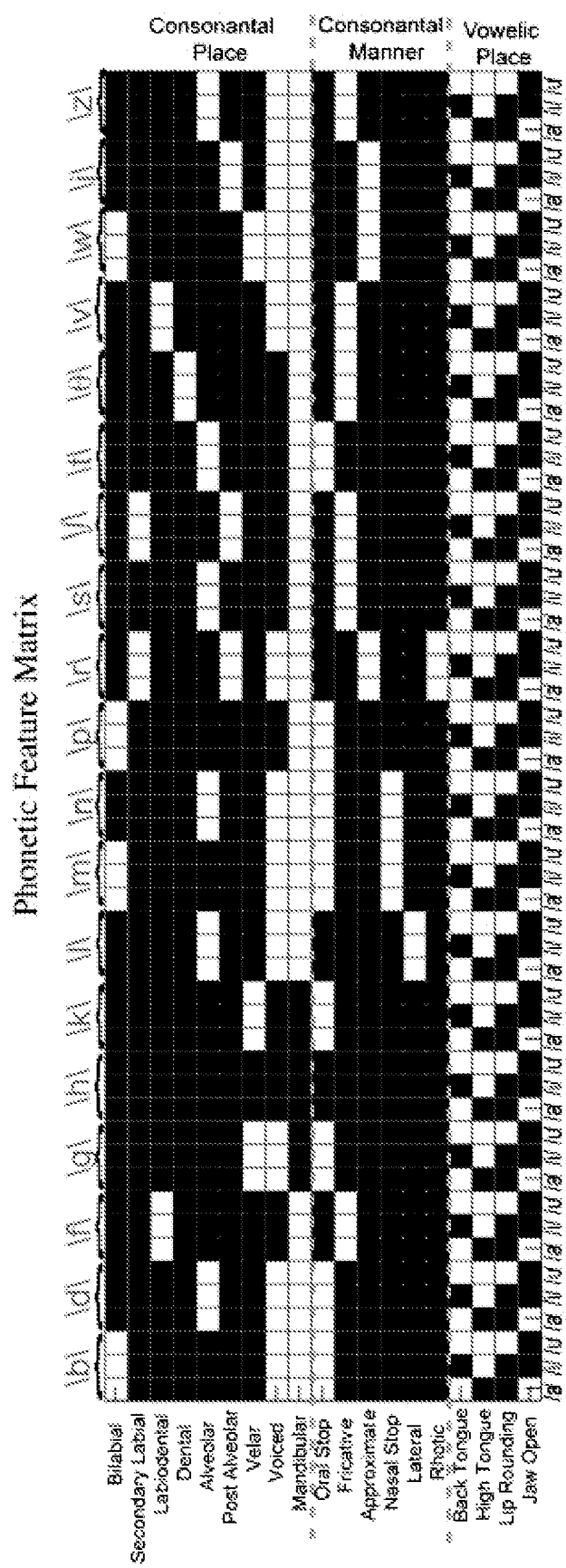
FIG. 17 depicts a phonetic feature matrix. For the analysis of phonetic structure of the CVs in the data set, a standard description derived from IPA was used. This feature matrix has nine features for the constriction location (~place of consonant articulation), six features for the constriction degree and shape (~manner of consonant articulation), as well as four features describing vocalic articulator configurations. IPA symbols for consonant (top) and vowel (bottom) segments are presented. White boxes correspond to 1, black to 0.
Figure 18:
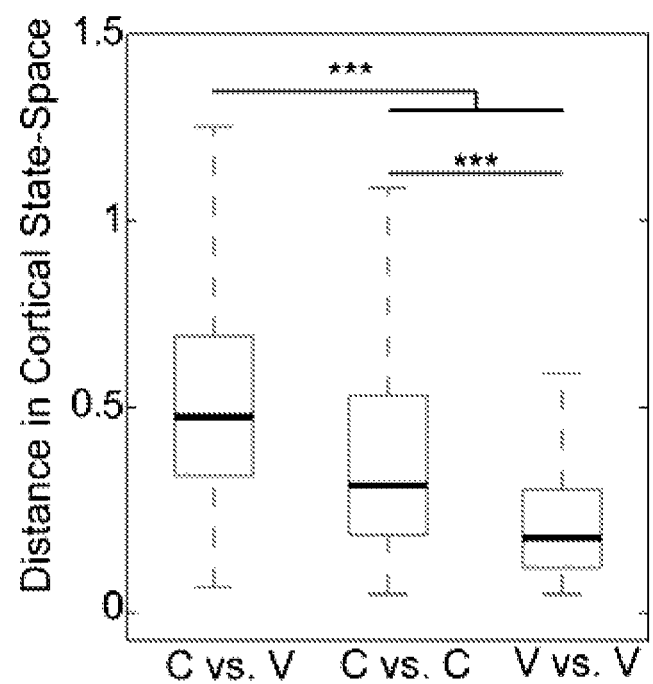
FIG. 18 shows a comparison of consonant and vowel representations. The distributions of distances comparing consonant and vowel representations are displayed. It was found that the distribution of distances comparing consonants and vowels was significantly greater than the consonant-consonant comparison or vowel-vowel comparison, and the consonant-consonant comparison was greater than the vowel-vowel comparison ($P<10^{-10}$ for all comparisons, Wilcoxon signed-rank test, n=4623 for all, bonferroni corrected for m=3 comparisons). Black line in plots correspond to median of data; grey boxes correspond to $25^{th}$ and $75^{th}$ percentiles (whiskers extend to ±~2.7 s.d.).

Across early time points (−375:120 ms), it was found that consonant features describing constriction location yielded a significantly greater correlation with the cortical state-space than constriction degree, which in turn was significantly more correlated than the upcoming vowel ($P<10$-10, Wilcoxon signed-rank test (WSRT), n=297 from 3 subjects; see FIG. 17 for phonetic feature sets). This analysis demonstrates that constriction location accounts for more structure of spatial activity patterns than does constriction degree/shape. Analogously, across later time points (125:620 ms), it was found that vowel features provided the greatest correlation (vowel configuration vs. others, $P<10$-10, WSRT, n=297 from 3 subjects).

Example 5: Dynamics of Phonetic Representations

The dynamics of neural populations have provided insight into the structure and function of many neural circuits. To determine the dynamics of phonetic representations, how state-space trajectories for CVs entered and departed target regions for phonetic clusters was investigated. Trajectories of individual CV syllables were visualized by plotting their locations in the first two PC dimensions versus time. PC1 and PC2 for Subject 1 are shown in FIG. 5, panels A and B.

How trajectories of different consonants transitioned to a single vowel /u/ was first examined (FIG. 5, panel A). The cortical state-space was initially unstructured, and then individual trajectories converged within phonetic clusters (e.g. labial, front tongue, dorsal tongue, and sibilant), while simultaneously cluster trajectories diverged from one another. These convergent and divergent dynamics gradually increased the separability of different phonetic clusters. Later, as each consonant transitioned to /u/, trajectories converged to a compact target region for the vowel. Finally, trajectories diverged randomly, presumably as articulators returned to neutral position. Analogous dynamics were observed during the production of a single consonant cluster (e.g. labials) transitioning to different vowels (/a/, /i/, and /u/) (FIG. 5, panel B).

The internal dynamical properties of the cortical state-space were quantified by calculating cluster separability, which measures the mean difference of between-cluster and within-cluster distances. The time course of cluster separability, averaged across subjects and CVs, is plotted in FIG. 5, panel C: separability peaked ~200 ms before the CV transition for consonants (onset, ~−300 ms), and at +250 ms for vowels (onset, ~50 ms). Further examined were the dynamics of correlations between the structure of the cortical state-space and phonetic features (averaged across subjects), which is plotted in FIG. 5, panel D. Across subjects, it was found that cluster separability and the correlation between cortical state-space organization and phonetic features were tightly linked for both consonants and vowels in a time-dependent fashion ($R^2$ range=[0.42 0.98], $P<10^{-10}$ for all). This demonstrates that the dynamics of clustering in the cortical state-space is strongly coupled to the degree to which the cortical state reflects the phonetic structure of the vocalization.

The dynamic structure of the cortical state-space during production of all CV syllables is summarized in FIG. 5, panel E. In this visualization, the center of each colored tube is located at the centroid of the corresponding phonetic cluster. Tube diameter corresponds to cluster density and color saturation represents the correlation between the structure of the cortical state-space and phonetic features. This visualization highlights that, as the cortical state comes to reflect phonetic structure (coloring), different phonetic clusters diverged from one another, while the trajectories within clusters converged. Furthermore, it was observed correlates of the earlier articulatory specification for sibilants (red, e.g. /sh/, /z/, /s/). Additionally, with all CVs on the same axes, it was observed that consonants occupy a substantially distinct region of cortical state-space compared to vowels, despite sharing the same articulators. The distribution of distances comparing consonant and vowel representations was significantly greater than the consonant-consonant comparison or vowel-vowel comparison ($P<10$-10 for all comparisons, WSRT, n=4623 for all, FIG. 16). Finally, the consonant-to-vowel sequence reveals a periodic structure, which is sub-specified for consonant and vowel features.

Example 6: Spatiotemporal Speech Production Signal Patterns for Consonant-Vowel Syllables Spatiotemporal speech production signal patterns for the various consonant-vowel syllables were generated using a 16×16 ECoG array placed on the speech motor cortex of a subject. FIG. 19, panel A shows the position of the array relative to the subject's brain, indicating that the array is disposed over the subject's speech motor cortex (including the vSMC). Panels B-T show the spatiotemporal speech production signal patterns for the consonant vowel syllables indicated in the respective panels.

Discussion

Our broad-coverage, high-resolution, direct cortical recordings allowed us to examine the spatial and temporal profiles of speech articulator representations in human vSMC. Cortical representations were somatotopically organized, and punctuated by sites tuned for a preferred articulator and co-modulated by other articulators. The dorsal-ventral layout of articulators recapitulates the rostral-to-caudal layout of the vocal tract. However, it was found an additional laryngeal representation located at the dorsal-most end of vSMC. This dorsal laryngeal representation appears to be absent in non-human primates, suggesting a unique feature of vSMC for the specialized control of speech. Pre- and post-central gyrus neural activity occurred before vocalization, which may reflect the integration of motor commands with proprioceptive information for rapid feedback control during speaking.

Just as focal stimulation is insufficient to evoke speech sounds, it is not any single articulator representation, but rather the coordination of multiple articulator representations across the vSMC network that generates speech. Analysis of spatial patterns of activity revealed an emergent hierarchy of network states, which organized phonemes by articulatory features. This functional hierarchy of network states contrasts with the anatomical hierarchy often considered in motor control. The cortical state-space organization likely reflects the coordinative patterns of articulatory motions during speech, and is strikingly similar to a theorized cross-linguistic hierarchy of phonetic features ("feature geometry"). In particular, the findings support gestural theories of speech control over alternative acoustic (hierarchy primarily organized by constriction degree) or vocal tract geometry theories (no hierarchy of constriction location and degree).

The vSMC population exhibited convergent and divergent dynamics during production of different phonetic features. The dynamics of individual phonemes were superimposed on a slower oscillation characterizing the transition between consonants and vowels, which occupied distinct regions of the cortical state-space. Although trajectories could originate or terminate in different regions, they consistently passed through the same (target) region of the state-space for shared phonetic features. Large state-space distances between consonant and vowel representations may explain why it is more common to substitute consonants with one another, and same for vowels, but very rarely across categories in speech errors (i.e. slips of the tongue').

Demonstrated herein is that a relatively small set of articulator representations can flexibly combine to create the large variety of speech sounds in American English. The major organizational features found here define many phonologies throughout the world. Consequently, these cortical organizational principles are predicted to be conserved, with further specification for unique articulatory properties across different languages.

Example 7: Vowel Variability and Coarticulation in the Human Sensory-Motor Cortex Speech is thought to be generated from invariant movement plans for the production of elemental speech sounds called phonemes. However, variability exists in speech production—some of which is inherent to vocal control, and some reflects contextual effects of surrounding phonemes. To examine if and how cortical activity covaries with speech variability, high-resolution, multi-electrode neural activity was recorded directly from human ventral sensory-motor cortex (vSMC) during the production of consonant-vowel syllables. It was found that single-trial vSMC activity was predictive of the produced acoustic parameters of different vowels, and different renditions of the same vowel. vSMC activity for vowels was influenced by the preceding consonant, and vSMC activity for consonants was influenced by upcoming vowels. vSMC population representations for individual phonemes were biased towards population representations for adjacent phonemes. These results demonstrate that vSMC representations for phonemes are not invariant and provide evidence of a cortical source for coarticulation.

Materials and Methods

The following are general materials and protocols used in Example 7. The experimental protocol was approved by the Human Research Protection Program at the University of California, San Francisco.

Subjects and Experimental Task

Three native English speaking human subjects underwent chronic implantation of a high-density, subdural electrocortigraphic (ECoG) array over the left hemisphere (two subjects) or right hemisphere (one subject) as part of their clinical treatment of epilepsy. Subjects gave their written informed consent before the day of surgery. All subjects had self-reported normal hearing and underwent neuro-psychological language testing (including the Boston Naming and verbal fluency tests) and were found to be normal. Each subject read aloud consonant-vowel syllables (CVs) composed of 18-19 consonants (19 consonants for two subjects, 18 consonants for one subject), followed by one of three vowels. Each CV was produced between 15 and 100 times total. Across these three subjects, data were taken on 24 different recording sessions. Because it was observed that the recorded ECoG signal from a patient could vary from block-to-block, these different recording sessions were used as the samples across which statistical tests were performed.

Data Acquisition and Signal Processing

Cortical field potentials were recorded with ECoG arrays and a multichannel amplifier optically connected to a digital signal processor (Tucker-Davis Technologies [TDT], Alachua, Fla.). The spoken syllables were recorded with a microphone, digitally amplified, and recorded inline with the ECoG data. ECoG signals were acquired at 3052 Hz. The acoustic signal was acquired at 22 kHz.

The time series from each channel was visually and quantitatively inspected for artifacts or excessive noise (typically 60 Hz line noise). These channels were excluded from all subsequent analysis and the raw recorded ECoG signal of the remaining channels were then common average referenced and used for spectro-temporal analysis. For each (useable) channel, the time-varying analytic amplitude was extracted from eight bandpass filters (Gaussian filters, logarithmically increasing center frequencies (70-150 Hz) and semi-logarithmically increasing band-widths) with the Hilbert transform. The high-gamma (high-$\gamma$) power was then calculated by averaging the analytic amplitude across these eight bands, and then this signal was down-sampled to 200 Hz. High-$\gamma$ power was z-scored relative to the mean and standard deviation of baseline data for each channel. Throughout, High-$\gamma$ power refers to this z-scored measure, denoted below as H$\gamma$.

Acoustic Formant Extraction

The recorded speech signal was transcribed off-line by a certified speech pathologist using WaveSurfer (http://www.speech.kth.se/wavesurfer/). The vowel formant, $F_0$-$F_4$, was measured as a function of time for each utterance of a vowel using an inverse filter method (Watanabe, 2001; Ueda et al., 2007). Briefly, the signal is inverse filtered with an initial estimate of $F_2$ and then the dominant frequency in the filtered signal is used as an estimate of $F_1$. The signal is then inverse filtered again, this time with an inverse of the estimate of $F_1$, and the output is used to refine the estimate of $F_2$. This procedure is repeated a couple of times and is also used to find $F_3$ and $F_4$. The inverse filter method converges on very accurate estimates of the vowel formants, without making assumptions inherent in the more widely used linear predictive coding (LPC) method. For the extraction of the $F_0$ (pitch), standard auto-correlation methods were used.

Statistical Testing

Figure 20:
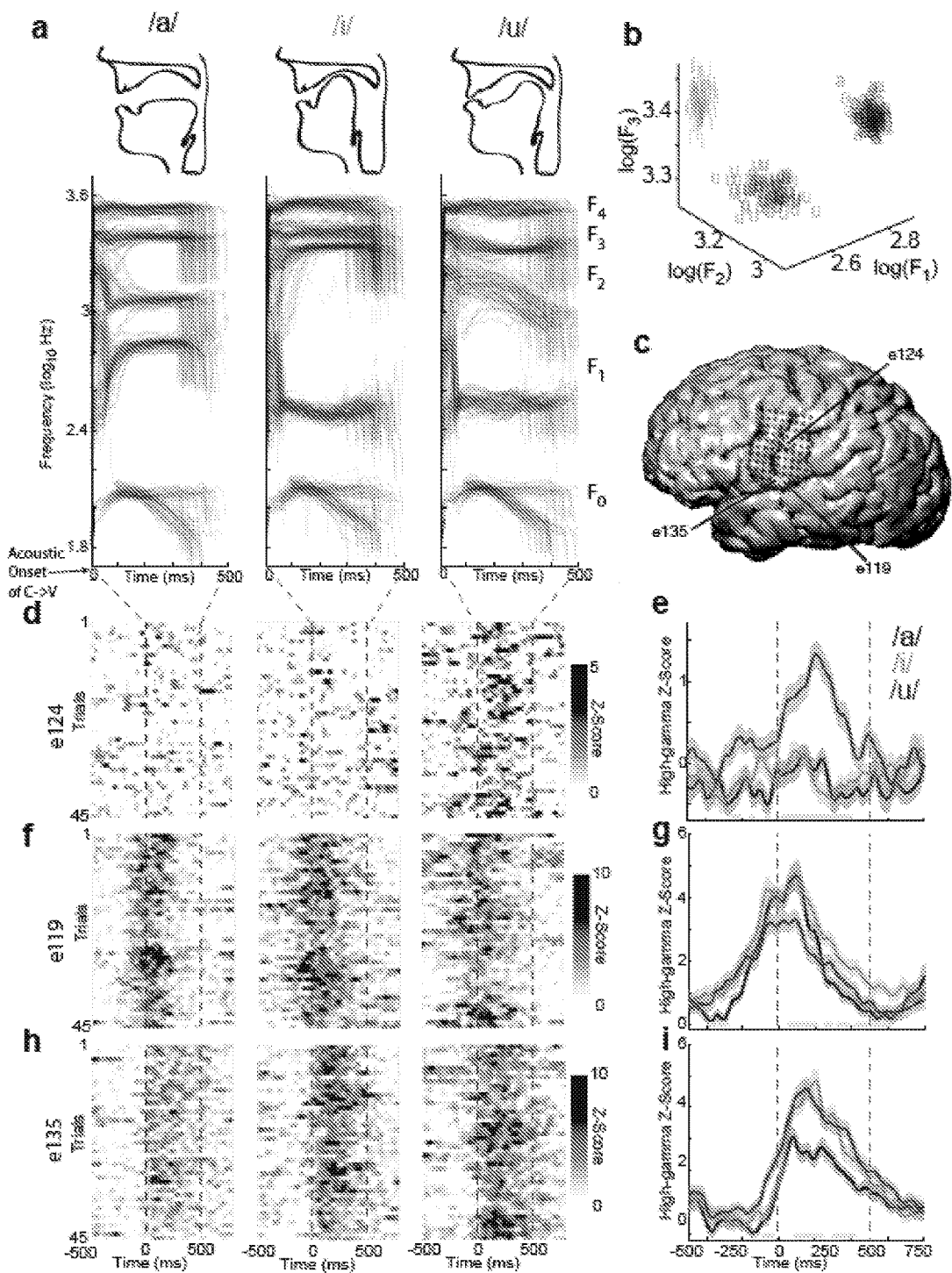
FIG. 20 shows single-utterance vowel acoustics and vSMC neural activity. Panel A shows a schematic of vocal tracts (top) and measured formant traces (bottom, $F_0:F_4$) from more than 100 utterances each of /a/ (left), /i/ (center), and /u/ (right) from one recording session. Formant values were extracted from the central ⅕th of each vowel utterance. Time point 0 is the acoustic onset of the consonant-to-vowel transition. Panel B shows a scatter plot of the vowels in the space formed by $F_1$, $F_2$, $F_3$ ($\log_{10}$ scale) extracted from the traces in Panel A. The vowels /a/, /i/, and /u/ occupy distinct regions of the formant space. Panel C shows a lateral view of the left hemisphere from the same subject with location of electrodes over the ventral half of the sensory-motor cortex highlighted by small dots. The larger dots correspond to electrodes in Panels D-I. Panels D-I show neural activity (high-gamma amplitude, z-scored) vs. time from the electrodes demarcated in Panel C during speech production.

Times with statistically significant differences in Hγ across vowel comparisons in FIG. 20 (e, g, i) were times in which any of three rank-sum tests on pair-wise comparisons resulted in a p-value of less than $10^{-3}$. Statistical significance of the across block distribution of model performance ($R^2$, FIGS. 21, 22, 23, and 25) was performed against the null-hypothesis of 0 with t-tests (see Cross-validation and Regularization Procedure, below). Comparisons between distributions of different $R^2$ distributions (FIG. 22, Panels B-D and FIG. 25, Panels B and C) were performed with Wilcoxon-Signed Rank test. Statistical significance of phoneme-separability (FIG. 26, Panel C) was determined with t-tests against the expected value of 0 under the null-hypothesis (see Quantification of state-space organization, below). Throughout, the results of statistical tests were deemed significant if the Bonferroni corrected probability of incorrectly rejecting the null hypothesis was less than 0.05.

Correlation Coefficient

The Person product-moment correlation coefficient (R) was used to quantify the linear relationship between two variables (x and y):

$$R(x, y) = \frac{\text{cov}(x, y)}{\sigma_x \sigma_y} \quad (9)$$

where $\sigma_x$ and $\sigma_y$ are the sample standard deviations of x and y, respectively.

Acoustic Analysis

The mean formants values were extracted from the central 20% of each vowel utterance, and $\log_{10}$ of these values was used for subsequent analysis. The discriminability of the cardinal vowels (V∈[/a/, /i/, /u/]) was quantified based on individual formant and formant ratio features ($F_i$, i∈[0 1 2 3 4 1/0 2/1 3/2]) using the d' metric. d' is the difference between the mean of two distributions divided by the square root of the product of their standard deviations:

$$d'(F_i^V, F_i^{V'}) = \frac{\mu F_i^V - \mu F_i^{V'}}{\sqrt{\sigma F_i^V \sigma F_i^{V'}}} \quad (10)$$

where $F_i^V$, $F_i^{V'}$ denote the values of formant feature i for vowel V and V'. To summarize the discriminability of a feature, d' for the three vowel comparisons (e.g. /a/ vs. /i/) was calculated, and average these values across comparisons.

PCA and Cortical Features

Principal components analysis (PCA) was performed on the set of all vSMC electrodes for dimensionality reduction and orthogonalization. This also ensures that the matrices in the calculation of least mean squared error estimators (from regressions below) were well scaled. PCA was performed independently for each non-overlapping 10 ms window preceding the acoustic measurement window. First, for each electrode ($e_j$ of which there are n) and syllable utterance (s, of which there are m), the mean high-gamma activity was calculated in 10 ms windows with a non-overlapping two-sample moving average of the Hγ with time lag τ. The Hγ$_j$(τ,s) were used as entries in the n×m data matrix D, with rows corresponding to channels (of which there are n) and columns corresponding to the number of utterances within a recording block (of which there are m). Each electrode's activity was z-scored across utterances to normalize response variability across electrodes. PCA was performed on the n×n covariance matrix Z derived from D. The singular-value decomposition of Z was used to find the eigenvector matrix M and associated eigenvalues λ. The PCs derived in this way serve as a spatial filter of the electrodes, with each electrode $e_j$ receiving a weighting in $PC_i$ equal to $m_{ij}$, the i-j$^{th}$ element of M, the matrix of eigenvectors. Because an object of this study was to examine whether vSMC activity could be used to predict both large acoustic variability (cross-vowel variability) and smaller acoustic variability (with-in vowel variability), the leading 40 eigenvectors were included in the analysis. For each utterance (s), projected was the vector Hγ(τ,s) of high-gamma activity across electrodes into the leading 40 eigenvectors ($M^{40}$):

$$\Psi(\tau,s) = M^{40} \cdot H\gamma(\tau,s) \Psi(\tau,s) = M^{40} \cdot H\gamma(\tau,s) \quad (11)$$

The approach described above identifies principal components (spatial filters) derived only from the spatial structure of the data (structure of Hγ across electrodes); the temporal structure of the Hγ population does not enter into M in any way. Thus, the PC's are completely local in time.

Formant Decoding Model

For each non-overlapping 10 ms time window (τ) preceding the behavioral measurement, the Ψ(τ,s) (equation 11) served as the basis for training and testing optimal linear predictors of single-trial vowel formant features using a 5-fold cross-validation procedure (described below). A simple linear model was used to predict the formant features ($F_i$(s)) for a syllable (s) from Ψ(τ,s):

$$\hat{F}_i(s) = \beta \cdot \Psi(\tau,s) + \beta_0 \hat{F}_i(s) = \beta \cdot \psi(\tau,s) + \beta_0 \quad (12)$$

where $\hat{F}_i(s)$ is the best linear estimate of $F_i(s)$ based on the cortical features. The vector of weights β that minimized the mean squared error between $\hat{F}_i(s)$ and $F_i(s)$ was found through multi-linear regression and cross-validation with regularization (see below).

Formant Encoding Model

A linear encoding model was used to understand the relative contributions of formant features (F(s)) to variations in the associated high-gamma activity of single electrodes (Hγ$_j$(τ,s)) at different lags relative to the acoustic measurement window:

$$H\widetilde{\gamma_j(\tau,}s) = \beta \cdot F(s) + \beta_0 H\widetilde{\gamma_j(\tau,}s) = \beta \cdot F(s) + \beta_0 \quad (13)$$

This model was trained and tested using the same cross-validation procedure describe below, except that no regularization was used; performance was quantified by equation: $R(\widehat{H\gamma_l(\tau,s)}, H\gamma(\tau,s))$. Separate encoding models (5) were trained based on formants ($F(s)=[F_0(s)\ F_1(s)\ F_2(s)\ F_3(s)\ F_4(s)]$) and formant ratios ($F(s)=[F_{1/0}(s)\ F_{2/1}(s)\ F_{3/2}(s)]$). These models were fit separately because of the explicitly strong correlation between formants and formant ratios.

Cross-Validation and Regularization Procedure

A cross-validation procedure was used to train and test separate decoding/encoding models for within and across vowel acoustic features. Separate models were trained/tested for each time-point (dt=10 ms) and recording block. The procedure is as follows. First, 200 random 80% subsets of the data were used to derive linear weights for the models (equations 12 and 13), and the performance (equation 9) of these models was validated on the remaining 20% of the data not used in training. From this, a distribution of 200 weights ($\beta*^{obs}$) was arrived at for each formant. Second, to derive null distributions of weights ($\beta*^{rnd}$) and model performance ($R^2_{rnd}$), each vowel formant was randomly permuted (200 times) independently relative to $H\gamma$ on a trial-by-trial basis, and the same cross-validation procedure described above was used to derive model weights from training data and model performance on test data. For predicting acoustics from cortical features (equation 12), the dimensionality of the cortical features ($\Psi$) was reduced by comparing the distributions of model weights between the observed and randomized data sets to identify cortical features (i.e., PC projections) with weight distributions that were different between the two conditions. Specifically, cortical features ($\Psi_j$) were retained if the mean of the distribution of weight magnitudes ($|\beta_{j*}^{obs}|$) was greater than the mean plus one standard deviation of the distribution of weight magnitudes derived from the randomization procedure ($|\beta_{j*}^{rnd}|$). Finally, decoders were again trained based only on this reduced set of cortical features to arrive at optimal weights ($\beta*^{reg}$) and determined decoding performance ($R^2_{reg}$) on test data used 5-fold cross-validation. This 'regularization' resulted in improved decoding performance (up to ~10%) on validation data. The choice of threshold (mean plus one standard deviation of null distribution) was chosen by visual examination of the weight distributions. An optimization of this threshold may have resulted in better model performance; however, because the chosen threshold resulted in good decoding performance, this optimization was not done to reduce computational run-time.

The decoding performance for each block and decoding condition was taken as the mean of $R^2_{reg}$ values across random test samples. This quantifies the expected value of predictive decoding performance across randomly selected training and test samples. The scatter plots in FIG. 2 (Panel A) and FIG. 3 (Panel A) were constructed by taking the expected predicted formant values for a given data point from all validation sets that contained that data point (i.e. the average predicted value across different cross-validation randomizations).

It was confirmed that the expected value of $R^2$ under the null hypothesis for our data and procedure was 0 by examining the distributions of $R^2_{rnd}$. Across all blocks, times and conditions, $R^2_{rnd}$ had a median very close to 0 (median<0.001 for all). As there are more cortical features in the model used to derive $R^2_{rnd}$ than $R^2_{reg}$, comparing $R^2_{reg}$ to $R^2_{rnd}$ is a conservative approach for statistical testing. Therefore, the significance of the across block distributions of $R^2_{reg}$ was gauged for each feature and time-window by performing t-tests against the null-hypothesis of 0. The conclusions of significance were insensitive to different statistical tests.

Analysis of Perseverative Co-Articulation of Vowel Acoustics

A linear model was used to account for the co-articulation effect of the preceding consonant on the formants of vowels. In agreement with previous studies, it was observed that perseverative coarticulation was mediated by which of three major oral articulators (lips, coronal tongue and dorsal tongue) is required for production of the preceding consonant. Therefore, the effect of perseverative co-articulation was modeled for all of the formant features of each vowel by a linear model based on a 3×1 binary vector indicating which articulator was engaged by the preceding consonant (see Extended Data FIG. 1). The articulatory contributions to perseverative co-articulation on formants was quantified and removed using a linear model based on the major articulator of the preceding consonant:

$$\hat{F}_i(s) = \beta \cdot A(s) + \beta_0 \quad (14)$$

This model was fit separately for each vowel, formant feature, and time during the vowel; performance was quantified by equation: $R^2(\hat{F}_i(s), F_i(s))$. A randomization procedure was used to gauge the expected $R^2$ values under the null hypothesis. The results of this analysis are presented in FIG. 23.

The effects of perseverative co-articulation were removed by calculating the residual formant features:

$$F_i^{res}(s) = F_i(s) - \hat{F}_i(s) \quad (15)$$

Therefore, $F_i^{res}(s)$ is the best estimate of the formant features unaffected by (the linear effect of) perseverative co-articulation. Linear decoders to predict $F_i^{res}(s)$ from the cortical features ($\Psi$) was trained and tested as described above.

Dimensionality Reduction

The objective of dimensionality reduction was to derive a 'cortical state-space' to investigate the organization of the vSMC network associated with different consonant-vowel syllables through time. In particular, two related, but not redundant, hypotheses were tested: 1) the identity of adjacent phonemes imparts structure to the state-space representation of activity generating individual phonemes, and 2) the relative location of single-trial trajectories during one phoneme decay smoothly and overlap in time with state-space representations of other phonemes. Specific CV contrasts were used for this analysis. The state-spaces for specific syllable contrasts designed to test the above hypothesis were derived independently. For the examination of perseverative co-articulation, consonants with differing major oral articulators but with the same constriction degree [(/b/ /d/ /g/), (/p/ /t/ /k/), (/w/ /l/ /j/)]transitioning to the different cardinal vowels (e.g. /bu/ vs. /du/ vs. /gu/) were contrasted. Analogously, for anticipatory co-articulation, the different cardinal vowels following each of the consonants (e.g. /ga/ vs. /gi/ vs. /gu/) were contrasted.

Specifically, the goal of the dimensionality reduction scheme was to find a low-dimensional space derived from single trial cortical activity that maximized the separability of specific CV contrasts through time. To this end, a two-step dimensionality reduction scheme was devised, in which Gaussian Process Factor Analysis (GPFA) was followed by Linear Discriminant Analysis (LDA). This approach is similar to previous studies of population neural activity aiming to identify specific axes in state-space (Briggman et al, 2006; Mante et al, 2013). Following dimensionality reduction, DC offsets and differences in scaling across time were removed by z-scoring the single-trial distribution of state-space locations across CV syllable contrasts locally at each point in time. This allowed us to examine the temporal profile with which the relative state-space locations at a given time point was correlated with the relative locations at other times. The local z-scoring procedure, which is a simple translation and scaling, did not change the qualitative structure of the data, but made the quantification of the conservation of relative state-space locations across time more straightforward.

GFPA is an unsupervised dimensionality reduction algorithm designed to simultaneously perform temporal smoothing (under the assumption of Gaussian process dynamics) and dimensionality reduction (with the Factor Analysis model). First, because GPFA assumes non-negative values, the across time minimum was added to the z-scored high-gamma activity for each electrode and trial. Data from all blocks with-in a subject were combined for this analysis. GPFA was then performed on activity across electrodes and time for specific CV contrasts. Across all CV contrasts, optimal smoothing had a standard deviation of 25 ms and the first nine latent dimensions were kept for further analysis ($G^9$). It was observed that the different CV contrasts examined were separable across several latent dimensions from GPFA, and so LDA was applied at consonant and vowel time-points, using contrasting phonemes as class identifiers. LDA is a supervised dimensionality reduction algorithm that finds the projection that maximizes the linear discriminability of the (user defined) clusters. LDA can be thought of as a discrete version of the general linear model decoders used in the results. Multiclass linear discriminants analysis (LDA) was performed on the GPFA representation ($G^{10}$) by computing the matrix $L^* = L\Sigma^{-1/2}$, where L and $\Sigma$ are the class centroids and common with-in class covariance matrices, respectively. Classes were determined by the specific phoneme contrasts examined. The singular-value decomposition of the covariance matrix of $L^*$ was then taken, and projected $G^9$ into the 9-dimensions of the corresponding eigenspace (LDA necessarily results in a n−1 dimensional space). Because there were three classes for each contrast the vast majority of the structure was captured by the first two latent dimensions after LDA projection ($L^2$). Quantification was therefore performed in these dimensions.

Quantification in State-Space Organization

The dynamic organization of the cortical state-space was quantified using two complimentary metrics. First, the time course of cross-trial phoneme separability (see the Examples herein above) of different consonants and vowels transitioning to/from individual phonemes was examined. This quantifies the difference in the average distance between phonemes and the average distance within a phoneme, so larger values correspond to tighter distributions within a phoneme and larger distances between phonemes. The empirical null distribution for this metric was found by randomly permuting trial identity 200 times. This distribution was tightly centered on 0, as expected.

Second, examined was the time course with which the exact relative locations of single-trial trajectories during consonants and vowels were correlated while transitioning to a single adjacent phoneme. Here, the state-space trajectories for single-trials were averaged over a 25 ms window centered on the times of average peak cluster-separability for consonants (Tc) and vowels (Tv). This served as the estimate of state-space region in $L^2$ for particular consonant ($L^2_{Tc}$) and vowel ($L^2_{Tv}$) contrasts. The vector of these values across trials associated with the syllable contrasts described above was then correlated through time using the 'state-space' autocorrelation function (e.g. $R(L^2_{Tc}(t), L^2_{Tc}(t-\tau))$. The empirical null distribution for this metric was found by randomly permuting trial identity across contrasts 200 times. The null distribution was tightly centered on 0, as expected.

In addition, the organization of state-space dynamics was examined by calculating correlation coefficients as described above after randomizing within and across syllables in a given contrast. To examine the time course of single-trial auto-correlations due purely to being part of a specific consonant-vowel syllable, trials (200 times) were randomized strictly within a given consonant-vowel syllable, and calculated the state-space auto-correlation function as described above. To examine the time-course of correlations between the state-space location for a consonant and the other consonants, and for a given vowel with the other vowels, trials were randomized strictly across the syllables for a given contrast. The correlation for a contrast was taken as the average across randomizations.

Introduction

Communication through spoken language relies on a speaker's ability to articulate sounds that are identifiable to a listener as the meaningful units—consonants and vowels—of a language. To maximize communicative clarity, a speaker presumably generates motor commands that differ greatly across phonemes but differ little within multiple renditions of a given phoneme. Indeed, it is commonly hypothesized that the neural representation of different phonemes or syllables are invariant to the differences across multiple renditions. In fluent speakers, the ventral half of the primary sensory-motor cortex (vSMC, Brodmann areas 1, 2, 3, 6b, and 43) is thought to exert precise control of the vocal tract-control that has likely been optimized through evolution, learning, and extensive practice. Despite this, multiple utterances of a given phoneme by the same speaker are not identical. Some variability in the production of the same phoneme is likely inherent to repeated production of any behavior, while some reflects the surrounding phonetic context. Understanding if and how cortical activity is related to various types of behavioral "variability" is critical for disentangling different linguistic and (speech) motor control theories, which often make similar predictions about the average relationship between brain activity and behavior, but different predictions about how activity covaries with variations in behavior.

Previous examination of average activity has shown that individual vSMC electrodes are preferentially active when a particular articulator of the vocal tract (e.g. lips, tongue, jaw, larynx) is engaged in production of a phoneme (see previous Examples herein). Furthermore, phonemes were represented as spatially distributed, dynamic patterns of (average) activity across the vSMC population (see previous Examples herein). These findings raise questions about the role of the vSMC in speech control, such as whether vSMC activity is related to the acoustics associated with different phonemes on a single-utterance basis ("across-phoneme" variability), and if so, which acoustic features are most tightly controlled. Furthermore, it is unknown whether vSMC neural activity has any relationship to the utterance-to-utterance variability in the production of the same phoneme ("within phoneme" variability). Indeed, the standard theory of generative linguistics assumes invariant cortical representations of phonemes, implying that much of the variability in production results from peripheral factors (e.g. noisy synaptic transmission at the neuromuscular junction, or from the biomechanics of the vocal tract). Linking vSMC activity to within-phoneme variability on a single-utterance basis would demonstrate that vSMC representations for phonemes are not invariant.

In natural, continuous speech, phonemes are not produced in isolation, but rather in the context of phoneme sequences. The production of a phoneme can be influenced by surrounding phonemes, a process known as coarticulation. Coarticulation is a primary reason why connected speech is not simply the concatenation of discrete, segmented units, but instead reflects a smoothed trajectory through the speech sequence. The role of the cortex in coarticulation is a central question in linguistics because it directly addresses the representational nature of phonemes in speech production. Understanding the anticipatory/perseverative effects of coarticulation in the vSMC will provide insight into the segmental units of speech production representations.

Investigating the cortical sources of speech variability requires analyzing the trial-by-trial relationship between high-resolution cortical activity and behavior in humans. To accomplish this, cortical activity was recorded directly from the surface of ventral sensorimotor cortex (vSMC) in neurosurgical patients who read aloud a large number of consonant-vowel syllables.

Results

Three neurosurgical patients were implanted with high-density multi-electrode arrays as part of their clinical work-up for epilepsy surgery. Intracranial cortical recordings were synchronized with microphone recordings as subjects read aloud consonant-vowel (CV) syllables commonly used in American English (19 consonants followed by either /a/, /u/, or /i/, Extended Data FIG. 1). This task was designed to sample across a broad range of phonetic features for both consonants and vowels (Extended Data FIG. 1). In particular, /a/, /i/, and /u/ are considered 'cardinal' vowels, as they span the articulatory and acoustic space of all vowels, and are the most conserved in the languages of the world. The cardinal vowels were chosen to examine key questions about co-variation between cortical activity and vowel production in the context of simple consonant-vowel syllables, not the general encoding/decoding of all vowels.

Single-Utterance Acoustics of Vowels and Cortical Activity

To better understand the relationship between vSMC activity and speech production, examined was the magnitude and dynamics with which the acoustic parameters of cardinal vowels covaried with cortical activity on a single-utterance basis. The fundamental frequency ($F_0$) and the first four vowel formants ($F_1$-$F_4$) were extracted as a function of time (see Materials and Methods for the present Example), and calculated formant ratios (Extended Data FIG. 2). The bottom row of FIG. 20 (Panel A) plots single-trial formant traces vs. time (individual black lines) from more than 100 syllables containing –/a/, –/i/ and –/u/ from a male subject during one recording session. Here, formants are aligned to the acoustic onset of the consonant-to-vowel transition (t=0). Vowel formants have an extended duration and reach an acoustic steady state, allowing for accurate measurement. The fundamental frequency ($F_0$) is determined by the vibration frequency of the glottis, while the formants $F_1$ and $F_2$ and ratios $F_1/F_0$ and $F_2/F_1$ are directly related to the physical shape of the vocal tract which is itself determined by the configuration of the tongue, lips, and jaw. Specifically, the production of /a/ is accomplished by depressing the tongue towards the bottom of the mouth (FIG. 20, Panel A, left-top); production of /i/ is accomplished by raising the front of the tongue towards the soft-palate and is optionally accompanied by narrowing of space between the lips (FIG. 20, Panel A, center-top); production of /u/ is accomplished by raising the back of the tongue towards the soft-palate and protruding/rounding the lips (to lengthen the vocal tract) (FIG. 20, Panel A, right-top). These different vocal tract configurations give rise to formant structures for /a/, /i/, and /u/ that are quite distinct (FIG. 20, Panel A), which can be visualized by extracting the formant values from the midpoint (average of middle $\frac{1}{5}^{th}$) of each vowel utterance (FIG. 20, Panel B, Extended Data FIG. 2-3). Across utterances, variability in the acoustics was observed with multiple productions of the different vowels (FIG. 20, Panels A and B), although the means for each feature were generally stable across utterances of a vowel within a recording session (Extended Data FIG. 2).

Neural activity from 80-90 electrodes located directly on the surface of the ventral sensory-motor cortex (vSMC) (FIG. 20, Panel C) was recorded (see previous examples herein). The focus was on the high-gamma frequency component of cortical field potentials (70-150 Hz), which correlates well with multi-unit firing rates (see previous examples herein). For each electrode, the time-varying high-gamma amplitude was normalized to baseline statistics by transforming to z-scores. These direct cortical recordings yielded robust high-gamma activity that differed between the cardinal vowels. Shown in FIG. 20, Panels D-I, is single-trial high-gamma activity recorded from an electrode in the lip area (e124) and two electrodes in the tongue area (e119 and e135) during the production of /ja/, /ji/, and /ju/ (/j/ is the American English sound 'y'), and the corresponding averages (here, data was temporally aligned to the acoustic onset of the consonant to vowel transition). It was found that electrode 124 was selectively active during /u/, the production of which involves lip rounding (FIG. 20, Panels D and E, dots demarcate times with $P<10^{-3}$ from rank-sum tests between vowels). In contrast, while both electrode 119 and electrode 135 are active during all three cardinal vowels, the relative magnitude of activity differentiates one of the vowels from the others. For example, the activity of electrode 119 (FIG. 20, Panels F and G) differed significantly between the vowels at various times, while activity of electrode 135 (FIG. 20, Panels H and I) is consistently greater for /i/ and /u/ (both 'high-tongue' vowels) than for /a/ (a 'low-tongue' vowel), suggesting that e135 is involved in raising the tongue. Together, these examples illustrate that the activity of individual electrodes differentially contribute to vowel production, and emphasize that the vowels are produced by the pattern of activation across multiple cortical sites.

Neural Decoding and Encoding of Across Vowel Acoustics

To quantify how well vowel formant features could be predicted from the population of recorded vSMC activity, cross-validation was used to train and evaluate regularized linear decoders. The cortical features used for decoding were spatial principal components derived independently at each point in time (see Materials and Methods). It was found that such decoders were able to predict single-trial acoustics with high accuracy. In FIG. 21 (Panel A), the $F_2/F_1$ ratio predicted by the decoder is plotted vs. the actual values for one subject. The predicted values are in good agreement with the actual values; for this subject, 81% of the variability in $F_2/F_1$ across the cardinal vowels could be accurately predicted from the vSMC population neural activity. Also note that the best-fit lines of predicted vs. actual $F_2/F_1$ within vowels had very shallow slopes (FIG. 21, Panel A, the upper, middle, and lower dashed lines correspond to regression within /i/, /u/, and /a/ respectively). This suggests that decoders trained to predict across-vowel acoustic variability do a poor job at predicting within-vowel variability.

The time course of decoding performance was examined by training separate decoders on cortical data at different lags relative to the measured acoustics (FIG. 21, Panel B). At each point in time preceding the onset of acoustic measurement, (acoustic measurements were taken as the mean values from the central $\frac{1}{5}^{th}$ of each vowel utterance, onset of central $\frac{1}{5}^{th}$ denoted here as t=0), decoding performance was quantified by calculating the percent of acoustic variance ($R^2$) predicted by the optimal decoder for that time. Our decoding analysis was restricted to the time before the onset of acoustic measurement to focus on vSMC cortical activity preceding the acoustics. The upper trace in FIG. 21, Panel B summarizes decoding accuracy for $F_2/F_1$ (mean±s.e.; N=24 recordings sessions from three subjects) as a function of the lag in cortical data relative to the measured acoustics (t=0). The decoding time course revealed three epochs, with highest decoding during vowel times (i.e. the time when vowel features are represented, t=0: −280, right-most marks along x-axis), high decoding performance during consonant times (i.e. when consonant features are represented) t=−290: −500, middle marks), and a sharp drop in decoding performance during pre-vocal times (t=−510: −650, left-most marks) (see previous examples herein). Note that the very early significant decoding performance may in part reflect the self-paced, list-reading nature of the task. Together, these results demonstrate that the acoustics of cardinal vowels can be predicted with high accuracy from the population of vSMC activity, and high-accuracy decoding extends into consonant times.

Different acoustic features have very different within vs. across vowel statistics (Extended Data FIG. 2-3). For example, $F_2/F_1$ was an acoustic feature which discriminated /a/, /i/, and /u/ from one another and was also amongst the most variable within individual vowels (Extended Data FIG. 3). Therefore, how decoding performance varied as a function of vowel discriminability was examined. For example, it was found that the third formant ($F_3$: FIG. 21, Panel B, middle trace) has smaller within vowel variability but reduced cross-vowel discriminability relative to $F_2/F_1$ (Extended Data FIG. 3). $F_3$ was decoded with less accuracy across all times, though the temporal structure of decoding performance was similar. In contrast, fundamental frequency ($F_0$) varies little across vowels and within vowels, and had significantly reduced decoding performance across all times (though still greater than chance). Across features, it was found that, during peak vowel decoding times (t=−80: −180 ms; shaded area on FIG. 21, Panel B), predictive performance varied widely across acoustic features ($R^2$ range: [0.15 0.80]). Plotted in FIG. 21, Panel C is the average decoding performance for each acoustic feature as a function of how discriminable the vowels are based on that feature (quantified with the discriminability metric d', N=24 blocks, dashed line is from linear regression). It was found that decoding performance of vowel features was well predicted by the discriminability of the feature, with 93% of the decoding performance across features being explained by vowel discriminability. In particular, ~75% of the variance of those features associated with $F_1$ could be decoded from vSMC activity. From an articulatory standpoint, modulations of $F_1$ are related to both the height of the tongue in the mouth and the area between the lips.

A linear decoding model was additionally used to describe the activity of individual electrodes as an optimal weighted combination of the same cross-vowel formant features used in the decoding analysis. Plotted in FIG. 21, Panel D is the time course of cross-validated 'encoding' performance from the top 10% of electrodes per subject (N=25 electrodes from three subjects). It was found that a model based on formants and a model using formant ratios could predict high-gamma activity at individual electrodes equally well across all times, despite the fact that the formant ratio model had fewer parameters. Correlations increased gradually from low-levels 600 ms before the acoustic measurement, then rose sharply to a peak at ~−60 ms, and then declined slightly. This time course is qualitatively different from the dynamics observed for population decoding, though significant encoding performance extended far before the acoustic measurement, as with the decoding results. It was found qualitatively similar patterns of predictive performance (extracted from the shaded region in FIG. 21, Panel D) across features for encoding and decoding models (FIG. 21, Panel E).

Neural Decoding and Encoding of within Vowel Acoustics

It was found that decoders trained to predict the across-vowel variability did a poor job at predicting within-vowel variability (e.g., FIG. 21, Panel A). For each acoustic feature, the within-vowel variability describes the single utterance deviations from the mean of each vowel (Extended Data FIG. 2-3). Therefore, unlike the across-vowel variability, which must be utilized to acoustically discriminate one vowel from the others, the within-vowel variability is often considered 'noise' that interferes with vowel identification. For speech production, the observed poor performance of cross-vowel decoders to predict within-vowel variability raises the question of whether within-vowel variability is related to variability in vSMC during individual vowels, or due to peripheral 'noise' (e.g. noisy transmission at the neuro-muscular junction), or variability that arises in the nervous system independently of vSMC (e.g. the cerebellum). If the vSMC activity generating a vowel is invariant (i.e. categorical), there should be no relationship between the within vowel acoustic variations and the utterance-by-utterance fluctuations in cortical activity, and so decoding performance during the vowel epoch should be at chance levels (i.e. $R^2$~0).

Different decoders were trained for each vowel and formant feature separately and found that even the within-vowel variability can be predicted from vSMC activity, albeit to a lesser extent than the across vowel acoustics. For example, FIG. 22, Panel A plots the predicted values of $F_2/F_1$ vs. the actual values for the same data in FIG. 21, Panel A, and shows that within vowel regression lines (dashed upper-most, middle, and lower-most lines for /i/, /u/, and /a/ respectively) had slopes near unity (thin dashed line extending from 0,0 to 1,1). Across acoustic features, within vowel decoders (red, mean±s.e.; N=24) for /u/ (FIG. 22, Panel B), /a/ (FIG. 22, Panel C), and /i/ (FIG. 22, Panel D) predicted significantly larger amounts of acoustic variability than expected by chance ($P<10^{-10}$ for all, t-test). Within-vowel decoders also outperformed the across-vowel decoders (mean±s.e.; N=24; $P<10^{-10}$ for all, Wilcoxon Sign-Rank Test), which were near chance levels for most features. Across the cardinal vowels, it was found that decoding performance was generally largest for /u/ and smallest for /i/. This could reflect the highly configurable nature of articulations involved in /u/, and the reduced articulatory control involved in /i/, which could result in increased controlled variability for /u/ relative to /i/.

It was found that within the cardinal vowels, some features were more accurately decoded than others. In particular, the features associated with $F_2$ were much more accurately predicted than other features within the vowel /u/, while the differentiation of decoding performance across features was less pronounced for /a/ and /i/ (FIG. 22, Panels B-D). Qualitatively similar patterns of within-vowel predictive performance across formant features were found using a linear encoding model to predict single-trial high-gamma activity at individual electrodes as weighted combination of formant features. Optimal linear combinations of both formants and formant ratios resulted in peak mean correlation coefficients of R=0.14 (Extended Data FIG. 4). Plotted in FIG. 22, Panel E is the correlation coefficients for each feature contributing to the formant (left of the vertical line) and formant ratio (right of the vertical line) encoding models. Together, these results show that a significant portion of the within-vowel acoustic fluctuations have a source in vSMC, demonstrating that the vSMC representation of the cardinal vowels is not invariant at the phoneme level.

Coarticulation in Vowel Acoustics and vSMC Activity

During natural speech, vowels are rarely produced in isolation, but are instead produced in the context of sequences of other phonemes. Previous linguistic studies have shown that vowel formants can differ depending on which articulator is engaged in the production of preceding consonants. Evidence of perseveratory (i.e. carry-over) coarticulation in the vowel formants and corresponding vSMC activity was therefore investigated. Plotted in FIG. 23, Panel A are single-trial $F_2/F_1$ traces from one recording session (same as in FIG. 20, Panels A and B) for /u/, /a/, and /i/, with each trace corresponding to the major articulator of the preceding consonant (labials [e.g. /b/, /p/]; dorsal tongue [e.g., /g/, /k/]; coronal tongue [e.g., /d/, /t/]). This revealed clear evidence of perseveratory coarticulation in the vowel acoustics attributable to the articulators utilized by preceding consonants, especially for /u/. For example, $F_2/F_1$ for /u/ is higher than average when preceded by dorsal tongue consonants, and lower than average when preceded by labial consonants. At each moment in time during the vowel, the magnitude of perseveratory coarticulation was estimated by determining how much of the variability in formant features could be explained by an optimal linear weighting of the major articulator engaged by the preceding consonants (e.g. lips, coronal tongue, dorsal tongue, FIG. 23, Panel B).

Across /u/, /a/, and /i/, this analysis revealed that the ability to predict acoustic variability in vowels based on the articulator of preceding consonant peaked 75-125 ms after the consonant-to-vowel transition. During the central $\frac{1}{5}^{th}$ of each vowel (FIG. 23, Panel B, shaded region), it was found that the perseveratory coarticulation effect on $F_2/F_1$ was large for /u/(~38%), modest for /a/ (~12%), and minimal for /i/ (~6%). Across vowels and acoustic features, it was found a large range of perseveratory coarticulation magnitudes: 3-40% for /u/, 3-17% for /a/, and 3-9% for /i/ (FIG. 23, Panel C, chance is ~2%). The observed pattern of perseveratory coarticulation in the produced vowel acoustics (FIG. 23, Panel C) qualitatively resembles the pattern of within vowel decoding performance across features and vowels (FIG. 22, Panels B-D). This suggests that a portion of the explained acoustic variability may be due to a systematic relationship between cortical activity and perseveratory coarticulation in vowel acoustics.

Qualitative evidence of perseveratory coarticulation in the vSMC activity was observed by visually comparing the high-gamma activity during the production of /a/, /i/ and /u/ when preceded by the consonants /b/, (FIG. 24, Panel A), /d/, (FIG. 24, Panel B), and /g/, (FIG. 24, Panel C). The stop-plosive consonants /b/, /d/, and /g/ are produced by the formation and release of complete occlusion of the vocal tract by the lips, coronal tongue, and dorsal tongue, respectively. The plots in FIG. 24, Panels A-C show the average high-gamma activity of four electrodes distributed along the dorsal-ventral axis of vSMC (burgundy-to-black with increasing distance from Sylvian Fissure). Examination of cortical activity during the production of the vowels revealed qualitative differences across electrodes reflecting preceding articulator engagement. For example, during /u/ (arrows pointing downward to the left), electrodes in tongue areas were more active when preceded by /d/ relative to /b/ and /g/. Analogously, it is possible to examine if the cortical activity generating consonants depends on the upcoming vowel. During /b/ (arrows pointing downward and to the right in FIG. 24, Panel A), the tongue electrodes are more active when the upcoming vowel is /i/ compared to /a/ and /u/. Furthermore, an electrode in the lip area is more active during /d/ when the upcoming vowel is /u/ relative to /a/ and /i/ (arrows pointing downward and to the right in FIG. 24, Panel B). This last example may reflect anticipatory lip rounding for the vowel /u/ during the lip-neutral consonant /d/. These results demonstrate that the multi-electrode patterns of vSMC activity generating individual phonemes can depend on both the preceding and following phonemic context.

A Cortical Source for Coarticulation

Whether the preceding consonant affects the cortical activity generating an individual vowel was quantitatively determined. It was reasoned that if the effects of perseveratory coarticulation observed in vowel formants are mediated purely by the passive dynamical properties (i.e. inertia) of the vocal tract, then these contextual variations in acoustics would not co-vary with vSMC activity. This predicts that removing the effects of perseveratory co-articulation on formant features would increase decoding performance by 'de-noising' the acoustics. Conversely, if the vSMC activity for vowels depends on the preceding consonant, then removing perseveratory coarticulatory effects from the acoustics should reduce decoding performance during vowel times by removing a controlled source of variation. Additionally, significant decoding performance during vowel times that persists after accounting for the acoustic consequences of the preceding consonant would imply that the ability to decode within-vowel fluctuations is not purely due to coarticulatory effects. Therefore, compared was the performance between decoders trained on original formant feature values and decoders trained on residual formant feature values after removing the effects of perseveratory co-articulation (residuals of from the linear model described in FIG. 23).

Plotted in FIG. 25, Panel A is the time course of within vowel (/u/: top, /a/: upper-middle, /i/: bottom-middle) $R^2$'s for decoders trained to predict the original $F_2/F_1$ values (upper-most traces for /u/ and /a/), and for decoders trained to predict the residual $F_2/F_1$ values after subtracting the (linear) effects of the preceding consonant articulator (lower-most traces for /u/ and /a/). The average decoding performance for all features during the vowel phase (FIG. 25, Panel B; Tv: right shaded region in FIG. 25, Panel A) and during the consonant phase (FIG. 25, Panel C; Tc: left shaded region in FIG. 25, Panel A) are also plotted. Focusing on /u/ (top row of FIG. 25, Panels A-C), for which perseveratory coarticulation was largest, during the consonant phase (FIG. 25, Panel A, Tc: left-most shading) removing the effect of preceding articulators on formant features resulted in significant reduction in decoding performance for features associated with $F_2$ (FIG. 25, Panel C *: $P<10^{-3}$, WSRT), as expected methodologically. Crucially, decoding performance was also significantly reduced during the vowel phase (FIG. 25, Panel A, Tv: right-most shading) for features associated with $F_2$ and $F_3$ (FIG. 25, Panel B *: $P<10^{-3}$, WSRT). Qualitatively similar results were observed for /a/ (FIG. 25, Panels A-C), though with greatly reduced magnitude, while no significant effects were found for /i/ (FIG. 25, Panels A-C). Across vowels and features, decoding performance changes due to removing perseveratory coarticulation were largest for features that were most co-articulated (e.g. $F_2$ for /u/ and /a/), and smaller for those that were less coarticulated (e.g. $F_0$). This emphasizes that the ability to decode within vowel feature variability was influenced by the degree to which that feature was coarticulated. These analyses demonstrate that the activity generating a vowel can depend on the preceding consonant.

It was found that removing the effects of perseveratory coarticulation equalized decoding performance across features and across vowels, although small differences remained (e.g. $F_2$ vs. $F_4$ for /u/ during vowel times). Nonetheless, it was found that a modest, but significant amount of residual with-in vowel acoustic variability (9-15%) could be accurately predicted from vSMC activity (distributions of cross-validated $R^2$ were all significantly greater than 0). This implies that some of the variability within the production of a vowel has a source in vSMC.

The high-decoding performance of across-vowel formant features observed during consonant times is strongly suggestive of anticipatory coarticulation in vSMC activity. However, the early decoding performance could reflect perseveratory coarticulation, as observed for within vowel decoders above (FIG. 25, Panel C). It was reasoned that if vSMC activity during consonant times depends on the identity of upcoming vowels, then removing perseveratory coarticulation from the acoustics should minimally affect cross-vowel decoding performance during consonant times. In the bottom row of FIG. 25, Panels A-C, the across-vowel $R^2$'s were compared for decoders trained on formant features and decoders trained on residual formant features after removing perseveratory coarticulation. It was found that removing the effects of perseveratory coarticulation on vowel formant features minimally affected across-vowel decoding performance during vowel times (FIG. 25, Panel A, Tv: right-most shading; FIG. 25, Panel B) and consonant times (FIG. 25, Panel A, Tc: left-most shading; FIG. 25, Panel C). However, across-vowel decoding of the residuals of $F_2$ associated features resulted in subtle, but consistent (and statistically significant), increases in decoding performance across vowels (FIG. 25, Panels B and C, bottom *: $P<10^{-3}$, WSRT). These analyses demonstrate that the cortical activity generating consonants can be highly influenced by the upcoming vowel.

Anticipatory and Perseveratory Dynamics Across the vSMC Network

The decoding results described above, which utilized methodology that was local in time, demonstrates that there is structure in the vSMC network during consonants and vowels that depends on the upcoming/preceding phoneme. However, because of the temporal locality, the network dynamics generating consonant-vowel syllables cannot be uniquely determined from this analysis. Indeed, the observed time-courses of decoding performance are consistent with several different dynamic network organizations. To gain insight into network dynamics, a combination of unsupervised (GPFA of single utterance cortical activity) and supervised (LDA projection for specific syllable contrasts) dimensionality reduction techniques (see Materials and Methods for the present Example) was used to find a low-dimensional cortical state-space corresponding to spatial activity patterns across the vSMC network. How surrounding phonemes affect network trajectories was examined for individual phonemes to gain a more mechanistic understanding into coarticulation using specific syllable contrasts (Methods).

To understand how the network dynamics for consonants were affected by the identity of the upcoming vowel, trajectories of individual consonants transitioning to the vowels /a/, /i/ and /u/ were examined. FIG. 26, Panel A displays the average (mean±s.e.) trajectories derived from single-trial vSMC network activity associated with /ga/, /gi/, and /gu/. Observed was a clear separability of the state-space trajectories reflecting the upcoming vowel identity during the latter portion of the /g/-consonant phase (box in Panel A) as well as earlier times. Furthermore, the relative positions of trajectories during different vowels are preserved through the transition from the preceding consonant. That is, the state-space trajectories through the /g/ 'sub-space' are biased towards the state-space location of the upcoming vowel. Analogously, to understand how the network dynamics for individual vowels depend on the preceding consonant, trajectories of labial, coronal tongue, and dorsal tongue consonants transitioning to either /a/, /i/, or /u/ were examined. FIG. 26, Panel B displays average trajectories derived from single-trial cortical activity associated with /bu/, /du/, and /gu/. During the early vowel time (Tv, box in Panel B), there is clear separability of state-space trajectories according to the preceding consonant identity, and the relative positions during consonants is preserved through the transition to the upcoming vowel.

The dynamic organization of the vSMC state-space was quantified using two complimentary metrics. First, the time course of cross-trial phoneme separability (see Materials and Methods for the present Example) for individual labial, coronal tongue, and dorsal tongue consonants transitioning to a single vowel (e.g. [/bu/ /du/ /gu/] was examined, FIG. 26, Panel C, upper trace, mean±s.e., n=78 syllable contrasts), as well as for the vowels /a/, /i/, and /u/ when transitioning from individual consonants (e.g. [/ga/ /gi/ /gu/], FIG. 26, Panel C, lower trace, mean±s.e., n=162 syllable contrasts). This metric quantifies the difference between within phoneme distances and across phoneme distances in the cortical state-space for a given contrast, with larger values corresponding to more separable state-space trajectories for an individual phoneme. This analysis showed that the identity of adjacent phonemes imparts significant structure during both the peak consonant times (separability>0, $P<10^{-5}$, n=162, t-test) and peak vowel times ($P<10^{-7}$, N=78, t-test). Furthermore, significant separability for consonants and vowels extended across multiple production epochs (FIG. 26, Panel C, *: $P<10^{-5}$, : $P<0.01$, *: $P<0.05$, t-test). This demonstrates that the vSMC network organization for a given phoneme can be structured by the identity of upcoming phonemes (anticipatory coarticulation) and preceding phonemes (perseveratory coarticulation).

How single-trial state-space locations associated with different consonants/vowels persisted through the transition to/from a single adjacent phoneme was further examined. The vector of single-trial state-space locations for different phoneme contrasts transitioning to/from an adjacent phoneme at different lags was auto-correlated. For example, the vector for consonants could correspond to the location of all single-trial trajectories associated with /bu/, /du/, and /gu/ for a given subject. This analysis tests for systematic biases of single-trial state-space trajectories during a phoneme that reflect the state-space location of adjacent phonemes. The trace having the highest peak on the left in FIG. 26, Panel D shows the average state-space auto-correlation function derived from single-trial trajectories centered in consonant times (average state centered at black triangle) for labial, coronal tongue, and dorsal tongue consonants transitioning to individual vowels (mean±s.e., N=78, e.g. FIG. 26, Panel B). Likewise, the trace having the highest peak on the right in FIG. 26, Panel D is the average state-space auto-correlation function derived from single-trial trajectories centered in vowel times (average state determined at red triangle) for /a/, /i/, and /u/ transitioning from individual consonants (mean±s.e., N=162, e.g. FIG. 7a). The average state-space auto-correlations for both consonants and vowels exhibited an initial rapid decay followed by a slower decline. These correlation functions extended through the adjacent phonological segment and beyond.

In addition, the time-course of correlations resulting from randomizing single-trials across different levels of sequence structure were measured to provide further understanding into the dynamic organization of the vSMC network during CV sequences (see Extended Data FIGS. 10-11). Examined were the dynamics of correlations due only to being associated with a specific consonant-vowel syllable by randomizing trials strictly within a syllable (Materials and Methods), which removes single-trial correlations but preserves the mean structure associated with the syllable. The correlations from being in a syllable were much smaller than the observed correlations of single-trial trajectories (FIG. 26, Panel D, lower traces). This demonstrates that long-time organization observed in the state-space auto-correlations corresponds to structure above and beyond that due to simply being associated with a specific syllable. To examine the correlation between trajectories for a given consonant and the other consonants, and for a given vowel with the other vowels, trials were randomized strictly across the different phonemes for a given contrast (Methods). The correlations strictly across phonemes were negative on average and generally small (FIG. 26, Panel D, lower traces). Together, these results demonstrate that the trajectories through phoneme sub-spaces are biased towards surrounding phoneme sub-spaces, and that these biases reflect long-time correlations on the level of single-trials that is preserved across the consonant-vowel transition.

Discussion

High-resolution electrophysiological recordings directly from the surface of human speech sensory-motor cortex were used to examine if and how neural activity covaried with different types of variability in the acoustics of spoken vowels. It was found that vSMC population activity could predict the acoustic parameters associated with different vowels with high accuracy. Furthermore, even a portion of the variability within a vowel could be predicted from the vSMC population, demonstrating a cortical source for within-vowel fluctuations. Significant decoding performance for different vowels extended through the preceding consonant phase, demonstrating that cortical activity during consonants can be modulated by the upcoming vowel. The effects of preceding consonant articulations on vowel acoustics were quantitatively identified. These effects demonstrate that vSMC activity during vowel production covaried with this perseverative coarticulation. Finally, it was found that trajectories through vSMC state-space regions for an individual phoneme were biased towards the state-space regions for adjacent phonemes.

vSMC Control of Vowel Acoustics

The cardinal vowels /a/, /i/, and /u/ are important phonemes in speech, as they are found in most human languages and outline the acoustic and articulatory space of all vowels. To better understand the cortical processes generating vowel acoustics, the covariation between vSMC neural activity and the acoustics of these vowels was examined on a single-trial basis. Examining the relationship between vSMC and speech on a single-trial basis benefits from both the high spatio-temporal resolution of the ECoG grids and the high signal-to-noise ratio of high-gamma band activity.

It was found that vSMC population activity preceding measured vocalizations could predict large amounts (upwards of 75%) of across vowel acoustic structure between /a/, /i/, and /u/ (FIG. 21). Performance in predicting different acoustic features was well predicted by the degree to which those features could statistically discriminate the vowels. For example, the produced variability in $F_1$ and $F_2$, (which are determined by vocal tract shape through positioning the tongue, lips and jaw) was well predicted by vSMC activity; $F_1$ and $F_2$ are also critical for determining vowel identity. In contrast, the variability in pitch ($F_0$, which is controlled by the larynx) was modestly predicted by vSMC activity during our particular task in which pitch change or prosodic voice modulation is not an important articulatory goal. This suggests that, during speech production, vSMC is exerting precise control for the generation of task relevant parameters, while relaxing control for the generation of task irrelevant parameters. Although it was found that vSMC activity was directly linked to the acoustics of produced vowels, it cannot be concluded that the representation of vowels in vSMC is in acoustic coordinates. The results from the previous Examples herein on consonants showed that individual sites in vSMC represent the speech articulators. As a consequence, the organization of vSMC representations of phonemes reflects articulatory relations, not acoustic relations. Indeed, the acoustic features that were most accurately predicted (those associated with $F_1$ and $F_2$), are precisely those features that are most directly related to the positioning of the tongue, lips and jaw.

It has traditionally been assumed that variability across repeated movements towards the same target/goal largely reflects 'noise', perhaps introduced at the neuromuscular junction, or due to biomechanical properties of the skeletomuscular system (i.e. the inertia of the articulators). However, recent electrophysiological recordings from motor cortices in non-humans (e.g. Macaque PMd/M1 and songbird RA) demonstrate that a portion of movement variability has a source in the central nervous system, although such studies do not exist for humans. In line with these findings, it was found that vSMC population activity could accurately predict a significant fraction of the variability within a given vowel (FIG. 22). As expected, the magnitude of within vowel decoding was modest in comparison to across vowel decoding. Furthermore, a modest but significant fraction of within vowel variability (10-15%) could be accurately predicted after quantitatively controlling for effects of different preceding consonants on vowel acoustics (perseverative coarticulation, FIG. 25). This observation implies that the ability to decode within vowel acoustics is not purely a result of coarticulation. Together, these results demonstrate that the cortical activity generating individual vowels is not invariant, but instead can be linked to utterance-to-utterance fluctuations in their production.

A Cortical Basis for Coarticulation

The present Example demonstrates that cortical activity generating individual phonemes exhibits both anticipatory and perseverative coarticulation reflecting surrounding phonemes. Specifically, population decoding showed that vSMC activity during the production of consonants was predictive of the upcoming vowel (anticipatory coarticulation), and that the activity generating a vowel depends on the major articulator of the preceding consonant (perseveratory coarticulation). Furthermore, by examining the dynamic organization of the vSMC network, it was found that state-space trajectories through individual 'phoneme sub-spaces' were biased towards the 'phoneme sub-space' of the adjacent phoneme. These two approaches showed a general temporal correspondence between single-trial decoding performance and the internal organization of vSMC network states, and provide complementary insight into cortical functioning during speech production. Together, these data and analysis provide a definitive demonstration that vSMC activity for phonemes exhibit anticipatory and perseveratory biases towards adjacent phonemes during the production of consonant-vowel syllables.

It is likely that higher-order brain areas (e.g. Broca's area, supplementary motor area) contain more invariant representations than those found here for vSMC. Indeed, the observed perseveratory coarticulation in vSMC activity could result from invariant input command signals. For example, the previous Examples herein demonstrate that human vSMC represents phonemes in terms of the articulations that generate them. Therefore, during the production of a consonant-vowel sequence, the articulatory requirements of different consonants could leave the vSMC network in different initial states when the activity for the vowel begins. These differences in 'initial conditions' could bias subsequent network states that generate the vowel, and thus result in differences in vowel acoustics that depend on the articulations required for the preceding consonant (a sort of 'network inertia' effect). Therefore, in addition to the dynamic biomechanical properties of the vocal tract, perseveratory coarticulation may in part reflect the 'inertial' properties of the dynamical system instantiated by vSMC during speech production. That said, the high decoding performance for vowel acoustics during the consonant phase (FIG. 25), coupled with the observed anticipatory bias in state-space trajectories (FIG. 26), demonstrates that the vSMC network state generating a consonant anticipates the identity of upcoming vowels. Such anticipatory modulations cannot result from 'network inertia' effects that potentially explain results of perseveratory coarticulation. Both the anticipatory and perseverative biases reduce the 'distance traveled' between sequentially activated network states. These biases in network trajectories towards surrounding phoneme states appear to reflect overt, top-down control signals that optimize vSMC for rapid sequence production (speed) and minimize the time-dependent accumulation of behavior deteriorating neural noise (accuracy).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of decoding speech from the brain of a subject, comprising:
   detecting speech production signals from at least three electrodes directly in contact with the speech motor cortex of a subject while the subject produces or imagines producing a speech sound, wherein the speech motor cortex comprises ventral sensorimotor cortex;
   deriving a speech production signal pattern from the detected speech production signals;
   correlating the speech production signal pattern with a reference speech production signal pattern corresponding to features of speech associated with at least two speech articulators selected from the group consisting of lips, tongue, larynx, and jaw, to decode speech from the brain of the subject; and
   producing the speech decoded from the brain of the subject, wherein the speech is produced in an audible form or in a text form.

2. The method of claim 1, wherein the at least three electrodes comprises at least 10 electrodes.

3. The method of claim 1, wherein the at least three electrodes comprises at least 20 electrodes.

4. The method of claim 1, wherein the speech production signals are detected from a region of the ventral sensorimotor cortex selected from: the pre-central gyrus, the post-central gyms, and combinations thereof.

5. The method of claim 1, wherein the at least three electrodes are directly in contact with the speech motor cortex by implantation on the surface of the speech motor cortex.

6. The method of claim 5, wherein the speech production signals are detected using electrocorticography (ECoG).

7. The method of claim 1, wherein the at least three electrodes are directly in contact with the speech motor cortex by insertion of the electrodes into the speech motor cortex.

8. The method of claim 1, wherein detecting speech production signals comprises detecting local field potentials from the speech motor cortex using the at least three electrodes.

9. The method of claim 8, wherein the speech production signals comprise the high-gamma frequency component (85-175 Hz) of the local field potentials.

10. The method of claim 1, wherein the detecting comprises detecting a time-course of speech production signals from each of the least three electrodes.

11. The method of claim 10, wherein the time-course of speech production signals is detected beginning from 250 milliseconds or more prior to the onset of the speech sound.

12. The method of claim 1, wherein the speech sound is selected from the group consisting of: a phoneme, formant acoustics of a vowel, a diphone, a triphone, a consonant-vowel transition, a syllable, a word, a phrase, a sentence, and combinations thereof.

13. The method of claim 12, wherein the speech sound is a syllable.

14. The method of claim 1, wherein deriving a speech production signal pattern comprises performing time-frequency analysis of speech production signals detected from each of the at least three electrodes.

15. The method of claim 14, wherein the time-frequency analysis is performed using a method selected from the group consisting of: Fast Fourier Transform (FFT), wavelet transform, Hilbert transform, and bandpass filtering.

16. The method of claim 1, wherein the at least three electrodes are distributed across the speech motor cortex such that speech production signals corresponding to at least three speech articulators are detected.

17. The method of claim 16, wherein the at least three speech articulators are selected from the group consisting of: the larynx, the lips, the jaw, and the tongue.

18. The method of claim 1, wherein the subject has a speech impairment.

19. The method of claim 1, wherein the method is carried out using a receiver unit, comprising:
- a wireless receiver in communication with a wireless transmitter that receives the speech production signals detected from the at least three electrodes;
- a speech generator;
- a processor; and
- a memory comprising instructions for execution by the processor for deriving the speech production signal pattern from the detected speech production signals, correlating the speech production signal pattern with the reference speech production signal pattern to decode the speech sound, and producing the speech sound using the speech generator.

* * * * *